US006265411B1

(12) United States Patent
Thomas et al.

(10) Patent No.: US 6,265,411 B1
(45) Date of Patent: *Jul. 24, 2001

(54) OXINDOLE DERIVATIVES

(75) Inventors: Andrew Peter Thomas, Macclesfield (GB); Jean-Jacques Marcel Lohmann, Reims Cedex (FR); Laurent Francois Andre Hennequin, Reims Cedex (FR); Patrick Ple, Reims Cedex (FR)

(73) Assignee: Zeneca Limited, London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/180,310

(22) PCT Filed: May 2, 1997

(86) PCT No.: PCT/GB97/01211

§ 371 Date: Nov. 6, 1998

§ 102(e) Date: Nov. 6, 1998

(87) PCT Pub. No.: WO97/42187

PCT Pub. Date: Nov. 13, 1997

(30) Foreign Application Priority Data

| May 6, 1996 | (EP) | 96400956 |
| May 6, 1996 | (EP) | 96400957 |
| Dec. 17, 1996 | (EP) | 96402762 |
| Dec. 17, 1996 | (EP) | 96402763 |

(51) Int. Cl.[7] .................... A61K 31/505; C07D 247/02
(52) U.S. Cl. .......................... 514/259; 544/284
(58) Field of Search ............... 544/284; 514/259

(56) References Cited

U.S. PATENT DOCUMENTS

| Re. 36,265 | 7/1999 | Spada et al. | 514/249 |
| 5,409,930 | 4/1995 | Spada et al. | 514/248 |

(List continued on next page.)

FOREIGN PATENT DOCUMENTS

| 0 326 330 A2 | 8/1989 | (EP) . |
| 0 602 851 A1 | 6/1994 | (EP) . |
| 0 743 308 | 11/1996 | (EP) . |

(List continued on next page.)

OTHER PUBLICATIONS

Gazit et al. Tyrophostins IV–Highly Potent Inhibitors...Relationship Study of 4–Anilidoquinazolines. Bioorganic & Medicinal Chemistry, vol. 4. No. 8, 1996, pp. 1203–1207.
Sinyak, et al., Synthesis and Biological Properties of Derivatives of 4–Heterylmercaptoquinazoline, Zaporozh'e Medical Institute pp. 103–106, translated from Khimiko–farmatsevticheskii Zhurnal, vol. 20, No. 2, Feb. 1986, 168–171, original aarticle submitted 12/29/84.

*Primary Examiner*—Mukund J. Shah
*Assistant Examiner*—Sudhaker B. Patel
(74) *Attorney, Agent, or Firm*—Pillsbury Winthrop LLP

(57) ABSTRACT

The invention relates to compounds of formula (I),

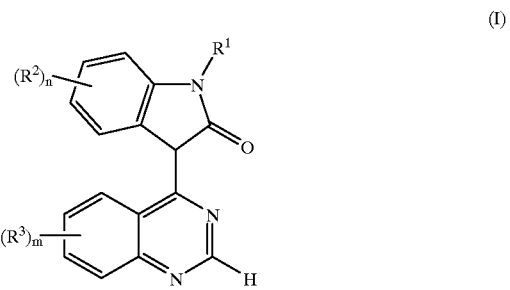

wherein:
$R^2$ represents hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylthio, $C_{1-4}$alkylsulphinyl, $C_{1-4}$alkylsulphonyl, carbamoyl, $N-C_{1-4}$alkylcarbamoyl, $N,N-di(C_{1-4}$alkyl)carbamoyl, aminosulphonyl, $N-C_{1-4}$alkylaminosulphonyl, $N,N-di(C_{1-4}$alkyl)aminosulphonyl, $C_{1-4}$alkylsulphonylamino, or a group $R^4X^1$ wherein $X^1$ represents a direct bond, $C_{2-4}$alkanoyl, $-CONR^5R^6-$, $-SO_2NR^7R^8-$ or $-SO_2R^9-$ (wherein $R^5$ and $R^7$, each independently represents hydrogen or $C_{1-2}$alkyl and $R^6$, $R^8$ and $R^9$ each independently represents $C_{1-4}$alkyl and wherein $R^4$ is linked to $R^6$, $R^8$ or $R^9$) and $R^4$ represents an optionally substituted group selected from phenyl and a 5 or 6-membered heterocyclic group; n is an integer from 0 to 4, $R^1$ represents hydrogen, $C_{1-4}$alkyl, $C_{1-4}$alkoxymethyl, di($C_{1-4}$alkoxy)methyl or $C_{1-4}$alkanoyl; m is an integer from 0 to 4; and $R^3$ represents hydroxy, halogeno, nitro, trifluoromethyl, $C_{1-3}$alkyl, cyano, amino or $R^{10}X^2$ (wherein $X^2$ represents a direct bond, $-CH_2-$, or a single or double heteroatom linker group including $-S-$, $-SO-$ and $-NR^{15}-$ (wherein $R^{15}$ represents hydrogen, $C_{1-3}$alkyl or $C_{1-3}$alkoxyC$_{2-3}$alkyl), and $R^{10}$ is an alkenyl or alkynyl chain optionally substituted by for example hydroxy, amino, nitro, alkyl, cycloalkyl, alkoxyalkyl, or an optionally substituted group selected from pyridone, phenyl and a heterocyclic ring, which alkyl, alkenyl or alkynyl chain may have a heteroatom linker group, or $R^{10}$ is an optionally substituted group selected from pyridone, phenyl and a heterocyclic ring. The compounds of formula (I) and the pharmaceutically acceptable salts thereof inhibit the effects of VEGF and FGF, properties of value in the treatment of a number of disease states including cancer and rheumatoid arthritis.

19 Claims, No Drawings

U.S. PATENT DOCUMENTS

| | | | |
|---|---|---|---|
| 5,411,963 | 5/1995 | Dreikorn et al. | 514/259 |
| 5,480,883 | 1/1996 | Spada et al. | 514/249 |
| 5,646,153 | 7/1997 | Spada et al. | 514/259 |
| 5,650,415 | 7/1997 | Tang et al. | 514/312 |
| 5,710,158 | 1/1998 | Myers et al. | 514/259 |
| 5,712,395 | 1/1998 | App et al. | 544/344 |
| 5,714,493 | 2/1998 | Myers et al. | 514/259 |
| 5,721,237 | 2/1998 | Myers et al. | 514/259 |
| 5,736,534 | 4/1998 | Arnold | 514/63 |
| 5,792,771 | 8/1998 | App et al. | 514/254 |
| 6,002,008 | 12/1999 | Wissner et al. | 546/160 |
| 6,037,320 | 5/2000 | Spada et al. | 514/244 |

FOREIGN PATENT DOCUMENTS

| | | |
|---|---|---|
| 0 787 722 A1 | 8/1997 | (EP) . |
| 19614718 | 10/1997 | (EP) . |
| 0 837 063 A1 | 4/1998 | (EP) . |
| WO 87/04321 | 7/1987 | (WO) . |
| WO 92/14716 | 9/1992 | (WO) . |
| WO 92/16527 | 10/1992 | (WO) . |
| WO 92/20642 | 11/1992 | (WO) . |
| WO 95/19169 | 7/1995 | (WO) . |
| WO 95/21613 | 8/1995 | (WO) . |
| WO 96/29331 | 9/1996 | (WO) . |
| WO 96/30370 | 10/1996 | (WO) . |
| WO 96/39145 | 12/1996 | (WO) . |
| WO 96/40648 | 12/1996 | (WO) . |
| WO 96/40673 | 12/1996 | (WO) . |
| WO 97/02266 | 1/1997 | (WO) . |
| WO 97/03069 | 1/1997 | (WO) . |
| WO 97/17329 | 5/1997 | (WO) . |
| WO 97/22596 | 6/1997 | (WO) . |
| WO 97/28161 | 8/1997 | (WO) . |
| WO 97/30034 | 8/1997 | (WO) . |
| WO 97/30035 | 8/1997 | (WO) . |
| WO 97/32856 | 9/1997 | (WO) . |
| WO 97/34876 | 9/1997 | (WO) . |
| WO 98/02434 | 1/1998 | (WO) . |
| WO 98/13350 | 4/1998 | (WO) . |
| WO 98/13354 | 4/1998 | (WO) . |
| WO 98/23613 | 6/1998 | (WO) . |

OXINDOLE DERIVATIVES

The present invention relates to oxindole derivatives, processes for their preparation, pharmaceutical compositions containing them as active ingredient, methods for the treatment of disease states associated with angiogenesis and/or increased vascular permeability, to their use as medicaments and to their use in the manufacture of medicaments for use in the production of antiangiogenic and/or vascular permeability reducing effects in warm-blooded animals such as humans.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57–66; Folkman, 1995, Nature Medicine 1: 27–31). Alteration of vascular permeability is thought to play a role in both normal and pathological physiological processes (Cullinan-Bove et al, 1993, Endocrinology 133: 829–837; Senger et al, 1993, Cancer and Metastasis Reviews, 12: 303–324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36:139–155) and vascular permeability (Connolly et al, 1989, J. Biol. Chem. 264: 20017–20024). Antagonism of VEGF action by sequestration of VEGF with antibody can result in inhibition of tumour growth (Kim et al, 1993, Nature 362: 841–844). Basic FGF (bFGF) is a potent stimulator of angiogenesis (e.g. Hayek et al, 1987, Biochem. Biophys. Res. Commun. 147: 876–880) and raised levels of FGFs have been found in the serum (Fujimoto et al, 1991, Biochem. Biophys. Res. Commun. 180: 386–392) and urine (Nguyen et al, 1993, J. Natl. Cancer. Inst. 85: 241–242) of patients with cancer.

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tyrosine kinase receptor, Flt4. Two of these related RTKS, Flt and KDR, have been shown to bind VEGF with high affinity (De Vries et al, 1992, Science 255: 989–991; Terman et al, 1992, Biochem. Biophys. Res. Comm. 1992, 187: 1579–1586). Binding of VEGF to these receptors expressed in heterologous cells has been associated with changes in the tyrosine phosphorylation status of cellular proteins and calcium fluxes.

The present invention is based on the discovery of compounds that surprisingly inhibit the effects of VEGF and FGF, properties of value in the treatment of disease states associated with angiogenesis and/or increased vascular permeability such as cancer, diabetes, psoriasis, rheumatoid arthritis, Kaposi's sarcoma, haemangioma, acute and chronic nephropathies, atheroma, arterial restenosis, autoimmune diseases, acute inflammation and ocular diseases with retinal vessel proliferation. Compounds of the present invention possess higher potency against VEGF receptor tyrosine kinase and against FGF R1 receptor tyrosine kinase than against epidermal growth factor (EGF) receptor tyrosine kinase. Furthermore, compounds of the present invention, possess substantially higher potency against VEGF receptor tyrosine kinase and against FGF R1 receptor tyrosine kinase than against EGF receptor tyrosine kinase. Compounds of the invention which have been tested possess activity against VEGF receptor tyrosine kinase and against FGF R1 receptor tyrosine kinase such that they may be used in an amount sufficient to inhibit VEGF receptor tyrosine kinase and FGF R1 receptor tyrosine kinase whilst demonstrating no significant activity against EGF receptor tyrosine kinase. Thus compounds of the present invention possess good VEGF receptor tyrosine kinase activity and good FGF R1 receptor tyrosine kinase activity. Compounds with both VEGF receptor tyrosine kinase activity and FGF R1 receptor tyrosine kinase activity are believed to be of particular value in the treatment of disease states associated with angiogenesis and/or increased vascular permeability.

According to one aspect of the present invention there are provided compounds of the formula I:

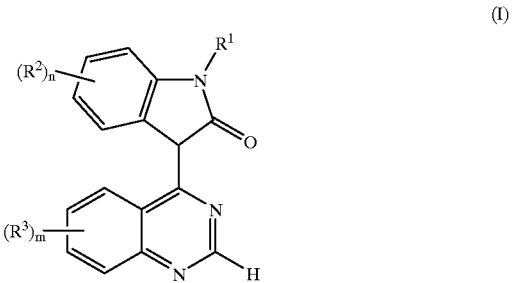

(I)

wherein:
R$^2$ represents hydroxy, halogeno, C$_{1-3}$alkyl, C$_{1-3}$alkoxy, C$_{1-3}$alkanoyloxy, trifluoromethyl, cyano, amino or nitro, and additional values for R$^2$ are C$_{2-4}$alkanoyl, C$_{1-4}$alkanoylamino, C$_{1-4}$alkoxycarbonyl, C$_{1-4}$alkylthio, C$_{1-4}$alkylsulphinyl, C$_{1-4}$alkylsulphonyl, carbamoyl, N-C$_{1-4}$alkylcarbamoyl, N,N-di(C$_{1-4}$alkyl) carbamoyl, aminosulphonyl, N-C$_{1-4}$akylaminosulphonyl, N,N-di(C$_{1-4}$alkyl) aminosulphonyl, C$_{1-4}$alkylsulphonylamino, or a group R$^4$X$^1$ wherein X$^1$ represents a direct bond, C$_{2-4}$alkanoyl, —CONR$^5$R$^6$—, —SO$_2$NR$^7$R$^8$— or —SO$_2$R$^9$— (wherein R$^5$ and R$^7$, each independently represents hydrogen or C$_{1-2}$alkyl and R$^6$, R$^8$ and R$^9$ each independently represents C$_{1-4}$alkyl and wherein R$^4$ is linked to R$^6$, R$^8$ or R$^9$) and R$^4$ represents phenyl or a 5 or 6-membered heterocyclic group with one or two heteroatoms, selected independently from O, S and N, which heterocyclic group may be saturated or unsaturated and which phenyl or heterocyclic group may bear one or two substituents selected from hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl;

n is an integer from 0 to 4;

$R^1$ represents hydrogen, $C_{1-4}$alkyl, $C_{1-4}$alkoxymethyl, di($C_{1-4}$alkoxy)methyl or $C_{1-4}$alkanoyl;

m is an integer from 0 to 4; and $R^3$ represents hydroxy, halogeno, nitro, trifluoromethyl, $C_{1-3}$alkyl, cyano, amino or $R^{10}X^2$ (wherein $X^2$ represents —O—, —CH$_2$—, —S—, —SO—, —SO$_2$—, —NR$^{11}$CO—, —CONR$^{12}$—, —SO$_2$NR$^{13}$—, —NR$^{14}$SO$_2$— or —NR$^{15}$ (wherein $R^{11}$, $R^{12}$, $R^{13}$, $R^{14}$ and $R^{15}$ each independently represents hydrogen, $C_{1-3}$alkyl or $C_{1-3}$alkoxyC$_{2-3}$alkyl), or $X^2$ represents a direct bond, and $R^{10}$ is selected from one of the following fifteen groups:

1) hydrogen or $C_{1-5}$alkyl which may be unsubstituted or which may be substituted with one or more groups selected from hydroxy, fluoro and amino;
2) $C_{1-5}$alkylX$^3$COR$^{16}$ (wherein $X^3$ represents —O— or —NR$^{17}$— (in which $R^{17}$ represents hydrogen, $C_{1-3}$alkyl or $C_{1-3}$alkoxyC$_{2-3}$alkyl) and $R^{16}$ represents $C_{1-3}$alkyl, —NR$^{18}$R$^{19}$— or —OR$^{20}$— (wherein $R^{18}$, $R^{19}$ and $R^{20}$ which may be the same or different each represents hydrogen, $C_{1-3}$alkyl or $C_{1-3}$alkoxyC$_{2-3}$alkyl));
3) $C_{1-5}$alkylX$^4$R$^{21}$ (wherein $X^4$ represents —O—, —S—, —SO—, —SO$_2$—, —OCO—, —NR$^{22}$CO—, —CONR$^{23}$—, —SO$_2$NR$^{24}$—, —NR$^{25}$SO$_2$— or —NR$^{26}$— (wherein $R^{22}$, $R^{23}$, $R^{24}$, $R^{25}$ and $R^{26}$ each independently represents hydrogen, $C_{1-3}$alkyl or $C_{1-3}$alkoxyC$_{2-3}$alkyl) and $R^{21}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);
4) $C_{1-5}$alkylX$^5$C$_{1-5}$alkylX$^6$R$^{27}$ (wherein $X^5$ and $X^6$ which may be the same or different are each —O—, —S—, —SO—, —SO$_2$—, —NR$^{28}$CO—, —CONR$^{29}$—, —SO$_2$NR$^{30}$—, —NR$^{31}$SO$_2$— or —NR$^{32}$— (wherein $R^{28}$, $R^{29}$, $R^{30}$, $R^{31}$ and $R^{32}$ each independently represents hydrogen, $C_{1-3}$alkyl or $C_{1-3}$alkoxyC$_{2-3}$alkyl) and $R^{27}$ represents hydrogen or $C_{1-3}$alkyl);
5) $C_{1-5}$alkylR$^{33}$ (wherein $R^{33}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);
6) $C_{2-5}$alkenylR$^{33}$ (wherein $R^{33}$ is as defined hereinbefore);
7) $C_{2-5}$alkynylR$^{33}$ (wherein $R^{33}$ is as defined hereinbefore);
8) $R^{34}$ (wherein $R^{34}$ represents a pyridone group, a phenyl group or a 5 or 6-membered aromatic heterocyclic group with 1 to 3 heteroatoms selected from O, N and S, which pyridone, phenyl or heterocyclic group may carry up to 5 substituents selected from halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —CONR$^{35}$R$^{36}$ and —NR$^{37}$COR$^{38}$ (wherein $R^{35}$, $R^{36}$, $R^{37}$ and $R^{38}$, which may be the same or different, each represents hydrogen, $C_{1-4}$alkyl or $C_{1-3}$alkoxyC$_{2-3}$alkyl)) and an additional possible substituent of $R^{34}$ is hydroxy;
9) $C_{1-5}$alkylR$^{34}$ (wherein $R^{34}$ is as defined hereinbefore);
10) $C_{2-5}$alkenylR$^{34}$ (wherein $R^{34}$ is as defined hereinbefore);
11) $C_{2-5}$alkynylR$^{34}$ (wherein $R^{34}$ is as defined hereinbefore);
12) $C_{1-5}$alkylX$^7$R$^{34}$ (wherein $X^7$ represents —O—, —S—, —SO—, —SO$_2$—, —NR$^{39}$CO—, —CONR$^{40}$—, —SO$_2$NR$^{41}$—, —NR$^{42}$SO$_2$— or —NR$^{43}$— (wherein $R^{39}$, $R^{40}$, $R^{41}$, $R^{42}$ and $R^{43}$ each independently represents hydrogen, $C_{1-3}$alkyl or $C_{1-3}$alkoxyC$_{2-3}$alkyl) and $R^{34}$ is as defined hereinbefore);
13) $C_{2-5}$alkenylX$^8$R$^{34}$ (wherein $X^8$ represents —O—, —S—, —SO—, —SO$_2$—, —NR$^{44}$CO—, —CONR$^{45}$—, —SO$_2$NR$^{46}$—, —NR$^{47}$SO$_2$— or —NR$^{48}$— (wherein $R^{44}$, $R^{45}$, $R^{46}$, $R^{47}$ and $R^{48}$ each independently represents hydrogen, $C_{1-3}$alkyl or $C_{1-3}$alkoxyC$_{2-3}$alkyl) and $R^{34}$ is as defined hereinbefore);
14) $C_{2-5}$alkynylX$^9$R$^{34}$ (wherein $X^9$ represents —O—, —S—, —SO—, —SO$^2$—, —NR$^{49}$CO—, —CONR$^{50}$—, —SO$_2$NR$^{51}$—, —NR$^{52}$SO$_2$— or —NR$^{53}$— (wherein $R^{49}$, $R^{50}$, $R^{51}$, $R^{52}$ and $R^{53}$ each independently represents hydrogen, $C_{1-3}$alkyl or $C_{1-3}$alkoxyC$_{2-3}$alkyl) and $R^{34}$ is as defined hereinbefore); and
15) $C_{1-3}$alkylX$^{10}$C$_{1-3}$alkylR$^{34}$ (wherein $X^{10}$ represents —O—, —S—, —SO—, —SO$_2$—, —NR$^{54}$CO—, —CONR$^{55}$—, —SO$_2$NR$^{56}$—, —NR$^{57}$SO$_2$— or —NR$^{58}$— (wherein $R^{54}$, $R^{55}$, $R^{56}$, $R^{57}$ and $R^{58}$ each independently represents hydrogen, $C_{1-3}$alkyl or $C_{1-3}$alkoxyC$_{2-3}$alkyl) and $R^{34}$ is as defined hereinbefore); and additional groups of values of $R^{10}$ are:
16) $R^{33}$ (wherein $R^{33}$ is as defined hereinbefore); and
17) $C_{1-3}$alkylX$^{10}$C$_{1-3}$alkylR$^{33}$ (wherein $X^{10}$ and $R^{33}$ are as defined hereinbefore))];

and salts thereof.

Advantageously $X^1$ represents a direct bond $C_{2-4}$alkanoyl, —CONR$^5$R$^6$—, —SO$_2$NR$^7$R$^8$— or —SO$_2$R$^9$— (wherein $R^5$ and $R^7$, each independently represents hydrogen or $C_{1-2}$alkyl and $R^6$, $R^8$ and $R^9$ each independently represents $C_{1-3}$alkyl and wherein $R^4$ is linked to $R^6$, $R^8$ or $R^9$).

Preferably $X^1$ represents a direct bond $C_{2-4}$alkanoyl, —CONR$^5$R$^6$—, —SO$_2$NR$^7$R$^8$— or —SO$_2$R$^9$— (wherein $R^5$ and $R^7$, each independently represents hydrogen and $R^6$, $R^8$ and $R^9$ each independently represents $C_{1-3}$alkyl and wherein $R^4$ is linked to $R^6$, $R^8$ or $R^9$).

Advantageously $R^2$ represents hydroxy, halogeno, $C_{1-2}$alkyl, $C_{1-2}$alkoxy, trifluoromethyl, cyano, nitro, $C_{2-3}$alkanoyl, $C_{1-3}$alkanoylamino, $C_{1-3}$alkoxycarbonyl, $C_{1-3}$alkylthio, $C_{1-3}$alkylsulphinyl, $C_{1-3}$alkylsulphonyl, carbamoyl, N-C$_{1-3}$alkylcarbamoyl, N,N-di(C$_{1-3}$alkyl)carbamoyl, aminosulphonyl, N-C$_{1-3}$alkylaminosulphonyl, N,N-di(C$_{1-3}$alkyl)aminosulphonyl, $C_{1-3}$alkylsulphonylamino, or a group $R^4X^1$ (wherein $X^1$ is as defined hereinbefore and $R^4$ represents phenyl or a 5 or 6-membered heterocyclic group with one or two heteroatorns, selected independently from O, S and N, which heterocyclic group may be saturated or unsaturated and which phenyl or heterocyclic group may bear one or two substituents selected from hydroxy, halogeno, $C_{1-2}$alkyl, $C_{1-2}$alkoxy, $C_{1-2}$alkanoyloxy, trifluoromethyl, cyano, amino, nitro and $C_{1-4}$alkoxycarbonyl).

Preferably $R^2$ represents halogeno, trifluoromethyl, cyano, nitro, $C_{2-3}$alkanoyl, $C_{1-3}$alkoxycarbonyl, $C_{1-3}$alkylsulphinyl, $C_{1-3}$alkylsulphonyl, carbamoyl. $\underline{N}$-$C_{1-3}$alkylcarbamoyl, $\underline{N},\underline{N}$-di($C_{1-3}$alkyl)carbamoyl, aminosulphonyl, $\underline{N}$-$C_{1-3}$alkylaminosulphonyl, $\underline{N},\underline{N}$-di($C_{1-3}$alkyl)aminosulphonyl, or a group $R^4X^1$ (wherein $X^1$ is as defined hereinbefore and $R^4$ represents phenyl or a 5 or 6-membered heterocyclic group with one or two heteroatoms, selected independently from O, S and N, of which at least one is N, which heterocyclic group may be saturated or unsaturated and which phenyl or heterocyclic group may bear one or two substituents selected from hydroxy, halogeno, $C_{1-2}$alkyl, $C_{1-2}$alkoxy, $C_{1-2}$alkanoyloxy, trifluoromethyl, cyano, amino, nitro and $C_{1-4}$alkoxycarbonyl).

More preferably $R^2$ represents halogeno, trifluoromethyl, cyano, nitro, $C_{2-3}$alkanoyl, $C_{1-3}$alkoxycarbonyl, $C_{1-3}$alkylsulphinyl, $C_{1-3}$alkylsulphonyl, carbamoyl, $\underline{N}$-$C_{1-3}$alkylcarbamoyl, $\underline{N},\underline{N}$-di($C_{1-3}$alkyl)carbamoyl, aminosulphonyl, $\underline{N}$-$C_{1-3}$alkylaminosulphonyl, $\underline{N},\underline{N}$-di($C_{1-3}$alkyl)aminosulphonyl, or a group $R^4X^1$ (wherein $X^1$ is as defined hereinbefore and $R^4$ represents pyrrolidinyl, piperazinyl, piperidinyl, morpholino, thiomorpholino, phenyl, pyridyl, imidazolyl, thiazolyl, thienyl, triazolyl or pyridazinyl which phenyl or heterocyclic group may bear one or two substituents selected from hydroxy, halogeno, $C_{1-2}$alkyl, $C_{1-2}$alkoxy, $C_{1-2}$alkanoyloxy, trifluoromethyl, cyano, amino, nitro and $C_{1-4}$alkoxycarbonyl).

Especially preferred values of $R^2$ are halogeno, trifluoromethyl, cyano, nitro, $C_{2-3}$alkanoyl, $C_{1-3}$alkoxycarbonyl, $C_{1-3}$alkylsulphinyl, $C_{1-3}$alkylsulphonyl, carbamoyl, $\underline{N}$-$C_{1-3}$alkylcarbamoyl, $\underline{N},\underline{N}$-di($C_{1-3}$alkyl)carbamoyl, aminosulphonyl, $\underline{N}$-$C_{1-3}$alkylaminosulphonyl, $\underline{N},\underline{N}$-di($C_{1-3}$alkyl)aminosulphonyl, or a group $R^4X^1$ (wherein $X^1$ is as defined hereinbefore and $R^4$ represents pyrrolidinyl, piperazinyl, piperidinyl, morpholino, thiomorpholino, imidazolyl or triazolyl which heterocyclic group is linked to $X^1$ via a nitrogen atom and which heterocyclic group may bear one or two substituents selected from hydroxy, halogeno, $C_{1-2}$alkyl, $C_{1-2}$alkoxy, $C_{1-2}$alkanoyloxy, trifluoromethyl, cyano, amino, nitro and $C_{1-4}$alkoxycarbonyl).

In another aspect of the present invention $R^2$ represents hydroxy, halogeno, $C_{1-3}$alkyl, $C_{1-3}$alkoxy, trifluoromethyl, cyano, amino or nitro.

In another aspect of the present invention $R^2$ represents hydroxy, halogeno, $C_{1-3}$alkyl, $C_{1-3}$alkoxy or trifluoromethyl, especially hydroxy, chloro, fluoro, methyl or methoxy.

Preferably n is an integer from 0 to 2.

Preferably $R^1$ represents hydrogen, $C_{1-4}$alkoxymethyl, di($C_{1-4}$alkoxy)methyl or $C_{1-4}$alkanoyl, especially hydrogen.

Preferably m is an integer from 0–2, most preferably 2.

Advantageously $X^2$ represents —O—, —S—, —NR$^{11}$CO—, —NR$^{14}$SO$_2$— or —NR$^{15}$— (wherein $R^{11}$, $R^{14}$ and $R^{15}$ each independently represents hydrogen, $C_{1-2}$alkyl or $C_{1-2}$alkoxyethyl).

Preferably $X^2$ represents —O—, —S—, —NR$^{11}$CO—, —NR$^{14}$SO$_2$— (wherein $R^{11}$ and $R^{14}$ each independently represents hydrogen or $C_{1-2}$alkyl) or NH.

More preferably $X^2$ represents —O—, —S—, —NR$^{11}$CO— (wherein $R^{11}$ represents hydrogen or $C_{1-2}$alkyl) or NH.

Particularly $X^2$ represents —O— or —NR$^{11}$CO— (wherein $R^{11}$ represents hydrogen or $C_{1-2}$alkyl), more particularly —O— or —NHCO—, especially —O—.

Advantageously $X^3$ represents —O— or NR$^{17}$ (wherein $R^{17}$ represents hydrogen, $C_{1-3}$alkyl or $C_{1-2}$alkoxyethyl).

Advantageously $X^4$ represents —O—, —S—, —SO—, —SO$_2$—, —NR$^{22}$CO—, —NR$^{25}$SO$_2$— or —NR$^{26}$— (wherein $R^{22}$, $R^{25}$ and $R^{26}$ each independently represents hydrogen, $C_{1-2}$alkyl or $C_{1-2}$alkoxyethyl).

Preferably $X^4$ represents —O—, —S—, —SO—, —SO$_2$— or —NR$^{26}$— (wherein $R^{26}$ represents hydrogen, $C_{1-2}$alkyl or $C_{1-2}$alkoxyethyl).

More preferably $X^4$ represents —O— or —NR$^{26}$— (wherein $R^{26}$ represents hydrogen or $C_{1-2}$alkyl).

Advantageously $X^5$ and $X^6$ which may be the same or different each represents —O—, —S—, —SO—, —SO$_2$— or —NR$^{32}$— (wherein $R^{32}$ represents hydrogen, $C_{1-3}$alkyl or $C_{1-2}$alkoxyethyl).

Preferably $X^5$ and $X^6$ which may be the same or different each represents —O—, —S— or —NR$^{32}$— (wherein $R^{32}$ represents hydrogen, $C_{1-2}$alkyl or $C_{1-2}$alkoxyethyl).

More preferably $X^5$ and $X^6$ which may be the same or different each represents —O— or —NH—.

Advantageously $X^7$ represents —O—, —S— or —NR$^{43}$— (wherein $R^{43}$ represents hydrogen, $C_{1-2}$alkyl or $C_{1-2}$alkoxyethyl).

Preferably $X^7$ represents —O— or —NR$^{43}$— (wherein $R^{43}$ represents hydrogen or $C_{1-2}$alkyl).

Advantageously $X^8$ represents —O—, —S— or —NR$^{48}$— (wherein $R^{48}$ represents hydrogen, $C_{1-2}$alkyl or $C_{1-2}$alkoxyethyl).

Preferably $X^8$ represents —O— or —NR$^{48}$— (wherein $R^{48}$ represents hydrogen or $C_{1-2}$alkyl).

Advantageously $X^9$ represents —O—, —S— or —NR$^{53}$— (wherein $R^{53}$ represents hydrogen, $C_{1-2}$alkyl or $C_{1-2}$alkoxyethyl).

Preferably $X^9$ represents —O— or —NR$^{53}$— (wherein $R^{53}$ represents hydrogen or $C_{1-2}$alkyl).

Advantageously $X^{10}$ represents —O—, —S— or —NR$^{58}$— (wherein $R^{58}$ represents hydrogen, $C_{1-2}$alkyl or $C_{1-2}$alkoxyethyl).

Preferably $X^{10}$ represents —O— or —NR$^{58}$— (wherein $R^{58}$ represents hydrogen or $C_{1-2}$alkyl).

$R^{33}$ is preferably pyrrolidinyl, piperazinyl, piperidinyl, morpholino or thiomorpholino which group may carry one or two substituents selected from oxo, hydroxy, halogeno, $C_{1-2}$alkyl, $C_{1-2}$hydroxyalkyl and $C_{1-2}$alkoxy.

$R^{34}$ preferably represents a pyridone group or a 5 or 6-membered aromatic heterocyclic group with 1 to 3 heteroatoms selected from O, N and S, which pyridone group or heterocyclic group may be substituted as hereinbefore defined.

Where $R^{34}$ is a 5 or 6-membered aromatic heterocyclic group, it preferably has 1 or 2 heteroatoms, selected from O, N and S, of which more preferably one is N, and may be substituted as hereinbefore defined.

$R^{34}$ is particularly a pyridone, pyridyl, imidazolyl, thiazolyl, thienyl, triazolyl or pyridazinyl group which group may be substituted as hereinbefore defined, more particularly a pyridone, pyridyl, imidazolyl, thiazolyl or triazolyl group, especially a pyridone, pyridyl, imidazolyl or triazolyl group which group may be substituted as hereinbefore defined.

In one embodiment of the invention $R^{34}$ represents a pyridone, phenyl or 5 or 6-membered aromatic heterocyclic group with 1 to 3 heteroatoms selected from O, N and S, which group may preferably carry up to 2 substituents, more preferably up to one substituent, selected from the group of substituents as hereinbefore defined.

In the definition of $R^{34}$, conveniently substituents are selected from halogeno, $C_{1-4}$alkyl, $C_{1-4}$alkoxy and cyano, more conveniently substituents are selected from chloro, fluoro, methyl and ethyl.

Conveniently $R^3$ represents hydroxy, halogeno, nitro, trifluoromethyl, $C_{1-3}$alkyl, cyano, amino or $R^{10}X^2$ [wherein $X^2$ is as hereinbefore defined and $R^{10}$ is selected from one of the following fifteen groups:

1) $C_{1-5}$alkyl which may be unsubstituted or substituted with one or more fluorine atoms, or $C_{2-5}$alkyl which may be unsubstituted or substituted with one or more groups selected from hydroxy and amino;
2) $C_{2-3}$alkylX$^3$COR$^{16}$ (wherein $X^3$ is as hereinbefore defined and $R^{16}$ represents $C_{1-3}$alkyl, —NR$^{18}$R$^{19}$— or —OR$^{20}$— (wherein $R^{18}$, $R^{19}$ and $R^{20}$ which may be the same or different are each $C_{1-2}$alkyl or $C_{1-2}$alkoxyethyl));
3) $C_{2-4}$akylX$^4$R$^{21}$ (wherein $X^4$ is as hereinbefore defined and $R^{21}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-3}$alkoxy and which cyclic group may bear one or two substituents selected from oxo, hydroxy, halogeno, $C_{1-4}$alkyl, $C_{1-4}$hydroxyalkyl and $C_{1-4}$alkoxy);
4) $C_{2-3}$alkylX$^5$C$_{2-3}$alkylX$^6$R$^{27}$ (wherein $X^5$ and $X^6$ are as hereinbefore defined and $R^{27}$ represents hydrogen or $C_{1-3}$alkyl);
5) $C_{1-5}$alkylR$^{59}$ (wherein $R^{59}$ is a 5 or 6 membered saturated heterocyclic group with one or two heteroatoms, selected independently from O, S and N, which heterocyclic group is linked to $C_{1-5}$alkyl through a carbon atom and which heterocyclic group may bear one or two substituents selected from oxo, hydroxy, halogeno, $C_{1-4}$alkyl, $C_{1-4}$hydroxyalkyl and $C_{1-4}$alkoxy) or $C_{2-5}$alkylR$^{60}$ (wherein $R^{60}$ is a 5 or 6 membered saturated heterocyclic group with one or two heteroatoms of which one is N and the other is selected independently from O, S and N, which heterocyclic group is linked to $C_{2-5}$alkyl through a nitrogen atom and which heterocyclic group may bear one or two substituents selected from oxo, hydroxy, halogeno, $C_{1-4}$alkyl, $C_{1-4}$hydroxyalkyl and $C_{1-4}$alkoxy);
6) $C_{3-4}$alkenylR$^{61}$ (wherein $R^{61}$ represents $R^{59}$ or $R^{60}$ as defined hereinbefore);
7) $C_{3-4}$alkynylR$^{61}$ (wherein $R^{61}$ represents $R^{59}$ or $R^{60}$ as defined hereinbefore);
8) $R^{34}$ (wherein $R^{34}$ is as defined hereinbefore);
9) $C_{1-5}$alkylR$^{34}$ (wherein $R^{34}$ is as defined hereinbefore);
10) $C_{3-5}$alkenylR$^{34}$ (wherein $R^{34}$ is as defined hereinbefore);
11) $C_{3-5}$alkynylR$^{34}$ (wherein $R^{34}$ is as defined hereinbefore);
12) $C_{1-5}$alkylX$^7$X$^{34}$ (wherein $X^7$ and $R^{34}$ are as defined hereinbefore);
13) $C_{4-5}$alkenylX$^8$R$^{34}$ (wherein $X^8$ and $R^{34}$ are as defined hereinbefore);
14) $C_{4-5}$alkynylX$^9$R$^{34}$ (wherein $X^9$ and $R^{34}$ are as defined hereinbefore); and
15) $C_{2-3}$alkylX$^{10}$C$_{1-2}$alkylR$^{34}$ (wherein $X^{10}$ and $R^{34}$ are as defined hereinbefore); and additional convenient values of $R^{10}$ are:
16) $R^{33}$ (wherein $R^{33}$ is as defined hereinbefore); and
17) $C_{2-3}$alkylX$^{10}$C$_{1-2}$alkylR$^{33}$ (wherein $X^{10}$ and $R^{33}$ are as defined hereinbefore)].

Advantageously $R^3$ represents hydroxy, halogeno, nitro, trifluoromethyl, $C_{1-3}$alkyl, cyano, amino or $R^{10}X^2$ [wherein $X^2$ is as hereinbefore defined and $R^{10}$ is selected from one of the following fifteen groups:

1) $C_{1-4}$alkyl which may be unsubstituted or substituted with one or more fluorine atoms, or $C_{2-4}$alkyl which may be unsubstituted or substituted with one or two groups selected from hydroxy and amino;
2) $C_{2-3}$alkylX$^3$COR$^{16}$ (wherein $X^3$ is as hereinbefore defined and $R^{16}$ represents —NR$^{18}$R$^{19}$— or —OR$^{20}$— (wherein $R^{18}$, $R^{19}$ and $R^{20}$ which may be the same or different are each $C_{1-2}$alkyl or $C_{1-2}$alkoxyethyl));
3) $C_{2-4}$alkylX$^4$R$^{21}$ (wherein $X^4$ is as hereinbefore defined and $R^{21}$ is a group selected from $C_{1-3}$alkyl, cyclopentyl, cyclohexyl, pyrrolidinyl and piperidinyl which group is linked to $X^4$ through a carbon atom and which $C_{1-3}$alkyl group may bear one or two substituents selected from oxo, hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);
4) $C_{2-3}$alkylX$^5$C$_{2-3}$alkylX$^6$R$^{27}$ (wherein $X^5$ $^{and\ X6}$ are as hereinbefore defined and $R^{27}$ represents hydrogen or $C_{1-3}$alkyl);
5) $C_{1-4}$alkylR$^{62}$ (wherein $R^{62}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-4}$alkyl through a carbon atom and which group may carry one or two substituents selected from oxo, hydroxy, halogeno, $C_{1-2}$alkyl, $C_{1-2}$hydroxyalkyl and $C_{1-2}$alkoxy) or $C_{2-4}$alkylR$^{63}$ (wherein $R^{63}$ is a group selected from morpholino, thiomorpholino, pyrrolidin-1-yl, piperazin-1-yl and piperidino which group may carry one or two substituents selected from oxo, hydroxy, halogeno, $C_{1-2}$alkyl, $C_{1-2}$hydroxyalkyl and $C_{1-2}$alkoxy);
6) $C_{3-4}$alkenylR$^{64}$ (wherein $R^{64}$ represents $R^{62}$ or $R^{63}$ as defined hereinbefore);
7) $C_{3-4}$alkynylR$^{64}$ (wherein $R^{64}$ represents $R^{62}$ or $R^{63}$ as defined hereinbefore);
8) $R^{34}$ (wherein $R^{34}$ is as defined hereinbefore);
9) $C_{1-4}$alkylR$^{34}$ (wherein $R^{34}$ is as defined hereinbefore);
10) 1-$R^{34}$prop-1-en-3-yl or 1-$R^{34}$but-2-en4-yl (wherein $R^{34}$ is as defined hereinbefore with the proviso that when $R^{10}$ is 1-$R^{34}$prop-1-en-3-yl, $R^{34}$ is linked to the alkenyl group via a carbon atom);
11) 1-$R^{34}$prop-1-yn-3-yl or 1-$R^{34}$but-2-yn-4-yl (wherein $R^{34}$ is as defined hereinbefore with the proviso that when $R^{10}$ is 1-$R^{34}$prop-1-yn-3-yl, $R^{34}$ is linked to the alkynyl group via a carbon atom);
12) $C_{1-5}$alkylX$^7$R$^{34}$ (wherein $X^7$ and $R^{34}$ are as defined hereinbefore);
13) 1-($R^{34}$X$^8$)but-2-en-4-yl (wherein $X^8$ and $R^{34}$ are as defined hereinbefore);
14) 1-($R^{34}$X$^9$)but-2-yn-4-yl (wherein $X^9$ and $R^{34}$ are as defined hereinbefore); and 15) $C_{2-3}$alkyl$X^{10}C_{1-2}$alkyl$R^{34}$ (wherein $X^{10}$ and $R^{34}$ are as defined hereinbefore); and additional advantageous values of $R^{10}$ are:
16) $R^{33}$ (wherein $R^{33}$ is as defined hereinbefore); and
17) $C_{2-3}$alkyl$X^{10}C_{1-2}$alkyl$R^{33}$ (wherein $X^{10}$ and $R^{33}$ are as defined hereinbefore)].

Preferably $R^3$ represents hydroxy, halogeno, nitro, trifluoromethyl, $C_{1-3}$alkyl, cyano, amino or $R^{10}X^2$ [wherein $X^2$ is as hereinbefore defined and $R^{10}$ is selected from one of the following thirteen groups:

1) $C_{1-3}$alkyl which may be unsubstituted or substituted with one or more fluorine atoms, or $C_{2-3}$alkyl which may be unsubstituted or substituted with one or two groups selected from hydroxy and amino;
2) 2-(3,3-dimethylureido)ethyl, 3-(3,3-dimethylureido) propyl, 2-(3-methylureido)ethyl, 3-(3-methylureido) propyl, 2-ureidoethyl, 3-ureidopropyl, 2-N,N-dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-carbamoyloxy)propyl;
3) $C_{2-3}$alkyl$X^4R^{21}$ (wherein $X^4$ is as defined hereinbefore and $R^{21}$ is a group selected from $C_{1-2}$alkyl, cyclopentyl, cyclohexyl, pyrrolidinyl and piperidinyl which group is linked to $X^4$ through a carbon atom and which $C_{1-2}$alkyl group may bear one or two substituents selected from hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);
4) $C_{2-3}$alkyl$X^5C_{2-3}$alkyl$X^6R^{27}$ (wherein $X^5$ and $X^6$ are as hereinbefore define hydrogen or $C_{1-2}$alkyl);
5) $C_{1-2}$alkyl$R^{62}$ (wherein $R^{62}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-2}$alkyl through a carbon atom and which group may carry one substituent selected from oxo, hydroxy, halogeno, $C_{1-2}$alkyl, $C_{1-2}$hydroxyalkyl and $C_{1-2}$alkoxy) or $C_{2-3}$alkyl$R^{63}$ (wherein $R^{63}$ is a group selected from morpholino, thiomorpholino, piperidino, piperazin-1-yl and pyrrolidin-1-yl which group may carry one substituent selected from oxo, hydroxy, halogeno, $C_{1-2}$alkyl, $C_{1-2}$hydroxyalkyl and $C_{1-2}$alkoxy);
6) $R^{34}$ (wherein $R^{34}$ is as defined hereinbefore);
7) $C_{1-4}$alkyl$R^{34}$ (wherein $R^{34}$ is as defined hereinbefore);
8) 1-$R^{34}$but-2-en4-yl (wherein $R^{34}$ is as defined hereinbefore);
9) 1-$R^{34}$but-2-yn4-yl (wherein $R^{34}$ is as defined hereinbefore);
10) $C_{1-5}$alkyl$X^7R^{34}$ (wherein $X^7$ and $R^{34}$ are as defined hereinbefore);
11) 1-($R^{34}X^8$)but-2-en-4-yl (wherein $X^8$ and $R^{34}$ are as defined hereinbefore);
12) 1-($R^{34}X^9$)but-2-yn-4-yl (wherein $X^9$ and $R^{34}$ are as defined hereinbefore); and
13) ethyl$X^{10}$methyl$R^{34}$ (wherein $X^{10}$ and $R^{34}$ are as defined hereinbefore); and additional preferred values of $R^{10}$ are:
14) $R^{33}$ (wherein $R^{33}$ is as defined hereinbefore); and
15) ethyl$X^{10}$ methyl$R^{33}$ (wherein $X^{10}$ and $R^{33}$ are as defined hereinbefore)].

More preferably $R^3$ represents hydroxy, $C_{1-3}$alkyl, amino or $R^{10}X^2$ [wherein $X^2$ is as hereinbefore defined and $R^{10}$ represents methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl) ethyl, 2-(methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino) propyl, 2-methylthiazol-4-ylmethyl, 2-acetamidothiazol-4-ylmethyl, 1-methylimidazol-2-ylmethyl, 2-(imidazol-1-yl) ethyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-thiomorpholinoethyl, 3-thiomorpholinopropyl, 2-(2-methoxyethoxy)ethyl, 2-(4-methylpiperazin-1-yl)ethyl or 3-(4-methylpiperazin-1-yl) propyl and additional more preferred values of $R^{10}$ are 3-(methylsulphinyl)propyl, 3-(methylsulphonyl)propyl, 2-(2-methylimidazol-1-yl)ethyl, 2-(5-methyl-1,2,4-triazol-1-yl)ethyl, morpholino, 2-((N(1-methylimidazol4-ylsulphonyl)-N-methyl)amino)ethyl, 2-((N-(3-morpholinopropylsulphonyl)-N-methyl)amino)ethyl, 2-((N-methyl-N-4-pyridyl)amino)ethyl and 3-(4-oxidomorpholino)propyl].

Where one of the $R^3$ substituents is $R^{10}X^2$ the substituent $R^{10}X^2$ is preferably at the 6 or 7-position of the quinazoline ring, more preferably at the 7-position of the quinazoline ring.

In a particular aspect of the current invention there are provided compounds of the formula 1a:

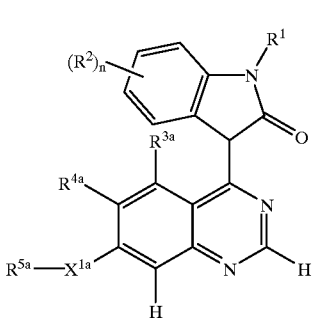

(Ia)

[wherein:
$R^1$, $R^2$ and n are as defined hereinbefore;
$R^{3a}$ represents hydrogen, hydroxy, methoxy, amino, nitro or halogeno;
$R^{4a}$ represents hydrogen, hydroxy, halogeno, cyano, nitro, trifluoromethyl, $C_{1-3}$alkyl, $C_{1-3}$alkoxy, $C_{1-3}$alkylthio, or —NR$^{6a}$R$^{7a}$— (wherein R$^{6a}$ and R$^{7a}$, which may be the same or different, each represents hydrogen or $C_{1-3}$alkyl), and an additional value of R$^{4a}$ is R$^{8a}$(CH$_2$)$_{za}$X$^{2a}$ (wherein R$^{8a}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy, za is an integer from 0 to 4 and $X^{2a}$ represents a direct bond, —O—, —CH$_2$—, —S—, —SO—, —SO$_2$—, —NR$^{9a}$CO—, —CONR$^{10a}$—, —SO$_2$NR$^{11a}$—, —NR$^{12a}$SO$_2$— or —NR$^{13a}$— (wherein $R^{9a}$, $R^{10a}$, $R^{11a}$, $R^{12a}$ and $R^{13a}$ each independently represents hydrogen, $C_{1-3}$alkyl or $C_{1-3}$alkoxyC$_{2-3}$alkyl));

$X^{1a}$ represents —O—, —CH$_2$—, —S—, —SO—, —SO$_2$—, —NR$^{14a}$CO—, —CONR$^{15a}$—, —SO$_2$NR$^{16a}$—, —NR$^{17a}$SO$_2$— or —NR$^{18a}$— (wherein $R^{14a}$, $R^{15a}$, $R^{16a}$, $R^{17a}$ and $R^{18a}$ each independently represents hydrogen, $C_{1-3}$alkyl or $C_{1-3}$alkoxyC$_{2-3}$alkyl) or $X^{1a}$ represents a direct bond;

$R^{5a}$ is selected from one of the following fifteen groups:

1) hydrogen or $C_{1-5}$alkyl which may be unsubstituted or which may be substituted with one or more groups selected from hydroxy, fluoro and amino;

2) $C_{1-5}$alkylX$^{3a}$COR$^{19a}$ (wherein $X^{3a}$ represents —O— or —NR$^{20a}$— (in which $R^{20a}$ represents hydrogen, $C_{1-3}$alkyl or $C_{1-3}$ alkoxyC$_{2-3}$alkyl) and $R^{19a}$ represents $C_{1-3}$alkyl, —NR$^{21a}$R$^{22a}$— or —OR$^{23a}$— (wherein $R^{21a}$, $R^{22a}$ and $R^{23a}$ which may be the same or different each represents hydrogen, $C_{1-3}$alkyl or $C_{1-3}$alkoxyC$_{2-3}$alkyl));

3) $C_{1-5}$alkylX$^{4a}$R$^{24a}$ (wherein $X^{4a}$ represents —O—, —S—, —SO—, —SO$_2$—, —OCO—, —NR$^{25a}$CO—, —CONR$^{26a}$—, —SO$_2$NR$^{27a}$—, —NR$^{28a}$SO$_2$— or —NR$^{29a}$— (wherein $R^{25a}$, $R^{26a}$, $R^{27a}$, $R^{28a}$ and $R^{29a}$ each independently represents hydrogen, $C_{1-3}$alkyl or $C_{1-3}$alkoxyC$_{2-3}$alkyl) and $R^{24a}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);

4) $C_{1-5}$alkylX$^{5a}$C$_{1-5}$alkylX$^{6a}$R$^{30a}$ (wherein $X^{5a}$ and $X^{6a}$ which may be the same or different are each —O—, —S—, —SO—, —SO$_2$—, —NR$^{31a}$CO—, —CONR$^{32a}$—, —SO$_2$NR$^{33a}$—, —NR$^{34a}$SO$_2$— or —NR$^{35a}$— (wherein $R^{31a}$, $R^{32a}$, $R^{33a}$, $R^{34a}$ and $R^{35a}$ each independently represents hydrogen, $C_{1-3}$alkyl or $C_{1-3}$alkoxyC$_{2-3}$alkyl) and $R^{30a}$ represents hydrogen or $C_{1-3}$alkyl);

5) $C_{1-5}$alkylR$^{36a}$ (wherein $R^{36a}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyi, $C_{1-4}$hydroxyalkyl and $C_{1-4}$alkoxy);

6) $C_{2-5}$alkenylR$^{36a}$ (wherein $R^{36a}$ is as defined hereinbefore);

7) $C_{2-5}$alkynylR$^{36a}$ (wherein $R^{36a}$ is as defined hereinbefore);

8) $R^{37a}$ (wherein $R^{37a}$ represents a pyridone group, a phenyl group or a 5 or 6-membered aromatic heterocyclic group with 1 to 3 heteroatoms selected from O, N and S, which pyridone, phenyl or heterocyclic group may carry up to 5 substituents selected from halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —CONR$^{38a}$R$^{39a}$ and —NR$^{40a}$COR$^{41a}$ (wherein $R^{38a}$, $R^{39a}$, $R^{40a}$ and $R^{41a}$, which may be the same or different, each represents hydrogen, $C_{1-4}$alkyl or $C_{1-3}$alkoxyC$_{2-3}$alkyl)) and an additional possible substituent of $R^{37a}$ is hydroxy;

9) $C_{1-5}$alkylR$^{37a}$ (wherein $R^{37a}$ is as defined hereinbefore);

10) $C_{2-5}$alkenylR$^{37a}$ (wherein $R^{37a}$ is as defined hereinbefore);

11) $C_{2-5}$alkynylR$^{37a}$ (wherein $R^{37a}$ is as defined hereinbefore);

12) $C_{1-5}$alkylX$^{7a}$R$^{37a}$ (wherein $X^{7a}$ represents —O—, —S—, —SO—, —SO$_2$—, —NR$^{42a}$CO—, —CONR$^{43a}$—, —SO$_2$NR$^{44a}$—, —NR$^{45a}$SO$_2$— or —NR$^{46a}$— (wherein $R^{42a}$, $R^{43a}$, $R^{44a}$, $R^{45a}$ and $R^{46a}$ each independently represents hydrogen, $C_{1-3}$alkyl or $C_{1-3}$alkoxyC$_{2-3}$alkyl) and $R^{37}$a is as defined hereinbefore);

13) $C_{2-5}$-alkenylX$^{8a}$R$^{37a}$ (wherein $X^{8a}$ represents —O—, —S—, —SO—, —SO$_2$—, —NR$^{47a}$CO—, —CONR$^{48a}$—, —SO$_2$NR$^{49a}$—, —NR$^{50a}$SO$_2$— or —NR$^{51a}$— (wherein $R^{47a}$, $R^{48a}$, $R^{49a}$, $R^{50}$ and $R^{51a}$ each independently represents hydrogen, $C_{1-3}$alkyl or $C_{1-3}$alkoxyC$_{2-3}$alkyl) and $R^{37a}$ is as defined hereinbefore);

14) $C_{2-5}$alkynylX$^{9a}$R$^{37a}$ (wherein $X^{9a}$ represents —O—, —S—, —SO—, —SO$_2$—, —NR$^{52a}$CO—, —CONR$^{53a}$—, —SO$_2$NR$^{54a}$—, —NR$^{55a}$SO$_2$— or —NR$^{56a}$— (wherein $R^{52a}$, $R^{53a}$, $R^{54a}$, $R^{55a}$ and $R^{56a}$ each independently represents hydrogen, $C_{1-3}$alkyl or $C_{1-3}$alkoxyC$_{2-3}$alkyl) and $R^{37a}$ is as defined hereinbefore); and 15) $C_{1-3}$alkylX$^{10a}$C$_{1-3}$alkylR$^{37a}$ (wherein $X^{10a}$ represents —O—, —S—, —SO—, —SO$_2$—, —NR$^{57a}$CO—, —CONR$^{58a}$—, —SO$_2$NR$^{59a}$—, —NR$^{60a}$SO$_2$— or —NR$^{61a}$— (wherein $R^{57a}$, $R^{58a}$, $R^{59a}$, and $R^{60a}$ and $R^{61a}$ each independently represents hydrogen, $C_{1-3}$alkyl or $C_{1-3}$alkoxyC$_{2-3}$alkyl) and $R^{37a}$ is as defined hereinbefore) and additional groups of values of $R^{5a}$ are:

16) $R^{36a}$ (wherein $R^{36a}$ is as defined hereinbefore); and

17) $C_{1-3}$alkylX$^{10a}$C$_{1-3}$alkylR$^{36a}$ (wherein $X^{10a}$ and $R^{36a}$ are as defined hereinbefore)];

and salts thereof.

Preferably $R^{3a}$ represents hydrogen, amino, nitro or halogeno, but especially hydrogen.

Advantageously $X^{2a}$ represents —O—, —S—, —NR$^{9a}$CO—, —NR$^{12a}$SO$_2$— or —NR$^{13a}$— (wherein $R^{9a}$, $R^{12a}$ and $R^{13a}$ each independently represents hydrogen, $C_{1-2}$alkyl or $C_{1-2}$alkoxyethyl).

Preferably $X^{2a}$ represents —O—, —S—, —NR$^{9a}$CO—, —NR$^{12a}$SO$_2$— (wherein $R^{9a}$ and $R^{12a}$ each independently represents hydrogen or $C_{1-2}$alkyl) or NH.

More preferably $X^{2a}$ represents —O—, —S—, —NR$^{9a}$CO— (wherein $R^{9a}$ represents hydrogen or $C_{1-2}$alkyl) or NH.

Particularly $X^{2a}$ represents —O— or —NR$^{9a}$CO—0 (wherein $R^{9a}$ represents hydrogen or $C_{1-2}$alkyl), more particularly —O— or —NHCO—, especially —O—.

Preferably za is an integer from 1 to 3.

Preferably $R^{8a}$ is a group selected from pyrrolidinyl, piperazinyl, piperidinyl, morpholino and thiomorpholino which group may carry one or two substituents selected from oxo, hydroxy, halogeno, $C_{1-2}$alkyl, $C_{1-2}$hydroxyalkyl and $C_{1-2}$alkoxy.

Advantageously $R^{4a}$ represents hydrogen, hydroxy, cyano, nitro, trifluoromethyl, $C_{1-3}$alkyl, $C_{1-3}$alkoxy or amino and an additional advantageous value of $R^{4a}$ is $R^{8a}(CH_2)_{za}X^{2a}$ (wherein $R^{8a}$, $X^{2a}$ and za are as defined hereinbefore).

Preferably $R^{4a}$ is hydrogen, hydroxy, cyano, nitro, trifluoromethyl, methyl, ethyl, methoxy or ethoxy, and an additional preferred value of $R^{4a}$ is $R^{8a}(CH_2)_{za}X^{2a}$ (wherein $R^{8a}$, $X^{2a}$ and za are as defined hereinbefore).

More preferably $R^{4a}$ is hydrogen, hydroxy, cyano, nitro, trifluoromethyl, methyl, ethyl, methoxy, ethoxy or $R^{8a}(CH_2)_{za}X^{2a}$ (wherein $R^{8a}$ is a group selected from pyrrolidinyl, piperazinyl, piperidinyl, morpholino and thiomorpholino which group may carry one or two substituents selected from oxo, hydroxy, halogeno, $C_{1-2}$alkyl, $C_{1-2}$hydroxyalkyl and $C_{1-2}$alkoxy, $X^{2a}$ is —O—, —S—, —NR$^{9a}$CO—, —NR$^{12a}$SO$_2$— (wherein $R^{9a}$ and $R^{12a}$ each independently represents hydrogen or $C_{1-2}$alkyl) or NH and za is an integer from 1 to 3).

Particularly $R^{4a}$ represents hydrogen, hydroxy, cyano, nitro, trifluoromethyl, methyl or methoxy and an additional more preferred value of $R^{4a}$ is $R^{8a}(CH_2)_{za}X^{2a}$ (wherein $R^{8a}$, $X^{2a}$ and za are as defined hereinbefore).

More particularly $R^{4a}$ represents hydrogen or methoxy. $R^{4a}$ especially represents methoxy.

Advantageously $X^{1a}$ represents —O—, —S—, —NR$^{14a}$CO—, —NR$^{17a}$SO$_2$— or —NR$^{18a}$— (wherein $R^{14a}$, $R^{17a}$ and $R^{18a}$ each independently represents hydrogen, $C_{1-2}$alkyl or $C_{1-2}$alkoxyethyl).

Preferably $X^{1a}$ represents —O—, —S—, —NR$^{14a}$CO—, —NR$^{17a}$SO$_2$— (wherein $R^{14a}$ and $R^{17a}$ each independently represents hydrogen or $C_{1-2}$alkyl) or NH.

More preferably $X^{1a}$ represents —O—, —S—, —NR$^{14a}$CO— (wherein $R^{14a}$ represents hydrogen or $C_{1-2}$alkyl) or NH.

Particularly $X^{1a}$ represents —O— or —NR$^{14a}$CO— (wherein $R^{14a}$ represents hydrogen or $C_{1-2}$alkyl), more particularly —O— or —NHCO—, especially —O—.

Advantageously $X^{3a}$ represents —O— or NR$^{20a}$ (wherein $R^{20a}$ represents hydrogen, $C_{1-3}$alkyl or $C_{1-2}$alkoxyethyl).

Advantageously $X^{4a}$ represents —O—, —S—, —SO—, —SO$_2$—, —NR$^{25a}$CO—, —NR$^{28a}$SO$_2$— or —NR$^{29a}$— (wherein $R^{25a}$, $R^{28a}$ and $R^{29a}$ each independently represents hydrogen, $C_{1-2}$alkyl or $C_{1-2}$alkoxyethyl).

Preferably $X^{4a}$ represents —O—, —S—, —SO—, —SO$_2$— or —NR$^{29a}$— (wherein $R^{29a}$ represents hydrogen, $C_{1-2}$alkyl or $C_{1-2}$alkoxyethyl).

More preferably $X^{4a}$ represents —O— or —NR$^{29a}$— (wherein $R^{29a}$ represents hydrogen or $C_{1-2}$alkyl).

Advantageously $X^{5a}$ and $X^{6a}$ which may be the same or different each represents —O—, —S—, —SO—, —SO$_2$— or —NR$^{35a}$— (wherein $R^{35a}$ represents hydrogen, $C_{1-3}$alkyl or $C_{1-2}$alkoxyethyl).

Preferably $X^{5a}$ and $X^{6a}$ which may be the same or different each represents —O—, —S— or —NR$^{35a}$— (wherein $R^{35a}$ represents hydrogen, $C_{1-2}$alkyl or $C_{1-2}$alkoxyethyl).

More preferably $X^{5a}$ and $X^{6a}$ which may be the same or different each represents —O— or —NH—.

Advantageously $X^{7a}$ represents —O—, —S— or —NR$^{46a}$— (wherein $R^{46a}$ represents hydrogen, $C_{1-2}$alkyl or $C_{1-2}$alkoxyethyl).

Preferably $X^{7a}$ represents —O— or —NR$^{46a}$— (wherein $R^{46a}$ represents hydrogen or $C_{1-2}$alkyl).

Advantageously $X^{8a}$ represents —O—, —S— or —NR$^{51a}$— (wherein $R^{51a}$ represents hydrogen, $C_{1-2}$alkyl or $C_{1-2}$alkoxyethyl).

Preferably $X^{8a}$ represents —O— or —NR$^{51a}$— (wherein $R^{51a}$ represents hydrogen or $C_{1-2}$alkyl).

Advantageously $X^9$ represents —O—, —S— or —NR$^{56a}$— (wherein $R^{56a}$ represents hydrogen, $C_{1-2}$alkyl or $C_{1-2}$alkoxyethyl).

Preferably $X^{9a}$ represents —O— or —NR$^{56a}$— (wherein $R^{56a}$ represents hydrogen or $C_{1-2}$alkyl).

Advantageously $X^{10a}$ represents —O—, —S— or —NR$^{61a}$— (wherein $R^{61a}$ represents hydrogen, $C_{1-2}$alkyl or $C_{1-2}$alkoxyethyl).

Preferably $X^{10a}$ represents —O— or —NR$^{61a}$— (wherein $R^{61a}$ represents hydrogen or $C_{1-2}$alkyl).

$R^{36a}$ is preferably pyrrolidinyl, piperazinyl, piperidinyl, morpholino or thiomorpholino which group may carry one or two substituents selected from oxo, hydroxy, halogeno, $C_{1-2}$alkyl, $C_{1-2}$hydroxyalkyl and $C_{1-2}$alkoxy.

$R^{37a}$ preferably represents a pyridone group or a 5 or 6-membered aromatic heterocyclic group with 1 to 3 heteroatoms selected from O, N and S, which pyridone group or heterocyclic group may be substituted as hereinbefore defined.

Where $R^{37a}$ is a 5 or 6-membered aromatic heterocyclic group, it preferably has 1 or 2 heteroatoms, selected from O, N and S, of which more preferably one is N, and may be substituted as hereinbefore defined.

$R^{37a}$ is particularly a pyridone, pyridyl, imidazolyl, thiazolyl, thienyl, triazolyl or pyridazinyl group which group may be substituted as hereinbefore defined, more particularly a pyridone, pyridyl, imidazolyl, thiazolyl or triazolyl group, especially a pyridone, pyridyl, imidazolyl or triazolyl group which group may be substituted as hereinbefore defined.

In one embodiment of the invention $R^{37a}$ represents a pyridone, phenyl or 5 or 6-membered aromatic heterocyclic group with 1 to 3 heteroatoms selected from O, N and S, which group may preferably carry up to 2 substituents, more preferably up to one substituent, selected from the group of substituents as hereinbefore defined.

In the definition of $R^{37a}$, conveniently substituents are selected from halogeno, $C_{1-4}$alkyl, $C_{1-4}$alkoxy and cyano, more conveniently substituents are selected from chloro, fluoro, methyl and ethyl.

Conveniently $R^{5a}$ is selected from one of the following fifteen groups:

1) $C_{1-5}$alkyl which may be unsubstituted or substituted with one or more fluorine atoms, or $C_{2-5}$alkyl which may be unsubstituted or substituted with one or more groups selected from hydroxy and amino;

2) $C_{2-3}$alkylX$^{3a}$COR$^{19a}$ (wherein $X^{3a}$ is as hereinbefore defined and $R^{19a}$ represents $C_{1-3}$alkyl, —NR$^{21a}$R$^{22a}$— or —OR$^{23a}$— (wherein $R^{21a}$, $R^{22a}$ and $R^{23a}$ which may be the same or different are each $C_{1-2}$alkyl or $C_{1-2}$alkoxyethyl));

3) $C_{2-4}$alkylX$^{4a}$R$^{24a}$ (wherein $X^{4a}$ is as hereinbefore defined and $R^{24a}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-3}$alkoxy and which cyclic group may bear one or two substituents selected from oxo, hydroxy, halogeno, $C_{1-4}$alkyl, $C_{1-4}$hydroxyalkyl and $C_{1-4}$alkoxy);

4) $C_{2-3}$alkylX$^{5a}$C$_{2-3}$alkylX$^{6a}$R$^{30a}$ (wherein $X^{5a}$ and $X^{6a}$ are as hereinbefore defined and $R^{30a}$ represents hydrogen or $C_{1-3}$alkyl);

5) $C_{1-5}$alkylR$^{62a}$ (wherein $R^{62a}$ is a 5 or 6 membered saturated heterocyclic group with one or two heteroatoms, selected independently from O, S and N, which heterocyclic group is linked to $C_{1-5}$alkyl through a carbon atom and which heterocyclic group may bear one or two substituents selected from halogeno, $C_{1-4}$alkyl, $C_{1-4}$hydroxyalkyl and $C_{1-4}$alkoxy) or $C_{2-5}$alkyl$R^{63a}$ (wherein $R^{63a}$ is a 5 or 6 membered saturated heterocyclic group with one or two heteroatoms of which one is N and the other is selected independently from O, S and N, which heterocyclic group is linked to $C_{2-5}$alkyl through a nitrogen atom and which heterocyclic group may bear one or two substituents selected from halogeno, $C_{1-4}$alkyl, $C_{1-4}$hydroxyalkyl and $C_{1-4}$alkoxy);

6) $C_{3-4}$alkenyl$R^{64a}$ (wherein $R^{64a}$ represents $R^{62a}$ or $R^{63a}$ as defined hereinbefore);

7) $C_{3-4}$alkynyl$R^{64a}$ (wherein $R^{64a}$ represents $R^{62a}$ or $R^{63a}$ as defined hereinbefore);

8) $R^{37a}$ (wherein $R^{37a}$ is as defined hereinbefore);

9) $C_{1-5}$alkyl$R^{37a}$ (wherein $R^{37a}$ is as defined hereinbefore);

10) $C_{3-5}$alkenyl$R^{37a}$ (wherein $R^{37a}$ is as defined hereinbefore);

11) $C_{3-5}$alkynyl$R^{37a}$ (wherein $R^{37a}$ is as defined hereinbefore);

12) $C_{1-5}$alkyl$X^{7a}R^{37a}$ (wherein $X^{7a}$ and $R^{37a}$ are as defined hereinbefore);

13) $C_{4-5}$alkenyl$X^{8a}R^{37a}$ (wherein $X^{8a}$ and $R^{37a}$ are as defined hereinbefore);

14) $C_{4-5}$alkynyl$X^{9a}R^{37a}$ (wherein $X^{9a}$ and $R^{37a}$ are as defined hereinbefore); and 15) $C_{2-3}$alkyl$X^{10a}C_{1-2}$alkyl$R^{37a}$ (wherein $X^{10a}$ and $R^{37a}$ are as defined hereinbefore) and additional convenient groups of values of $R^{5a}$ are:

16) $R^{36a}$ (wherein $R^{36a}$ is as defined hereinbefore); and

17) $C_{2-3}$alkyl$X^{10a}C_{1-2}$alkyl$R^{36a}$ (wherein $X^{10a}$ and $R^{36a}$ are as defined hereinbefore).

Advantageously $R^{5a}$ is selected from one of the following fifteen groups:

1) $C_{1-4}$alkyl which may be unsubstituted or substituted with one or more fluorine atoms, or $C_{2-4}$alkyl which may be unsubstituted or substituted with one or two groups selected from hydroxy and amino;

2) $C_{2-3}$alkyl$X^{3a}COR^{19a}$ (wherein $X^{3a}$ is as hereinbefore defined and $R^{19a}$ represents —$NR^{21a}R^{22a}$— or —$OR^{23a}$— (wherein $R^{21a}$, $R^{22a}$ and $R^{23a}$ which may be the same or different are each $C_{1-2}$alkyl or $C_{1-2}$alkoxyethyl));

3) $C_{2-4}$alkyl$^{4a}R^{24a}$ (wherein $X^{4a}$ is as hereinbefore defined and $R^{24a}$ is a group selected from $C_{1-3}$alkyl, cyclopentyl, cyclohexyl, pyrrolidinyl and piperidinyl which group is linked to $X^{4a}$ through a carbon atom and which $C_{1-3}$alkyl group may bear one or two substituents selected from oxo, hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{2-3}$alkyl$X^{5a}C_{2-3}$alkyl$X^{6a}R^{30a}$ (wherein $X^{5a}$ and $X^{6a}$ are as hereinbefore defined and $R^{30a}$ represents hydrogen or $C_{1-3}$alkyl);

5) $C_{1-4}$alkyl$R^{65a}$ wherein $R^{65a}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-4}$alkyl through a carbon atom and which group may carry one or two substituents selected from oxo, hydroxy, halogeno, $C_{1-2}$alkyl, $C_{1-2}$hydroxyalkyl and $C_{1-2}$alkoxy) or $C_{2-4}$alkyl$R^{66a}$ (wherein $R^{66a}$ is a group selected from morpholino, thiomorpholino, pyrrolidin-1-yl, piperazin-1-yl and piperidino which group may carry one or two substituents selected from oxo, hydroxy, halogeno, $C_{1-2}$alkyl, $C_{1-2}$hydroxyalkyl and $C_{1-2}$alkoxy);

6) $C_{3-4}$alkenyl$R^{67a}$ (wherein $R^{67a}$ represents $R^{65a}$ or $R^{66a}$ as defined hereinbefore);

7) $C_{3-4}$alkynyl$R^{67a}$ (wherein $R^{67a}$ represents $R^{65a}$ or $R^{66a}$ as defined hereinbefore);

8) $R^{37a}$ (wherein $R^{37a}$ is as defined hereinbefore);

9) $C_{1-4}$alkyl$R^{37a}$ (wherein $R^{37a}$ is as defined hereinbefore);

10) 1-$R^{37a}$prop-1-en-3-yl or 1-$R^{37a}$but-2-en4-yl (wherein $R^{37a}$ is as defined hereinbefore with the proviso that when $R^{5a}$ is 1-$R^{37a}$prop-1-en-3-yl, $R^{37a}$ is linked to the alkenyl group via a carbon atom);

11) 1-$R^{37a}$prop-1-yn-3-yl or 1-$R^{37a}$but-2-yn-4-yl (wherein $R^{37a}$ is as defined hereinbefore with the proviso that when $R^{5a}$ is 1-$R^{37a}$prop-1-yn-3-yl, $R^{37a}$ is linked to the alkynyl group via a carbon atom);

12) $C_{1-5}$alkyl$X^{7a}R^{37a}$ (wherein $X^{7a}$ and $R^{37a}$ are as defined hereinbefore);

13) 1-($R^{37a}X^{8a}$)but-2-en-4-yl (wherein $X^{8a}$ and $R^{37a}$ are as defined hereinbefore);

14) 1-($R^{37a}X^{9a}$)but-2-yn-4-yl (wherein $X^{9a}$ and $R^{37a}$ are as defined hereinbefore); and 15) $C_{2-3}$alkyl$X^{10a}C_{1-2}$alkyl$R^{37a}$ (wherein $X^{10a}$ and $R^{37a}$ are as defined hereinbefore) and additional advantageous groups of values of $R^{5a}$ are:

16) $R^{36a}$ (wherein $R^{36a}$ is as defined hereinbefore); and

17) $C_{2-3}$alkyl$X^{10a}C_{1-2}$alkyl$R^{36a}$ (wherein $X^{10a}$ and $R^{36a}$ are as defined hereinbefore).

Preferably $R^{5a}$ is selected from one of the following thirteen groups:

1) $C_{1-3}$alkyl which may be unsubstituted or substituted with one or more fluorine atoms, or $C_{2-3}$alkyl which may be unsubstituted or substituted with one or two groups selected from hydroxy and amino;

2) 2-(3,3-dimethylureido)ethyl, 3-(3,3-dimethylureido) propyl, 2-(3-methylureido)ethyl, 3-(3-methylureido) propyl, 2-ureidoethyl, 3-ureidopropyl, 2(N,N-dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl;

3) $C_{2-3}$alkyl$X^{4a}R^{24a}$ (wherein $X^{4a}$ is as defined hereinbefore and $R^{24a}$ is a group selected from $C_{1-2}$alkyl, cyclopentyl, cyclohexyl, pyrrolidinyl and piperidinyl which group is linked to $X^{4a}$ through a carbon atom and which $C_{1-2}$alkyl group may bear one or two substituents selected from hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{2-3}$alkyl$X^{5a}C_{2-3}$alkyl$X^{6a}R^{30a}$ (wherein $X^{5a}$ and $X^{6a}$ are as hereinbefore defined and $R^{30a}$ represents hydrogen or $C_{1-2}$alkyl);

5) $C_{1-2}$alkyl$R^{65a}$ (wherein $R^{65a}$ is a group selected from pyrrolidinyl, piperazinyl, piperidinyl, 1,3-dioxolan-2- yl, 1,3-dioxan-2-yl, 1,3-dithiolan-2-yl and 1,3-dithian-2-yl, which group is linked to $C_{1-2}$alkyl through a carbon atom and which group may carry one substituent selected from oxo, hydroxy, halogeno, $C_{1-2}$alkyl, $C_{1-2}$hydroxyalkyl and $C_{1-2}$alkoxy) or $C_{2-3}$alkyl$R^{66a}$ (wherein $R^{66a}$ is a group selected from morpholino, thiomorpholino, piperidino, piperazin-1-yl and pyrrolidin-1-yl which group may carry one substituent selected from oxo, hydroxy, halogeno, $C_{1-2}$alkyl, $C_{1-2}$hydroxyalkyl and $C_{1-2}$alkoxy);

6) $R^{37a}$ (wherein $R^{37a}$ is as defined hereinbefore);

7) $C_{1-4}$alkyl$R^{37a}$ (wherein $R^{37}$a is as defined hereinbefore);

8) 1-$R^{37a}$but-2-en-4-yl (wherein $R^{37a}$ is as defined hereinbefore);

9) 1-$R^{37a}$but-2-yn-4-yl (wherein $R^{37a}$ is as defined hereinbefore);

10) $C_{1-5}$alkyl$X^{7a}R^{37a}$ (wherein $X^{7a}$ and $R^{37a}$ are as defined hereinbefore);

11) 1-($R^{37a}X^{8a}$)but-2-en-4-yl (wherein $X^{8a}$ and $R^{37a}$ are as defined hereinbefore);

12) 1-($R^{37a}X^{9a}$)but-2-yn-4-yl (wherein $X^{9a}$ and $R^{37a}$ are as defined hereinbefore); and 13) ethyl$X^{10a}$methyl$R^{37a}$ (wherein $X^{10a}$ and $R^{37a}$ are as defined hereinbefore) and additional preferred groups of values of $R^{5a}$ are:

14) $R^{36a}$ (wherein $R^{36a}$ is as defined hereinbefore); and 15) ethyl$X^{10a}$methyl$R^{36a}$ (wherein $X^{10a}$ and $R^{36a}$ are as defined hereinbefore).

More preferably $R^{5a}$ represents methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino) propyl, 2-methylthiazol-4-ylmethyl, 2-acetamidothiazol-4-ylmethyl, 1-methylimidazol-2-ylmethyl, 2-(imidazol-1-yl)ethyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl 2-(4-pyridyloxy)ethyl, 2-(4-pyridylamino)ethyl, 2-(4-oxo-1,4-dihydro-1-pyridyl)ethyl, 2-thiomorpholinoethyl, 3-thiomorpholinopropyl, 2-2-methoxyethoxy)ethyl, 2-(4-methylpiperazin-1-yl)ethyl or 3-(4-methylpiperazin-1-yl) propyl and additional more preferred values of $R^{5a}$ are 3-(methylsulphinyl)propyl, 3-(methylsulphonyl)propyl, 2-(2-methylimidazol-1-yl)ethyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 2-((N-methyl-N-4-pyridyl)amino)ethyl and 3-(4-oxidomorpholino)propyl.

In a further aspect of the current invention there are provided compounds of the formula Ib:

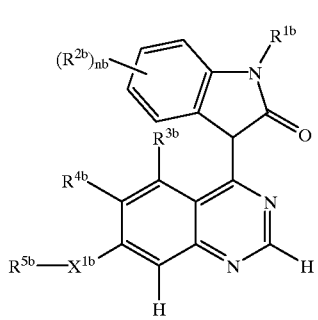

(Ib)

[wherein:

$R^{1b}$ represents hydrogen;

$R^{2b}$ represents halogeno, trifluoromethyl, cyano, nitro, $C_{2-4}$alkanoyl, $C_{1-3}$alkoxycarbonyl, $C_{1-3}$alkylsulphinyl, $C_{1-3}$alkylsulphonyl, carbamoyl, N-$C_{1-3}$alkylcarbamoyl, N,N-di($C_{1-3}$alkyl)carbamoyl, aminosulphonyl, N-$C_{1-3}$alkylaminosulphonyl, N,N-di($C_{1-3}$alkyl)aminosulphonyl, or a group $R^{6b}X^{2b}$ (wherein $X^{2b}$ represents a direct bond, $C_{2-4}$alkanoyl, —CONR$^{7b}R^{8b}$—, —SO$_2$NR$^{9b}R^{10b}$— or —SO$_2R^{11b}$— (wherein $R^{7b}$ and $R^{9b}$, each independently represents hydrogen and $R^{8b}$, $R^{10b}$ and $R^{11b}$ each independently represents $C_{1-3}$alkyl and wherein $R^{6b}$ is linked to $R^{8b}$, $R^{10b}$ or $R^{11b}$) and $R^{6b}$ represents pyrrolidinyl, piperazinyl, piperidinyl, morpholino, thiomorpholino, imidazolyl or triazolyl which heterocyclic group is linked to $X^{2b}$ via a nitrogen atom and which heterocyclic group may bear one or two substituents selected from hydroxy, halogeno, $C_{1-2}$alkyl, $C_{1-2}$alkoxy, $C_{1-2}$alkanoyloxy, trifluoromethyl, cyano, amino, nitro and $C_{1-4}$alkoxycarbonyl);

nb is an integer from 0 to 2;

$R^{3b}$ represents hydrogen;

$R^{4b}$ represents represents hydrogen, hydroxy, cyano, nitro, trifluoromethyl, methyl, methoxy or a group $R^{12b}(CH_2)_{zb}X^{3b}$ (wherein $R^{12b}$ represents a group selected from pyrrolidinyl, piperazinyl, piperidinyl, morpholino and thiomorpholino which group may carry one or two substituents selected from oxo, hydroxy, halogeno, $C_{1-2}$alkyl, $C_{1-2}$hydroxyalkyl and $C_{1-2}$alkoxy, zb is an integer from 1 to 3 and $X^{3b}$ represents —O— or —NR$^{13b}$CO— (wherein $R^{13b}$ represents hydrogen or $C_{1-2}$alkyl));

$X^{1b}$ represents —O— or —NR$^{14b}$CO— (wherein $R^{14b}$ represents hydrogen or $C_{1-2}$alkyl); and $R^{5b}$ represents methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino) propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-methylthiazol-4- ylmethyl, 2-acetamidothiazol-4-ylmethyl, 1-methylimidazol-2-ylmethyl, 2-(imidazol-1-yl)ethyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl 2-(4-pyridyloxy)ethyl, 2-(4-pyridylamino)ethyl, 2-(4-oxo-1,4-dihydro-1-pyridyl)ethyl, 2-thiomorpholinoethyl, 3-thiomorpholinopropyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 2-(2-methylimidazol-1-yl)ethyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 2-((N-methyl-N-4-pyridyl)amino)ethyl or 3-(4-oxidomorpholino)propyl;]

and salts thereof.

Preferred compounds are 7-methoxy-6-(3-morpholinopropoxy)-4-(oxindol-3-yl)quinazoline, 4-(5-cyanooxindol-3-yl)-6-methoxy-7-(2-methoxyethoxy)quinazoline, 7-(2-(imidazol-1-yl)ethoxy)6-methoxy-4-oxindol-3-yl)quinazoline.

4-(5-cyanooxindol-3-yl)-6-methoxy-7-(3-morpholinopropoxy)quinazoline, 4-(5-cyanooxindol-3-yl)-6-methoxy-7-(2-([N-methyl-N-(4-pyridyl)]amino)ethoxy)quinazoline, 6-methoxy4-(5-methoxycarbonyloxindol-3-yl)-7-(3-morpholinopropoxy)quinazoline, 4-(6-fluorooxindol-3-yl)-7-(2-(imidazol-1-yl)ethoxy)-6-methoxyquinazoline, 4-(7-hydroxyoxindol-3-yl)-6-methoxy-7-(3-morpholinopropoxy)quinazoline, 6-methoxy-7-(2-methoxyethoxy)-5-nitrooxindol-3-yl)quinazoline, 6-methoxy-7-(3-morpholinopropoxy)-4-(5-nitrooxindol-3-yl)-quinazoline, 4-(5-acetamidooxindol-3-yl)-6-methoxy-7-(2-methoxyethoxy)quinazoline, 4-(5-acetyloxindol-3-yl)-6-methoxy-7-(2-methoxyethoxy)quinazoline, 6-methoxy-4-(5-methylsulphonyloxindol-3-yl)-7-(3-morpholinopropoxy)quinazoline, 6-methoxy-4-(5-methylsulphinyloxindol-3-yl)-7-(3-morpholinopropoxy)quinazoline, 7-(2-(imidazol-1-yl)ethoxy)-6-methoxy-4-(5-(2-morpholinoethylaminosulphonyl)oxindol-3-yl)quinazoline, 7-(2-methoxyethoxy)-4-(5-nitrooxindol-3-yl)quinazoline, 6-methoxy-7-(2-methoxyethoxy)-4-(6-trifluoromethyloxindol-3-yl)quinazoline, 4-(6-cyanooxindol-3-yl)-7-(3-morpholinopropoxy)quinazoline, 4-(6-cyanooxindol-3-yl)-6-methoxy-7-(3-morpholinopropoxy)quinazoline, 4-(6-bromooxindol-3-yl)-7-(3-morpholinopropoxy)quinazoline, 4-(5-aminosulphonyloxindol-3-yl)-6-methoxy-7-(3-morpholinopropoxy)quinazoline, 4-(oxindol-3-yl)-6-morpholinoquinazoline, 4-(5-cyanooxindol-3-yl)-6-methoxy-7-(2-(pyrrolidin-1-yl)ethoxy)quinazoline, 6-methoxy-4-(5-methylthiooxindol-3-yl)-7-(3-morpholinopropoxy)quinazoline, 6-methoxy-7-(2-methoxyethoxy)-4-(5-(2-morpholinoethylaminosulphonyl)oxindol-3-yl)quinazoline, 6,7-dimethoxy-4-(5-(2-morpholinoetylaminosulphonyl)oxindol-3-yl)quinazoline, 4-(5-cyanooxindol-3-yl)-7-(2-methoxyethoxy)quinazoline, 7-(3-morpholinopropoxy)-4-(5-nitrooxindol-3-yl)quinazoline, 4-(6-cyanooxindol-3-yl)-6-methoxy-7-(2-methoxyethoxy)quinazoline, 6-methoxy-7-(2-methoxyethoxy)-4-(5-methylaminosulphonyloxindol-3-yl)quinazoline, 4-(5-N,N-dimethylaminosulphonyloxindol-3-yl)-6-methoxy-7-(2-methoxyethoxy)quinazoline, 6-methoxy-4-(oxindol-3-yl)-7-(2(pyrrolidin-1-yl)ethoxy)quinazoline, 4-(5-bromooxindol-3-yl)-6-methoxy-7-(3-morpholinopropoxy)quinazoline, 6-methoxy-4-(oxindol-3-yl)-7-(3-(pyrrolidin-1-yl)propoxy)quinazoline, 7-(3-morpholinopropoxy)-4-(oxindol-3-yl)quinazoline, 6-methoxy-7-(2-([N-methyl-N-(3-morpholinopropylsulphonyl)]amino)ethoxy)-4-(oxindol-3-yl)quinazoline and 6-methoxy-7-(2-([N-methyl-N-(1-methyl-1H-imidazol-4-ylsulphonyl)]amino)ethoxy)-4-(oxindol-3-yl)quinazoline and and salts thereof, particularly hydrochloride salts thereof.

More preferred compounds are 6,7-dimethoxy-4-(6-fluorooxindol-3-yl)quinazoline, 6,7-dimethoxy-4-(oxindol-3-yl)quinazoline, 7-(2-methoxyethoxy)-1-(oxindol-3-yl)quinazoline, 4-(5-bromooxindol-3-yl)-6-methoxy-7-(2-methoxyethoxy)quinazoline, 4-(5-hydroxyoxindol-3-yl)-6-methoxy-7-(3-morpholinopropoxy)quinazoline, 6-methoxy-7-(3-morpholinopropoxy)-4-(6-trifluoromethyloxindol-3-yl)quinazoline, 4-(5-aminosulponyloxindol-3-yl)-6-methoxy-7-(2-methoxyethoxyquinazoline, 4-(5-cyanooxindol-3-yl)-7-(3-morpholinopropoxy)quinazoline, 6-methoxy-7-(2-(2-methoxyethoxy)ethoxy)-4-(oxindol-3-yl)quinazoline and 4-(5-aminosulphonyloxindol-3-yl)-6-methoxy-7-(2-(2-methoxyethoxy)ethoxy)quinazoline and salts thereof, particularly hydrochloride salts thereof.

Especially preferred compounds are 4-(5-fluorooxindol-3-yl)-6-methoxy-7-(3-morpholinopropoxy)quinazoline, 4-(5-fluorooxindol-3-yl)-6-methoxy-7-(2-methoxyethoxy)quinazoline, 4-(5-cyanooxindol-3-yl)-7-(2-(imidazol-1-yl)ethoxy)-6-methoxyquinazoline and 7-(3-morpholinopropoxy)-4-(6-trifluoromethyloxindol-3-yl)quinazoline and salts thereof, particularly hydrochloride salts thereof.

More especially preferred compounds are 4-(6-fluorooxindol-3-yl)-6-methoxy-7-(3-morpholinopropoxy)quinazoline, 6-methoxy-7-(2-methoxyethoxy)-4-oxindol-3-yl)quinazoline and 6-methoxy-7-(3-morpholinopropoxy)-4-(oxindol-3-yl)quinazoline and salts thereof, particularly hydrochloride salts thereof.

In another aspect of the present invention particularly preferred compounds by virtue of their good activity against VEGF receptor tyrosine kinase activity and their lack of significant activity against epidermal growth factor (EGF) receptor tyrosine kinase include:

6-methoxy-7-(2-methoxyethoxy)-4-(oxindol-3-yl) quinazoline,
6-methoxy-7-(3-morpholinopropoxy)-4-(oxindol-3-yl) quinazoline,
4-(5-fluorooxindol-3-yl)-6-methoxy-7-(3-morpholinopropoxy)quinazoline,
4-(5-bromooxindol-3-yl)-6-methoxy-7-(2-methoxyethoxy) quinazoline,
4-(5-fluorooxindol-3-yl)-6-methoxy-7-(2-methoxyethoxy) quinazoline,
4-(5-hydroxyoxindol-3-yl)-6-methoxy-7-(3-morpholinopropoxy)quinazoline,
6,7-dimethoxy-4-(6-fluorooxindol-3-yl)quinazoline,
4-(6-fluorooxindol-3-yl)-6-methoxy-7-(3-morpholinopropoxy)quinazoline,
7-(2-methoxyethoxy)-4-(oxindol-3-yl)quinazoline,
6,7-dimethoxy-4-(oxindol-3-yl)quinazoline,
and salts thereof, particularly hydrochloride salts thereof.

For the avoidance of doubt it is to be understood that where in this specification a group is qualified by 'hereinbefore defined' or 'defined hereinbefore' the said group encompasses the first occurring and broadest definition as well as each and all of the preferred definitions for that group.

In this specification unless stated otherwise the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1–6 carbon atoms, preferably 1–4 carbon atoms. The term "alkoxy" as used herein, unless stated otherwise includes "alkyl" —O— groups in which "alkyl" is as hereinbefore defined. The term "aryl" as used herein unless stated otherwise includes reference to a $C_{6-10}$ aryl group which may, if desired, carry one or more substituents selected from halogeno, alkyl, alkoxy, nitro, trifluoromethyl and cyano, (wherein alkyl and alkoxy are as hereinbefore defined). The term "aryloxy" as used herein unless otherwise stated includes "aryl" —O— groups in which "aryl" is as hereinbefore defined. The term "sulphonyloxy" as used herein refers to alkylsulphonyloxy and arylsulphonyloxy groups in which "alkyl" and "aryl" are as hereinbefore defined. The term "alkanoyl" as used herein unless otherwise stated includes formyl and alkylC=O groups in which "alkyl" is as defined hereinbefore, for example $C_2$alkanoyl is ethanoyl and refers to $CH_3C$=O, $C_1$alkanoyl is formyl and refers to CHO. In this specification unless stated otherwise the term "alkenyl" includes both straight and branched chain alkenyl groups but references to individual alkenyl groups such as 2-butenyl are specific for the straight chain version only. Unless otherwise stated the term "alkenyl" advantageously refers to chains with 2–5 carbon atoms, preferably 3–4 carbon atoms. In this specification unless stated otherwise the term "alkynyl" includes both straight and branched chain alkynyl groups but references to individual alkynyl groups such as 2-butynyl are specific for the straight chain version only. Unless otherwise stated the term "alkynyl" advantageously refers to chains with 2–5 carbon atoms, preferably 3–4 carbon atoms.

Within the present invention it is to be understood that a compound of the formula I or a salt thereof may exhibit the phenomenon of tautomerism and that the formulae drawings within this specification can represent only one of the possible tautomeric forms. It is to be understood that the invention encompasses any tautomeric form which inhibits VEGF receptor tyrosine kinase activity and which inhibits FGF R1 receptor tyrosine kinase activity and is not to be limited merely to any one tautomeric form utilised within the formulae drawings. In particular the oxindole group can exist in at least two forms giving compounds of formulae I and II:

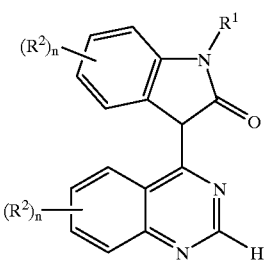

(I)

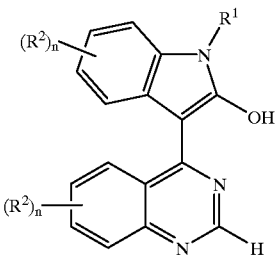

(II)

(wherein $R^1$, $R^2$, $R^3$, m and n are as hereinbefore defined). The formulae drawings within this specification can represent only one of the possible tautomeric forms and it is to be understood that the specification encompasses all possible tautomeric forms of the compounds drawn not just those forms which it has been possible to show graphically herein.

It is also to be understood that certain compounds of the formula I and salts thereof can exist in solvated as well as unsolvated forms such as, for example, hydrated forms. It is to be understood that the invention encompasses all such solvated forms which inhibit VEGF receptor tyrosine kinase activity and inhibit FGF R1 receptor tyrosine kinase activity.

For the avoidance of any doubt, it is to be understood that when $X^2$ is, for example, a group of formula —$NR^{11}CO$—, it is the nitrogen atom bearing the $R^{11}$ group which is attached to the quinazoline ring and the carbonyl (CO) group is attached to $R^{10}$, whereas when $X^2$ is, for example, a group of formula —$CONR^{12}$—, it is the carbonyl group which is attached to the quinazoline ring and the nitrogen atom bearing the $R^{12}$ group is attached to $R^{10}$. A similar convention applies to the other two atom $X^2$ linking groups such as —$NR^{14}SO_2$— and —$SO_2NR^{13}$—. When $X^2$ is —$NR^{15}$— it is the nitrogen atom bearing the $R^{15}$ group which is linked to the quinazoline ring and to $R^{10}$. An analogous convention applies to other groups. It is further to be understood that when $X^2$ represents —$NR^{15}$—and $R^{15}$ is $C_{1-3}$alkoxy$C_{2-3}$alkyl it is the $C_{2-3}$alkyl moiety which is linked to the nitrogen atom of $X^2$ and an analogous convention applies to other groups.

For the avoidance of any doubt, it is to be understood that in a compound of the formula I when $R^{10}$ is, for example, a group of formula $C_{1-5}$alkyl$X^{10}C_{1-5}$alkyl$R^{34}$, it is the terminal $C_{1-5}$alkyl moiety which is linked to $X^2$, similarly when $R^{10}$ is, for example, a group of formula $C_{2-5}$alkenyl$R^{34}$ it is the $C_{2-5}$alkenyl moiety which is linked to $X^2$ and an analogous convention applies to other groups. When $R^{10}$ is a group 1-$R^{34}$prop-1-en-3-yl it is the first carbon to which the group $R^{34}$ is attached and it is the third carbon which is linked to $X^2$ and an analogous convention applies to other groups.

For the avoidance of any doubt, it is to be understood that when $R^{34}$ carries a $C_{1-4}$aminoalkyl substituent it is the $C_{1-4}$alkyl moiety which is attached to $R^{34}$ whereas when $R^{34}$ carries a $C_{1-4}$alkylamino substituent it is the amino moiety which is attached to $R^{34}$ and an analogous convention applies to other groups.

For the avoidance of any doubt when $X^1$ is $C_{2-4}$alkanoyl it is the carbonyl moiety which is linked to the benz ring of the oxindole group and it is the alkyl moiety which is linked to $R^4$ and an analogous convention applies to other groups.

The present invention relates to the compounds of formula I as hereinbefore defined as well as to the salts thereof. Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

A compound of the formula I, or salt thereof, and other compounds of the invention (as hereinafter defined) may be prepared by any process known to be applicable to the preparation of chemically-related compounds. Such processes include, for example, those illustrated in European Patent Applications Publication Nos. 0520722, 0566226, 0602851, 0635498 and 0636608. Such processes, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus the following processes (a) to (h) and (i) to (viii) constitute further features of the present invention.

Synthesis of Compounds of Formula I (a) Compounds of the formula I and salts thereof may be prepared by the reaction of a compound of the formula III:

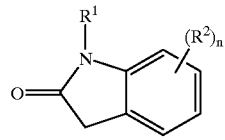

(III)

(wherein $R^3$ and m are as defined hereinbefore and $L^1$ is a displaceable moiety), with a compound of the formula IV:

(IV)

(wherein $R^1$, $R^2$ and n are as defined hereinbefore) whereby to obtain compounds of the formula I and salts thereof. A convenient displaceable moiety $L^1$ is, for example, a halogeno, alkoxy (preferably $C_{1-4}$alkoxy), aryloxy or sulphonyloxy group, for example a chloro, bromo, methoxy, phenoxy, methanesulphonyloxy or toluene4-sulphonyloxy group.

The reaction is advantageously effected in the presence of a base. Such a base is, for example, an organic amine base such as, for example, pyridine, 2,6-tutidine, collidine, 4-dimethylaminopyridine, triethylamine, morpholine, N-methylmorpholine or diazabicyclo[5.4.0]undec-7-ene, tetramethylguanidine or for example, an alkali metal or alkaline earth metal carbonate or hydroxide, for example sodium carbonate, potassium carbonate, calcium carbonate, sodium hydroxide or potassium hydroxide. Alternatively such a base is, for example, an alkali metal hydride, for example sodium hydride, or an alkali metal or alkaline earth metal amide, for example sodium amide, sodium bis (trimethylsilyl)arnide, potassium amide or potassium bis (trimethylsilyl)amide. The reaction is preferably effected in the presence of an inert solvent or diluent, for example an ether such as tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethylsulphoxide. The reaction is conveniently effected at a temperature in the range, for example, 10 to 150° C., preferably in the range 20 to 90° C.

When it is desired to obtain the acid salt, the free base may be treated with an acid such as a hydrogen halide, for example hydrogen chloride, sulphuric acid, a sulphonic acid, for example methane sulphonic acid, or a carboxylic acid, for example acetic or citric acid, using a conventional procedure.

(b) A compound of the formula I and salts thereof can be prepared by the deprotection of a compound of formula V:

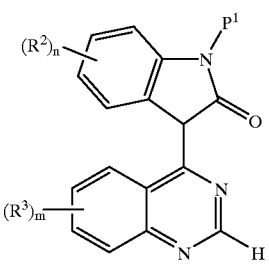

(V)

(wherein $R^2$, $R^3$, n and m are as hereinbefore defined and $P^1$ represents a protecting group). The choice of indole protecting group $P^1$ is within the standard knowledge of an organic chemist, for example those included in standard texts such as "Protective Groups in Organic Synthesis" T. W. Greene and R. G. M. Wuts, 2nd Ed. Wiley 1991, including N-sulphonyl derivatives (for example, p-toluenesulphonyl), carbamates (for example, t-butyl carbonyl), N-alkyl derivatives (for example, 2-chloroethyl, benzyl) and particularly amino acetal derivatives (for example, diethoxymethyl and benzyloxymethyl). The removal of such a protecting group may be effected by any of the procedures known for such a transformation, including those reaction conditions indicated in standard texts such as that indicated hereinbefore, or by a related procedure. The reaction conditions preferably being such that the unprotected derivative is produced without unwanted reactions at other sites within the starting or product compounds. For example, where the protecting group $P^1$ is diethoxymethyl, the transformation may conveniently be effected by treatment of the oxindole derivative with an acid (as defined hereinbefore in process (a)) preferably in the presence of a protic solvent or co-solvent such as water or an alcohol, for example methanol or ethanol. Such a reaction can be effected in the presence of an additional inert solvent or diluent (as defined hereinbefore in process (a)) advantageously at a temperature in the range 0 to 100° C., conveniently in the range 20 to 90° C.

(c) Compounds of the formula I and salts thereof wherein $R^1$ is hydrogen may also be prepared by the reduction and cyclisation of a compound of formula VI:

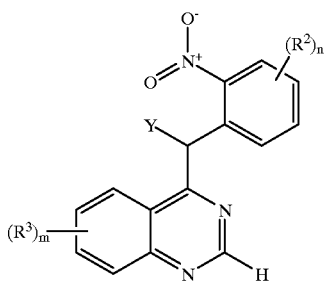

(VI)

(wherein $R^2$, $R^3$, m and n are as defined herein before and Y represents cyano, carboxy or $C_{1-4}$alkoxycarbonyl). The reduction of the nitro group may conveniently be effected as described in process (i) hereinafter. Where Y represents carboxy or $C_{1-4}$alkoxycarbonyl, the cyclisation to a compound of formiula I occurs spontaneously after reduction of the nitro group or may be promoted, if necessary, by heating in an inert solvent or diluent such as xylene, toluene or N,N-dimethylformarnide, optionally in the presence of an acid (as described hereinbefore in process (a)), advantageously at a temperature in the range of 20 to 150° C. preferably in the range 20 to 100° C. Where Y represents cyano, the cyclisation to a compound of formula I can be effected in the presence of an acid (as described hereinbefore in process (a)) or a Lewis acid, such as a haloborane derivative for example boron trifluoride, and an alcohol or thiol, such as methanol, ethanol or t-butanethiol, in an inert solvent or diluent (as defined hereinbefore in process (a)) and at a temperature in the range −20 to 50° C. preferably −5 to 10° C., followed by treatment with an aqueous acid, (as defined hereinbefore in process (a)), at a temperature in the range 20 to 150° C. preferably in the range 20 to 100° C.

(d) Compounds of formula I and salts thereof wherein at least one of the $R^2$ groups is hydroxy may also be prepared by the deprotection of a compound of formula VII:

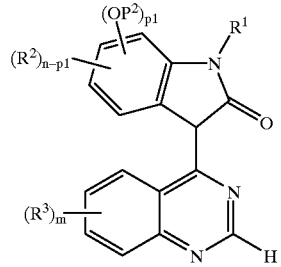

(VII)

(wherein $R^1$, $R^2$, $R^3$, n and m are as defined hereinbefore, $P^2$ represents a phenolic hydroxy protecting group and p1 is an integer from 1 to 4 equal to the number of protected hydroxy groups and such that n−p1 is equal to the number of $R^2$ substituents which are not protected hydroxy). The choice of phenolic hydroxy protecting group $P^2$ is within the standard knowledge of an organic chemist, for example those included in standard texts such as "Protective Groups in Organic Synthesis" T. W. Greene and R. G. M. Wuts, 2nd Ed. Wiley 1991, including ethers (for example, methyl, methoxymethyl, allyl, benzyl and benzyl substituted with up to 2 substituents selected from $C_{1-4}$alkoxy and nitro), silyl ethers (for example, t-butyldiphenylsilyl and t-butyldimethylsilyl), esters (for example, acetate and benzoate) and carbonates (for example, methyl, benzyl and benzyl substituted with up to 2 substituents selected from $C_{1-4}$alkoxy and nitro). The removal of such a phenolic hydroxy protecting group may be effected by any of the procedures known for such a transformation, including those reaction conditions indicated in standard texts such as that indicated hereinbefore, or by a related procedure. The reaction conditions preferably being such that the hydroxy derivative is produced without unwanted reactions at other sites within the starting or product compounds. For example, where the protecting group $P^2$ is benzyl, the transformation may conveniently be effected by treatment of the oxindole derivative with an acid (as defined hereinbefore in process (a)) particularly trifluoroacetic acid, preferably in the presence of an ether or thioether such as thioanisole. Such a reaction can be effected in the presence of an additional inert solvent or diluent (as defined hereinbefore in process (a)) advantageously at a temperature in the range 0 to 80° C., conveniently at about 40° C.

(e) Production of those compounds of formula I and salts thereof wherein at least one $R^3$ is $R^{10}X^2$ wherein $R^{10}$ is as defined hereinbefore and $X^2$ is —O—, —S—, —SO$_2$—, —CONR$^{12}$—, —SO$_2$NR$^{13}$— or —NR$^{15}$— (wherein $R^{12}$, $R^{13}$ and $R^{15}$ each independently represents hydrogen, $C_{1-3}$alkyl or $C_{1-3}$alkoxy$C_{2-3}$alkyl) can be achieved by the reaction, conveniently in the presence of a base (as defined hereinbefore in process (a)) of a compound of the formula VIII:

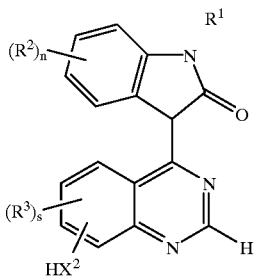

(VIII)

(wherein $R^1$, $R^2$, $R^3$, n and $X^2$ are as hereinbefore defined and s is an integer from 0 to 3) with a compound of formula IX:

$$R^{10}-L^1 \quad (IX)$$

(wherein $R^{10}$ and $L^1$ are as hereinbefore defined), $L^1$ is a displaceable moiety for example a halogeno or sulphonyloxy group such as a bromo or methanesulphonyloxy group. The reaction is preferably effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 50° C.

(f) Compounds of the formula I and salts thereof wherein at least one $R^3$ is $R^{10}X^2$ wherein $R^{10}$ is as defined hereinbefore and $X^2$ is —O—, —S—, or —$NR^{15}$— (wherein $R^{15}$ represents hydrogen, $C_{1-3}$alkyl or $C_{1-3}$alkoxy$C_{2-3}$alkyl) may be prepared by the reaction of a compound of the formula X:

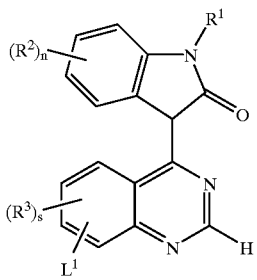

(X)

with a compound of the formula XI:

$$R^{10}-X^2-H \quad (XI)$$

(wherein $L^1$, $R^1$, $R^2$, $R^3$, $R^{10}$, n, s and $X^2$ are all as hereinbefore defined). The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

(g) Compounds of the formula I and salts thereof wherein at least one $R^3$ is $R^{10}X^2$ wherein $X^2$ is as defined hereinbefore and $R^{10}$ is $C_{1-5}$alkyl$R^{65}$, [wherein $R^{65}$ is selected from one of the following six groups:

1) $X^{11}C_{1-3}$alkyl (wherein $X^{11}$ represents —O—, —S—, —$SO_2$—, —$NR^{66}CO$— or —$NR^{67}SO_2$— (wherein $R^{66}$ and $R^{67}$ which may be the same or different are each hydrogen, $C_{1-3}$alkyl or $C_{1-3}$alkoxy$C_{2-3}$alkyl);

2) $NR^{68}R^{69}$ (wherein $R^{68}$ and $R^{69}$ which may be the same or different are each hydrogen, $C_{1-3}$alkyl or $C_{1-3}$alkoxy$C_{2-3}$alkyl);

3) $X^{12}C_{1-5}$alkyl$X^6R^{27}$ (wherein $X^{12}$ represents —O—, —S—, —$SO_2$—, —$NR^{70}CO$—, —$NR^{71}SO_2$— or $NR^{72}$ (wherein $R^{70}$, $RR^{71}$, and $R^{72}$ which may be the same or different are each hydrogen, $C_{1-3}$alkyl or $C_{1-3}$alkoxy$C_{2-3}$alkyl) and $X^6$ and $R^{27}$ are as defined hereinbefore);

4) $R^{60}$ (wherein $R^{60}$ is as defined hereinbefore);

5) $X^{13}R^{34}$ (wherein $X^{13}$ represents —O—, —S—, —$SO_2$—, —$NR^{73}CO$—, —$NR^{74}SO_2$—, or —$NR^{75}$— (wherein $R^{73}$, $R^{74}$, and $R^{75}$ which may be the same or different are each hydrogen, $C_{1-3}$alkyl or $C_{1-3}$alkoxy$C_{2-3}$alkyl) and $R^{34}$ is as defined hereinbefore); and 6) $X^{14}C_{1-5}$alkyl$R^{34}$ (wherein $X^{14}$ represents —)—, —S—, —$SO_2$—, —$NR^{76}CO$—, —$NR^{77}SO_2$— or —$NR^{78}$— (wherein $R^{76}$, $R^{77}$ and $R^{78}$ each independently represents hydrogen, $C_{1-3}$alkyl or $C_{1-3}$alkoxy$C_{2-3}$alkyl) and $R^{34}$ is as defined hereinbefore);]

may be prepared by reacting a compound of the formula XII:

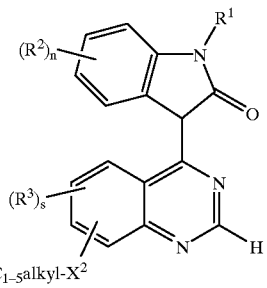

(XII)

(wherein $L^1$, $X^2$, $R^1$, $R^2$, $R^3$, n and s are as hereinbefore defined) with a compound of the formula XIII:

$$R^{65}-H \quad (XIII)$$

(wherein $R^{65}$ is as defined hereinbefore) to give a compound of the formula I or salt thereof The reaction may conveniently be effected in the presence of a base (as defined hereinbefore in process (a)) and advantageously in the presence of an inert solvent or diluent (as defined hereinbefore in process (a)), and at a temperature in the range, for example 0 to 150° C., conveniently at about 50° C.

Processes (a)–(d) and (g) are preferred over processes (e) and (f).

(h) The production of those compounds of the formula I and salts thereof wherein one or more of the substituents $(R^3)_m$ is represented by —$NR^{79}R^{80}$—, where one or both of $R^{79}$ and $R^{80}$ are $C_{1-3}$alkyl, may be effected by the reaction of compounds of formula I wherein the substituent $(R^3)_m$ is an amino group and an alkylating agent, preferably in the presence of a base as defined hereinbefore. Such alkylating agents are $C_{1-3}$alkyl moieties bearing a displaceable moiety as defined hereinbefore such as $C_{1-3}$alkyl halides for example $C_{1-3}$alkyl chloride, bromide or iodide. The reaction is preferably effected in the presence of an inert solvent or diluent (as defined hereinbefore in process (a)) and at a temperature in the range, for example, 10 to 100° C., conveniently at about ambient temperature. The production of compounds of formula I and salts thereof wherein one or more of the substituents $R^2$ or $R^3$ is an amino group may be effected by the reduction of a corresponding compound of formula I wherein the substituent(s) at the corresponding position(s) of the quinazoline and/or benz ring of the oxindole group is/are a nitro group(s). The reduction may conveniently be effected as described in process (i) hereinafter. The production of a compound of formula I and salts thereof wherein the substituent(s) at the corresponding position(s) of the quinazoline and/or benz ring of the oxindole group is/are a nitro group(s) may be effected by the processes described hereinbefore and hereinafter in processes (a–g) and (i–viii) using a compound selected from the compounds of the formulae (I–XXXIII) in which the substituent(s) at the corresponding position(s) of the quinazoline and/or benz ring of the oxindole group is/are a nitro group(s).

Synthesis of Intermediates (i) The compounds of formula III and salts thereof, constitute a further feature of the present invention. Such compounds in which $L^1$ is halogeno may for example be prepared by halogenating a compound of the formula XIV:

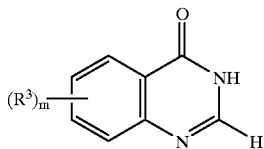

(XIV)

(wherein $R^3$ and m are as hereinbefore defined).

Convenient halogenating agents include inorganic acid halides, for example thionyl chloride, phosphorus(III) chloride, phosphorus(V)oxychloride and phosphorus(V) chloride. The halogenation reaction is conveniently effected in the presence of an inert solvent or diluent such as for example a halogenated solvent such as methylene chloride, trichloromethane or carbon tetrachloride, or an aromatic hydrocarbon solvent such as benzene or toluene. The reaction is conveniently effected at a temperature in the range, for example 10 to 150° C., preferably in the range 40 to 100° C.

The compounds of formula XIV and salts thereof which constitute a furter feature of the present invention may for example be prepared by reacting a compound of the formula XV:

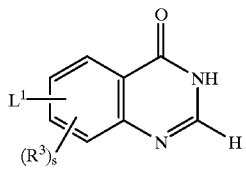

(XV)

(wherein $R^3$, s and $L^1$ are as hereinbefore defined) with a compound of the formula XI as hereinbefore defined. The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

The compounds of formula XIV and salts thereof may also be prepared by cyclising a compound of the formula XVI:

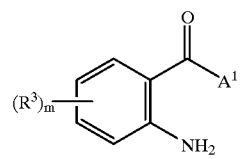

(XVI)

(wherein $R^3$ and m, are as hereinbefore defined, and $A^1$ is an hydroxy, alkoxy (preferably $C_{1-4}$alkoxy) or amino group) whereby to form a compound of formula XIV or salt thereof. The cyclisation may be effected by reacting a compound of the formula XVI, where $A^1$ is an hydroxy or alkoxy group, with formamide or an equivalent thereof effective to cause cyclisation whereby a compound of formula XIV or salt thereof is obtained, such as [3-(dimethylamino)-2-azaprop-2-enylidene]dimethylanmnonium chloride. The cyclisation is conveniently effected in the presence of formamide as solvent or in the presence of an inert solvent or diluent such as an ether for example 1,4-dioxan. The cyclisation is conveniently effected at an elevated temperature, preferably in the range 80 to 200° C. The compounds of formula XIV may also be prepared by cyclising a compound of the formula XVI, where $A^1$ is an amino group, with formic acid or an equivalent thereof effective to cause cyclisation whereby a compound of formula XXV or salt thereof is obtained. Equivalents of formic acid effective to cause cyclisation include for example a tri-$C_{1-4}$alkoxymethane, for example triethoxymethane and trimethoxymethane. The cyclisation is conveniently effected in the presence of a catalytic amount of an anhydrous acid, such as a sulphonic acid for example p-toluenesulphonic acid, and in the presence of an inert solvent or diluent such as for example a halogenated solvent such as methylene chloride, trichloromethane or carbon tetrachloride, an ether such as diethylether or tetrahydrofuran, or an aromatic hydrocarbon solvent such as toluene. The cyclisation is conveniently effected at a temperature in the range, for example 10 to 100° C., preferably in the range 20 to 50° C.

Compounds of formula XVI and salts thereof, which constitute a further feature of the present invention, may for example be prepared by the reduction of the nitro group in a compound of the formula XVII:

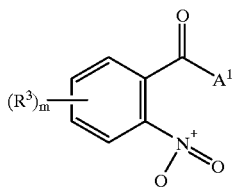

(XVII)

(wherein $R^3$, m and $A^1$ are as hereinbefore defined) to yield a compound of formula XVI as hereinbefore defined. The reduction of the nitro group may conveniently be effected by any of the procedures known for such a transformation. The reduction may be carried out, for example, by the hydrogenation of a solution of the nitro compound in the presence of an inert solvent or diluent as defined hereinbefore in the presence of a metal effective to catalyse hydrogenation reactions such as palladium or platinum. A further reducing agent is, for example, an activated metal such as activated iron (produced for example by washing iron powder with a dilute solution of an acid such as hydrochloric acid). Thus, for example, the reduction may be effected by heating the nitro compound and the activated metal in the presence of a solvent or diluent such as a mixture of water and alcohol, for example methanol or ethanol, to a temperature in the range, for example 50 to 150° C., conveniently at about 70° C.

Compounds of the formula XVII and salts thereof which constitute a further feature of the present invention, may for example be prepared by the reaction of a compound of the formula XVIII:

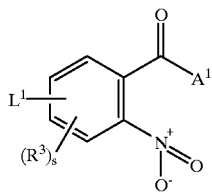

(XVIII)

(wherein $R^3$, s, $L^1$ and $A^1$ are as hereinbefore defined) with a compound of the formula XI as hereinbefore defined to give a compound of the formula XVII. The reaction of the compounds of formulae XVIII and XI is conveniently effected under conditions as described for process (f) hereinbefore.

Compounds of formula XVII and salts thereof wherein at least one $R^3$ is $R^{10}X^2$ and wherein $X^2$ is —O—, —S—, —$SO_2$—, —$CONR^{12}$—, —$SO_2NR^{13}$— or —$NR^{15}$— (wherein $R^{12}$, $R^{13}$ and $R^{15}$ each independently represents hydrogen, $C_{1-3}$alkyl or $C_{1-3}$alkoxy$C_{2-3}$alkyl), may for example also be prepared by the reaction of a compound of the formula XIX:

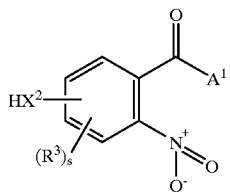

(XIX)

(wherein $R^3$, s, $A^1$ and $X^2$ are as hereinbefore defined) with a compound of the formula IX as hereinbefore defined to yield a compound of formula XVII as hereinbefore defined. The reaction of the compounds of formulae XIX and IX is conveniently effected under conditions as described for process (e) hereinbefore.

The compounds of formula III and salts thereof wherein at least one $R^3$ is $R^{10}X^2$ and wherein $X^2$ is —O—, —S—, —$SO_2$—, —$CONR^{12}$—, —$SO_2NR^{13}$— or —$NR^{15}$— (wherein $R^{12}$, $R^{13}$ and $R^{15}$ each independently represents hydrogen, $C_{1-3}$alkyl or $C_{1-3}$alkoxy$C_{2-3}$alkyl), may also be prepared for example by reacting a compound of the formula XX:

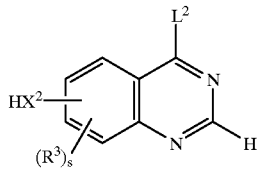

(XX)

(wherein $R^3$, $X^2$ and s are as hereinbefore defined, and $L^2$ represents a displaceable protecting moiety) with a compound of the formula IX as hereinbefore defined, whereby to obtain a compound of formula III in which $L^1$ is represented by $L^2$.

A compound of formula XX is conveniently used in which $L^2$ represents a phenoxy group which may if desired carry up to 5 substituents, preferably up to 2 substituents, selected from halogeno, nitro and cyano. The reaction may be conveniently effected under conditions as described for process (e) hereinbefore.

The compounds of formula XX and salts thereof which constitute a further feature of the present invention may for example be prepared by deprotecting a compound of the formula XXI:

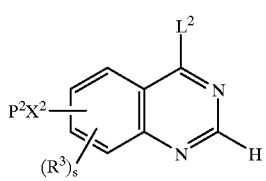

(XXI)

(wherein $R^3$, $P^2$, s and $L^2$ are as hereinbefore defined). Deprotection may be effected by techniques well known in the literature, for example where $P^2$ represents a benzyl group deprotection may be effected by hydrogenolysis or by treatment with trifluoroacetic acid.

One compound of formula III may if desired be converted into another compound of formula III in which the moiety $L^1$ is different. Thus for example a compound of formula III in which $L^1$ is other than halogeno, for example optionally substituted phenoxy, may be converted to a compound of formula III in which $L^1$ is halogeno by hydrolysis of a compound of formula III (in which $L^1$ is other than halogeno) to yield a compound of formula XIV as hereinbefore defined, followed by introduction of halide to the compound of formula XIV, thus obtained as hereinbefore defined, to yield a compound of formula III in which $L^1$ represents halogen.

(ii) Compounds of formula IV and salts thereof may be prepared by any of the known procedures, references include: "The Chemistry of Indoles" R. J. Sundberg page 341, 1970 Academic, New York, Gassman and Bergen, 1974, Jnl. Am. Chem. Soc., 96, 5508 and 5512, Quallich and Morrissey, 1993, Synthesis, 51, Cherest et al., 1989, Tetrahedron Letters, 30, 715, Marfat et al., 1987, Tetrahedron Letters, 28, 4027–4030.

(iii) The compounds of formula V and salts thereof, constitute a further feature of the present invention, and may for example be prepared by the reaction of a compound of formula III as hereinbefore defined with a compound of the formula XXII:

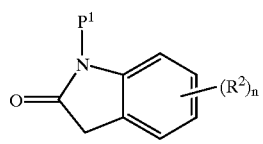

(XXII)

(wherein $R^2$, n and $P^1$ are as hereinbefore defined). The reaction may for example be effected as described for process (a) hereinbefore.

The compounds of formula V and salts thereof may also be prepared by reacting a compound of formula XXII:

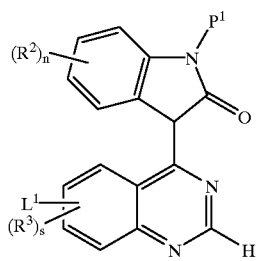

(XXIII)

(wherein $R^2$, $R^3$, $L^1$, n, s and $P^1$ are as hereinbefore defined) with a compound of formula XI as hereinbefore defined. The reaction may for example be effected as described for process (f) above.

The compounds of formula V and salts thereof wherein at least one $R^3$ is $R^{10}X^2$ and wherein $X^2$ is —O—, —S—, —SO$_2$—, —CONR$^{12}$—, —SO$_2$NR$^{15}$— or —NR$^{15}$— (wherein $R^{12}$, $R^{13}$ and $R^{15}$ each independently represents hydrogen, $C_{1-3}$alkyl or $C_{1-3}$alkoxy$C_{2-3}$alkyl), may also be prepared by reacting a compound of formula XXIV:

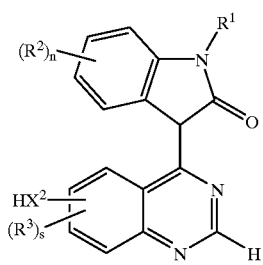

(XXIV)

(wherein $R^2$, $R^3$, $X^2$, n, s and $P^1$ are as hereinbefore defined) with a compound of the formula IX as hereinbefore defined. The reaction may for example be effected as described for process (e) hereinbefore.

The compounds of formula XXIII and salts thereof constitute a further feature of the present invention and may for example be prepared by reaction of a compound of formula XXV:

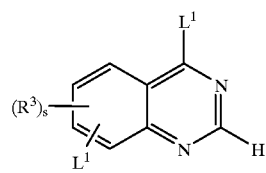

(XXV)

(wherein $R^3$, s and each $L^1$ are as hereinbefore defined, and the $L^1$ in the 4-position and the other $L^1$ in a further position on the quinazoline ring may be the same or different) with a compound of the formula XXII as hereinbefore defined. The reaction may be effected for example by a process as described in (a) above.

Compounds of the formula XXIV and salts thereof which constitute a farther feature of the present invention may be made by reacting compounds of the formulae XXI and XXII as hereinbefore defined, under conditions described in (a) hereinbefore, to give a compound of formula XXVI:

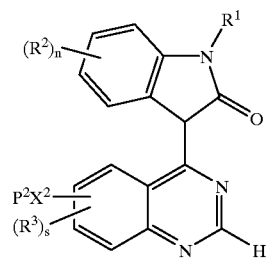

(XXVI)

(wherein $R^2$, $R^3$, $P^1$, $P^2$, $X^2$, s and n are as hereinbefore defined with the proviso that $X^2$ is not —CH$_2$—) and then deprotecting the compound of formula XXVI for example as described in (i) above.

(iv) Compounds of the formula VI and salts thereof constitue a further feature of the present invention and may be made by the reaction of a compound of formula III as hereinbefore defined with a compound of the formula XXVII:

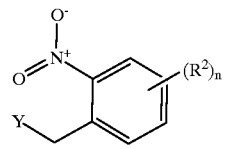

(XXVII)

(wherein $R^2$, n, and Y are as hereinbefore defined). The reaction may for example be effected as described for the process (a) hereinbefore.

(v) The compounds of formula VII and salts thereof, constitute a firther feature of the present invention, and may for example be prepared by the reaction of a compound of formula III as hereinbefore defined with a compound of the formula XXVIII:

(XXVIII)

(wherein $R^1$, $R^2$, n, p1 and $P^2$ are as hereinbefore defined). The reaction may for example be effected as described for process (a) hereinbefore.

The compounds of formula VII and salts thereof may also be prepared by reacting a compound of formula XXIX:

(XXIX)

(wherein $R^1$, $R^2$, $R^3$, $L^1$, n, p1, s and $P^2$ are as hereinbefore defined) with a compound of formula XI as hereinbefore defined. The reaction may for example be effected as described for process (f) above.

The compounds of formula VII and salts thereof wherein at least one $R^3$ is $R^{10}X^2$ and wherein $X^2$ is —O—, —S—, —SO$_2$—, —CONR$^{12}$—, —SO$_2$NR$^{13}$— or —NR$^{15}$— (wherein $R^{12}$, $R^{13}$ and $R^{15}$ each independently represents hydrogen, $C_{1-3}$alkyl or $C_{1-3}$alkoxy$C_{2-3}$alkyl), may also be prepared by reacting a compound of formula XXX:

(XXX)

(wherein $R^1$, $R^2$, $R^3$, $X^2$, n, s, p1 and $P^2$ are as hereinbefore defined) with a compound of the formula IX as hereinbefore defined. The reaction may for example be effected as described for process (e) hereinbefore.

The compounds of formula XXIX and salts thereof may for example be prepared by the reaction of a compound of formula XXV as hereinbefore defined with a compound of the formula XXVIII as hereinbefore defined. The reaction may be effected for example by a process as described in (a) above.

Compounds of the formula XXX and salts thereof may be made by reacting compounds of the formulae XXI and XXVIII as hereinbefore defined, under conditions described in (a) hereinbefore, to give a compound of formula XXXI:

(XXXI)

(wherein $R^1$, $R^2$, $R^3$, $P^2$, $X^2$, p1, n and s are as hereinbefore defined with the proviso that $X^2$ is not —CH$_2$—) and then deprotecting the compound of formula XXXI for example as described in (i) above.

(vi) Compounds of formula VIII as hereinbefore defined and salts thereof constitute a further feature of the present invention and may be made by deprotecting the compound of formula XXXII:

(XXXII)

(wherein $R^1$, $R^2$, $R^3$, $P^2$, $X^2$, s and n are as hereinbefore defined with the proviso that $X^2$ is not —CH$_2$—) by a process for example as described in (i) above.

Compounds of the formula XXXII and salts thereof which constitute a further feature of the present invention may be made by reacting compounds of the formulae XXI and IV as hereinbefore defined, under the conditions described in (a) hereinbefore, to give a compound of the formula XXXII or salt thereof.

(vii) Compounds of the formula X and salts thereof constitute a further feature of the present invention and may be made by reacting compounds of the formulae XXV and IV as hereinbefore defined, the reaction for example being effected by a process as described in (a) above.

(viii) Compounds of formula XII as defined hereinbefore and salts thereof constitute a further feature of the present invention and may for example be made by the reaction of compounds of formula VIII as defined hereinbefore with compounds of the formula XXXIII:

$L^1$—$C_{1-5}$alkyl-$L^1$ (XXXIII)

(wherein $L^1$ is as hereinbefore defined) to give compounds of formula XII or salts thereof. The reaction may be effected for example by a process as described in (e) above.

When a pharmaceutically acceptable salt of a compound of the formula I is required, it may be obtained, for example, by reaction of said compound with, for example, an acid using a conventional procedure, the acid having a pharmaceutically acceptable anion.

Many of the intermediates defined herein are novel, for example, those of the formulae III, V, VI, VII, VIII, X, XII, XIV, XV, XVI, XVII, XVIII, XIX, XX, XXI, XXIII, XXIV, XXV, XXVI, XXIX, XXX, XXXI and XXXII and these are provided as a further feature of the invention.

The identification of compounds which potently inhibit the tyrosine kinase activity associated with the VEGF receptors such as Flt and/or KDR and which inhibit angiogenesis and/or increased vascular permeability is desirable and is the subject of the present invention. These properties may be assessed, for example, using one or more of the procedures set out below:

(a) In Vitro Receptor Tyrosine Kinase Inhibition Test

This assay determines the ability of a test compound to inhibit tyrosine kinase activity. DNA encoding VEGF, FGF or EGF receptor cytoplasmic domains may be obtained ; by total gene synthesis (Edwards M, International Biotechnology Lab 5(3), 19–25, 1987) or by cloning. These may then be expressed in a suitable expression system to obtain polypeptide with tyrosine kinase activity. For example VEGF, FGF and EGF receptor cytoplasmic domains, which were obtained by expression of recombinant protein in insect cells, were found to display intrinsic tyrosine kinase activity. In the case of the VEGF receptor Flt (Genbank accession number X51602), a 1.7kb DNA fragment encoding most of the cytoplasmic domain, commencing with methionine 783 and including the termination codon, described by Shibuya et al (Oncogene, 1990, 5: 519–524), was isolated from cDNA and cloned into a baculovirus transplacement vector (for example pAcYMI (see The Baculovirus Expression System: A Laboratory Guide, L. A. King and R. D. Possee, Chapman and Hall, 1992) or pAc360 or pBlueBacHis (available from Invitrogen Corporation)). This recombinant construct was co-transfected into insect cells (for example Spodoptera frugiperda 21(Sf21)) with viral DNA (eg Pharmingen BaculoGold) to prepare recombinant baculovirus. (Details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W. H. Freeman and Co, New York). For other tyrosine kinases for use in assays, cytoplasmic fragments starting from methionine 806 (KDR, Genbank accession number L04947), methionine 668 (EGF receptor, Genbank accession number X00588) and methionine 399 (FGF R1 receptor, Genbank accession number X51803) may be cloned and expressed in a similar manner.

For expression of cFlt tyrosine kinase activity, Sf21 cells were infected with plaque-pure cFlt recombinant virus at a multiplicity of infection of 3 and harvested 48 hours later. Harvested cells were washed with ice cold phosphate buffered saline solution (PBS) (10 mM sodium phosphate pH7.4, 138 mM sodium chloride, 2.7 mM potassium chloride) then resuspended in ice cold HNTG/PMSF (20 mM Hepes pH7.5, 150 mM sodium chloride, 10% v/v glycerol, 1% v/v Triton X100, 1.5 mM magnesium chloride, 1 mM ethylene glycol-bis($\beta$aminoethyl ether) N,N,N',N'-tetraacetic acid (EGTA), 1 mM PMSF (phenylmethylsulphonyl fluoride); the PMSF is added just before use from a freshly-prepared 100 mM solution in methanol) using 1 ml HNTG/PMSF per 10 million cells. The suspension was centrifuged for 10 minutes at 13,000 rpm at 4° C., the supernatant (enzyme stock) was removed and stored in aliquots at −70° C. Each new batch of stock enzyme was titrated in the assay by dilution with enzyme diluent (100 mM Hepes pH 7.4, 0.2 mM sodium orthovanadate, 0.1% v/v Triton X100, 0.2 mM dithiothreitol). For a typical batch, stock enzyme is diluted 1 in 2000 with enzyme diluent and 50 $\mu$l of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 $\mu$l of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH7.4.

Test compounds were diluted with 10% dimethylsulphoxide (DMSO) and 25 $\mu$l of diluted compound was transferred to wells in the washed assay plates. "Total" control wells contained 10% DMSO instead of compound. Twenty-five microlitres of 40 mM manganese(II)chloride containing 8 $\mu$M adenosine-5'-triphosphate (ATP) was added to all test wells except "blank" control wells which contained manganese(II)chloride without ATP. To start the reactions 50$\mu$l of freshly diluted enzyme was added to each well and the plates were incubated at room temperature for 20 minutes. The liquid was then discarded and the wells were washed twice with PBST. One hundred microlitres of mouse IgG anti-phosphotyrosine antibody (Upstate Biotechnology Inc. product 05-321), diluted 1 in 6000 with PBST containing 0.5% w/v bovine serum albumin (BSA), was added to each well and the plates were incubated for 1 hour at room temperature before discarding the liquid and washing the wells twice with PBST. One hundred microlitres of horse radish peroxidase (HRP)-linked sheep anti-mouse Ig antibody (Amersham product NXA 931), diluted 1 in 500 with PBST containing 0.5% w/v BSA, was added and the plates were incubated for 1 hour at room temperature before discarding the liquid and washing the wells twice with PBST. One hundred microlitres of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20–60 minutes at room temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibtion of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL)+ 7.5% v/v foetal calf serum (FCS) and were plated out (at passage 2 to 8), in MCDB 131+2% v/v FCS+3$\mu$g/ml heparin+1$\mu$g/ml hydrocortisone, at a concentration of 1000 cells/well in 96 well plates. After a minimum of 4 hours they were dosed with the appropriate growth factor (i.e. VEGF 3ng/ml, EGF 3ng/ml or b-FGF 0.3 ng/ml) and compound. The cultures were then incubated for 4 days at 37° C. with 7.5% $CO_2$. On day 4 the cultures were pulsed with 1 $\mu$Ci/well of tritiated-thymidine (Amersharn product TRA 61) and incubated for 4 hours. The cells were harvested using a 96-well plate harvester (Tomtek) and then assayed for incorporation of tritium with a Beta plate counter. Incorporation of radioactivity into cells, expressed as cpm, was used to measure inhibition of growth factor-stimulated cell proliferation by compounds.

(c) In Vivo Rat Uterine Oedema Assay

This test measures the capacity of compounds to reduce the acute increase in uterine weight in rats which occurs in the first 4–6 hours following oestrogen stimulation. This early increase in uterine weight has long been known to be due to oedema caused by increased permeability of the uterine vasculature and recently Cullinan-Bove and Koos (Endocrinology, 1993,133:829–837) demonstrated a close temporal relationship with increased expression of VEGF mRNA in the uterus. We have found that prior treatment of the rats with a neutralising monoclonal antibody to VEGF significantly reduces the acute increase in uterine weight, confirming that the increase in weight is substantially mediated by VEGF.

Groups of 20 to 22-day old rats were treated with a single subcutaneous dose of oestradiol benzoate (2.5 μg/rat) in a solvent, or solvent only. The latter served as unstimulated controls. Test compounds were orally administered at various times prior to the administration of oestradiol benzoate. Five hours after the administration of oestradiol benzoate the rats were humanely sacrificed and their uteri were dissected, blotted and weighed. The increase in uterine weight in groups treated with test compound and oestradiol benzoate and with oestradiol benzoate alone was compared using a Student T test. Inhibition of the effect of oestradiol benzoate was considered significant when $p<0.05$.

According to a further aspect of the invention there is provided a pharmaceutical composition which comprises a compound of the formula I as defined hereinbefore or a pharmaceutically acceptable salt thereof, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square metre body area of the animal, i.e. approximately 0.1–100 mg/kg. A unit dose in the range, for example, 1–100 mg/kg, preferably 1–50 mg/kg is envisaged and this normally provides a thempeutically-effective dose. A unit dose form such as a tablet or capsule will usually contain, for example 1–250 mg of active ingredient.

According to a further aspect of the present invention there is provided a compound of the formula I or a pharmaceutically acceptable salt thereof as defined hereinbefore for use in a method of treatment of the human or animal body by therapy.

We have found that compounds of the present invention inhibit VEGF receptor tyrosine kinase activity and FGF R1 receptor tyrosine kinase activity and are therefore of interest for their antiangiogenic effects and/or their ability to cause a reduction in vascular permeability.

A further feature of the present invention is a compound of formula I, or a pharmaceutically acceptable salt thereof, for use as a medicament, conveniently a compound of formula I, or a pharmaceutically acceptable salt thereof, for use as a medicament for producing an antiangiogenic and/or vascular permeability reducing effect in a warm-blooded animal such as a human being.

Thus according to a further aspect of the invention there is provided the use of a compound of the formula I, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of a compound of formula I or a pharmaceutically acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The antiangiogenic and/or vascular permeability reducing treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be: surgery, radiotherapy or chemotherapy. Such chemotherapy may cover three main categories of therapeutic agent:

(i) other antiangiogenic agents that work by different mechanisms from those defined hereinbefore (for example linomide, inhibitors of integrin αvβ3 function, angiostatin, razoxin, thalidomide);

(ii) cytostatic agents such as antioestrogens (for example tamoxifen,toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor finction) and inhibitors of growth factor finction, (such growth factors include for example EGF, platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as-antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan).

As stated above the compounds defined in the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, acute and chronic nephropathies, atheroma, arterial restenosis, autoimmune diseases, acute inflammation and ocular diseases with retinal vessel proliferation. In particular such compounds of the invention are expected to slow advantageously the growth of primary and recurrent solid tumours of, for example, the colon, breast, prostate, lungs and skin. More particularly such compounds of the invention are expected to inhibit the growth of those primary and recurrent solid tumours which are associated with VEGF and/or FGF, especially those tumours which are significantly dependent on VEGF and/or FGF for their growth and spread, including for example, certain tumours of the colon, breast, prostate, lung, vulva and skin.

In addition to their use in therapeutic medicine, the compounds of formula I and their pharmaceutically acceptable salts are also useful as pharmacological tools in the development and standardisation of in vitro and in vivo test systems for the evaluation of the effects of inhibitors of VEGF receptor tyrosine kinase activity and FGF R1 receptor tyrosine kinase activity in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated in the following non-limiting Examples in which, unless otherwise stated:

[(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points are uncorrected and were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(vii) intermediates were not generally fully characterised and purity was assessed by thin layer chromatography (TLC), high-performance liquid chromatography (HPLC), infra-red (IR) or NMR analysis;

(viii) petroleum ether refers to that fraction boiling between 40–60° C (ix) the following abbreviations have been used:
DMF N,N-dimethylformamide
DMSO dimethylsulphoxide
TFA trifluoroacetic acid
THF tetrahydrofaran.]

EXAMPLE 1

Potassium bis(trimethylsilyl)amide (5 ml of a 0.5M solution in toluene, 2.5 mmol) was rapidly added at ambient temperature to a solution of 4-chloro-6,7-dimethoxyquinazoline (337 mg, 1.5 mmol) and 1-methyloxindole (368 mg, 2.5 mmol), (prepared according to the method described in J. Am. Chem. Soc 1945, 67, 1656), in THF (30ml). After 30 minutes, the precipitate was collected by filtration and washed with ether. A second precipitate was isolated from the filtrate. The two solids were mixed and purified by column flash chromatography using methylene chloride/methanol (96/4 and 94/6) as eluent. During the evaporation of the solvents, the compound crystallised. The solid was filtered off, washed with ether and dried under vacuum to give 6,7-dimethoxy-4-(1-methyloxindol-3-yl)quinazoline (103 mg, 20%) as red orange needles.

m.p. 233–235° C.

$^1$H NMR Spectrum: (DMSOd$_6$, TFA) 3.37(s, 3H); 3.85(s, 3H); 4.00(s, 3H); 7.11(t, 1H); 7.16(d, 1H); 7.26(t, 1H); 7.27(s, 1H); 7.72(d, 1H); 7.75(s, 1H); 8.90(s, 1H).

MS-ESI: 336 [MH]$^+$

| Elemental analysis: | Found | C 66.6 | H 5.3 | N 12.3 |
| $C_{19}H_{17}N_3O_3$ 0.4H$_2$O | Requires | C 66.6 | H 5.2 | N 12.3% |

The starting material was prepared as follows:

A mixture of 4,5-dimethoxyanthranilic acid (19.7 g) and formamide (10 ml) was stirred and heated at 190° C. for 5 hours. The mixture was allowed to cool to approximately 80° C. and water (50 ml) was added. The mixture was then allowed to stand at ambient temperature for 3 hours. The precipitate was collected by filtration, washed with water and dried to give 6,7-dimethoxy-3,4-dihydroquinazolin4-one (3.65 g).

To a portion (2.06 g) of the material so obtained were added thionyl chloride (20 ml) and DMF (1 drop) and the mixture stirred and heated at reflux for 2 hours. Excess thionyl chloride was removed by evaporation and the residue was partitioned between ethyl acetate and a saturated aqueous sodium hydrogen carbonate solution. The organic phase was washed with water, dried (MgSO$_4$) and the solvent removed by evaporation. The residue was purified by column chromatography using increasingly polar mixtures of methylene chloride and ethyl acetate as eluent to give 4-chloro-6,7-dimethoxyquinazoline (0.6 g, 27%).

EXAMPLE 2

Potassium bis(trimethylsilyl)amide (48 ml of a 0.5M solution in toluene, 24 mmol) was rapidly added to a solution of 4-chloro-6-methoxy-7-(2-methoxyethoxy) quinazoline (3.2 g, 11.9 mmol) and 1-diethoxymethyloxindole (4.0 g, 14.9 mmol), (prepared according to Synthesis 1975, 168), in THF (240 ml) at ambient temperature. After 2 hours, the precipitate was filtered off and washed with ether. The filtrate was evaporated. The residue was mixed with the precipitate and partitioned between methylene chloride and water and the organic phase washed with saturated aqueous sodium chloride solution. The organic layer was driied ($MgSO_4$) and the solvent removed by evaporation. The residue was purified by column flash chromatography using methylene chloride/methanol (95/5) as eluent. The purified product was triturated with a mixture of ether and petroleum ether to give 4-(1-diethoxymethyloxindol-3-yl)-6-methoxy-7-(2-methoxyethoxy)quinazoline (4.03 g, 74%) as a red orange solid.

m.p. 148–150° C.

$^1$H NMR Spectrum: ($DMSOd_6$, TFA) 1.07(t, 6H); 3.37(s, 3H); 3.45(q, 4H); 3.77–3.79(m, 2H); 3.85(s, 3H); 4.34–4.37 (m, 2H); 7.13–7.23(m, 2H); 7.28(s, 1H); 7.87(br d, 1H); 8.07(d, 1H); 8.64(s, 1H); 9.44(s, 1H).

MS-ESI: 490 [MNa]$^+$

| Elemental analysis: | Found | C 63.3 | H 6.6 | N 8.9 |
|---|---|---|---|---|
| $C_{25}H_{29}N_3O_6$ 0.4$H_2O$ | Requires | C 63.3 | H 6.3 | N 8.9% |

The starting material was prepared as follows:

A mixture of ethyl 4-hydroxy-3-methoxybenzoate (9.8 g, 50 mmol), 2-bromoethyl methyl ether (8.46 ml, 90 mmol) and potassium carbonate (12.42 g, 90 mmol) in acetone (60 ml) was heated at reflux for 30 hours. The mixture was allowed to cool and the solids removed by filtration. The volatiles were removed from the filtrate by evaporation and the residue triturated with hexane to give ethyl 3-methoxy-4-(2-methoxyethoxy)benzoate ( 1.3 g, 89%) as a white solid.

m.p. 57–60° C.

$^1$H NMR Spectrum: (DMSOd6) 1.31(t, 3H); 3.29(s, 3H); 3.32(s, 3H); 3.68(m, 2H); 4.16(m, 2H); 4.28(q, 2H); 7.06(d, 1H); 7.45(d, 1H); 7.56(dd, 1H).

MS-FAB: 255 [MH]$^+$

Ethyl 3-methoxy-4-(2-methoxyethoxy)benzoate (9.5 g, 37 mmol) was added in portions to stirred concentrated nitric acid (75 ml) at 0° C. The mixture was allowed to warm to ambient temperature and stirred for a fuirther 90 minutes. The mixture was diluted with water and extracted with methylene chloride, dried ($MgSO_4$) and the solvent removed by evaporation. The residue was triturated with hexane to give ethyl 5-methoxy4-(2-methoxyethoxy)-2-nitrobenzoate (10.6 g, 95%) as an orange solid.

m.p. 68–69° C.

$^1$H NMR Spectrum: ($DMSOd_6$) 1.27(t, 3H); 3.30(s, 3H); 3.69(m, 2H); 3.92(s, 3H); 4.25(m, 2H); 4.29(q, 2H); 7.30(s, 1H); 7.65(s, 1H)

MS-CI: 300 [MH]$^+$

A mixture of ethyl 5-methoxy-4-(2-methoxyethoxy)-2-nitrobenzoate (10.24 g, 34 mmol), cyclohexene (30 ml) and 10% palladium-on-charcoal catalyst (2.0 g) in methanol (150 ml) was heated at reflux for 5 hours. The reaction mixture was allowed to cool and diluted with methylene chloride. The catalyst was removed by filtration and the volatiles removed from the filtrate by evaporation. The residue was recrystallised from ethyl acetate/hexane to give ethyl 2-amino-5-methoxy-4-(2-methoxyethoxy) benzoate (8.0 g) as a buff solid. Formamide (80 ml) was added to this product and the mixture heated at 170° C. for 18 hours. About half the solvent was removed by evaporation under high vacuum and the residue was left to stand overnight. The solid product was collected by filtration, washed with ether and dried to give 6-methoxy-7-(2-methoxyethoxy)-3,4-dihydroquinazolin-4-one (5.3 g, 62% over two steps) as a grey solid.

$^1$H NMR Spectrum: ($DMSOd_6$) 3.35(s, 3H); 3.74(m, 2H); 3.89(s, 3H); 4.26(m, 2H); 7.15(s, 1H); 7.47(s, 1H); 7.98(s, 1H); 12.03(br s, 1H).

MS-CI: 251 [MH]$^+$

DMF (0.5 ml) was added to a mixture of 6-methoxy-7-(2-methoxyethoxy)3,4-dihydroquinazolin-4-one (5.1 g, 20 mmol) in thionyl chloride (50 ml). The mixture was stirred and heated at reflux for 3 hours, allowed to cool and the excess thionyl chloride removed by evaporation. The residue was suspended in methylene chloride and washed with aqueous sodium hydrogen carbonate solution. The aqueous phase was extracted with methylene chloride and the combined extracts dried ($MgSO_4$). The crude product was recrystallised from methylene chloride/hexane to give 4-chloro-6-methoxy-7-(2-methoxyethoxy)quinazoline (2.8 g, 51%) as a fine white solid.

$^1$H NMR Spectrum: ($DMSOd_6$) 3.37(s, 3H); 3.77(m, 2H); 4.01(s, 3H); 4.37(m, 2H); 7.40(s, 1H); 7.49(s, 1H); 8.88(s, 1H).

MS-CI: 269 [MH]$^+$

EXAMPLE 3

2M Hydrochloric acid (40 ml, 80 mmol) was added to a solution of 4-(1-diethoxymethyloxindol-3-yl)-6-methoxy-7-(2-methoxyethoxy)quinazoline (3.7 g, 79 mmol), (prepared as described in Example 2), in ethanol (300 ml) at 80° C. A precipitate rapidly appeared which then went into solution followed after 15 minutes by the formation of a new precipitate. The mixture was stirred for 45 minutes at 80° C., the solid was collected by filtration, washed with ethanol and then ether and dried under vacuum at 65° C. to give 6-methoxy-7-2-methoxyethoxy)-4-(oxindol-3-yl)quinazoline (2.42 g, 84%) as a red orange solid.

m.p. 262–268° C.

$^1$H NMR Spectrum: ($DMSOd_6$, TFA) 3.38(s, 3H); 3.78(t, 2H); 3.87(s, 3H); 4.33(t, 2H); 7.02–7.07(m, 2H); 7.18(t, 1H); 7.31(s, 1H); 7.70(d, 1H); 7.75(s, 1H); 8.94(s, 1H).

MS-ESI: 366 [MH]$^+$

| Elemental analysis: | Found | C 59.4 | H 5.3 | N 10.6 | Cl 4.8 |
|---|---|---|---|---|---|
| $C_{20}H_{19}N_3O_4$ 0.9$H_2O$ 0.55HCl | Requires | C 59.8 | H 5.4 | N 10.5 | Cl 4.9% |

EXAMPLE 4

2M Hydrochloric acid (0.54 ml, 1.08 mmol) was added to a solution of 4-(1-diethoxymethyloxindol-3-yl)-6-methoxy-7-(2-methoxyethoxy)quinazoline (250 mg, 0.53 mmol), (prepared as described in Example 2), in ethanol (10 ml) at ambient temperature. A precipitate rapidly appeared. The mixture was stirred for 30 minutes, the solid was collected by filtration washed with ethanol and then ether and dried under vacuum at 60° C. to give 4-(1-formyloxindol-3-yl)-6-methoxy-7-(2-methoxyethoxy)quinazoline (141 mg, 68%) as an orange solid.

m.p. 228–230° C.

$^1$H NMR Spectrun: (DMSOd$_6$, TFA) 3.36(s, 3H); 3.77(t, 2H); 3.84(s, 3H); 4.34(t, 2H); 7.13(t, 2H); 7.20(t, 1H); 7.27(s, 1H); 7.88(d, 1H); 7.96(s, 1H); 8.06(d, 1H); 8.60(s, 1H); 9.43(s, 1H).

MS-ESI: 316 [MNa]$^+$

| Elemental analysis: | Found | C 62.6 | H 5.1 | N 10.4 |
|---|---|---|---|---|
| C$_{21}$H$_{19}$N$_3$O$_5$ 0.4H$_2$O | Requires | C 63.0 | H 5.0 | N 10.5% |

EXAMPLE 5

4-Chloro-6-methoxy-7-(3-morpholinopropoxy)quinazoline (338 mg, 1 mmol) was dissolved in THF (20 ml) at 40° C., and 1-diethoxymethyloxindole (705 mg, 3 mmol), (prepared according to Synthesis 1975, 168), and sodium hydride (138 mg, 5.8 mmol, pre-washed with petroleum ether) were added successively to the solution at ambient temperature. After stirring for 45 minutes, the volatiles were removed by evaporation and the residue dissolved in methylene chloride. The solution was washed with an aqueous saturated sodium chloride solution, dried (MgSO$_4$) and the solvent removed by evaporation. The residue was purified by column flash chromatography using methylene chloride/ethyl acetate (1/1) followed by an increasingly polar mixture of methylene chloride and methanol (2 to 4%) as eluent. The purified product was triturated with ether. collected by filtration, washed with a 1/1 mixture of ether/petroleum ether and dried under vacuum to give 4-(1-diethoxymethyloxindol-3-yl)-6-methoxy-7-(3-morpholinopropoxy)quinazoline (425 mg, 84%) as a yellow-orange solid.

m.p. 174–176° C.

$^1$H NMR Spectrum: (CDCl$_3$, CD$_3$CO$_2$D) 1.26(t, 6H); 2.33–2.41(m, 2H); 3.24–3.28(m, 6H); 3.55–3.61(m, 2H); 3.75–3.82(m, 2H); 3.88(s, 3H); 3.95–3.97(m, 4H); 4.26–4.29(m, 2H); 6.48(s, 1H); 7.07(t, 1H); 7.14(t, 1H); 7.31(s, 1H); 7.63(d, 1H); 7.81(s, 1H); 8.27(s, 1H).

MS-ESI: 537 [MH]$^+$

| Elemental analysis: | Found | C 65.4 | H 7.1 | N 10.5 |
|---|---|---|---|---|
| C$_{29}$H$_{36}$N$_4$O$_6$ | Requires | C 64.9 | H 6.8 | N 10.4% |

The starting material was prepared as follows:

A mixture of 4-hydroxy-3-methoxybenzoic acid (4.5 g, 26.8 mmol), 3-morpholinopropyl chloride (9.5 g, 58.0 mmol), (prepared according to J. Am. Chem. Soc. 1945, 67, 736), potassium carbonate (8.0 g, 58 mmol), potassium iodide (1.0 g, 0.22 mmol) and DMF (80 ml) was stirred and heated at 100° C. for 3 hours. The solid was removed by filtration and the filtrate evaporated. The residue was dissolved in ethanol (50 ml), 2M sodium hydroxide (50 ml) was added and the mixture heated at 90° C. for 2 hours. After partial evaporation, the mixture was acidified with concentrated hydrochloric acid, washed with ether and then subjected to purification on a Diaion (trade mark of Mitsubishi) HP20SS resin column, eluting with water and then with a gradient of methanol (0 to 25%) in hydrochloric acid (pH2). Partial evaporation of the solvents and lyophilisation gave 3-methoxy-4-(3-morpholinopropoxy)benzoic acid (8.65 g, 97%).

$^1$H NMR Spectrum: (DMSOd$_6$, TFA) 2.17–2.24(m, 2H); 3.10–3.16(m, 2H); 3.30(t, 2H); 3.52(d, 2H); 3.71(t, 2H); 3.82(s, 3H); 4.01(brd, 2H); 4.14(t, 2H); 7.08(d, 1H); 7.48(d, 1H); 7.59(dd, 1H).

MS-ESI: 296 [MH]$^+$

Fuming nitric acid (1.5 ml, 36.2 mmol) was added slowly at 0° C. to a solution of 3-methoxy-4-(3-morpholinopropoxy)benzoic acid (7.78 g, 23.5 mmol) in TFA (25 ml). The cooling bath was removed and the reaction mixture stirred at ambient temperature for 1 hour. The TFA was removed by evaporation and ice was added to the residue. The precipitate was collected by filtration, washed with a minimum of water followed by toluene and ether. The solid was dried under vacuum over phosphorus pentoxide to give 5-methoxy-4-(3-morpholinopropoxy)-2-nitrobenzoic acid (7.54 g) which was used without flirther purification.

$^1$H NMR Spectrum: (DMSOd$_6$, TFA) 2.16–2.23(m, 2H); 3.10–3.17(m, 2H); 3.30(t, 2H); 3.52(d, 2H); 3.66(t, 2H); 3.93(s, 31H); 4.02(br d, 2H); 4.23(t, 2H); 7.34(s, 1H); 7.61(s, 1H).

MS-EI: 340 [M]$^+$

Thionyl chloride (15 ml) and DMF (0.05 ml) were added to 5-methoxy-4-(3-morpholinopropoxy)-2-nitrobenzoic acid (7.54 g). The mixture was heated at 50° C. for 1 hour, the excess thionyl chloride was removed by evaporation and by azeotroping with toluene (×2). The resulting solid was suspended in THF (200 ml) and ammonia was bubbled through the mixture for 30 minutes. The precipitate was removed by filtration and washed with THF. After concentration of the filtrate by evaporation, the product crystallised and was collected by filtration to give 5-methoxy-4-(3-morpholinopropoxy)-2-nitrobenzamide (5.25 g) as light yellow crystals which were used without further purification.

$^1$H NMR Spectrum: (DMSOd$_6$, TFA) 2.17–2.24(m, 2H); 3.11–3.18(m, 2H); 3.31(t, 2H); 3.53(d, 2H); 3.67(t, 2H); 3.93(s, 3H); 4.03(br d, 2H); 4.21(t, 2H); 7.17(s, 1H); 7.62(s, 1H).

MS-EI: 339 [M]$^+$

Concentrated hydrochloric acid (30 ml) was added to a suspension of 5-methoxy-4-(3-morpholinopropoxy)-2-nitrobenzamide (5.67 g) in methanol (150 ml) and the mixture was heated to 60° C. When the 5-methoxy-4-(3-morpholinopropoxy)-2-nitrobenzamide had dissolved, iron powder (5.6 g, 100 mmol) was added in portions to the reaction mixture which was then heated for 90 minutes. After cooling, the insolubles were removed by filtration through diatomaceous earth, the volatiles were removed from the filtrate by evaporation and the residue was purified on a Diaion (trade mark of Mitsubishi) HP20SS resin column, eluting with water and then with hydrochloric acid pH2). Concentration of the fractions by evaporation gave a precipitate which was collected by filtration and dried under vacuum over phosphorus pentoxide to give 2-amino-5-methoxy-4-(3-morpholinopropoxy)benzamide as a hydrochloride salt (4.67 g, 75%) as beige crystals.

$^1$H NMR Spectrum: (DMSOd$_6$, TFA) 2.22–2.28(m, 2H); 3.12(br t, 2H); 3.29(t, 2H); 3.51(d, 2H); 3.75(t, 2H); 3.87(s, 3H); 4.00(br d, 2H); 4.12(t, 2H); 7.06(s, 1H); 7.53(s, 1H).

MS-EI: 309 [M]$^+$

A mixture of 2-amino-5-methoxy-4-(3-morpholinopropoxy)benzamide (4.57 g, 12.25 mmol) and Gold's reagent (2.6 g, 15.89 mmol) in dioxane (35 ml) was heated at reflux for 5 hours. Acetic acid (0.55 ml) and sodium acetate (1.0 g) were added to the reaction mixture which was heated for a further 3 hours. The mixture was cooled to ambient temperature and the volatiles removed by evaporation. The residue was adjusted to pH7 with 2M sodium hydroxide and then purified on a Diaion (trade mark of Mitsubishi) HP20SS resin column, eluting with methanol (gradient of 0 to 60%) in water. Concentration of the fractions by evaporation gave a precipitate which was collected by filtration and dried under vacuum over phosphorus pentoxide to give 4-hydroxy-6-methoxy-7-(3-morpholinopropoxy)quinazoline (3.04 g, 78%) as a white solid.

$^1$H NMR Spectrum: (CDCl$_3$) 2.10(q, 2H); 2.48(m, 4H); 2.56(t, 2H); 3.72(t, 4H); 4.00(s, 3H); 4.24(t, 2H); 7.18(s, 1H); 7.60(s, 1H); 8.00(s, 1H); 10.86(br s, 1H).

MS-EI: 319 [M]$^+$

A mixture of 4-hydroxy-6-methoxy-7-(3-morpholinopropoxy)quinazoline (638 mg, 2 mmol) and thionyl chloride (8 ml) was heated at reflux for 30 minutes. Excess thionyl chloride was removed by evaporation and by azeotroping with toluene (×2). The residue was suspended in methylene chloride and 10% aqueous solution of sodium hydrogen carbonate was added to the mixture. The organic layer was separated, dried (MgSO$_4$) and the solvent removed by evaporation. The residue was triturated with ether, the solid was collected by filtration, washed with ether and dried under vacuum to give 4-chloro-6-methoxy-7-(3-morpholinopropoxy)quinazoline (590 mg, 87%).

$^1$H NMR Spectrum: (CDCl$_3$) 2.10–2.16(m, 2H); 2.48(br s, 4H); 2.57(t, 2H); 3.73(t, 4H); 4.05(s, 3H); 4.29(t, 2H); 7.36(s, 1H); 7.39(s, 1H); 8.86(s, 1H).

MS-ESI: 337 [MH]$^+$

EXAMPLE 6

2M Hydrochloric acid (3 ml, 6 mmol) was added to a solution of 4-(1-diethoxymethyloxindol-3-yl)-6-methoxy-7-3-morpholinopropoxy)quinazoline (295 mg, 0.55 mmol), (prepared as described in Example 5), in ethanol (20 ml) at 80° C. The mixture was stirred for 45 minutes at 80° C. After cooling of the reaction mixture, partial evaporation of the solvents led to the crystallisation of the compound. The solid was collected by filtration, washed with ethanol and then ether and dried under vacuum at 50° C. to give 6-methoxy-7-(3-morpholinopropoxy)-4-(oxindol-3-yl)quinazoline as a hydrochloride salt (207 mg, 84%) as an orange solid.

m.p. 180–183° C.

$^1$H NMR Spectrum: (DMSOd$_6$, TFA) 2.28–2.36(m, 2H); 3.13–3.20(m, 2H); 3.34–3.38(m, 2H); 3.56(br d, 2H); 3.74 (br t, 2H); 3.88(s, 3H); 4.04(dd, 2H); 4.31–4.34(m, 2H); 7.19(t, 1H); 7.34(s, 1H); 7.69(d, 1H); 7.79(s, 1H); 8.93(s, 1H).

MS-ESI: 435 [MH]$^+$

| Elemental analysis: | Found | C 55.1 | H 6.3 | N 10.7 | Cl 9.9 |
|---|---|---|---|---|---|
| C$_{24}$H$_{26}$N$_4$O$_4$ 2H$_2$O 1.45HCl | Requires | C 55.1 | H 6.1 | N 10.7 | Cl 9.8% |

EXAMPLE 7

Sodium hydride (80 mg, 3.4 mmol, pre-washed with petroleum ether) was added to a solution of 5-fluorooxindole (423 mg, 2.8 mmol), (prepared according to Synthesis 1993, 51), in THF (10 ml) at ambient temperature under argon. The resulting suspension was stirred for 30 minutes and a partial solution of 4-chloro-6-methoxy-7-(3-morpholinopropoxy) quinazoline (236 mg, 0.7 mmol), (prepared as described for the starting material in Example 5), in a 1/1 mixture of THF/DMF (14 ml), was added and the reaction mixture was stirred at ambient temperature for 15 hours. The volatiles were then removed by evaporation and the residue purified by column flash chromatography using an increasingly polar mixture of methylene chloride and methanol (2 to 10%) as eluent. The purified product was dissolved in a minimum volume of methanol and a 2.9M solution of hydrogen chloride in ether was added to the solution. During the evaporation of the solvents a solid precipitated which was collected by filtration, washed with ether and dried under vacuum to give 4-(5-fluorooxindol-3-yl)-4-methoxy-7-(3-morpholinopropoxy)quinazoline as a hydrochloride salt (298 mg, 81%).

m.p. 230–240° C.

$^1$H NMR Spectrum: (DMSOd$_6$, TFA) 2.28–2.33(m, 2H); 3.13–3.18(m, 2H); 3.35(t, 2H); 3.55(d, 2H); 3.74(br t, 2H); 3.89(s, 3H); 4.03(d, 2H); 4.33(t, 2H); 6.94–6.99(m, 2H); 7.34(s, 1H); 7.46(d, 1H); 7.81(s, 1H); 8.81(s, 1H).

MS-ESI: 453 [MH]$^+$

| Elemental analysis: | Found | C 54.4 | H 5.5 | N 10.3 | Cl 11.5 |
|---|---|---|---|---|---|
| C$_{24}$H$_{25}$N$_4$O$_4$F 0.6H$_2$O 1.75HCl | Requires | C 54.7 | H 5.3 | N 10.6 | Cl 11.8% |

EXAMPLE 8

2M Hydrochloric acid (2.75 ml, 5.5 mmol) was added to a solution of 4-(5-bromo-1-diethoxymethyloxindol-3-yl)-6-methoxy-7-(2-methoxyethoxy)quinazoline (300 mg, 0.55 mmol) in ethanol (20 ml) at 90° C. The mixture was heated for 1 hour, the solid product was collected by filtration and purified on a Diaion (trade mark of Mitsubishi) HP20SS resin column, eluting with acetonitrile (using a gradient of 0 to 100%) in hydrochloric acid (pH2). Concentration of the fractions by evaporation gave a precipitate which was collected by filtration, washed with water to give a solid which was purified again by column flash chromatography using an increasingly polar mixture of methylene chloride/methanol (95/5 to 80/20) as eluent. After evaporation of the solvent, the resulting solid was dissolved in a minimum volume of methanol and a 2.9M solution of hydrogen chloride in ether was added to the solution. The solid was collected by filtration, washed with ether and dried under vacuum to give 4-(5-bromooxindol-3-yl)-6-methoxy-7-(2-methoxyethoxy) quinazoline as a hydrochloride salt (74 mg, 30%) as an orange solid.

$^1$H NMR Spectrum: (DMSOd$_6$, TFA) 3.36(s, 3H); 3.78(t, 2H); 3.93(s, 3H); 4.34(t, 2H); 6.96(d, 1H); 7.26(dd, 1H); 7.31(s, 1H); 7.77(s, 1H); 7.79(d, 1H); 8.80(s, 1H).

MS-ESI: 444 [MH]$^+$

| Elemental analysis: | Found | C 49.4 | H 4.1 | N 8.6 | Cl 5.0 |
|---|---|---|---|---|---|
| C$_{20}$H$_{18}$N$_3$O$_4$Br 0.7H$_2$O 0.7HCl | Requires | C 49.8 | H 4.2 | N 8.7 | Cl 5.1% |

The starting material was prepared as follows:

A mixture of 5-bromooxindole (6.36 g, 30 mmol), (prepared according to J. Am. Chem. Soc. 1975, 67, 1656), and triethyl orthoformate (100 ml) was heated and stirred at reflux for 8 hours. The volatiles were removed by evaporation and the residue purified by column flash chromatography using petroleum ether/ether (7/3) as eluent. Evaporation of the solvents lead to a crystalline material which was collected, washed with a minimum of petroleum ether and dried under vacuum to give 5-bromo-1-diethoxymethyloxindole (6.43 g, 68%).

$^1$H NMR Spectrum: (CDCl$_3$) 1.23(t, 6H); 3.50–3.57(m, 2H); 3.58(s, 2H); 3.69–3.77(m, 2H); 6.22(s, 1H); 7.29–7.38 (m, 3H).

5-Bromo-1-diethoxymethyloxindole (942 mg, 3 mmol) and sodium hydride (138 mg, 5.8 mmol, pre-washed with petroleum ether) were added successively to a solution of 4-chloro-6-methoxy-7-(2-methoxyethoxy)quinazoline (269 mg, 1 mmol), (prepared as described for the starting material in Example 2), in THF (25 ml) at ambient temperature. After stirring for 2 hours at ambient temperature, the volatiles were removed by evaporation and the residue dissolved in methylene chloride. The solution was washed with an aqueous saturated sodium chloride solution, dried (MgSO$_4$) and the solvent evaporated. The residue was purified by column flash chromatography using an increasingly polar mixture of methylene chloride and ethyl acetate followed by a 7/3 mixture of methylene chloride/acetonitrile as eluent. The purified product was triturated with ether, collected by filtration, washed with a 1/1 mixture of ether/petroleum ether and dried under vacuum to give 4-(5-bromo-1-diethoxymethyloxindol-3-yl)-6-methoxy-7-(2-methoxyethoxy)quinazoline (400 mg, 73%) as a yellow-orange solid.

$^1$H NMR Spectrum: (CDCl$_3$) 1.25(t, 6H); 3.50(s, 3H); 3.52–3.60(m, 2H); 3.73–3.80(m, 2H); 3.89–3.91(m, 2H); 4.00(s, 3H); 4.35–4.37(m, 2H); 6.47(s, 1H); 7.19(d, 1H); 7.21(s, 2H); 7.48(s, 1H); 7.75(s, 1H); 7.81(dd, 1H); 8.11(s, 1H).

MS-ESI: 568 [MNa]$^+$

EXAMPLE 9

Sodium hydride (95 mg of a 60% suspension in paraffin oil, 2.4 mmol) was added to a solution of 5-fluoro-1-diethoxymethyloxindole (520 mg, 2.05 mmol) and 4-chloro-6-methoxy-7-(2-methoxyethoxy)quinazoline (220 mg, 0.82 mmol), (prepared as described for the starting material in Example 2), in THF (20 ml). After stirring for 2 hours at ambient temperature, the volatiles were removed by evaporation. The residue was partitioned beween methylene chloride and water, the organic layer was washed with water and then brine, dried (MgSO$_4$) and the solvent evaporated. The residue was purified by flash chromatography using an increasingly polar mixture of methylene chloride/ethyl acetate (100/0 to 0/100) as eluent to give 4-(5-fluoro-1-diethoxymethyloxindol-3-yl)-6-methoxy-7-(2-methoxyethoxy)quinazoline (300 mg, 68%) as a yellow solid.

m.p. 245–255° C.

1H NMR Spectrum: (DMSOd$_6$, CF$_3$CO$_2$D) 1.06(t, 6H); 3.36(s, 3H); 3.44(q, 4H); 3.78(t, 2H); 3.87(s, 3H); 4.33(t, 2H); 6.87–6.89(m, 1H); 7.20(s, 1H); 7.85–7.95(m, 1H); 8.0–8.5(dd, 1H); 8.20–8.25(m, 1H); 8.64(s, 1H); 9.38(s, 1H).

The starting material was prepared as follows:

A solution of 5-fluorooxindole (980 mg, 6.5 mmol), (prepared according to Synthesis 1993, 51), in triethyl orthoformate (25 ml) was stirred and heated at reflux for 8 hours. The volatiles were removed by evaporation and the crude product purified by flash chromatography using petroleum ether/ether 7/3 as eluent to give 5-fluoro-1-diethoxymethyloxindole (637 mg, 40%).

$^1$H NMR Spectrum: (CDCl$_3$) 1.23(t, 6H); 3.51–3.62(m, 4H); 3.69–3.77(m, 2H); 6.23(s, 1H); 6.92–6.98(m, 2H); 7.30–7.36(m, 1H).

EXAMPLE 10

A solution of 4-(5-fluoro-1-diethoxymethyloxindol-3-yl)-6-methoxy-7-(2-methoxyethoxy)quinazoline (255 mg, 0.52 mmol), (prepared as described in Example 9), in ethanol (25 ml) containing 2M hydrochloric acid (2.6 ml) was heated at 80° C. for 1 hour. The solid formed was collected by filtration, washed with ethanol and dried under vacuum. The solid was dissolved in hot DMF, the solution was diluted with ethyl acetate and thoroughly washed with water. The organic layer was dried (MgSO$_4$), the volatiles removed by evaporation and the resulting solid was dried under vacuum at 70° C. to give 4-(5-fluorooxindol-3-yl)-6-methoxy-7-(2-methoxyethoxy)quinazoline (49 mg, 25%).

m.p. 277–280° C.

$^1$H NMR Spectrum: (DMSOd$_6$, CF$_3$CO$_2$D) 3.36(s, 3H); 3.78(t, 2H); 3.88(s, 3H); 4.34(t,2H); 6.94–6.99(m, 2H); 7.30(s, 1H); 7.48(dd, 1H); 7.78(s, 1H); 8.83(s, 1H).

MS-ESI: 383 [MH]$^+$

| Elemental analysis: | Found | C 61.9 | H 5.0 | N 10.5 |
|---|---|---|---|---|
| C$_{20}$H$_{18}$N$_3$O$_4$F 0.1 ethyl acetate | Requires | C 62.5 | H 4.8 | N 10.7% |

EXAMPLE 11

A solution of oxindole (1.2 g, 9 mmol) in THF (10 ml) was added dropwise to a suspension of sodium hydride (360 mg of a 60% suspension in paraffin oil, 9 mmol) in THF (15 ml) over 15 minutes under nitrogen. The resulting white suspension was stirred for 15 minutes at ambient temperature and a solution of 7-benzyloxy-4-chloro-6-methoxyquinazoline (900 mg, 3 mmol) in THF (10 ml) was added followed by DMF (5 ml). The resulting reddish solution was stirred for 30 minutes at ambient temperature followed by 1 hour at 65° C. The mixture was concentrated to half its volume by evaporation and was partitioned between ethyl acetate and water. The aqueous layer was separated, adjusted to pH7 with 2M hydrochloric acid and the resulting precipitate was collected by filtration, washed with water, followed by ethyl acetate and ether and dried under vacuum to give 7-benzyloxy-6-methoxy4-(oxindol-3-yl)quinazoline (1 g, 83%) as a yellow solid.

m.p. 280–285° C.

$^1$H NMR Spectrum: (DMSOd$_6$, NaOD) 3.82(s, 3H); 5.23 (s, 2H); 6.6–6.75(m, 3H); 7.05(s, 1H); 7.3–7.45(m, 3H); 7.52(d, 2H); 8.1(d, 1H); 8.5(s, 1H); 8.8(s, 1H).

MS-ESI m/z: 398 [MH]$^+$

| Elemental analysis: | Found | C 71.8 | H 5.0 | N 10.6 |
|---|---|---|---|---|
| C$_{24}$H$_{19}$N$_3$O$_3$ 0.2H$_2$O | Requires | C 71.9 | H 4.9 | N 10.5% |

The starting material was prepared as follows:

A mixture of 2-amino-4-benzyloxy-5-methoxybenzamide (10 g, 0.04 mol), (prepared according to J. Med. Chem.

1977, vol 20, 146–149), and Gold's reagent (7.4 g, 0.05mol) in dioxane (100 ml) was stirred and heated to reflux for 24 hours. Sodium acetate (3.02 g, 0.037 mol) and acetic acid (1.65 ml, 0.029 mol) were added to the reaction mixture and it was heated for a further 3 hours. The volatiles were removed by evaporation, water was added to the residue, the solid was collected by filtration, washed with water and dried. Recrystallisation from acetic acid gave 7-benzyloxy-6-methoxy-3,4-dihydroquinazolin-4-one (8.7 g, 84%).

A mixture of 7-benzyloxy-6-methoxy-3,4-dihydroquinazolin-4-one (2.82 g, 0.01 mol), thionyl chloride (40 ml) and DMF (0.28 ml) was stirred and heated at reflux for 1 hour. The excess thionyl chloride was removed by evaporation and by azeotroping with toluene to give 7-benzyloxy4-chloro-6-methoxyquinazoline hydrochloride (3.45 g), which was subjected to an aqueous work-up with sodium hydroxide solution to give 7-benzyloxy-4-chloro-6-methoxyquinazoline.

EXAMPLE 12

A mixture of 4-(5-benzyloxy-1-diethoxymethyloxindol-3-yl)-6-methoxy-7-(3-morpholinopropoxy)quinazoline (240 mg, 0.38 mmol) and TFA (8 ml) was heated at reflux for 30 minutes. The TFA was removed by evaporation, the residue was triturated with ether, the solid was collected by filtration, washed with ether and dried under vacuum. The orange solid thus obtained was dissolved in a 1M hydrochloric acid solution (5 ml, 5 mmol) and heated at reflux for 40 minutes. After cooling, the reaction mixture was adjusted to pH2.3 with 6M sodium hydroxide and subjected to column chromatography on reverse phase silica gel (C18 10μ) with a gradient of methanol in water (30 to 100%) as eluent The fractions containing the compound were combined, the solution was adjusted to pH1.5 with concentrated hydrochloric acid and the solvents removed by evaporation The residue was triturated with methanol/ether, the solid was collected by filtration, washed with ether and dried under vacuum at 40° C. to give 4-(5-hydroxyoxindol-3-yl)-6-methoxy-7-(3-morpholinopropoxy)quinazoline as a hydrochloride salt (90 mg, 45%) as an orange solid.

m.p. 230–245° C.

$^1$H NMR Spectrum: (DMSOd$_6$, TFA) 2.27–2.34(m, 2H); 3.11–3.18(m, 2H); 3.33(t, 2H); 3.53(d, 2H); 3.76(t, 2H); 3.89(s, 3H); 4.02(d, 2H); 4.31(t, 2H); 6.61(dd, 1H); 6.81(d, 1H); 7.15(d, 1H); 7.33(s, 1H); 7.74(s, 1H); 8.86(s, 1H).

MS-ESI: 451 [MH]$^+$

| Elemental analysis: | Found | C 52.9 | H 6.2 | N 9.9 | Cl 9.5 |
|---|---|---|---|---|---|
| C$_{24}$H$_{26}$N$_4$O$_5$ 1.5H$_2$O 1.5HCl | Requires | C 54.2 | H 5.8 | N 10.5 | Cl 10.0% |

The starting material was prepared as follows:

A mixture of 5-benzyloxyoxindole (1.88 g, 7.9 mmol), (EP 0636608 A1), and triethyl orthoformate (180 ml) was heated at reflux with stirring for 3 hours. The volatiles were removed by evaporation and the residue was purified by column flash chromatography using petroleum ether/ether (7/3) as eluent. Evaporation of the solvents lead to a crystalline material which was collected by filtration and dried under vacuum to give 5-benzyloxy-1-diethoxymethyloxindole (1.96 g, 73%).

$^1$H NMR Spectrum: (CDCl$_3$) 1.23(t, 6H); 3.51–3.58(m, 2H); 3.55(s, 2H); 3.68–3.76(m, 2H); 5.03(s, 2H); 6.22(s, 1H); 6.85(dd, 1H); 6.90(d, 1H); 7.30–7.44(m, 6H).

MS-ESI: 341 [MNa]$^+$

| Elemental analysis: | Found | C 70.0 | H 4.2 | N 7.0 |
|---|---|---|---|---|
| C$_{20}$H$_{23}$NO$_4$ | Requires | C 70.4 | H 4.1 | N 6.8% |

4-Chloro-6-methoxy-7-(2-methoxyethoxy)quinazoline (200 mg, 0.59 mmol), (prepared as described for the starting material in Example 2), and sodium hydride (72 mg, 3 mmol, pre-washed with petroleum ether) were added successively to a solution of 5-benzyloxy-1-diethoxymethyloxindole (500 mg, 1.47 mmol) in THF (20 ml) at ambient temperature. After stirring for 2 hours at ambient temperature, the volatiles were removed by evaporation and the residue was taken up in methylene chloride. The solution was washed with saturated aqueous sodium chloride solution, dried (MgSO$_4$) and the solvent was removed by evaporation. The residue was purified by column flash chromatography using methylene chloride/ethyl acetate (1/1) followed by an increasingly polar mixture of methylene chloride/methanol (97/3 to 95/5) as eluent. The purified product was triturated with ether, collected by filtration, washed with ether and dried under vacuum to give 4-(5-benzytoxy-1-diethoxymethyloxindol-3-yl)-6-methoxy-7-(3-morpholinopropoxy)quinazoline (340 mg, 90%) as a yellow-orange solid.

$^1$H NMR Spectrum: (CDCl$_3$) 1.06(t, 6H); 2.25–2.31(m, 2H); 3.12–3.19(m, 2H); 3.36(t, 2H); 3.44(q, 4H); 3.55(d, 2H); 3.67(t, 3H); 3.86(s, 3H); 4.04(br d, 2H); 4.32(t, 2H): 5.10(s, 2H); 6.83(dd, 1H); 7.24(s, 1H); 7.33–7.36(br s, 1H); 7.40(t, 1H); 7.46(d, 1H); 7.58(br s, 1H); 7.95(d, 1H); 8.08(br s, 1H); 8.59(s, 1H); 9.36(s, 1H).

MS-ESI: 643 [MH]$^+$

EXAMPLE 13

A solution of 6-fluorooxindole (264 mg, 1.75 mmol), (prepared according to Synthesis 1993, 51), in THF (3 ml) was added dropwise under nitrogen to sodium hydride (42 mg, 1.75 mmol, pre-washed with hexane). After stirring the resulting mixture for 20 minutes at ambient temperature, 4-chloro-6,7-dimethoxyquinazoline (210 mg, 0.93 mmol), (prepared as described for the starting material in Example 1), was added as a solid, followed by DMF (4 ml). The reaction mixture was then heated at 85° C. for 1 hour, the solvent was removed by evaporation and the residue partitioned between ether and water. The aqueous layer was separated and neutralised with 2M hydrochloric acid and the solid was collected by filtration, washed with ether and dried under vacuum to give 6,7-dimethoxy4-(6-fluorooxindol-3-yl)quinazoline (255 mg, 81%) as a yellow solid.

m.p. 315° C. (decomposition)

$^1$H NMR Spectrum: (DMSOd$_6$, CF$_3$CO$_2$D) 3.85(s, 3H); 3.98(s, 3H); 6.75–6.9(m, 2H); 7.42(s, 1H); 7.65(m, 1H); 7.75(s, 1H); 8.75(s, 1H).

MS: 340 [MH]$^+$

| Elemental analysis: | Found | C 62.4 | H 4.4 | N 12.2 |
|---|---|---|---|---|
| C$_{18}$H$_{14}$N$_3$O$_3$F 0.23H$_2$O | Requires | C 63.0 | H 4.2 | N 12.2% |

EXAMPLE 14

A solution of 6-fluorooxindole (227 mg, 1.5 mmol), (prepared according to Synthesis 1993, 51), in THF (3 ml)

was added dropwise under nitrogen to sodium hydride (42 mg, 1.75 mmol, pre-washed with hexane). After stirring the resulting mixture for 20 minutes at ambient temperature, 4-chloro-6-methoxy-7-(3-morpholinopropoxy)quinazoline (169 mg, 0.5 mmol), (prepared as described for the starting material in Example 5), was added as a solid, followed by DMF (3 ml). The mixture was then heated at 75° C. for 1 hour, allowed to cool and the solvent removed by evaporation The mixture was partitioned between water and ether. The aqueous layer was separated and adjusted to pH8 with 2M hydrochloric acid and then extracted with ethyl acetate. The organic layer was washed with brine, dried and volatiles removed by evaporation. The residue was triturated with ether and collected by filtration. This solid was dissolved in methylene chloride/methanol, a 5M solution of hydrogen chloride in isopropanol (0.5 ml) was added and the volatiles removed by evaporation. The resulting solid was collected by filtration, washed with ether and dried under vacuum to give 4-(6-fluorooxindol-3-yl)-6-methoxy-7-(3-morpholinopropoxy)quinazoline hydrochloride (198 mg, 81%) as a yellow solid.

m.p. .195–200° C.

$^1$H NMR Spectrum: (DMSOd$_6$, CF$_3$CO$_2$D) 2.25–2.4(m, 2H); 3.05–3.2(m, 2H); 3.25–3.35(m, 2H); 3.52(d, 2H); 3.72–3.85(m, 2H); 3.9(s, 3H); 4.05(d, 2H); 4.3(t, 2H); 6.8–6.9(m, 2H); 7.32(s, 1H); 7.62–7.7(m, 1H); 7.78(s, 1H); 8.7–8.8(m, 1H).

MS: 453[MH]$^+$

| Elemental analysis: | Found | C 54.1 | H 5.7 | N 10.6 |
|---|---|---|---|---|
| C$_{24}$H$_{25}$N$_4$O$_4$F 0.8H$_2$O 1.8HCl | Requires | C 54.1 | H 5.4 | N 10.5% |

EXAMPLE 15

A solution of oxindole (319 mg, 2.4 mmol) in THF (3 ml) was added dropwise under nitrogen to sodium hydride (58 mg, 2.4 mmol, pre-washed with hexane) and the mixture stirred for 20 minutes at ambient temperature. A solution of 4-chloro-7-(2-methoxyethoxy)quinazoline (191 mg, 0.8 mmol) in DMF (3 ml) was added and the mixture then heated at 70° C. for 1 hour. The mixture was allowed to cool and the solvent removed by evaporation. The mixture was partitioned between water and ether. The aqueous phase was separated and adjusted to pH7 with 2M hydrochloric acid. The resulting solid was collected by filtration and washed with water and ethanol. This solid was then suspended in ether, recollected by filtration, washed with ether and dried under vacuum to give 7(2-methoxyethoxy)-4-(oxindol-3-yl)quinazoline (200 mg, 75%).

m.p. 245–248° C.

$^1$H NMR Spectrum: (DMSOd$_6$, CF$_3$CO$_2$D) 3.36(s, 3H); 3.75(t, 2H); 4.31(t, 2H); 6.92–7.05(m, 2H); 7.12–7.2(m, 2H); 7.3–7.4(dd, 1H); 7.65(d, 1H); 8.4(d, 1H); 8.8(s, 1H).

MS: 336 [MH]$^+$

| Elemental analysis: | Found | C 67.4 | H 5.3 | N 12.5 |
|---|---|---|---|---|
| C$_{19}$H$_{17}$N$_3$O$_3$ 0.07H$_2$O | Requires | C 67.8 | H 5.1 | N 12.5% |

The starting material was prepared as follows:

A solution of 2-amino-4-fluorobenzoic acid (3 g, 19.3 mmol) in formamide (30 ml) was heated at 150° C. for 6 hours. The reaction mixture was poured onto icewater 1/1 (250 ml). The precipitated solid was collected by filtration, washed with water and dried to give 7-fluoro-3,4-dihydroquinazolin-4-one (2.6 g, 82%).

Sodium (400 mg, 17 mmol) was added carefully to 2-methoxyethanol (10 ml) and the mixture heated at reflux for 30 minutes. 7-Fluoro-3,4-dihydroquinazolin-4one (750 mg, 4.57 mmol) was added to the resulting solution and the mixture heated at reflux for 15 hours. The mixture was cooled and poured into water (250 ml). The mixture was acidified to pH4 with concentrated hydrochloric acid. The resulting solid product was collected by filtration, washed with water and then with ether, and dried under vacuum to give 7-(2-methoxyethoxy)-3,4-dihydroquinazolin-4-one (580 mg, 58%).

A solution of 7-(2-methoxyethoxy)-3,4-dihydroquinazolin-4-one (500 mg, 2.2 mmol) in thionyl chloride (15 ml) and DMF (0.1 ml) was heated at reflux for 3 hours. The volatiles were removed by evaporation to give 4-chloro-7-(2-methoxyethoxy)quinazoline hydrochloride as a cream solid (520 mg, 83%).

A suspension of 4-chloro-7-(2-methoxyethoxy) quinazoline hydrochloride (500 mg, 1.8 mmol) in a mixture of water (20 ml) and ethyl acetate (20 ml) was diluted with a saturated solution of sodium hydrogen carbonate. After stirring at ambient temperature for 15 minutes the solution was extracted with ethyl acetate. The organic layer was washed with brine, dried (MgSO$_4$) and evaporated to give 4-chloro-7-(2-methoxyethoxy)quinazoline (345 mg, 80%).

EXAMPLE 16

A solution of oxindole (266 mg, 2.0 mmol) in THF (2 ml) was added dropwise under nitrogen to a stirred suspension of sodium hydride (80 mg, of a 60% dispersion in mineral oil, 2.0 mmol) in THF (1 ml). After stirring the resulting mixture for 15 minutes at ambient temperature, a solution of 4-chloro-6,7-dimethoxyquinazoline (449 mg, 2.0 mmol), (prepared as described for the starting material in Example 1), in THF (20 ml) was added. The mixture was stirred at ambient temperature for 2 hours, quenched with water and the volatiles removed by evaporation. The resulting solid was purified by flash chromatography eluting with methylene chloride/methanol (19/1). The purified product was triturated with methanol, collected by filtration, washed with ether and dried under vacuum to give 6,7-dimethoxy-4-(oxindol-3-yl)quinazoline (77 mg, 12%).

$^1$H NMR Spectrum: (DMSOd$_6$, CF$_3$CO$_2$D) 3.86(s, 3H); 3.98(s, 3H); 6.9–7.1(m, 4H); 7.22(s, 1H); 7.63(d, 1H); 7.79(s, 1H); 8.34(s, 1H).

MS: 322 [MH]$^+$

| Elemental analysis: | Found | C 66.6 | H 4.4 | N 12.7 |
|---|---|---|---|---|
| C$_{18}$H$_{15}$N$_3$O$_3$ 0.1H$_2$O | Requires | C 66.9 | H 4.7 | N 13.0% |

EXAMPLE 17

A solution of 4-(7-benzyloxyoxindol-3-yl)-6-methoxy-7-(3-morpholinopropoxy)quinazoline (210 mg, 0.39 mmol) in TFA (15 ml) and thioanisole (2.3 ml, 19 mmol) was stirred at ambient temperature for 20 hours. The volatiles were removed by evaporation and the residue was triturated with ether. The solid product was collected by filtration, washed with ether and dried under vacuum. The solid was dissolved in water (5 ml) containing 2M hydrochloric acid (2 drops) and purified by reverse phase C18 chromatography eluting with water/methanol a (gradient from 80/20 to 30/70). The purified solid was dissolved in methanol and 7.5M methanolic hydrogen chloride (0.2 ml) was added. The volatiles were removed by evaporation, the solid collected and dried under vacuum at 45° C. to give 4-(7-hydroxyoxindol-3-yl)-6-methoxy-7-(3-morpholinopropoxy)quinazoline hydrochloride (73 mg, 35%).

$^1$H NMR Spectrum: (DMSOd$_6$, CF$_3$CO$_2$D) 2.2–2.35(m, 2H); 3.15(t, 2H); 3.34(t, 2H); 3.54(d, 2H); 3.7(t, 2H); 3.86(s, 3H); 4.01(d, 2H); 4.29(t, 2H); 6.73(d, 1H); 6.88(t, 1H); 7.17(d, 1H); 7.30(s, 1H); 7.80(s, 1H); 8.96(s, 1H).

MS-ESI: 451 [MH]$^+$

| Elemental analysis: | Found | C 54.1 | H 5.8 | N 10.5 |
|---|---|---|---|---|
| C$_{24}$H$_{26}$N$_4$O$_5$ 0.3H$_2$O 2HCl | Requires | C 54.5 | H 5.5 | N 10.6% |

The starting material was prepared as follows:

7-Benzyloxy-3-methylthiooxindole (610 mg, 2.1 mmol), (EP 8226), was dissolved in hot ethanol (60 ml). The mixture was allowed to cool and Rainey Nickel (40 ml volume, prewashed with ethanol) was added and the mixture was stirred at ambient temperature for 1.5 hours. The insolubles were removed by filtration and the filter pad was thoroughly washed with ethanol. The solvent was removed from the filtrate by evaporation and the residue was purified by column chromatography eluting with ethyl acetate/petroleum ether (40/60) to give 7-benzyloxyoxindole (395 mg, 71%).

$^1$H NMR Spectrum: (CDCl$_3$) 3.55(s,2H); 5.1(s, 2H); 6.86(d, 2H); 6.95(t, 1H); 7.35–7.45(m, 5H); 7.52(br s, 1H).

MS-ESI: 262 [MNa]$^+$

| Elemental analysis: | Found | C 75.5 | H 5.8 | N 5.8 |
|---|---|---|---|---|
| C$_{15}$H$_{13}$NO$_2$ | Requires | C 75.3 | H 5.5 | N 5.8% |

Sodium hydride (36 mg, 1.5 mmol) was added in portions to a solution of 7-benzyloxyoxindole (360 mg, 1.5 mmol) in THF (8 ml), the mixture was stirred for 30 minutes at ambient temperature and a solution of 4-chloro-6-methoxy-7-(3-morpholinopropoxy)quinazoline (204 mg, 0.6 mmol), (prepared as described for the starting material in Example 5), in THF (4 ml) and DMF (1.5 ml) was added. The mixture was stirred for 30 minutes at ambient temperature followed by 1.5 hours at 65° C. The THF was removed by evaporation, the mixture was partitioned between ethyl acetate and water and the aqueous layer was adjusted to pH8 with 2M hydrochloric acid. The precipitated product was collected by filtration, washed with water, ethyl acetate, and ether, and dried under vacuum to give 4-(7-benzyloxyoxindol-3-yl)-6-methoxy-7-(3-morpholinopropoxy)quinazoline (190 mg, 58%).

$^1$H NMR Spectrum: (DMSOd$_6$, CF$_3$CO$_2$D) 2.2–2.35(m, 2H); 3.15(t, 2H); 3.34(t, 2H); 3.54(d, 2H); 3.71(t, 2H); 3.85(s, 3H); 4.05(d, 2H); 4.3(t, 2H); 5.26(s, 2H); 6.9–7.0(m, 2H); 7.22–7.38(m, 3H); 7.4(t, 2H); 7.59(d, 2H); 7.79(s, 1H); 8.8(s, 1H).

MS-ESI: 541 [MH]$^+$

| Elemental analysis: | Found | C 66.4 | H 6.0 | N 10.1 |
|---|---|---|---|---|
| C$_{31}$H$_{32}$N$_4$O$_5$ 1H$_2$O | Requires | C 66.6 | H 6.1 | N 10.0% |

EXAMPLE 18

A solution of oxindole (200 mg, 1.5 mmol) in THF (3 ml) was added dropwise under nitrogen to sodium hydride (60 mg, 1.5 mmol, prewashed with hexane) in THF (3 ml). After stirring for 20 minutes at ambient temperature, a solution of 4-chloro-6(3-morpholinopropoxy)-7-methoxyquinazoline (169 mg, 0.5 mmol) in DMF (3 ml) was added. The mixture was heated at 75° C. for 1 hour, allowed to cool and the volatiles removed by evaporation. The mixture was partitioned between water and ether. The aqueous layer was adjusted to pH8 with 2M hydrochloric acid. The resulting precipitate was collected by filtration, washed with water, and dried under vacuum. The solid was dissolved in methylene chloride/methanol and 3M ethereal hydrogen chloride (0.5 ml) was added. The mixture was diluted with ether, the solid was collected by filtration and dried under vacuum to give 7-methoxy-6-(3-morpholinopropoxy)-4-(oxindol-3-yl) quinazoline hydrochloride (175 mg, 69%).

$^1$H NMR Spectrum: (DMSOd$_6$, CF$_3$CO$_2$D) 2.3(m, 2H); 3.1 (t, 2H); 3.3(t, 2H); 3.5(d, 2H); 3.75(t, 2H); 3.99(s, 3H); 3.95–4.05(m, 2H); 4.15(t, 2H); 7.0(d, 1H); 7.05(t, 1H); 7.15(t, 1H); 7.33(s, 1H); 7.7(d, 1H); 7.8(s, 1H); 8.81(s, 1H).

MS-ESI: 435 [MH]$^+$

| Elemental analysis: | Found | C 56.0 | H 6.1 | N 10.8 |
|---|---|---|---|---|
| C$_{24}$H$_{26}$N$_4$O$_4$ 1H$_2$O 1.8HCl | Requires | C 55.6 | H 5.8 | N 10.8% |

The starting material was prepared as follows:

A suspension of 4-(3-chloro-4-fluoroanilino)-6-(3-morpholinopropoxy)-7-methoxyquinazoline (6.0 g 13.4 mmol), (WO 96 33980), in 6M hydrochloric acid (120 ml) was heated at reflux for 6 hours. The mixture was cooled to 0° C. and carefully neutralised with cooling by addition of concentrated aqueous ammonia. The resulting precipitate was collected by filtration, washed with dilute aqueous ammonia and water and dried under vacuum to give 7-methoxy-6-(3-morpholinopropoxy)-3,4-dihydroquinazolin-4-one (4.2 g).

$^1$H NMR Spectrum: (DMSOd$_6$) 2.4(m, 6H); 3.59(t, 4H); 3.75(t, 2H); 3.90(s, 3H); 4.12(t, 2H); 7.12(s, 1H); 7.43(s, 1H); 7.98(s, 1H); 12.0(br s, 1H).

MS-ESI: 320 [MH]$^+$

| Elemental analysis: | Found | C 58.6 | H 6.5 | N 12.7 |
|---|---|---|---|---|
| C$_{16}$H$_{21}$N$_3$O$_4$ 0.5H$_2$O | Requires | C 58.5 | H 6.7 | N 12.8% |

A solution of 7-methoxy-6-(3-morpholinopropoxy)-3,4-dihydroquinazolin4-one (990 mg, 3.1 mmol) in thionyl chloride (10 ml) and DMF (0.1 ml) was heated at 80° C. for 1.5 hours. The mixture was allowed to cool, toluene was added and the solvent was removed by evaporation. The residue was partitioned between ethyl acetate and water and the aqueous layer was adjusted to pH7.5 with 2M sodium hydroxide solution. The organic layer was separated, washed with brine, dried (MgSO$_4$) and the solvent removed by evaporation. The residue was purified by flash chromatography eluting with methylene chloride/methanol (119 followed by 95/5). The purified solid was triturated with hexane, collected by filtration and washed with ether to give 4-chloro-7-methoxy-6-(3-morpholinopropoxy)quinazoline (614 mg, 58%).

$^1$H NMR Spectrum: (CDCl$_3$) 2.12(m, 2H); 2.50(br s, 4H); 2.59(t, 2H); 3.73(t, 4H); 4.05(s, 3H); 4.27(t, 2H); 7.33(s, 1H); 7.40(s, 1H); 8.86(s, 1H).

EXAMPLE 19

A solution of 5,6-dimethoxyoxindole (107 mg, 0.56 mmol), (Chem Pharm Bull. 1971, 19, 1325–1327), in a mixture of THF (1 ml) and DMF (1 ml) was added dropwise under nitrogen to a suspension of sodiumn hydride (22 mg, 0.55 mmol, prewashed with hexane) in THF (1 ml). The mixture was stirred for 20 minutes at ambient temperature and a solution of 4-chloro-6-methoxy-7-(2-methoxyethoxy) quinazoline (50 mg, 0.18 mmol), (prepared as described for the starting material in Example 2), in THF (1 ml) was added dropwise. The mixture was heated at 60° C. for 1.5 hours, allowed to cool and partitioned between ethyl acetate and water. The aqueous layer was adjusted to pH7 with 1M hydrochloric acid. The organic layer was washed with brine, dried (MgSO$_4$), and volatiles removed by evaporation. The residue was purified by column flash chromatography eluting with methylene chloride/acetonitrile/methanol (60/38/2 followed by 60/35/5). The resulting solid was dissolved in methylene chloride/methanol and 3M ethereal hydrogen chloride was added. The mixture was concentrated by evaporation, the resulting precipitate was collected by filtration, washed with ether and dried under vacuum to give 4-(5,6-dimethoxyoxindol-3-yl)-6-methoxy-7-(2-methoxyethoxy)quinazoline hydrochloride (33 mg, 51%).

$^1$HNMR Spectrum: (DMSOd$_6$, CF$_3$CO$_2$D) 3.35(s, 3H); 3.67(s, 3H); 3.78(m, 2H); 3.82(s, 3H); 3.86(s, 3H); 4.3(m; 2H); 6.67(s, 1H); 7.20(s, 1H); 7.27(s, 1H); 7.67(s, 1H).

MS-ESI: 426 [MH]$^+$

| Elemental analysis: | Found | C 55.4 | H 5.5 | N 8.6 |
|---|---|---|---|---|
| C$_{22}$H$_{23}$N$_3$O$_6$ 0.7H$_2$O 1HCl | Requires | C 55.7 | H 5.4 | N 8.9% |

EXAMPLE 20

A solution of 5-cyanooxindole (285 mg, 1.8 mmol), (Tet. Lett., 1987, 28, 4027), in THF (12 ml) was added dropwise under nitrogen, to a suspension of sodium hydride (96 mg, 2.4 mmol, prewashed with hexane) in THF (5 ml). The mixture was stirred for 20 minutes at ambient temperature, and a solution of 4-chloro-6-methoxy-7-(2-methoxyethoxy) quinazoline (162 mg, 0.6 mmol), (prepared as described for the starting material in Example 2), in DMF (0.5 ml) in THF (3 ml) was added dropwise. The mixture was stirred for 20 minutes at ambient temperature and then 1 hour at 65° C. The solvent was removed by evaporation and the residue was purified by column flash chromatography eluting with methylene chloride/methanol (97/3 followed by 96/4 and 90/10). The solid was collected by filtration, resuspended in methylene chloride and 2M ethereal hydrogen chloride was added. The solid was collected by filtration, washed with ether and dried under vacuum at 60° C. to give 4-(5-cyanooxindol-3-yl)-6-methoxy-7-(2-methoxyethoxy) quinazoline hydrochloride (92 mg, 40%).

$^1$HNMR Spectrum: (DMSOd$_6$, CF$_3$CO$_2$D) 3.36(s, 3H); 3.8(m, 2H); 3.90(s, 3H); 4.34(t, 2H); 7.09(d, 1H); 7.28(s, 1H); 7.46(d, 1H); 7.94(s, 1H); 8.1(s, 1H); 8.70(s, 1H).

MS-ESI: 391 [MH]$^+$

| Elemental analysis: | Found | C 62.6 | H 4.7 | N 14.0 |
|---|---|---|---|---|
| C$_{21}$H$_{18}$N$_4$O$_4$ 0.1HCl 0.4H$_2$O | Requires | C 62.9 | H 4.7 | N 14.0% |

EXAMPLE 21

A solution of 5-nitrooxindole (400 mg, 2.2 mmol) in THF (4 ml) was added to sodium hydride (89 mg, 3.7 mmol, prewashed with THF) in THF (4 ml). The mixture was stirred for 30 minutes at ambient temperature and a solution of 4-chloro-6-methoxy-7-(2-methoxyethoxy)quinazoline (200 mg, 0.75 mmol), (prepared as described for the starting material in Example 2), in THF (3 ml) and DMF (1 ml) was added dropwise. The mixture was stirred for 1 hour at ambient temperature, followed by 1.5 hours at 70° C. The solvent was removed by evaporation and the residue was partitioned between ethyl acetate and water. The aqueous layer was adjusted to pH7 with 2M hydrochloric acid. The precipitated product was collected by filtration, washed with ether and dried under vacuum at 60° C. The solid was dissolved in methanol (10 ml) and 7.5M hydrogen chloride in methanol (2 ml) was added. The volatiles were removed by evaporation, the solid residue was triturated with ether, collected by filtration and dried under vacuum to give 6-methoxy-7-(2-methoxyethoxy)-4-(5-nitrooxindol-3-yl) quinazoline hydrochloride (173 mg, 57%).

$^1$H NMR Spectrum: (DMSOd$_6$, CF$_3$CO$_2$D) 3.36(s, 3H); 3.79(t, 2H); 3.87(s, 3H); 4.35(t, 2H); 7.1(d, 1H); 7.31(s, 1H); 7.95(br s, 1H); 8.01(d, 1H); 8.56(br s, 1H); 8.66(s, 1H).

MS-ESI: 411 [MH]$^+$

The starting material was prepared as follows:

Fuming nitric acid (1.58 ml, 39.4 mmol) was added dropwise to a solution of oxindole (5 g, 37.5 mmol) in concentrated sulphuric acid (25 ml) cooled by an ice bath and maintained below 5° C. The mixture was stirred for 30 minutes at 0° C. and then poured into water. The precipitate was collected by filtration and thoroughly washed with water. The solid was suspended in 50% acetic acid (100 ml) and heated at 90° C. for 1 hour. The mixture was allowed to cool, the solid product was collected by filtration, washed with water and dried under vacuum over phosphorus pentoxide at 40° C. to give 5-nitrooxindole (3.2 g, 48%).

$^1$H NMR Spectrum: (CDCl$_3$, CD$_3$CO$_2$D) 3.68(s, 2H); 7.05(d, 1H); 8.16(s, 1H); 8.22(s, 1H)

MS-EI: 178 [M]$^+$

| Elemental analysis: | Found | C 53.6 | H 3.5 | N 15.7 |
|---|---|---|---|---|
| C$_8$H$_6$N$_2$O$_3$ | Requires | C 53.9 | H 3.39 | N 15.7% |

EXAMPLE 22

A solution of oxindole (164 mg, 1.23 mmol) in THF (3 ml) was added dropwise under nitrogen, to sodiun hydride (49 mg, 1.23 mmol, prewashed with hexane) in THF (3 ml). The mixture was stirred for 30 minutes at ambient temperature and DMF (2 ml) and then 4-chloro-7-(2-(imidazol-1-yl)ethoxy)-6-methoxyquinazoline (125 mg, 0.41 mmol) was added. The mixture was heated at 60° C. for 30 minutes and the THF was removed by evaporation. The residue was partitioned between saturated aqueous ammonium chloride solution and ether. The organic layer was separated, dried ($MgSO_4$) and the solvent removed by evaporation. The solid was dissolved in methylene chloride (5 ml), methanol (0.5 ml) and isopropanol (3 ml) and SM isopropanolic hydrogen chloride (0.5 ml) was added. The mixture was concentrated by evaporation to 2 ml total volume and the resulting precipitated solid was collected by filtration, washed with isopropanol followed by ether and dried under vacuum to give 7-(2-(imidazol-1-yl)ethoxy)-6-methoxy4-(oxindol-3-yl)quinazoline hydrochloride (110 mg, 61%).

$^1$H NMR Spectrum: ($DMSOd_6$, $CF_3CO_2D$) 3.85(s, 3H); 4.62(m, 2H); 4.75(m, 2H); 7.0–7.1(m, 2H); 7.16(t, 1H); 7.35(s, 1H); 7.68(d, 1H); 7.73(s, 1H); 7.77(s, 1H); 7.84(s, 1H); 8.83(s, 1H); 9.2(s, 1H).

MS-ESI: 402 $[MH]^+$

| Elemental analysis: | Found | C 55.7 | H 5.3 | N 13.1 |
|---|---|---|---|---|
| $C_{22}H_{19}N_5O_3$ $1H_2O$ 1.6HCl | Requires | C 55.7 | H 5.5 | N 13.3% |

0.8isopropanol

The starting material was prepared as follows:

Sodium hydride (1.44 g of a 60% suspension in mineral oil, 36 mmol) was added in portions over 20 minutes to a solution of 7-benzyloxy-6-methoxy-3,4-dihydroquinazolin-4-one (8.46 g, 30 mmol), (prepared as described for the starting material in Example 11), in DMF (70 ml) and the mixture was stirred for 1.5 hours. Chloromethyl pivalate (5.65 g, 37.5 mmol) was added dropwise and the mixture stirred for 2 hours at ambient temperature. The mixture was diluted with ethyl acetate (lOOmi) and poured onto ice/water (400 ml) and 2M hydrochloric acid (4 ml). The organic layer was separated and the aqueous layer extracted with ethyl acetate, the combined extracts were washed with brine, dried ($MgSO_4$) and the solvent removed by evaporation. The residue was triturated with a mixture of ether and petroleum ether, the solid was collected by filtration and dried under vacuum to give 7-benzyloxy-6-methoxy-3-((pivaloyloxy)methyl)-3,4-dihydroquinazolin-4-one (10 g, 84%).

$^1$H NMR Spectrum: ($DMSOd_6$) 1.11(s, 9H); 3.89(s, 3H); 5.3(s, 2H); 5.9(s, 2H); 7.27(s, 1H); 7.35(m, 1H); 7.47(t, 2H); 7.49(d, 2H); 7.51(s, 1H); 8.34(s, 1H).

A mixture of 7-benzyloxy-6-methoxy-3-((pivaloyloxy)methyl)-3,4-dihydroquinazolin-4-one (7 g, 17.7 mmol) and 10% palladium-on-charcoal catalyst (700 mg) in ethyl acetate (250 ml), DMF (50 ml), methanol (50 ml) and acetic acid (0.7 ml) was stirred under hydrogen at atmospheric pressure for 40 minutes. The catalyst was removed by filtration and the solvent removed from the filtrate by evaporation. The residue was triturated with ether, collected by filtration and dried under vacuum to give 7-hydroxy-6-methoxy-3-((pivaloyloxy)methyl)-3,4-dihydroquinazolin-4-one (4.36 g, 80%).

$^1$H NMR Spectrum: ($DMSOd_6$) 1.1(s, 9H); 3.89(s, 3H); 5.89(s, 2H); 7.0(s, 1H); 7.48(s, 1H); 8.5(s, 1H).

Diethyl azodicarboxylate (435 mg, 2.5 mmol) was added dropwise to a suspension of 7-hydroxy-6-methoxy-3-((pivaloyloxy)methyl)-3,4-dihydroquinazolin4-one (612 mg, 2 mmol), 2-(imidazol-1-yl)ethanol (280 mg, 2.5 mmol), (J. Med. Chem. 1993, 25 4052–4060), and triphenylphosphine (655 mg, 2.5 mmol) in methylene chloride (10 ml) at 5° C. The mixture was stirred for 10 minutes at 5° C. and then 1 hour at ambient temperature. The mixture was poured directly on to a silica column and eluted with methylene chloride/methanol (95/5) to give 7-(2-(imidazol-1-yl)ethoxy)-6-methoxy-3-((pivaloyloxy)methyl)-3,4-dihydroquinazolin-4-one (640 mg, 80%).

$^1$H NMR Spectrum: ($CDCl_3$) 1.19(s, 9H); 3.98(s, 3H); 4.34(m, 2H); 4.45(m, 2H); 5.94(s, 1H); 7.02(s, 1H); 7.07(s, 1H); 7.11(s, 1H); 7.64(s, 1H); 7.67(s, 1H); 8.17(s, 1H).

MS-ESI: 423 $[MNa]^+$

| Elemental Analysis: | Found | C 58.3 | H 6.4 | N 13.9 |
|---|---|---|---|---|
| $C_{20}H_{24}N_4O_5$ $0.7H_2O$ | Requires | C 58.2 | H 6.2 | N 13.6% |

A solution of 7-(2-(imidazol-1-yl)ethoxy)-6-methoxy-3-((pivaloyloxy)methyl)-3,4-dihydroquinazolin-4-one (640 mg, 1.6 mmol) in saturated methanolic ammonia (10 ml) was stirred for 15 hours at ambient temperature. The volatiles were removed by evaporation, the solid was triturated with ether, collected by filtration and dried under vacuum to give 7-(2-(imidazol-1-yl)ethoxy)-6-methoxy-3,4-dihydroquinazolin-4-one (412 mg, 90%).

$^1$H NMR Spectrum: ($DMSOd_6$) 3.89(s, 3H); 4.4–4.5(m, 4H); 6.9(s, 1H); 7.16(s, 1H); 7.38(s, 1H); 7.47(s, 1H); 7.7(s, 1H); 7.99(s, 1H).

MS-ESI: 287 $[MH]^+$

| Elemental Analysis: | Found | C 57.8 | H 5.2 | N 19.3 |
|---|---|---|---|---|
| $C_{14}H_{14}N_4O_3$ $0.3H_2O$ | Requires | C 57.7 | H 5.1 | N 19.2% |

A mixture of 7-(2-(imidazol-1-yl)ethoxy)-6-methoxy-3,4-dihydroquinazolin-4-one (412 mg, 1.44 mmol), thionyl chloride (5 ml) and DMF (0.2 ml) was heated at reflux for 1 hour. The mixture was diluted with toluene and the volatiles were removed by evaporation. The residue was suspended in methylene chloride, cooled to 0° C. and aqueous sodium hydrogen carbonate solution was added. The resulting precipitate was collected by filtration and dried under vacuum to give 4-chloro-7-(2-(imidazol-1-yl)ethoxy)-6-methoxyquinazoline (258 mg, 59%).

$^1$H NMR Spectrum: ($DMSOd_6$) 4.01(s, 3H); 4.47(m, 2H); 4.53(m, 2H); 6.89(s, 1H); 7.27(s, 1H); 7.41(s, 1H); 7.49(s, 1H); 7.70(s, 1H); 8.88(s, 1H).

MS-ESI: 327 $[MNa]^+$

EXAMPLE 23

A solution of oxindole (232 mg, 1.74 mmol) in THF (3 ml) was added dropwise under nitrogen, to sodium hydride (70 mg, 1.74 mmol, prewashed with hexane) in THF (3 ml). The mixture was stirred for 30 minutes at ambient temperature and 4-chloro-6-methoxy-7-(4-pyridylmethoxy) quinazoline (175 mg, 0.58 mmol) and then DMF (2 ml) was added. The mixture was heated at 60° C. for 1 hour and the THF was removed by evaporation. The residue was partitioned between cooled 2M hydrochloric acid and ethyl acetate. The organic layer was extracted with 2M hydrochloric acid. The aqueous layers were combined, washed with ethyl acetate and ether, basified with aqueous sodium hydrogen carbonate and extracted with methylene chloride. The organic layer was washed with brine, dried ($MgSO_4$) and the solvent removed by evaporation. The residue was purified by chromatography on neutral aluminium oxide eluting with methylene chloride/methanol (90/10 followed by 80/20 and 75/25). The purified solid product was dissolved in methanol/methylene chloride and 5M methanolic hydrogen chloride (0.5 ml) was added. The volatiles were removed by evaporation, the residue was resuspended in ether, collected by filtration, washed with ether and dried under vacuum to give 6-methoxy4-(oxindol-3-yl)-7-(4-pyridylmethoxy)quinazoline hydrochloride (50 mg, 21%).

$^1$H NMR Spectrum: (DMSOd$_6$, CF$_3$CO$_2$D) 3.93(s, 3H); 5.75(s, 2H); 7–7.1(m, 2H); 7.18(t, 1H); 7.35(s, 1H); 7.75(d, 1H); 7.88(s, 1H); 8.17(d, 2H); 8.8(m, 1H); 9.05(d, 2H).

MS-ESI: 399 [MH]$^+$

The starting material was prepared as follows:

Diethyl azodicarboxylate (348 mg, 2 mmol) was added dropwise to a suspension of 7-hydroxy-6-methoxy-3-((pivaloyloxy)methyl)-3,4-dihydroquinazolin-4-one (457 mg, 1.5 mmol), (prepared as described for the starting material in Example 22), 4-pyridinemethanol (218 mg, 2 mmol), and triphenylphosphine (524 mg, 2 mmol) in methylene chloride (7 ml) at 5° C. The mixture was stirred for 10 minutes at 5° C. and then 1 hour at ambient temperature. The mixture was poured directly on to a silica column and eluted with methylene chloride/methanol (95/5) to give 6-methoxy-3-((pivaloyloxy)methyl)-7-(4-pyridylmethoxy)-3,4-dihydroquinazolin-4-one (510 mg, 85%).

$^1$H NMR Spectrum: (DMSOd$_6$) 1.11 (s, 9H); 3.93(s, 3H); 5.38(s, 2H); 5.9(s, 2H); 7.23(s, 1H); 7.46(d, 2H); 7.55(s, 1H); 8.35(s, 1H); 8.60(d, 2H).

MS-ESI: 420 [MNa]$^+$

| Elemental Analysis: | Found | C 63.2 | H 6.0 | N 10.6 |
|---|---|---|---|---|
| C$_{21}$H$_{23}$N$_3$O$_5$ | Requires | C 63.5 | H 5.8 | N 10.6% |

A solution of 6-methoxy-3-((pivaloyloxy)methyl)-7-(4-pyridylmethoxy)-3,4-dihydroquinazolin-4-one (500 mg, 1.26 mmol) in saturated methanolic ammonia (10 ml) was stirred for 20 hours at ambient temperature. The volatiles were removed by evaporation, the solid residue was triturated with ether, collected by filtration and dried under vacuum to give 6-methoxy-7-(4-pyridylmethoxy)-3,4-dihydroquinazolin-4-one (330 mg, 92%).

$^1$H NMR Spectrum: (DMSOd$_6$) 3.91(s, 3H); 5.5(s, 2H); 7.19(s, 1H); 7.4–7.5(m, 3H); 7.97(s, 1H); 8.6(d, 2H).

MS-EI: 283 [M]$^+$

| Elemental analysis: | Found | C 61.9 | H 5.1 | N 14.8 |
|---|---|---|---|---|
| C$_{15}$H$_{13}$N$_3$O$_3$ 0.4H$_2$O | Requires | C 62.0 | H 4.8 | N 14.5% |

A suspension of 6-methoxy-7-(4-pyridylmethoxy)-3,4-dihydroquinazolin-4-one (300 mg, 1.06 mmol) in thionyl chloride (5 ml) containing DMF (50 µl) was heated at reflux for 1 hour. The mixture was allowed to cool, diluted with toluene and the volatiles were removed by evaporation. The residue was dissolved in methylene chloride and a cooled solution of aqueous sodium hydrogen carbonate was added. The resulting precipitate was collected by filtration, washed with ether and dried under vacuum to give 4-chloro-6-methoxy-7-(4-pyridylmethoxy)quinazoline (175 mg, 55%).

$^1$H NMR Spectrum: (DMSOd$_6$) 4.05(s, 3H); 5.55(s, 2H); 7.47(s, 1H); 7.55(s, 1H); 7.64(d, 2H); 8.7(d, 2H); 8.89(s, 1H).

MS-ESI: 302 [MH]$^+$

EXAMPLE 24

Sodium hydride (62 mg, 2.7 mmol) was added to a solution of 1-diethoxymethyloxindole (317 mg, 1.35 mmol), (prepared as described for the starting material in Example 2), in THF (10 ml). The mixture was stirred for 10 minutes at ambient temperature and 4-chloro-6-methoxy-7-(3-pyrrolidin-1-yl)propoxy)quinazoline (145 mg, 0.45 mmol) in THF (5 ml) was added. The mixture was then stirred for 2 hours at ambient temperature, and was partitioned between methylene chloride and water. The organic layer was separated, washed with brine, dried (MgSO$_4$) and the solvent removed by evaporation. The residue was purified by column chromatography eluting with methylene chloride/methanol (a gradient from 95/5 to 50/50). The purified product was triturated with ether, collected by filtration, washed with ether and dried under vacuum to give 4-(1-diethoxymethyloxindol-3-yl)6-methoxy-7-(3-(pyrrolidin-1-yl)propoxy)quinazoline (218 mg, 94%).

$^1$H NMR Spectrum: (CDCl$_3$, CD$_3$CO$_2$D) 1.26(t, 6H); 2.05–2.15(m, 4H); 2.4(m, 2H); 3.3–3.5(m, 6H); 3.6(q, 2H); 3.8(q, 2H); 3.87(s, 3H); 4.3(t, 2H); 6.47(s, 1H); 7.05(t, 1H); 7.15(t, 1H); 7.29(s, 1H); 7.63(d, 2H); 7.8(s, 1H); 8.3(s, 1H).

MS-ESI: 521 [MH]$^+$

The starting material was prepared as follows:

A mixture of 4-hydroxy-3-methoxybenzoic acid (8.4 g, 50 mmol), 3-(pyrrolidin-1-yl)propyl chloride (14.75 g, 0.1 mol), (prepared according to J. Am. Chem. Soc. 1955, 77. 2272), potassium carbonate (13.8 g, 0.1 mol) and potassium iodide (1.66 g, 10 mmol) in DMF (150 ml) was stirred and heated at 100° C. for 3 hours. The mixture was allowed to cool and the insolubles were removed by filtration and the volatiles were removed from the filtrate by evaporation. The residue was dissolved in ethanol (75ml), 2M aqueous sodium hydroxide (75 ml) was added and the mixture was heated at 90° C. for 2 hours. The mixture was concentrated by evaporation, acidified with concentrated hydrochloric acid, washed with ether and then subjected to purification on a Diaion (trade mark of Mitsubishi) HP20SS resin column, eluting with water and then with a gradient of methanol (0 to 25%) in dilute hydrochloric acid (pH2.2). The methanol was removed by evaporation and the aqueous residue was freeze dried to give 3-methoxy-4-(3-(pyrrolidin-1-yl)propoxy)benzoic acid hydrochloride (12.2 g, 77%).

$^1$H NMR Spectrum: (DMSOd$_6$, CF$_3$CO$_2$D) 2.2(m, 2H); 3.15(t, 2H); 3.3(t, 2H); 3.5(d, 2H); 3.7(t, 2H); 3.82(s, 3H); 4.05(d, 2H); 4.15(t, 2H); 7.07(d, 1H); 7.48(s, 1H); 7.59(d, 1H).

MS-EI: 279 [M]$^+$

Fuming nitric acid (2.4 ml, 57.9 mmol) was added slowly at 0° C. to a solution of 3-methoxy-4-(3-(pyrrolidin-1-yl)propoxy)benzoic acid (12.15 g, 38.17 mmol) in TFA (40ml). The cooling bath was removed and the reaction mixture stirred at ambient temperature for 1 hour. The TFA was removed by evaporation and ice/water was added to the residue and the solvent removed by evaporation. The solid residue was dissolved in dilute hydrochloric acid (pH2.2), poured onto a Diaion (trade mark of Mitsubishi) HP20SS resin column and eluted with methanol (gradient 0 to 50%) in water. Concentration of the fractions by evaporation gave a precipitate which was collected by filtration and dried under vacuum over phosphorus pentoxide to give 5-methoxy-2-nitro-4-(3-(pyrrolidin-1-yl)propoxy)benzoic acid hydrochloride (12.1 g, 90%).

$^1$HNMR Spectrum: (DMSOd$_6$, TFA) 1.8–1.9 (m, 2H); 2.0–2.1(m, 2H); 2.1–2.2(m, 2H); 3.0–3.1(m, 2H); 3.3(t, 2H); 3.6–3.7(m, 2H); 3.95(s, 3H); 4.25(t, 2H); 7.35(s, 1H); 7.62 (s, 1H).

A solution of 5-methoxy-2-nitro-4-(3-(pyrrolidin-1-yl) propoxy)benzoic acid hydrochloride (9.63 g, 24 mmol) in thionyl chloride (20ml) and DMF (50 μl) was heated at 45° C. for 1.5 hours. The excess thionyl chloride was removed by evaporation and by azeotroping with toluene (×2). The resulting solid was suspended in THF (250 ml) and methylene chloride (100 ml) and ammonia was bubbled though the mixture for 30 minutes and the mixture stirred for a further 1.5 hours at ambient temperature. The volatiles were removed by evaporation, the residue was dissolved in water and applied to a Diaion (trade mark of Mitsubishi) HP20SS resin column and eluted with water/methanol (100/0 to 95/5). The solvent was removed by evaporation from the fractions containing product and the residue was dissolved in a minimum of methanol and the solution was diluted with ether. The resulting precipitate was collected by filtration, washed with ether and dried under vacuum to give 5-methoxy-2-nitro4-(3-(pyrrolidin-1-yl)propoxy)benzamide (7.23 g, 73%).

$^1$H NMR Spectrum: (DMSOd$_6$, CF$_3$CO$_2$D) 1.85–1.95(m, 2H); 2–2.1(m, 2H); 2.15–2.25(m, 2H); 3.0–3.1(m, 2H); 3.31(t, 2H); 3.62(t, 2H); 3.93(s, 3H); 4.2(t, 2H); 7.16(s, 1H); 7.60(s, 1H).

MS-EI: 323 [M]$^+$

Concentrated hydrochloric acid (5 ml) was added to a suspension of 5-methoxy-2-nitro-4-(3-(pyrrolidin-1-yl) propoxy)benzamide (1.5 g, 4.64 mmol) in methanol (20 ml) and the mixture was heated at 50° C. to give a solution. Iron powder (1.3 g, 23.2 mmol) was added in portions and the reaction mixture was then heated at reflux for 1 hour. The mixture was allowed to cool, the insolubles were removed by filtration through diatomaceous earth and the volatiles were removed from the filtrate by evaporation. The residue was purified on a Diaion (trade mark of Mitsubishi) HP20SS resin column, eluting with water and then with dilute hydrochloric acid (pH2). The fractions containing product were concentrated by evaporation and the resulting precipitate was collected by filtration and dried under vacuum over phosphorus pentoxide to give 2-amino-5-methoxy-4-(3-(pyrrolidin-1-yl)propoxy)benzamide hydrochloride (1.44 g, 85%).

$^1$H NMR Spectrum: (DMSOd$_6$, CF$_3$CO$_2$D) 1.9(br s, 2H); 2.05(br s, 2H); 2.2(br s, 2H); 3.05(br s, 2H); 3.3(t, 2H); 3.61(br s, 2H); 3.8(s, 3H); 4.11(t, 2H); 7.05(s, 1H); 7.53s, 1H).

MS-EI: 293 [M]$^+$

A mixture of 2-amino-5-methoxy-4-(3-(pyrrolidin-1-yl) propoxy)benzamide hydrochloride (5.92 g, 16.2 mmol),and Gold's reagent (3.5 g, 21.4 mmol) in dioxane (50 ml) was heated at reflux for 5 hours. Acetic acid (0.7 ml) and sodium acetate (1.33 g) were added to the reaction mixture which was heated at reflux for a further 5 hours. The mixture was allowed to cool and the volatiles were removed by evaporation. The residue was dissolved in water, adjusted to pH8 with 2M aqueous sodium hydroxide solution and purified on a Diaion (trademark of Mitsubishi) HP20SS resin column eluting with methanol (gradient 0–50%) in water. The fractions containing product were concentrated by evaporation and then freeze dried to give 4-hydroxy-6-methoxy-7-(3-(pyrrolidin-1-yl)propoxy)quinazoline (4.55 g, 83%).

$^1$H NMR Spectrum: (DMSOd$_6$, CF$_3$CO$_2$D) 1.9(m, 2H); 2.0–2.1(m, 2H); 2.2–2.3(m, 2H); 3.05(m, 2H); 3.34(t, 2H); 3.6–3.7(br s, 2H); 3.94(s, 3H); 4.27(t, 2H); 7.31(s, 1H); 7.55(s, 1H); 9.02(s, 1H).

A mixture of 4-hydroxy-6-methoxy-7-(3-(pyrrolidin-1-yl) propoxy)quinazoline (1.7 g, 5 mmol) and thionyl chloride (25 ml) containing DMF (0.2 ml) was heated at reflux for 3 hours. Excess thionyl chloride was removed by evaporation and by azeotroping with toluene (×2). The residue was suspended in ether and 10% aqueous solution of sodium hydrogen carbonate was added to the mixture. The organic layer was separated, dried (MgSO$_4$) and the solvent removed by evaporation to give 4-chloro-6-methoxy-7-(3-(pyrrolidin-1-yl)propoxy)quinazoline (1.94 g, quantitative).

$^1$H NMR Spectrum: (CDCl$_3$) 1.8(br s, 4H); 2.17(m, 2H); 2.6(br s, 4H); 2.7(t, 2H); 4.05(s, 3H); 4.3(t, 2H); 7.35(s, 1H); 7.38(s, 1H); 8.86(s, 1H).

MS-ESI: 322 [MH]$^+$

EXAMPLE 25

2M Hydrochloric acid (1.5 ml, 3 mmol) was added to a solution of 4-(1-diethoxymethyloxindol-3-yl)-6-methoxy-7-(3-(pyrrolidin-1-yl)propoxy)quinazoline (151 mg, 0.29 mmol), (prepared as described in Example 24), in ethanol (15 ml) at 80° C. and the mixture was stirred at 80° C. for 1.5 hours. The reaction mixture was allowed to cool, the solvent was removed by evaporation and the residue was purified by reverse phase C18 chromatography eluting with a gradient of acetonitrile in water (0–40%). The acetonitrile was removed by evaporation from the fractions containing product and concentrated hydrochloric acid (0.1 ml) was added to the aqueous phase. The solution was freeze dried to give 6-methoxy4-(oxindol-3-yl)-7-(3-(pyrrolidin-1-yl) propoxy)quinazoline hydrochloride (150 mg, 100%).

$^1$H NMR Spectrum: (DMSOd$_6$, CF$_3$CO$_2$D) 1.85–1.95(m, 2H); 2.0–2.1(m, 2H); 2.2–2.3(m, 2H); 3.0–3.1(m, 2H); 3.3–3.4(t, 2H); 3.6–3.7(m, 2H); 3.87(s, 3H); 4.3(t, 2H); 7.0–7.1(m, 2H); 7.15–7.2(t, 1H); 7.33(s, 1H); 7.68(d, 1H); 7.8(s, 1H); 8.9(s, 1H).

MS-ESI: 419 [MH]$^+$

| Elemental analysis: | Found | C 53.9 | H 6.4 | N 10.7 |
| --- | --- | --- | --- | --- |
| C$_{24}$H$_{26}$N$_4$O$_3$ 3H$_2$O 1.6HCl | Requires | C 54.3 | H 6.3 | N 10.7% |

EXAMPLE 26

A solution of 5-cyanooxindole (213 mg, 1.35 mmol), (Tet. Lett., 1987, 28, 4027), in DMF (3 ml) was added dropwise to a suspension of sodium hydride (54 mg, 1.35 mmol, prewashed with hexane) in DMF (2 ml). The mixture was stirred for 20 minutes at ambient temperature, 4-chloro-6-methoxy-7-(3-morpholinopropoxy)quinazoline (152 mg, 0.45 mmol), (prepared as described for the starting material in Example 5), was added and the mixture was heated at 70° C. for 1 hour. The mixture was allowed to cool and then was diluted with water and adjusted to pH1 with 2M hydrochloric acid. The solution was washed with ether and then basified with aqueous sodium hydrogen carbonate solution. The resulting precipitate was collected by filtration, washed with water, ether and dried under vacuum. The solid was purified by flash chromatography eluting with methylene chloride/methanol (90/10 followed by 80/20). The purified solid was dissolved in methylene chloride/methanol and 5M methanolic hydrogen chloride (0.5 ml) was added. The solution was concentrated by evaporation to a total volume of 2 ml and ether (15 ml) was added. The resulting solid was collected by filtration, washed with ether and dried under vacuum to give 4-(5-cyanooxindol-3-yl)-6-methoxy-7-(3-morpholinopropoxy)quinazoline hydrochloride (120 mg, 50%).

¹H NMR Spectrum: (DMSOd₆, CF₃CO₂D) 2.32(m, 2H); 3.15(t, 2H); 3.35(t, 2H); 3.54(d, 2H); 3.75(t, 2H); 3.91(s, 3H); 4.05(d, 2H); 4.33(t, 2H); 7.10(d, 1H); 7.31(s, 1H); 7.47(d, 1H); 7.97(s, 1H); 8.06(s, 1H); 8.67(s, 1H).

MS-ESI: 460 [MH]⁺

| Elemental analysis: | Found | C 54.9 | H 5.4 | N 12.9 |
|---|---|---|---|---|
| $C_{25}H_{25}N_5O_4$ 1.1H₂O 1.75HCl | Requires | C 55.3 | H 5.4 | N 12.9% |

EXAMPLE 27

A solution of 5-nitrooxindole (1.26 g, 7.1 mmol), (prepared as described for the starting material in Example 21), in THF (10 ml) was added dropwise to sodium hydride (284 mg, 7.1 mmol, prewashed with THF) in THF (15 ml). The mixture was stirred for 30 minutes at ambient temperature and a solution of 4-chloro-6-methoxy-7-(3-morpholinopropoxy)quinazoline (600 mg, 1.8 mmol, (prepared as described for the starting material in Example 5), in THF (10 ml) and DMF (3 ml) was added dropwise. The mixture was stirred for 30 minutes at ambient temperature, then heated at 75° C. for 1.5 hours. DMF (4 ml) was added and the mixture stirred for 12 hours at ambient temperature. The solvent was removed by evaporation, the residue was partitioned between ethyl acetate and water and the aqueous layer was adjusted to pH8 with 2M hydrochloric acid. The precipitated product was collected by filtration, washed with water and dried under vacuum. The solid was dissolved in a mixture of DMF and dilute hydrochloric acid (pH2) and was purified on a Diaion (trade mark of Mitsubishi) HP20SS resin column, eluting with a gradient of methanol and dilute hydrochloric acid (pH2). The purified solid was dissolved in methanol and 7M ethanolic hydrogen chloride (1.5 ml) was added. The volatiles were removed by evaporation and the solid residue was triturated with a mixture of methanol and ether. The solid was collected by filtration and dried under vacuum to give 6-methoxy-7-(3-morpholinopropoxy)-4-(5-nitrooxindol-3-yl)-quinazoline hydrochloride (275 mg, 29%).

¹H NMR Spectrum: (DMSOd₆, CF₃CO₂D) 1.9–2.1(m, 2H); 2.9(t, 2H); 3.06(t, 2H); 3.25(d, 2H); 3.41(t, 2H); 3.57(s, 3H); 3.72(d, 2H); 4.04(t, 2H); 6.8(d, 1H); 7.02(s, 1H); 7.65–7.75(m, 2H); 8.2(br s, 1H); 8.31(s, 1H).

MS-ESI: 480 [MH]⁺

| Elemental analysis: | Found | C 50.5 | H 5.5 | N 11.9 |
|---|---|---|---|---|
| $C_{24}H_{25}N_5O_6$ 2.5H₂O 1.3HCl | Requires | C 50.4 | H 5.5 | N 12.2% |

EXAMPLE 28

A solution of oxindole (259 mg, 1.95 mmol) in THF (3 ml) was added dropwise to a suspension of sodium hydride (78 mg, 1.95 mmol, prewashed with hexane) in THF (3 ml). The mixture was stirred for 30 minutes at ambient temperature and a solution of 4-chloro-6-methoxy-7-(2-(pyrrolidin-1-yl)ethoxy)quinazoline (200 mg, 0.65 mmol) in DMF (3 ml) was added dropwise. The mixture was heated at 60° C. for 30 minutes, the THF was removed by evaporation and the residue was partitioned between methylene chloride and water. The organic layer was separated, washed with brine, dried (MgSO₄) and the solvent removed by evaporation. The solid residue was purified by chromatography on neutral aluminium oxide eluting with methylene chloride/methanol (80/20). The purified solid was dissolved in methylene chloride containing methanol and 3M ethereal hydrogen chloride was added. The volatiles were removed by evaporation and the residue was suspended in ether. The solid was collected by filtration, washed with ether and dried under vacuum to give 6-methoxy-4-(oxindol-3-yl)-7-(2-(pyrrolidin-1-yl)ethoxy)quinazoline hydrochloride (55 mg, 18%).

¹H NMR Spectrum: (DMSOd₆, CF₃CO₂D) 1.85–1.95(m, 2H); 2.05–2.2(m, 2H); 3.15–3.3(m, 2H); 3.65–3.8(m, 4H); 3.88(s, 3H); 4.57(m, 2H); 7.0–7.1(m, 2H); 7.16(t, 1H); 7.38(s, 1H); 7.68(d, 1H); 7.81(s, 1H); 8.82(br s, 1H).

MS-ESI: 405 [MH]⁺

| Elemental Analysis: | Found | C 56.1 | H 5.9 | N 11.0 |
|---|---|---|---|---|
| $C_{23}H_{24}N_4O_3$ 1H₂O 1.95HCl | Requires | C 56.0 | H 5.7 | N 11.3% |

The starting material was prepared as follows:

Diethyl azodicarboxylate (566 mg, 3.25 mmol) was added dropwise to a solution of 7-hydroxy-6-methoxy-3-((pivaloyloxy)methyl)-3,4-dihydroquinazolin-4-one (765 mg, 2.5 mmol), (prepared as described for the starting material in Example 22), 1-(2-hydroxyethyl)pyrrolidine (374 mg, 3.25 mmol) and triphenylphosphine (851 mg, 3.25 mmol) in methylene chloride (15 ml). The mixture was stirred for 1 hour at ambient temperature and further triphenylphosphine (861 mg, 3.25 mmol) followed by diethyl azodicarboxylate (566 mg, 3.25 mmol) was added. The mixture was stirred for 1 hour at ambient temperature and the solvent was removed by evaporation. The residue was dissolved in ethyl acetate/ether and extracted with 2M hydrochloric acid. The aqueous layer was basified by addition of solid sodium hydrogen carbonate and extracted with methylene chloride. The combined extracts were dried (MgSO₄), and the solvent removed by evaporation. The resulting oil was purified by column chromatography on neutral aluminium oxide eluting with methylene chloride/methanol (90/10 followed by 80/20) to give 6-methoxy-3-((pivaloyloxy)methyl)-7-(2-(pyrrolidin-1-yl)ethoxy)-3,4-dihydroquinazolin-4-one (550 mg, 55%).

¹H NMR Spectrum: (DMSOd₆, CF₃CO₂D) 1.12(s, 9H); 1.75–1.85(m, 2H); 2–2.1(m, 2H); 3.15–3.25(m, 2H); 3.65–3.75(m, 4H); 3.93(s, 3H); 4.50(t, 2H); 5.93(s, 2H); 7.31(s, 1H); 7.57(s, 1H); 8.41(s, 1H).

MS-ESI: 404 [MH]⁺

A solution of 6-methoxy-3-((pivaloyloxy)methyl)-7-(2-(pyrrolidin-1-yl)ethoxy)-3,4-dihydroquinazolin-4-one (524 mg, 1.3 mmol) in methanol saturated with ammonia (10 ml) was stirred for 20 hours at ambient temperature. The volatiles were removed by evaporation and the solid residue was triturated with ether, collected by filtration and dried under vacuum to give 6-methoxy-7-(2-(pyrrolidin-1-yl)ethoxy)-3,4-dihydroquinazolin-4-one (230 mg, 61%).

¹H NMR Spectrum: (DMSOd₆, CF₃CO₂D) 1.9–2.0(m, 2H); 2.05–2.2(m, 2H); 3.15–3.3(m, 2H); 3.6–3.8(m, 4H); 3.98(s, 3H); 4.53(t, 2H); 7.38(s, 1H); 7.61(s, 1H); 9.13(s, 1H).

A solution of 6methoxy-7-(2-(pyrrolidin-1-yl)ethoxy)-3,4-dihydroquinazolin-4-one (228 mg, 7.9 mmol) in thionyl chloride (5 ml) and DMF (0.2 ml) was heated at reflux for 1 hour. Toluene was added and the volatiles were removed by evaporation. The residue was dissolved in methylene chloride and cooled aqueous sodium hydrogen carbonate solution was added. The organic layer was separated, washed with brine, dried (MgSO$_4$) and the solvent removed by evaporation to give 4-chloro-6-methoxy-7-(2-(pyrrolidin-1-yl)ethoxy)quinazoline (200 mg, 82%).

MS-[ESI]: 307 [M.]$^+$

EXAMPLE 29

A solution of 1-acetyloxindole (251 mg, 1.6 mmol), ( J. Med. Chem. 1986, 1838), in DMF (3 ml) was added to a suspension of sodium hydride (50 mg, 2.4 mmol) in DMF (10 ml) and the mixture stirred for 10 minutes at ambient temperature. 4-Chloro-6-methoxy-7-(2-methoxyethoxy) quinazoline (108 mg, 0.4 mmol), (prepared as described for the starting material in Example 2), in DMF (3 ml) was added and the mixture stirred for 1.5 hours at ambient temperature. The solvent was removed by evaporation and the residue was partitioned between methylene chloride and water. The organic layer was separated, washed with water, brine, dried (MgSO$_4$) and the solvent removed by evaporation. The residue was purified by column chromatography eluting with methylene chloride/ethyl acetate (70/30). The purified product was recrystallised from methylene chloride/ ether, collected by filtration, washed with ether and dried under vacuum to give 4-(1-acetyloxindol-3-yl)-6-methoxy-7-(2-methoxyethoxy)quinazoline (77 mg, 47%).

$^1$H NMR Spectrum: (CDCl$_3$) 2.82(s, 3H); 3.49(s, 3H); 3.87(s, 3H); 3.90(m, 2H); 4.36(m, 2H); 7.1–7.2(m, 2H); 7.22(s, 1H); 7.61(d, 1H); 7.76(s, 1H); 8.16(s, 1H); 8.37(d, 1H).

MS-EI: 407 [M.]$^+$

| Elemental analysis: | Found | C 64.5 | H 5.4 | N 10.4 |
|---|---|---|---|---|
| C$_{22}$H$_{21}$N$_3$O$_5$ | Requires | C 64.9 | H 5.2 | N 10.3% |

EXAMPLE 30

A solution of 5-acetamidooxindole (212 mg, 1.1 mmol), (Zh. Obshch. Khim 1956, 26, 2019–2022), in DMF (2 ml) was added dropwise to sodium hydride.(89 mg, 2.23 mmol, prewashed with THF) in DMF (2 ml). The mixture was stirred for 5 minutes at ambient temperature and a solution of 4-chloro-6-methoxy-7-(2-methoxyethoxy)quinazoline (100 mg, 0.37 mmol), (prepared as described for the starting material in Example 2), in DMF (2 ml) was added. The mixture was stirred for 1.5 hours at ambient temperature, the solvent was removed by evaporation and the mixture was partitioned between methylene chloride and water. The aqueous layer was adjusted to pH7 with 2M hydrochloric acid. The organic layer was separated, dried (MgSO$_4$) and the solvent was removed by evaporation. The residue was purified by chromatography eluting with methanol/ methylene chloride (gradient from 5/95 to 15/85). The purified solid was dissolved in methylene chloride and 4M methanolic hydrogen chloride (4ml) was added. The volatiles were removed by evaporation, the solid residue was triturated with ether, collected by filtration, washed with ether and dried under vacuum at 60° C. to give 4-(5-acetamidooxindol-3-yl)-6-methoxy-7-(2-methoxyethoxy) quinazoline hydrochloride (95 mg, 56%).

$^1$H NMR Spectrum: (DMSOd$_6$, CF$_3$CO$_2$D) 2.01(s, 3H); 3.36(s, 3H); 3.78(t, 2H); 3.84(s, 3H); 4.33(t, 2H); 6.9(d, 1H); 7.3(s, 1H); 7.34(d, 1H); 7.68(s, 1H); 8.17(s, 1H); 8.9(s, 1H).

MS-EI: 422 [M]$^+$

| Elemental analysis: | Found | C 54.4 | H 5.1 | N 11.9 |
|---|---|---|---|---|
| C$_{22}$H$_{22}$N$_4$O$_5$ 1.3H$_2$O 1HCl | Requires | C 54.8 | H 5.3 | N 11.6% |

EXAMPLE 31

A solution of 5-methylthiooxindole (668 mg, 3.7 mmol) in DMF (3 ml) was added to a suspension of sodium hydride (149 mg, 3.7 mmol, prewashed with THF) in DMF (3 ml). The mixture was stirred for 30 minutes at ambient temperature and a solution of 4-chloro-6-methoxy-7-(3-morpholinopropoxy)quinazoline (420 mg, 1.2 mmol), (prepared as described for the starting material in Example 5), in DMF (3 ml) was added dropwise. The mixture was stirred for 1.5 hours at ambient temperature and the solvent was removed by evaporation. The residue was partitioned between water and ether and the aqueous layer was adjusted to pH8 with 2M hydrochloric acid. The precipitated product was collected by filtration, washed with water and dried under vacuum over phosphorus pentoxide. The solid was purified by column chromatography eluting with methylene chloride/methanol (95/5 followed by 90/10). The purified solid was dried under vacuum to give the product as the free base (450 mg, 75%). The free base product (100 mg) was dissolved in methylene chloride/methanol and a solution of 2.5M ethereal hydrogen chloride (1.5 ml) was added. The volatiles were removed by evaporation to give 6-methoxy4-(5-methylthiooxindol-3-yl)-7-(3-morpholinopropoxy) quinazoline hydrochloride (108 mg).

$^1$H NMR Spectrum: (DMSOd$_6$, CF$_3$CO$_2$D) 2.25–2.35(m, 2H); 2.42(s, 3H); 3.15(t, 2H); 3.35(t, 2H); 3.54(d, 2H); 3.75(t, 2H); 3.91(s, 3H); 4.05(d, 2H); 4.32(t, 2H); 7.01(d, 1H); 7.15(d, 1H); 7.33(s, 1H); 7.63(s, 1H); 7.79(s, 1H); 8.8(s, 1H).

MS-EI: 480 [M]$^+$

| Elemental analysis: | Found | C 53.3 | H 5.8 | N 9.7 |
|---|---|---|---|---|
| C$_{25}$H$_{28}$N$_4$O$_4$S 1.5H$_2$O 1.55HCl | Requires | C 53.2 | H 5.8 | N 9.9% |

The starting material was prepared as follows:

A solution of methyl 5-fluoro-2-nitrophenylacetate (3 g, 14 mmol), (Synthesis 1993, 51), in DMSO (10 ml) was added to a suspension of sodium thiomethoxide (1.08 g, 15.5 mmol) in anhydrous DMSO (10 ml). The mixture was stirred for 10 minutes at ambient temperature and further sodium thiomethoxide (100 mg, 1.5 mmol) was added. The mixture was stirred for 15 minutes at ambient temperature and was then partitioned between ethyl acetate and water. The organic layer was separated, washed with water, brine, dried (MgSO$_4$) and the solvent removed by evaporation. The residue was purified by column chromatography eluting with ethyl acetate/petroleum ether (15/85) to give methyl 5-methylthio-2-nitrophenylacetate (2.68 g, 81%).

$^1$H NMR Spectrum: (CDCl$_3$) 2.54(s, 3H); 3.71(s, 3H); 4.01(s, 2H); 7.09(s, 1H); 7.23(d, 1H); 8.10(d, 1H).

MS-EI: 240 [M]$^+$

Iron powder (2.36 g, 42 mmol) was added in portions to a solution of methyl 5-methylthio-2-nitrophenylacetate (2.55 g, 10.6 mmol) in acetic acid (30 ml) and the mixture was heated at 100° C. for 1 hour. The mixture was allowed to cool and the insolubles were removed by filtration and the filter pad was thoroughly washed with acetic acid and then ethyl acetate. The volatiles were removed from the filtrate by evaporation and the residue was dissolved in ethyl acetate and was washed with 1M hydrochloric acid (50 ml×3), water, brine and dried (MgSO$_4$). The solvent was removed by evaporation and the residue was purified by column chromatography eluting with ethyl acetate/petroleum ether (1/1) to give 5-methylthiooxindole (1.48 g, 78%).

m.p. 120–122° C.

$^1$H NMR Spectrum: (CDCl$_3$) 2.46(s, 3H); 3.53(s, 2H); 6.81(d, 1H); 7.15–7.30(m, 2H); 8.21(br s, 1H).

MS-EI: 179 [M]$^+$

| Elemental analysis: | Found | C 60.2 | H 5.2 | N 7.8 |
|---|---|---|---|---|
| C$_9$H$_9$NOS | Requires | C 60.3 | H 5.1 | N 7.8% |

EXAMPLE 32

3-Chloroperoxybenzoic acid (186 mg, 0.78 mmol) was added to a solution of 6-methoxy-4-(5-methylthiooxindol-3-yl)-7-(3-morpholinopropoxy)quinazoline (170 mg, 0.35 mmol), (prepared as described for the free base product in Example 31), in methylene chloride (40 ml) and the mixture stirred for 2 hours at ambient temperature. The mixture was diluted with water (5 ml) and ether (15 ml) and the aqueous layer was adjusted to pH2 by addition of 1M hydrochloric acid. The aqueous layer was separated and applied to a reverse phase C18 column and eluted with a gradient of methanol/1% aqueous acetic acid (0/100 to 100/0). The purified product was dissolved in methanol and concentrated hydrochloric acid (3drops) was added. The volatiles were removed by evaporation, the solid residue was collected and dried under vacuum to give 6-methoxy-4-(5-methylsulphinyloxindol-3-yl)-7-(4-oxidomorpholinopropoxy)quinazoline hydrochloride (100 mg, 60%).

$^1$H NMR Spectrum: (DMSOd$_6$, CF$_3$CO$_2$D) 2.45(m, 2H); 2.67(s, 3H); 2.7–2.9(m, 4H); 3.94(s, 3H); 3.94–3.99(br s, 6H); 4.37(t, 2H); 7.13(d, 1H); 7.34(d, 1H); 7.36(s, 1H); 7.78(s, 1H); 8.0(s, 1H); 8.76(s, 1H).

MS-ESI: 513 [MH]$^+$

EXAMPLE 33

5-methylsuphonyloxindole (350 mg, 1.66 mmol) was added to a suspension of sodium hydride (66 mg, 1.66 mmol) in DMF (5 ml) and the mixture was stirred for 30 minutes at ambient temperature. 4-Chloro-6-methoxy-7-(2-methoxyethoxy)quinazoline (148.5 mg, 0.55 mmol), (prepared as described for the starting material in Example 2), was added as a solid followed by DMF (1 ml). The mixture was heated at 50° C. for 1.5 hours and then allowed to cool. The mixture was partitioned between water and ether and the aqueous layer was adjusted to pH7 with 2M hydrochloric acid. The precipitated product was collected by filtration, washed with water, ether and dried under vacuum. The solid was adsorbed on silica and purified by column chromatography eluting with methylene chloride/methanolxacetonitrile (60/5/35). The purified solid was dissolved in methylene chloride/methanol and 7M ethanolic hydrogen chloride (1 ml) was added. The volatiles were removed by evaporation, the solid residue triturated with ether, collected by filtration, washed with ether and dried under vacuum to give 6-methoxy-7-(2-methoxyethoxy)4-(5-methylsuphonyloxindol-3-yl)quinazoline hydrochloride (170 mg, 70%).

$^1$H NMR Spectrum: (DMSOd$_6$, CF$_3$CO$_2$D) 3.1(s, 3H); 3.36(s, 3H); 3.78(m, 2H); 3.93(s, 3H); 4.36(t, 2H); 7.18(d, 1H); 7.33(s, 1H); 7.64(d, 1H); 7.77(s, 1H); 8.13(s, 1H); 8.72(s, 1H).

MS-ESI: 444 [MH]$^+$

| Elemental analysis: | Found | C 51.0 | H 4.9 | N 8.8 |
|---|---|---|---|---|
| C$_{21}$H$_{12}$N$_3$O$_6$S 1H$_2$O 0.85HCl | Requires | C 51.2 | H 4.9 | N 8.5% |

The starting material was prepared as follows:

3-Chloroperoxybenzoic acid (919 mg, 3.8 mmol) was added to a solution of 5-methylthiooxindole (343 mg, 1.9 mmol), (prepared as described for the starting material in Example 31), in methylene chloride (100 ml) cooled at 5° C. and the mixture stirred for 2 hours at ambient temperature. Further 3-chloroperoxybenzoic acid (100 mg) was added and the mixture stirred for a fuirther 1 hour. The volatiles were removed by evaporation, the residue was triturated with ether, collected by filtration and dried under vacuum to give 5-methylsuphonyloxindole (363 mg, 90%).

$^1$H NMR Spectrum: (DMSOd$_6$, CF$_3$CO$_2$D) 3.14(s, 3H); 3.60(s, 2H); 7.01 (d, 1H); 7.7–7.8(m, 2H).

EXAMPLE 34

Sodium hydride (58 mg, 2.4 mmol) was added to solution of 5-(2-morpholinoacetyl)oxindole (312 mg, 1.2 mmol) and 4-chloro-6-methoxy-7-(2-methoxyethoxy)quinazoline (160 mg, 0.6 mmol), (prepared as described for the starting material in Example 2), in DMF (15 ml). The mixture was stirred for 1.5 hours at ambient temperature and the volatiles were removed by evaporation. The residue was purified by column chromatography eluting with methylene chloride/methanol (96/4 followed by 94/6). The purified solid product was triturated with ether, collected by filtration, washed with ether and dried under vacuum. The solid was dissolved in methylene chloride (10 ml) and methanol (10 ml) and 1M methanolic hydrogen chloride (2 ml) was added. The volatiles were removed by evaporation and the solid residue was suspended in ether, collected by filtration, washed with ether and dried under vacuum to give 6-methoxy-7-(2-methoxyethoxy)-4-(5-(2-morpholinoacetyl)oxindol-3-yl)quinazoline hydrochloride (136 mg, 39%).

$^1$H NMR Spectrum: (DMSOd$_6$, CF$_3$CO$_2$D) 3.25(t, 2H); 3.36(s, 3H); 3.46(d, 2H); 3.78(m, 2H); 3.8–3.9(m, 2H); 3.86(s, 3H); 4.0(d, 2H); 4.35(m, 2H); 5.08(s, 2H); 7.15(d, 1H); 7.35(s, 1H); 7.78(d, 1H); 7.85(s, 1H); 8.31(s, 1H); 8.73(s, 1H).

MS-ESI: 493 [MH]$^+$

| Elemental analysis: | Found | C 53.5 | H 5.8 | N 9.7 |
|---|---|---|---|---|
| C$_{26}$H$_{28}$N$_4$O$_6$ 2H$_2$O 1.5HCl | Requires | C 53.5 | H 5.3 | N 9.6% |

The starting material was prepared as follows:

Potassium carbonate (800 mg, 5.8 mmol) followed by potassium iodide (30 mg, 0.2 mmol) and morpholine (500 μl, 5.7 mmol) were added to a solution of 5-(2-chloroacetyl) oxindole (1.05 g, 5 mmol), (J. Med. Chem. 1991, 1860), in DMF (20 ml) and the mixture was stirred for 1 hour at ambient temperature. The solvent was removed by evaporation and the residue was purified by reverse phase column chromatography on a Diaion (trade mark of Mitsubishi) HP20SS resin column, eluting with water/methanol (a gradient from 100/0 to 30/70). The purified product was then purified by chromatography on silica eluting with methylene chloride/methanol (95/5) to give 5-(2-morpholinoacetyl) oxindole (673 mg, 51%).

$^1$H NMR Spectrum: (DMSOd$_6$, CD$_3$CO$_2$D) 3.57(s, 2H); 5.06(s, 2H); 6.93(d, 1H); 7.83(s, 1H); 7.9(d, 1H).

EXAMPLE 35

Using a procedure analogous to that described in Example 49, 5-nitrooxindole (240 mg, 1.4 mmol), (prepared as described for the starting material in Example 21), was added to sodium hydride (80 mg, 1.9 mmol) in THF (15ml) and the solution was treated with 4-chloro-7-(2-methoxyethoxy)quinazoline (170 mg, 0.7 mmol), (prepared as described for the starting material in Example 15), in DMF (5 ml) to give, after work-up and purification, 7-(2-methoxyethoxy)-4-(5-nitrooxindol-3-yl)quinazoline (87 mg, 32%).

$^1$H NMR Spectrum: (DMSOd$_6$, CF$_3$CO$_2$D) 3.3(s, 3H); 3.7(t, 2H); 4.25(t, 2H); 7.0(d, 1H); 7.15(d, 1H); 7.22(dd, 1H); 7.95(dd, 1H); 8.5(d, 1H); 8.65(s, 1H); 8.75(s, 1H); 11.4(s, 1H).

MS-ESI: 381 [MH]$^+$

| Elemental analysis: | Found | C 57.9 | H 4.1 | N 14.7 |
|---|---|---|---|---|
| C$_{19}$H$_{16}$N$_4$O$_5$ 0.7H$_2$O | Requires | C 58.1 | H 4.5 | N 14.3% |

EXAMPLE 36

Using a procedure analogous to that described in Example 49, 5-cyanooxindole (250 mg, 1.6 mmol), (Tet. Lett., 1987, 28, 4027), was added to sodium hydride (100 mg, 2.5 mmol) in THF (15 ml) and the solution was treated with 4-chloro-7-(2-methoxyethoxy)quinazoline (200 mg, 0.84 mmol), (prepared as described for the starting material in Example 15), in DMF (5 ml) to give, after work-up and purification, 4-(5-cyanooxindol-3-yl)-7-(2-methoxyethoxy)quinazoline (160 mg, 53%).

$^1$H NMR Spectrum: (DMSOd$_6$, CF$_3$CO$_2$D) 3.3(s, 3H); 3.7(t, 2H); 4.3(t, 2H); 7.05(d, 1H); 7.15(d, 1H); 7.3(dd, 1H); 7.45(d, 1H); 7.95(s, 1H); 8.45(d, 1H), 8.8(s, 1H), 11.3(s, 1H).

MS-ESI: 359 [M-H]$^+$

| Elemental analysis: | Found | C 64.6 | H 4.5 | N 15.4 |
|---|---|---|---|---|
| C$_{20}$H$_{16}$N$_4$O$_3$ 0.6H$_2$O | Requires | C 64.7 | H 4.7 | N 15.1% |

EXAMPLE 37

Using a procedure anologous to that described in Example 26, oxindole (240 mg, 1.8 mmol) was added to sodium hydride (110 mg, 2.75 mmol) in THF (15 ml) and the solution was treated with 4-chloro-7-(3-morpholinopropoxy)quinazoline (400 mg, 1.3 mmol) in DMF (5 ml) to give, after work-up and purification, 7-(3-morpholinopropoxy)-4-(oxindol-3-yl)quinazoline (160 mg, 30%).

$^1$H NMR Spectrum; (DMSOd$_6$, CF$_3$CO$_2$D) 2.2(m, 2H); 3.1(t, 2H); 3.3(t, 2H); 3.5(d, 2H); 3.7(t, 2H); 4.0(m, 2H); 4.25(t, 2H); 6.92(d, 1H); 7.1(d, 1H); 7.15(d, 1H); 7.22(dd, 1H); 7.6(d, 1H); 8.4(d, 1H); 8.6(s, 1H), 10.05(br s, 1H), 10.9(br s, 1H).

MS-ESI: 405 [MH]$^+$

| Elemental analysis: | Found | C 65.9 | H 5.9 | N 13.9 |
|---|---|---|---|---|
| C$_{23}$H$_{24}$N$_4$O$_3$ 0.7H$_2$O | Requires | C 66.2 | H 6.1 | N 13.4% |

The starting material was prepared as follows:

A solution of 2-amino-4-fluorobenzoic acid (3 g, 19.3 mmol) in formamide (30 ml) was heated at 150° C. for 6 hours. The reaction mixture was poured onto ice/water (1/1) (250 ml). The precipitated solid was collected by filtration, washed with water and dried to give 7-fluoro-3,4-dihydroquinazolin-4-one (2.6 g, 82%).

Sodium metal (4.4 g, 191 mmol) was added to benzyl alcohol (100 ml) at ambient temperature and the mixture stirred for 30 minutes then heated at 80° C. for 1 hour. The mixture was then cooled to 40° C. and 7-fluoro-3,4-dihydroquinazolin-4-one (7.8 g, 47 mmol), was added. The reaction mixture was stirred at 130° C. for 4 hours and allowed to cool to ambient temperature and stirred for 18 hours. The solution was quenched with water (800 ml) and acidified to pH3 with concentrated hydrochloric acid. The resulting precipitate was collected by filtration, washed with water and ether and dried for 4 hours at 60° C. under high vacuum to give 7-benzyloxy-3,4-dihydroquinazolin-4-one (7.02 g, 63%).

7-Benzyloxy-3,4-dihydroquinazolin-4-one (7.0 g, 27 mmol) was suspended in dry DMF (50 ml) and cooled to 5–10° C., then sodium hydride was added (1.22 g of a 60% suspension in mineral oil, 30 mmol). The reaction mixture was allowed to return to ambient temperature and chloromethyl pivalate (4.75 g, 31.5 mmol) was added over 10 minutes and the mixture stirred for 1 hour. The reaction mixture was quenched with water (250 ml), the aqueous phase adjusted to pH5 and extracted with ether (300 ml×3). The combined ether phases were washed with brine, dried (MgSO$_4$) and the solvent removed by evaporation. The solid residue was triturated with isohexane, collected by filtration and dried under vacuum to give 7-benzyloxy-3-((pivaloyloxy)methyl)-3,4-dihydroquinazolin-4-one (9.1 g, 90%).

7-benzyloxy-3-((pivaloyloxy)methyl)-3,4-dihydroquinazolin-4-one (8.0 g, 22 mmol) was dissolved in TFA (40ml) and the mixture heated at reflux for 3 hours then allowed to cool to ambient temperature and stirred for 18 hours. The TFA was removed by evaporation and the residue resuspended in a mixture of ether and aqueous sodium hydrogen carbonate solution. The solid was collected by filtration, washed with water and ether and dried at 40° C. for 3 hours under high vacuum to give 7-hydroxy-3-((pivaloyloxy)methyl)-3,4-dihydroquinazolin-4-one (5.42 g, 90%).

Morpholine (94 g, 1.08 mol) was added dropwise to a solution of 3-bromo-1-propanol (75 g, 0.54 mol) in toluene (750 ml) and the reaction then heated at 80° C. for 4 hours. The mixture was allowed to cool to ambient temperature and the precipitated solid was removed by filtration. The volatiles were removed from the filtrate and the resulting yellow oil was purified by distillation at 0.4–0.7 mmHg to give 4-(3-hydroxypropyl)morpholine (40 g, 50%) as a colourless oil.

b.p. 68–70° C. (~0.5 mmHg)

hu 1H NMR Spectrum: (DMSOd$_6$) 1.65–1.78(m, 2H); 2.50(t, 4H); 2.60(t, 2H); 3.68(t, 4H); 3.78(t, 2H); 4.90(br d, 1H).

7-Hydroxy-3-((pivaloyloxy)methyl)-3,4-dihydroquinazolin-4-one (750 mg, 2.7 mmol) was suspended in methylene chloride (40 ml) at 5° C. and 4-(3-hydroxypropyl)morpholine (490 mg, 3.4 mmol) and triphenylphosphine (890 mg, 3.4 mmol) were added. The mixture was stirred for 5 minutes and diethyl azodicarboxylate (590 mg, 3.4 mmol) was added over 5 minutes at 5° C. The reaction mixture was stirred at 5° C. for 30 minutes then at ambient temperature for 1 hour. The solution was then purified directly by column flash chromatography eluting with methylene chloride, and then ethyl acetate, acetonitrile/ ethyl acetate (20/80), and acetonitrile/ethyl acetate/ammonia (50/50/0.5). The purified product was triturated with ether/ isohexane and collected by filtration to give 7-(3-morpholinopropoxy)-3-((pivaloyloxy)methyl)-3,4-dihydroquinazolin-4-one (745 mg, 68%).

7-(3-Morpholinopropoxy)-3-((pivaloyloxy)methyl)-3,4-dihydroquinazolin-4-one (680 mg, 1.6 mmol) was stirred in methanolic ammonia (20 ml) at 40° C. for 6 hours then for 18 hours at ambient temperature. The solvent was removed by evaporation, the residue was triturated with ether/ isohexane and collected by filtration to give 7-(3-morpholinopropoxy)-3,4-dihydroquinazolin-4-one (450 mg, 92%) as a white solid.

$^1$H NMR Spectrum: (DMSOd$_6$) 1.9(quin, 2H); 2.35(t, 4H); 2.4(t, 2H); 3.55(t, 4H); 4.15(t, 2H); 7.05(m, 2H); 7.97(d, 1H); 8.02(s, 1H).

MS: 290 [MH]$^+$

A mixture of 7-(3-morpholinopropoxy)-3,4-dihydroquinazolin-4-one (500 mg, 1.7 mmol), thionyl chloride (10 ml) and DMF (0.1 ml) was heated at reflux for 2 hours. The volatiles were removed by evaporation and the residue azeotroped with toluene. The crude product was partitioned between methylene chloride (50 ml) and saturated aqueous sodium hydrogen carbonate solution (50 ml) and the mixture stirred for 10 minutes. The organic phase was separated and the aqueous phase extracted with methylene chloride. The combined extracts were dried (MgSO4) and the solvent removed by evaporation to give 4-chloro-7-(3-morpholinopropoxy)quinazoline (425 mg, 80%).

EXAMPLE 38

A solution of 5-cyanooxindole (284 mg, 1.8 mmol), (Tet. Lett., 1987, 28, 4027), in DMF (4 ml) was added dropwise, to sodium hydride (72 mg, 1.8 mmol, prewashed with hexane) in DMF (4 ml) under nitrogen. The mixture was stirred for 15 minutes at ambient temperature and 4-chloro-6-methoxy-7-(2-(pyrrolidin-1-yl)ethoxy)quinazoline (184 mg, 0.6 mmol), (prepared as described for the starting material in Example 28), was added as a solid. The mixture was heated at 60° C. for 45 minutes and then solvent was removed by evaporation. Water was added to the residue and the mixture was adjusted to pH2 with 2M hydrochloric acid. The insolubles were removed by filtration and the filtrate was extracted with ether. The aqueous layer was adjusted to pH8 with 2M aqueous sodium hydroxide solution and was concentrated by evaporation to half initial volume. The precipitate was collected by filtration, washed with water and ether, and dried under vacuum. The solid was dissolved in methylene chloride/methanol and 2.9M ethereal hydrogen chloride was added. The volatiles were removed by evaporation, the solid residue was suspended in ether, collected by filtration, washed with ether and dried under vacuum to give 4-(5-cyanooxindol-3-yl)-6-methoxy-7-(2-(pyrrolidin-1-yl)ethoxy)quinazoline hydrochloride (110 mg, 40%).

$^1$H NMR Spectrum: (DMSOd$_6$, D$_2$O+NaOD) 1.7(br s, 4H); 2.5–2.6(m, 4H); 2.86(t, 2H); 3.80(s, 3H); 4.16(t, 2H); 6.65(d, 1H); 6.81(d, 1H); 6.89(s, 1H); 8.1(br s, 1H); 8.40(s, 1H); 9.14(br s, 1H).

MS-ESI: 430 [MH]$^+$

| Elemental analysis: | Found | C 55.0 | H 5.4 | N 13.1 |
|---|---|---|---|---|
| C$_{24}$H$_{23}$N$_5$O$_3$ 1.8H$_2$O 1.7HCl | Requires | C 55.0 | H 5.4 | N 13.3% |

EXAMPLE 39

A solution of 5-cyanooxindole (2.96 g, 18.7 mmol), (Tet. Lett., 1987, 28, 4027), in DMF (35 ml) was added dropwise under nitrogen to sodium hydride (749 mg, 18.7 mmol, prewashed with hexane) in DMF (15 ml). The mixture was stirred for 30 minutes at ambient temperature and 4-chloro-7-(2-(imidazol-1-yl)ethoxy)-6-methoxyquinazoline (1.98 g, 18.7 mmol), (prepared as described for the starting material in Example 22), was added as a solid. The mixture was heated at 55° C. for 45 minutes, allowed to cool and poured into a mixture of methylene chloride (400 ml) and saturated aqueous ammonium chloride solution (400 ml). The resulting precipitate was collected by filtration, resuspended in water and stirred for 15 minutes at ambient temperature. The solid was collected by filtration, washed with water and then ether, and dried under vacuum to give a white solid. This solid was suspended in methylene chloride (50 ml) and methanol (50 ml) and 2.2M ethereal hydrogen chloride (6 ml) was added. The mixture was stirred for 15 minutes at ambient temperature, the solid product was collected by filtration, washed with ether and dried under vacuum at 60° C. to give 4-(5-cyanooxindol-3-yl)-7-(2-(imidazol-1-yl) ethoxy)-6-methoxyquinazoline hydrochloride (2 g, 61%).

$^1$H NMR Spectrum: (DMSOd$_6$, CF$_3$CO$_2$D) 3.9(s, 3H); 4.65(t, 2H); 4.76(t, 2H); 7.06(d, 1H); 7.3(s, 1H); 7.45(d, 1H); 7.74(s, 1H); 7.85(s, 1H); 8.01(br s, 1H); 8.08(br s, 1H); 8.58(s, 1H); 9.2(s, 1H).

MS-ESI: 427 [MH]$^+$

| Elemental analysis: | Found | C 52.8 | H 4.0 | N 15.9 |
|---|---|---|---|---|
| C$_{23}$H$_{18}$N$_6$O$_3$ 1.5H$_2$O 1.95HCl | Requires | C 52.7 | H 4.4 | N 16.0% |

EXAMPLE 40

A solution of 5-acetyloxindole (352 mg, 2 mmol), (EP 0155828 A2), in DMF (5 ml) was added to a suspension of sodium hydride (80 mg, 2 mmol, prewashed with hexane) in DMF (1 ml) and the mixture stirred for 30 minutes at ambient temperature. 4-Chloro-6-methoxy-7-(2-methoxyethoxy)quinazoline (180 mg, 0.67 mmol), (prepared as described for the starting material in Example 2), was added and the mixture was heated at 50° C. for 1.5 hours. The mixture was partitioned between water and ether and the aqueous layer was adjusted to pH7 with 2M hydrochloric acid. The precipitate was collected by filtration, washed with water and dried under vacuum. The solid was dissolved in methylene chloride/methanol (30 ml/30 ml) and 7M ethanolic hydrogen chloride (1 ml) was added. The mixture was left to stand for 15 minutes at ambient temperature, the resulting precipitate was collected by filtration, washed with ether and dried under vacuum to give 4-(5-acetyloxindol-3-yl)-6-methoxy-7-(2-methoxyethoxy) quinazoline hydrochloride (195 mg, 71%).

$^1$H NMR Spectrum: (DMSOd$_6$, CF$_3$CO$_2$D) 2.52(s, 3H); 3.37(s, 3H); 3.80(t, 2H); 3.85(s, 1H); 4.35(t, 2H); 7.09(d, 1H); 7.33(s, 1H); 7.78(s, 1H); 7.88(d, 1H); 8.25(s, 1H); 8.85(s, 1H).

MS-ESI: 408 [MH]$^+$

| Elemental analysis: | Found | C 57.3 | H 5.0 | N 8.7 |
|---|---|---|---|---|
| C$_{22}$H$_{21}$N$_3$O$_5$ 1.2H$_2$O 0.95HCl | Requires | C 57.0 | H 5.3 | N 9.0% |

EXAMPLE 41

Using an analogous procedure to that described for Example 38, 5-cyanooxindole (284 mg, 1.8 mmol), (Tet. Lett., 1987, 28, 4027), was treated with sodium hydride (72 mg, 1.8 mmol) and 4-chloro-6-methoxy-7-(2-([N-methyl-N-(4-pyridyl)]amino)ethoxy)-3,4-dihydroquinazolin-4-one (207 mg, 0.6 mmol) to give 4-(5-cyanooxindol-3-yl)-6-methoxy-7-(2-([N-methyl-N-(4-pyridyl)]amino)ethoxy) quinazoline hydrochloride (83 mg, 28%).

$^1$H NMR Spectrum: (DMSOd$_6$, CF$_3$CO$_2$D) 3.3(s, 3H); 3.8(s, 3H); 4.16(t, 2H); 4.48(t, 2H); 7.05(br s, 1H); 7.1(d, 1H); 7.27(s, 1H); 7.35(br s, 1H); 7.47(s, 1H); 7.90(s, 1H); 8.05(s, 1H); 8.2–8.35(br s, 2H); 8.69(s, 1H).

MS-ESI: 467 [MH]$^+$

| Elemental analysis: | Found | C 55.9 | H 4.6 | N 15.2 |
|---|---|---|---|---|
| C$_{26}$H$_{22}$N$_6$O$_3$ 1.6H$_2$O 1.7HCl | Requires | C 56.0 | H 4.9 | N 15.1% |

The starting material was prepared as follows:

Diethyl azodicarboxylate (1.1 ml, 7 mmol) was added dropwise to a solution of 7-5 hydroxy-6-methoxy-3-((pivaloyloxy)methyl)-3,4-dihydroquinazolin-4-one (1.7 g, 5.55 mmol), (prepared as described for the starting material in Example 22), 2-([N-methyl-N-4-pyridyl)]amino)ethanol (1.06 g, 7mmol), (EP 0359389 A1), and triphenylphosphine (1.8 g, 7 mmol) in methylene chloride (29 ml). The mixture was stirred for 1 hour at ambient temperature, then purified directly by flash chromatography eluting with methylene chloride/methanol (90/10). The purified solid was triturated with ether and collected by filtration to give 6-methoxy-7-(2-([N-methyl-N-(4-pyridyl)]amino)ethoxy)-3-((pivaloyloxy)methyl)-3,4-dihydroquinazolin-4-one (2.29 g, 94%).

$^1$H NMR Spectrum: (DMSOd$_6$, CF$_3$CO$_2$D) 1.12(s, 9H); 3.3(s, 3H); 3.84(s, 3H); 4.11(t, 2H); 4.42(t, 2H); 5.92(s, 2H); 7.0(br s, 1H); 7.19(s, 1H); 7.3(br s, 1H); 7.5(s, 1H); 8.27(d, 2H); 8.4(s, 1H).

MS-ESI: 411 [MH]$^+$

| Elemental analysis: | Found | C 60.5 | H 12.2 | N 6.4 |
|---|---|---|---|---|
| C$_{23}$H$_{28}$N$_4$O$_5$ 0.8H$_2$O | Requires | C 60.7 | H 12.3 | N 6.5% |

A solution of 6-methoxy-7-(2-([N-methyl-N-(4-pyridyl)]amino)ethoxy)3-((pivaloyloxy)methyl)-3,4-dihydroquinazolin-4-one (2.24 g, 5 mmol) in methanol saturated with ammonia (30 ml) was stirred at ambient temperature for 17 hours. The solvent was removed by evaporation, the solid residue was resuspended in ether, collected by filtration, washed with ether and dried under vacuum to give 6-methoxy-7-(2-([N-methyl-N-(4-pyridyl)] amino)ethoxy)-3,4dihydroquinazolin-4-one (1.45 g, 95%).

$^1$H NMR Spectrum: (DMSOd$_6$) 3.04(s, 3H); 3.83(t, 2H); 3.85(s, 3H); 4.3(t, 2H); 6.7(s, 2H); 7.12(s, 1H); 7.4(s, 1H); 7.96(s, 1H); 8.1(d, 2H).

MS-ESI: 327 [MH]$^+$

| Elemental analysis: | Found | C 59.0 | H 5.9 | N 16.5 |
|---|---|---|---|---|
| C$_{17}$H$_{18}$N$_4$O$_3$ 1H$_2$O | Requires | C 59.3 | H 5.8 | N 16.3% |

A solution of 6-methoxy-7-(2-([N-methyl-N-(4-pyridyl)]amino)ethoxy)-3,4-dihydroquinazolin-4-one (1.5 g, 4.6 mmol) in thionyl chloride (18 ml) and DMF (0.7 ml) was heated at reflux for 1 hour. The mixture was allowed to cool, toluene was added and the volatiles were removed by evaporation. The residue was dissolved in methylene chloride and aqueous sodium hydrogen carbonate solution was added. The organic layer was separated, washed with brine, dried (MgSO$_4$), and the volatiles removed by evaporation. The residue was purified by flash chromatography eluting with methylene chloride/methanol (95/5 followed by 90/10) to give 4-chloro-6-methoxy-7-(2-([N-methyl-N-(4-pyridyl)] amino)ethoxy)-3,4-dihydroquinazolin-4-one (463 mg, 30%).

$^1$H NMR Spectrum: (DMSOd$_6$) 3.05(s, 3H); 3.89(t, 2H); 3.97(s, 3H); 4.4(t, 2H); 6.7(d, 2H); 7.39(s, 1H); 7.46(s, 1H); 8.11(d, 2H); 8.87(s, 1H).

MS-ESI: 345 [MH]$^+$

EXAMPLE 42

5-Methylsuphonyloxindole (262 mg, 1.24 mmol), (prepared as described for the starting material in Example 33), was added to a suspension of sodium hydride (50 mg, 1.24 mmol) in DMF (5 ml) and the mixture stirred for 30 minutes at ambient temperature. 4-Chloro-6-methoxy-7-(3-morpholinopropoxy)quinazoline (140 mg, 0.41 mmol), prepared as described for the starting material in Example 5), was added and the mixture heated at 50° C. for 1.5 hours. The mixture was allowed to cool and was then partitioned between water and ether and the aqueous layer was adjusted to pH8 with 2M hydrochloric acid. The organic phase was separated and the aqueous phase was extracted with ethyl acetate. The organic extracts were combined and the volatiles removed by evaporation. The residue was dissolved in methylene chloride and the organic layer was washed with brine, dried (MgSO$_4$) and the solvent removed by evaporation. The residue was purified by column chromatography, eluting with methanol/acetonitrile/methylene chloride (10/30/60 followed by 15/25/60). The purified solid was dissolved in methanol/methylene chloride and 7M ethanolic hydrogen chloride (1.5 ml) was added. The mixture was stirred for 10 minutes at ambient temperature, the solvent was removed by evaporation. The residue was triturated with ether, collected by filtration, washed with ether and dried under vacuum to give 6-methoxy-4-(5-methylsuphonyloxindol-3-yl)-7-(3-morpholinopropoxy) quinazoline hydrochloride (95 mg, 39%).

$^1$H NMR Spectrm: (DMSOd$_6$, CF$_3$CO$_2$D) 2.3(t, 2H); 3.09(s, 3H); 3.18(t, 2H); 3.36(t, 2H); 3.54(d, 2H); 3.72(t, 2H); 3.94(s, 3H); 4.04(d, 2H); 4.33(t, 2H); 7.18(d, 1H); 7.34(s, 1H); 7.64(d, 1H); 7.79(s, 1H); 8.11(s, 1H); 8.68(s, 1H).

MS-ESI: 513 [MH]+

| Elemental analysis: | Found | C 48.0 | H 5.3 | N 8.5 |
| --- | --- | --- | --- | --- |
| $C_{25}H_{28}N_4O_6S$ 2.2$H_2O$ 1.85HCl 0.1methylene chloride | Requires | C 48.0 | H 5.5 | N 8.9% |

EXAMPLE 43

A solution of 5-acetyloxindole (272 mg, 1.56 mmol), (EP 0155828 A2), in DMF (1.5 ml) was added dropwise to a suspension of sodium hydride (62 mg, 1.56 mmol, prewashed with hexane) in DMF (3 ml) and, the mixture stirred for 30 minutes at ambient temperature. 4-Chloro-6-methoxy-7-(3-morpholinopropoxy)quinazoline (175 mg, 0.52 mmol), (prepared as described for the starting material in Example 5), was added and the mixture was heated at 50° C. for 1.5 hours. The mixture was poured into a mixture of ether (30 ml), ethyl acetate (30 ml) and water (50 ml). The aqueous layer was separated and adjusted to pH7.8 with 2M hydrochloric acid and extracted with methylene chloride. The organic extracts were washed with water, brine, dried (MgSO$_4$) and the solvent removed by evaporation. The residue was purified by column chromatography eluting with methylene chloride/methanol (90/10). The purified solid was dissolved in methylene chloride/methanol and 7M ethanolic hydrogen chloride (1.5 ml) was added. The volatiles were removed by evaporation, the residue collected and dried under vacuum to give 4-(5-acetyloxindol-3-yl)-6-methoxy-7-(3-morpholinopropoxy)quinazoline hydrochloride (135 mg, 48%).

$^1$H NMR Spectrum: (DMSOd$_6$, CD$_3$CO$_2$D) 2.33(m, 2H); 2.54(s, 3H); 3.15(t, 2H); 3.37(t, 2H); 3.54(d, 2H); 3.73(t, 2H); 3.85(s, 3H); 4.03(d, 2H); 4.33(t, 2H); 7.09(d, 1H); 7.35(s, 1H); 7.8(s, 1H); 7.87(d, 1H); 8.25(s, 1H); 8.8(s, 1H).

MS-ESI: 477 [MH]+

| Elemental analysis: | Found | C 56.2 | H 5.9 | N 10.1 |
| --- | --- | --- | --- | --- |
| $C_{26}H_{28}N_4O_5$ 0.6$H_2O$ 1.8HCl 0.08ethanol | Requires | C 56.6 | H 5.7 | N 10.0% |

EXAMPLE 44

Using a procedure analogous to that described in Example 26, 5-nitrooxindole (250 mg, 1.4 mmol), (prepared as described for the starting material in Example 21, was added to sodium hydride (110 mg, 2.75 mmol) in THF (15 ml) and the solution was treated with 4-chloro-7-(3-morpholinopropoxy)quinazoline (400 mg, 1.3 mmol), (prepared as described for the starting material in Example 37), in DMF (5 ml) to give, after work-up and purification, 7-(3-morpholinopropoxy)-4-(5-nitrooxindol-3-yl) quinazoline (110 mg, 19%).

$^1$H NMR Spectrum: (DMSOd$_6$, CF$_3$CO$_2$D) 2.2–2.3(m, 2H); 3.1(t, 2H); 3.3(t, 2H); 3.5(d, 2H); 3.7(t, 2H); 4.0(m, 2H); 4.25(t, 2H); 7.0(d, 1H); 7.1(d, 1H); 7.18(dd, 1H); 7.95(dd, 1H); 8.55(s, 1H), 8.7 (m, 2H), 11.2(br s, 1H).

MS-ESI: 450 [MH]+

| Elemental analysis: | Found | C 58.4 | H 5.1 | N 14.9 |
| --- | --- | --- | --- | --- |
| $C_{23}H_{23}N_5O_5$ 1.3$H_2O$ | Requires | C 58.4 | H 5.5 | N 14.8% |

EXAMPLE 45

Using a procedure analogous to that described in Example 26, 5-cyanooxindole (250 mg, 1.5 mmol), (Tet. Lett., 1987, 28, 4027), was added to sodium hydride (110 mg, 2.75 mmol) in THF (15 ml) and the solution was treated with 4-chloro-7-(3-mozpholinopropoxy)quinazoline (400 mg, 1.3 mmol), (prepared as described for the starting material in Example 37), in DMF (5 ml) to give, after work-up and purification, 4-(5-cyanooxindol-3-yl)-7-(3-morpholinopropoxy)quinazoline (110 mg, 20%).

$^1$H NMR Spectrum: (DMSOd$_6$, CF$_3$CO$_2$D) 2.2–2.3(m, 2H); 3.1(t, 2H); 3.3(t, 2H); 3.5(d, 2H); 3.65(t, 2H); 3.95(d, 2H); 4.2(t, 2H); 6.95(d, 1H); 7.1(d, 1H); 7.2(dd, 1H); 7.4(dd, 1H); 8.1(br s, 1H); 8.5(s, 1H), 8.6(m, 1H), 11.0(br s, 1H).

MS-ESI: 428 [M–H]+

| Elemental analysis: | Found | C 65.2 | H 5.5 | N 15.8 |
| --- | --- | --- | --- | --- |
| $C_{24}H_{23}N_5O_3$ 0.6$H_2O$ | Requires | C 65.5 | H 5.5 | N 15.9% |

EXAMPLE 46

A solution of 5-methylsulphinyloxindole (303 mg, 1.55 mmol) in DMF (3.5 ml) was added to a suspension of sodium hydride (62 mg, 1.55 mmol, prewashed with hexane) in DMF (1.5 ml) and the mixture stirred for 30 minutes at ambient temperature. 4-Chloro-6-methoxy-7-(3-morpholinopropoxy)quinazoline (175 mg, 0.51 mmol), (prepared as described for the starting material in Example 5), was added and the mixture was stirred for 1.5 hours at 50° C. and then partitioned between water and ether. The aqueous layer was adjusted to pH7–8 with 2M hydrochloric acid and the volatiles removed by evaporation. The residue was purified by column chromatography eluting with methylene chloride/methanol (9/1). The semi-purified solid was dissolved in dilute hydrochloric acid (pH2) and purified by reverse phase C18 chromatography eluting with methanol/dilute hydrochloric acid (pH2) (gradient from 0/100 to 30/70). The methanol was removed by evaporation, the aqueous residue was freeze dried to give 6-methoxy-4-(5-methylsulphinyloxindol-3-yl)-7-(3-morpholinopropoxy) quinazoline hydrochloride (80 mg, 27%).

$^1$H NMR Spectrum: (DMSOd$_6$, CF$_3$CO$_2$D) 2.3(m, 2H); 2.67(s, 3H); 3.16(t, 2H); 3.35(t, 2H); 3.54(d, 2H); 3.73(t, 2H); 3.9(s, 3H); 4.02(d, 2H); 4.33(t, 2H); 7.13(d, 1H); 7.33(t, 1H); 7.36(s, 1H); 7.78(s, 1H); 8.0(s, 1H); 8.77(s, 1H).

MS-ESI: 497 [MH]+

| Elemental analysis: | Found | C 51.4 | H 5.9 | N 9.7 |
| --- | --- | --- | --- | --- |
| $C_{25}H_{28}N_4O_5S$ 0.8$H_2O$ 2HCl | Requires | C 51.4 | H 5.5 | N 9.6% |

The starting material was prepared as follows:

3-Chloroperoxybenzoic acid (400 mg, 1.7 mmol) was added in portions to a solution of 5-methylthiooxindole (300 mg, 1.7 mmol), (prepared as described for the starting material in Example 31), cooled at 5° C. and the mixture stirred for 1 hour at 5° C. and then for 1 hour at ambient temperature. The solvent was removed by evaporation and the residue was triturated with ether. The precipitate was collected by filtration, washed with ether and dried under vacuum. The solid was purified by flash chromatography eluting with methylene chloride/acetonitrile/methanol (60/32/8). The purified product was triturated with ether, the solid was collected by filtration and dried under vacuum to give 5-methylsulphinyloxindole (355 mg, 81%).

$^1$H NMR Spectrum: (DMSOd$_6$) 2.7(s, 3H); 3.58(s, 2H); 6.98(d, 1H); 7.51(d, 1H); 7.55(s, 1H); 10.67(br s, 1H).

MS-EI: 195 [M]$^+$

EXAMPLE 47

A solution of 5-methoxycarbonyloxindole (169 mg, 0.88 mmol), (Eur. J. Med. Chem. 1983, 18, 107–111), in DMF (2 ml) was added dropwise under nitrogen to sodium hydride (35 mg, 0.88 mmol, prewashed with hexane) in DMF (1.5 ml). The mixture was stirred for 20 minutes at ambient temperature and 4-chloro-6-methoxy-7-(3-morpholinopropoxy)quinazoline (100 mg, 0.3 mmol), (prepared as described for the starting material in Example 5), was added as a solid. The mixture was heated at 60° C. for 45 minutes, allowed to cool and partitioned between ethyl acetate and water. The aqueous layer was adjusted to pH8. The organic layer was separated, washed with brine, dried (MgSO$_4$) and the solvent removed by evaporation. The residue was purified by column chromatography eluting with methylene chloride/methanol (92/8). The solid was dissolved in methylene chloride/methanol and 3M ethereal hydrogen chloride (1 ml) was added. The volatiles were removed by evaporation, the solid residue suspended in ether, collected by filtration, washed with ether and dried under vacuum to give 4-(5-methoxycarbonyloxindol-3-yl)-6-methoxy-7-(3-morpholinopropoxy)quinazoline hydrochloride (55 mg. 32%).

$^1$H NMR Spectrum: (DMSOd$_6$, CF$_3$CO$_2$D) 2.25–2.4(m, 2H); 3.15(t, 2H); 3.35(t, 2H); 3.58(d, 2H); 3.75(t, 2H); 3.82(s, 3H); 3.90(s, 3H); 4.05(d, 2H); 4.35(t, 2H); 7.1(d, 1H); 7.35(s, 1H); 7.8(d, 1H); 7.82(s, 1H); 8.3(s, 1H); 8.8(s, 1H).

MS-ESI: 493 [MH]$^+$

| Elemental analysis: | Found | C 50.9 | H 6.2 | N 9.1 |
|---|---|---|---|---|
| C$_{26}$H$_{28}$N$_4$O$_6$ 3H$_2$O 1.85HCl | Requires | C 50.9 | H 5.9 | N 9.1% |

EXAMPLE 48

A solution of 5-(2-morpholinoethylaminosulphonyl) oxindole (363 mg, 1.1 mmol) in DMF (3 ml) was added dropwise to a suspension of sodium hydride (89 mg, 2.2 mmol, prewashed with hexane) and the mixture stirred for 30 minutes at ambient temperature. 4-Chloro-6-methoxy-7-(2-methoxyethoxy)quinazoline (100 mg, 0.37 mmol), (prepared as described for the starting material in Example 2), was added and the mixture heated at 50° C. for 30 minutes. DMF (5 ml) and DMSO (1.5 ml) were added and the mixture heated at 60° C. for 45 minutes, the volatiles were removed by evaporation and the residue was partitioned between methylene chloride and saturated aqueous ammonium chloride solution. The organic layer was separated, washed with brine, dried (MgSO$_4$) and the solvent removed by evaporation. The residue was purified by column chromatography eluting with methylene chloride/acetonitrile/methanol (60/35/5 followed by 60/30/10). The purified product was triturated with ether, collected by filtration and dried under vacuum. The solid was dissolved in methylene chloride/methanol and SM ethereal hydrogen chloride (1.5 ml) was added. The mixture was stirred for 30 minutes at ambient temperature, the volatiles were removed by evaporation and the solid residue was triturated with ether, collected by filtration and dried under vaccum to give 6-methoxy-7-(2-methoxyethoxy)4-(5-(2-morpholinoethylaminosulphonyl)oxindol-3-yl)quinazoline hydrochloride (110 mg, 46%).

$^1$H NMR Spectrum: (DMSOd$_6$, CD$_3$CO$_2$D) 2.97(t, 2H); 3.06(t, 2H); 3.15(t, 2H); 3.36(s, 3H); 3.36(m, 2H); 3.67(t, 2H); 3.78(t, 2H); 3.9(m, 2H); 3.92(s, 3H); 4.35(t, 2H); 7.15(d, 1H); 7.33(s, 1H); 7.57(d, 1H); 7.76(s, 1H); 8.07(s, 1H); 8.69(s, 1H).

MS-ESI: 558 [MH]$^+$

| Elemental analysis: | Found | C 47.7 | H 5.4 | N 11.0 |
|---|---|---|---|---|
| C$_{26}$H$_{31}$N$_5$O$_7$S 1.1H$_2$O 2HCl | Requires | C 48.0 | H 5.5 | N 10.8% |

The starting material was prepared as follows:

A solution of 5-chlorosulphonyloxindole (1 g, 4.3 mmol), (prepared as described for the starting material in Example 60), and 4-(2-aminoethyl)morpholine (620 µl, 4.7 mmol) in ethanol (20 ml) was heated at 65° C. for 1 hour. The solvent was removed by evaporation, the residue was partitioned between methylene chloride and water and the aqueous layer was adjusted to pH7–8 with 5% aqueous sodium hydrogen carbonate solution. The organic layer was separated, washed with brine, dried (MgSO$_4$) and the solvent removed by evaporation. The residue was purified by column chromatography eluting with methylene chloride/methanol (95/5) to give 5-(2-morpholinoethylaminosulphonyl)oxindole (750 mg, 54%).

$^1$H NMR Spectrum: (CDCl$_3$) 2.31(t, 4H); 2.44(t, 2H); 3.01(t, 2H); 3.60(s, 2H); 3.64(t, 4H); 5.16(br s, 1H); 6.97(d, 1H); 7.74(s, 1H); 7.78(d, 1H); 8.1(br s, 1H).

EXAMPLE 49

6-Trifluoromethyloxindole (270 mg, 1.3 mmol) was dissolved in dry, degassed DMF (5 ml) under argon. Sodium hydride (63 mg, 1.6 mmol) was added and the suspension stirred for 30 minutes at ambient temperature. A solution of 4-chloro-6-methoxy-7-(2-methoxyethoxy)quinazoline (111 mg, 0.332 mmol), (prepared as described for the starting material in Example 2), in dry, degassed DMF (5 ml) was added dropwise and the mixture heated at 100° C. for 2 hours. The mixture was allowed to cool and the DMF was removed by evaporation. The residue was purified by flash column chromatography eluting with methylene chloride/methanol (100/0 and then 15/1). The purified orange solid was triturated with ether, collected by filtration and dried under vacuum at 40° C. to give 6-methoxy-7-(2-methoxyethoxy)-4-(6-trifluoromethyloxindol-3-yl)quinazoline (100 mg, 52%).

$^1$H NMR Spectrum: (CDCl$_3$) 3.32(s, 3H); 3.74(t, 2H); 3.84(s, 3H); 4.32(t, 2H); 7.2(s, 1H); 7.3(m, 2H); 7.68(s, 1H); 7.78(d, 1H); 8.82(s, 1H); 11.25(s, 1H).

MS-ESI: 434 [MH]+

| Elemental analysis: | Found | C 56.2 | H 4.0 | N 9.2 |
|---|---|---|---|---|
| $C_{21}H_{18}N_3O_4F_3$ 0.7$H_2O$ | Requires | C 56.6 | H 4.4 | N 9.4% |

The starting material was prepared as follows:

Dibenzyl malonate (55.6 ml, 222 mmol) was added dropwise to a suspension of sodium hydride (8.9 g of a 60% suspension in mineral oil, 222 mmol) in DMF under argon and the reaction mixture stirred at ambient temperature for 30 minutes. 2-Bromo-5-trifluoromethyl-1-nitrobenzene (30 g, 111 mmol) was then added and the solution stirred for 18 hours. The reaction mixture was poured onto ice and extracted with ether (1200 ml). The ether layer was washed with water, brine, dried (MgSO$_4$), and the solvent removed by evaporation. The resulting red oil was purified by flash chromatography eluting with methylene chloride/isohexane (1/1) to give dibenzyl (2-nitro4-trifluoromethyl) phenylmalonate as a yellow oil (30 g, 57%) which crystallised on standing.

Lithium chloride (5.3 g, 130 mmol) and water (1.14 g, 40 mmol) were added to a solution of dibenzyl (2-nitro-4-trifluoromethyl)phenylmalonate (30 g, 60 mmol) in DMSO (500 ml) under argon and the resulting solution was heated to 100° C. for 4 hours. The reaction mixture was allowed to cool to ambient temperature then diluted with ethyl acetate (1000 ml). The organic phase was separated, washed with water, brine, dried (MgSO$_4$), and the solvent removed by evaporation. The resulting red oil was purified by flash chromatography eluting with ethyl acetate/isohexane (1/5) to give benzyl (2-nitro4-trifluoromethyl)phenylacetate as a yellow solid (16.6 g, 77%).

Tin(II)chloride dihydrate (50.8 g, 230 mmol) was added to a solution of benzyl (2-nitro4-trifluoromethyl) phenylacetate (15.3 g, 45 mmol) in ethyl acetate (250 ml), and the mixture heated at reflux for 2 hours under argon. Concentrated aqueous ammonia was added to give an aqueous phase of pH8. The mixture was stirred for 30 minutes and the insoluble material was removed by filtration through diatomaceous earth. The filtrate was purified by column chromatography eluting with isohexanes/ethyl acetate (3/2) to give 6-trifluoromethyloxindole as a white solid (7.2 g, 80%).

$^1$H NMR Spectrum: (CDCl$_3$) 3.6(s, 2H); 7.15(s, 1H); 7.3(m, 2H); 9.0(br s, 1H).

MS: 200 [M–H]+

| Elemental analysis: | Found | C 53.5 | H 3.0 | N 7.1 |
|---|---|---|---|---|
| $C_9H_6NO$ $F_3$ | Requires | C 53.7 | H 3.0 | N 7.0% |

EXAMPLE 50

A solution of 6-fluorooxindole (407 mg, 2.7 mmol), (Synthesis 1993, 51), in DMF (6 ml) was added dropwise to sodium hydride (108 mg, 2.7 mmol, prewashed with hexane) in DMF (6 ml). The mixture was stirred for 30 minutes at ambient temperature and 4-chloro-7-(2-(imidazol-1-yl)ethoxy)-6-methoxyquinazoline (274 mg, 0.9 mmol), (prepared as described for the starting material in Example 22), was added as a solid. The mixture was heated at 65° C. for 30 minutes, allowed to cool and was partitioned between saturated aqueous ammonium chloride solution and methylene chloride. The organic layer was separated, dried (MgSO$_4$), and the solvent removed by evaporation. The residue was triturated with ether, collected by filtration, washed with ether and dried under vacuum. The solid was dissolved in methylene chloride/methanol and 5M ethereal hydrogen chloride (4 ml) was added. The mixture was concentrated by evaporation to 5 ml total volume and the resulting solid was collected by filtration, washed with ether and dried under vacuum to give 4-(6-fluorooxindol-3-yl)-7-(2-(imidazol-1-yl)ethoxy)-6-methoxyquinazoline hydrochloride (175 mg, 40%).

$^1$H NMR Spectrum: (DMSOd$_6$, CF$_3$CO$_2$D) 3.86(s, 3H); 4.62(t, 2H); 4.76(t, 2H); 6.8–6.9(m, 2H); 7.34(s, 1H); 7.65–7.70(m, 1H); 7.73(s, 2H); 7.84(s, 1H); 8.79(s, 1H); 9.22(s, 1H).

MS-ESI: 420 [MH]+

| Elemental analysis: | Found | C 52.2 | H 4.2 | N 14.0 |
|---|---|---|---|---|
| $C_{22}H_{18}FN_5O_3$ 0.7$H_2O$ 1.95HCl | Requires | C 52.5 | H 4.3 | N 13.9% |

EXAMPLE 51

Using an analogous procedure to that described in Example 50, 5-bromooxindole (318 mg, 1.5 mmol), (prepared according to J. Am. Chem. Soc. 1975, 67, 1656), was treated with sodium hydride (60 mg, 1.5 mmol) in DMF (4 ml) and 4-chloro-6-methoxy-7-(3-morpholinopropoxy) quinazoline (169 mg, 0.5 mmol), (prepared as described for the starting material in Example 5), to give 4-(5-bromooxindol-3-yl)-6-methoxy-7-(3-morpholinopropoxy) quinazoline hydrochloride (108 mg, 35%).

$^1$H NMR Spectrum: (DMSOd$_6$, CF$_3$CO$_2$D) 2.2–2.3(m, 2H); 3.15(t, 2H); 3.35(t, 2H); 3.54(d, 2H); 3.73(t, 2H); 3.93(s, 3H); 4.04(d, 2H); 4.33(t, 2H); 6.95(d, 1H); 7.25(d, 1H); 7.33(s, 1H); 7.76(s, 1H); 7.8(s, 1H); 8.73(s, 1H).

MS-ESI: 515 [MH]+

| Elemental analysis: | Found | C 47.2 | H 4.6 | N 8.9 |
|---|---|---|---|---|
| $C_{24}H_{25}N_4O_4Br$ 1.8$H_2O$ 1.8HCl | Requires | C 47.1 | H 5.0 | N 9.2% |

EXAMPLE 52

Using a procedure analogous to that described in Example 26, 6-trifluoromethyloxindole (250 mg, 1.25 mmol), (prepared as described for the starting material in Example 49), was added to sodium hydride (100 mg, 2.5 mmol) in DMF (15 ml) and the solution was reacted with 4-chloro-7-(3-morpholinopropoxy)quinazoline (300 mg, 1.0 mmol), (prepared as described for the starting material in Example 37), in DMF (5 ml) to give, after work-up and purification, 7-(3-morpholinopropoxy)-4-(6-trifluoromethyloxindol-3-yl)quinazoline (80 mg, 16%).

$^1$H NMR Spectrum: (DMSOd$_6$, CF$_3$CO$_2$D) 2.2(m, 2H); 3.1(m, 2H); 3.3(t, 2H); 3.5(d, 2H); 3.7(t, 2H); 4.0(d, 2H); 4.25(t, 2H); 7.1–7.2(m, 4H); 7.75(d, 1H); 8.4(d, 1H); 8.85(s, 1H), 11.2(br s, 1H).

MS-ESI: 473 [MH]+

| Elemental analysis: | Found | C 59.3 | H 4.7 | N 11.7 |
|---|---|---|---|---|
| $C_{24}H_{23}F_3N_4O_3$ 0.6$H_2O$ | Requires | C 59.6 | H 5.1 | N 11.6% |

EXAMPLE 53

Sodium hydride (53 mg, 1.33 mmol) was added to a solution of 6-trifluoromethyloxindole (200 mg, 0.995 mmol), (prepared as described for the starting material in Example 49), in dry, degassed DMF and the suspension stirred for 15 minutes at ambient temperature. A solution of 4-chloro-6-methoxy-7-(3-morpholinopropoxy)quinazoline (111 mg, 0.332 mmol), (prepared as described for the starting material in Example 5), in a dry, degassed mixture of DMF (5 ml) and THF (2 ml) was added dropwise and the reaction mixture was heated at 60° C. for 3 hours. The mixture was allowed to cool, the DMF was removed by evaporation, 1M hydrochloric acid was added until the aqueous phase was pH8 and ethyl acetate was added to dissolve the resulting precipitate. The organic phase was separated and the aqueous phase re-extracted with ethyl acetate (50 ml×3). The ethyl acetate fractions were combined, dried (MgSO$_4$) and the solvent removed by evaporation. The residue was purified by flash column chromatography eluting with methylene chloride/methanol (10/1). The purified product was triturated with boiling ether and collected by filtration to give 6-methoxy-7-(3-morpholinopropoxy)-4-(6-trifluoromethyloxindol-3-yl) quinazoline (51 mg, 31%).

$^1$H NMR Spectrum: (DMSOd$_6$, CF$_3$CO$_2$D) 2.2(m, 2H), 3.1(m, 2H), 3.3(t, 2H), 3.5(m, 2H), 3.65(t, 2H), 3.82(s, 3H), 3.9(m, 2H), 4.28(t, 2H), 7.22(s, 1H), 7.3(m, 2H), 7.68(s, 1H), 7.74(d, 1H), 8.86(s, 1H), 11.54(s, 1H).

MS: 503 [MH]+

| Elemental analysis: | Found | C 57.0 | H 4.7 | N 10.5 |
|---|---|---|---|---|
| $C_{25}H_{25}N_4O_4F_3$ 1.2$H_2O$ | Requires | C 57.1 | H 5.3 | N 10.7% |

EXAMPLE 54

A solution of 5-carbamoyloxindole (391 mg, 2.2 mmol) in DMF (5 ml) was added dropwise to sodium hydride (89 mg, 2.2 mmol, prewashed with hexane) in DMF (3.5 ml). The mixture was stirred for 20 minutes at ambient temperature and 4-chloro-6-methoxy-7-(3-morpholinopropoxy) quinazoline (250 mg, 0.74 mmol), (prepared as described for the starting material in Example 5), was added as a solid and the mixture was heated at 60° C. for 1 hour. The volatiles were removed by evaporation and the residue was partitioned between ethyl acetate and water. The aqueous layer was adjusted to pH8.5 with 2M hydrochloric acid. The precipitate was collected by filtration, washed with water and dried under vacuum. The solid was dissolved in methylene chloride/methanol and 3M ethereal hydrogen chloride (2 ml) was added. The mixture was concentrated by evaporation and the resulting precipitate was collected by filtration, washed with ether and dried under vacuum to give 4-(5-carbamoyloxindol-3-yl)-6-methoxy-7-(3-morpholinopropoxy)quinazoline hydrochloride (184 mg, 45%).

$^1$H NMR Spectrum: (DMSOd$_6$, CF$_3$CO$_2$D) 2.3–2.4(m, 2H); 3.16(t, 2H); 3.35(t, 2H); 3.54(d, 2H); 3.75(t, 2H); 3.92(s, 3H); 4.04(d, 2H); 4.32(t, 2H); 7.03(d, 1H); 7.36(s, 1H); 7.77(d, 1H); 7.8(s, 1H); 8.31(s, 1H); 8.88(s, 1H).

MS-ESI: 478 [MH]+

| Elemental analysis: | Found | C 52.1 | H 5.7 | N 12.0 |
|---|---|---|---|---|
| $C_{25}H_{27}N_5O_5$ 2$H_2O$ 1.7HCl | Requires | C 52.2 | H 5.7 | N 12.2% |

The starting material was prepared as follows:

A solution of 5-cyanooxindole (1.2 g, 7.6 mmol), (Tet. Let., 1987, 28, 4027), in 85% sulphuric acid (8 ml) was heated at 80° C. for 6 hours. The mixture was allowed to cool, poured into ice/water and the mixture was adjusted to pH5 with 2M sodium hydroxide solution. The solid product was collected by filtration, washed with water, and dried under vacuum at 60° C. over phosphorus pentoxide to give 5-carbamoyloxindole (1.02 g, 76%).

$^1$H NMR Spectrum: (DMSOd$_6$) 3.52(s, 2H); 6.83(d, 1H); 7.14(br s, 1H); 7.74(s, 1H); 7.74(d, 1H); 7.76(br s, 1H); 10.6(s, 1H)

MS-EI: 176 [M]+

EXAMPLE 55

A solution of 5-(2-morpholinoethylaminosulphonyl) oxindole (364 mg, 1.1 mmol), (prepared as described for the starting material in Example 48), in DMF (3.5 ml) was added dropwise to a suspension of sodium hydride (90 mg, 2.2 mmol, prewashed with hexane) in DMF (1.5 ml). The mixture was stirred for 30 minutes at ambient temperature and 4-chloro-6,7dimethoxyquinazoline (84 mg, 0.37 mmol), (prepared as described for the starting material in Example 1), was added as a solid followed by DMSO (2 ml). The mixture was stirred for 45 minutes at 60° C., allowed to cool and partitioned between methylene chloride and saturated aqueous ammonium chloride solution. The organic layer was separated, washed with brine, dried (MgSO$_4$) and the solvent removed by evaporation. The residue was purified by column chromatography eluting with methylene chloride/methanol (95/5 followed by 92/8). The purified solid was triturated with ether, collected by filtration; washed with ether and dried under vacuum. The solid was dissolved in methylene chloride/methanol and 2M ethereal hydrogen chloride (1 ml) was added. The volatiles were removed bv evaporation, the solid residue triturated with ether, collected by filtration, washed with ether and dried under vacuum to give 6,7-dimethoxy-4-(5-(2-morpholinoethylaminosulphonyl)oxindol-3-yl)quinazoline hydrochloride (106 mg, 50%).

$^1$H NMR Spectrum: (DMSOd$_6$, CF$_3$CO$_2$D) 2.99(t, 2H); 3.1(t, 2H); 3.15(t, 2H); 3.37(d, 2H); 3.67(t, 2H); 3.92(s, 3H); 3.9(br s, 2H); 4.01(s, 3H); 7.15(d, 1H); 7.32(s, 1H); 7.56(d, 1H); 7.77(s, 1H); 8.08(s, 1H); 8.7(s, 1H).

MS-ESI: 514 [MH]+

| Elemental analysis: | Found | C 48.7 | H 5.1 | N 11.6 |
|---|---|---|---|---|
| $C_{24}H_{27}N_5O_6S$ 1.2$H_2O$ 1.5HCl | Requires | C 48.9 | H 5.3 | N 11.9% |

EXAMPLE 56

Using a procedure anaolgous to that described in Example 26, 6-cyanooxindole (250 mg, 1.6 mmol), (prepared as described for the starting material in Example 57), was added to sodium hydride (100 mg, 2.5 mmol) in DMF (15 ml) and the solution was treated with 4-chloro-7-(3-morpholinopropoxy)quinazoline (300 mg, 1.0 mmol), (prepared as described for the starting material in Example 37), in DMF (5 ml) to give, after work-up and purification, 4-(6-cyanooxindol-3-yl)-7-(3-morpholinopropoxy) quinazoline (90 mg, 20%).

$^1$H NMR Spectrun: (DMSOd$_6$, CF$_3$CO$_2$D) 2.2(m, 2H); 3.1(t, 2H); 3.3(t, 2H); 3.5(d, 2H0; 3.6(t, 2H); 4.0(m, 2H); 4.25(t, 2H); 7.1–7.3(m, 4H); 7.75(d, 1H); 8.5(d, 1H); 8.55(s, 1H), 11.0(s, 1H).

MS-ESI: 429 [M–H]$^+$

| Elemental analysis: | Found | C 62.9 | H 5.4 | N 15.6 |
|---|---|---|---|---|
| C$_{24}$H$_{23}$N$_5$O$_3$ 1.6H$_2$O | Requires | C 62.9 | H 5.7 | N 15.3% |

EXAMPLE 57

Sodium hydride (100 mg, 2.6 mmol) was added to a solution of 6-cyanooxindole (350 mg, 2.2 mmol) in dry degassed DMF (10 ml) under argon and the suspension stirred for 30 minutes at ambient temperature. A solution of 4-chloro-6-methoxy-7-(2-methoxyethoxy)quinazoline (200 mg, 0.74mmol), (prepared as described for the starting material in Example 2), in dry degassed DMF (2 ml) was added dropwise and the reaction mixture was heated at 60° C. for 2 hours. The mixture was allowed to cool and the DMF was removed by evaporation and the residue was partitioned between ethyl acetate (50 ml) and water (50 ml). The organic phase was separated and the aqueous phase was extracted with ethyl acetate (50 ml×3). The organic extracts were combined, dried (MgSO$_4$) and the solvent removed by evaporation. The solid residue was purified by flash column chromatography eluting with methylene chloride/methanol/ ammonia (99/1/1 and then 95/5/1). The purified solid was triturated in hot ether and collected by filtration and then triturated in hot methylene chloride/methanol (1/1), collected by filtration and dried to give 4-(6-cyanooxindol-3-yl)-6-methoxy-7-(2-methoxyethoxy)quinazoline (84 mg, 29%).

$^1$H NMR Spectrum: (CDCl$_3$) 3.34(s, 3H); 3.74(t, 2H); 3.84(s, 3H); 4.52(t, 2H); 7.32(m, 3H); 7.7(m, 2H); 8.70(s, 1H); 11.32(s, 1H).

MS: 391 [M]$^+$

| Elemental analysis: | Found | C 62.8 | H 4.5 | N 14.3 |
|---|---|---|---|---|
| C$_{21}$H$_{18}$N$_4$O$_4$ 0.3H$_2$O | Requires | C 62.8 | H 4.4 | N 14.1% |

The starting material was prepared as follows:

Diethyl malonate (44.6ml, 293 mmol) was added dropwise over 1.5 hours to a suspension of sodium hydride (11.7 g of a 60% suspension in mineral oil, 293 mmol) in DMF under argon and the reaction mixture was stirred at ambient temperature for 30 minutes. The resulting solution was added dropwise over 1 hour to a solution of 2-chloro-5-cyano-1-nitrobenzene (24.3 g, 133 mmol) in DMF (75 ml) cooled with a dry ice/acetone bath. The temperature of the cooling bath was adjusted to prevent the freezing of the red reaction mixture. After the addition was completed, the reaction was left to rise to ambient temperature over 2 hours. The resulting red solution was poured slowly into a stirred mixture of ice (100 ml) and 1M hydrochloric acid (10 ml). The resulting yellow precipitate was collected by filtration, washed with water until the filtrate was at pH7.0 and then dried under vacuum to give diethyl (4-cyano-2-nitrophenyl) malonate (39.6 g, 97%).

Lithium chloride (10.7 g, 255 mmol) and water (2.3 g, 127 mmol) were added to a solution of diethyl (4-cyano-2-nitrophenyl)malonate (39 g, 127 mmol) in DMSO (700 ml) under argon and the solution was heated at 100° C. for 4 hours. The reaction mixture was allowed to cool and then poured slowly into stirred ice water (1000 ml). The resulting pale yellow precipitate was colllected by filtration, washed with water (100 ml×4) and dried under vacuum to give ethyl (4-cyano-2-nitrophenyl)acetate (27.1 g, 91%).

Iron powder (11.5 g, 205.2 mmol) was added to a saturated solution of ethyl(4-cyano-2-nitrophenyl)acetate (12 g, 51.3 mmol) in hot glacial acetic acid and the reaction mixture was stirred at 100° C. for 2 hours. The mixture was allowed to cool and poured into stirred ice water (1000 ml). The aqueous mixture was extracted with ethyl acetate, the extracts were combined, dried (MgSO$_4$) and the solvent removed by evaporation. The solid residue was recrystallised from ethyl acetate to give 6-cyanooxindole (6.94 g, 85%).

$^1$H NMR Spectrum: (CDCl$_3$) 3.58(s, 2H), 7.1(s, 1H), 7.38(s, 2H).

MS: 157 [M–H]$^+$

EXAMPLE 58

A solution of 5-(2-morpholinoethylaminosulphonyl) oxindole (320 mg, 0.98 mmol), (prepared as described for the starting material in Example 48), in DMF (3.5 ml) was added to a suspension of sodium hydride (39.4 mg, 0.98 mmol, prewashed with THF) in DMF (1.5 ml). The mixture was stirred for 30 minutes at ambient temperature and 4-chloro-7-(2-(imidazol-1-yl)ethoxy)-6-methoxyquinazoline (100 mg, 0.32 mmol), (prepared as described for the starting material in Example 22), was added. The mixture was stirred for 1 hour at 60° C., allowed to cool and partitioned between methylene chloride and saturated aqueous ammonium chloride solution. The organic layer was separated, washed with brine, dried (MgSO$_4$) and the solvent removed by evaporation. The residue was purified by column chromatography eluting with methanoymethylene chloride (5/95 to 15/85). The purified product was triturated with ether, collected by filtration and dried under vacuum. The solid was dissolved in methylene chloride/ methanol and 2.2M ethereal hydrogen chloride (1 ml) was added. The volatiles were removed by evaporation, the solid residue was triturated with ether, collected by filtration and dried under vacuum to give 7-(2-(imidazol-1-yl)ethoxy)-6-methoxy-4-(5-(2-morpholinoethylaminosulphonyl)oxindol-3-yl)quinazoline hydrochloride (153 mg, 64%).

$^1$H NMR Spectrum: (DMSOd$_6$, CF$_3$CO$_2$D) 2.94(t, 2H); 3.10(t, 2H); 3.15(t, 2H); 3.36(d, 2H); 3.65(t, 2H); 3.91(s, 3H); 4.0(d, 2H); 4.65(t, 2H); 4.76(t, 2H): 7.12(d, 1H); 7.35(s, 1H); 7.5(d, 1H); 7.74(s, 1H); 7.82(s, 1H); 7.84(s, 1H); 8.07(br s, 1H); 8.57(s, 1H); 9.21(s, 1H).

MS-ESI: 594 [MH]$^+$

| Elemental analysis: | Found | C 46.0 | H 4.9 | N 13.3 |
|---|---|---|---|---|
| C$_{28}$H$_{31}$N$_7$O$_6$S 1.6H$_2$O 2.85HCl | Requires | C 46.3 | H 5.1 | N 13.5% |

EXAMPLE 59

Sodium hydride (80 mg, 2.07 mmol) was added to a solution of 6-cyanooxindole (280 mg, 1.78 mmol), (prepared as described for the starting material in Example 57), in dry, degassed DMF (10 ml) and the suspension stirred for 15 minutes at ambient temperature. A solution of 4-chloro-6-methoxy-7-(3-morpholinopropoxy)quinazoline (200 mg, 0.59 mmol), (prepared as described for the starting material in Example 5), in a dry, degassed mixture of DMF (2 ml) and THF (2 ml) was added dropwise and the reaction mixture was heated at 60° C. for 3 hours. The mixture was allowed to cool, the solvents were removed by evaporation and the residue was partitioned between ethyl acetate and water. The organic phase was separated and the aqueous phase extracted with ethyl acetate (50 ml×3). The ethyl acetate fractions were combined, dried ($MgSO_4$), the solvent removed by evaporation and the residue was purified by flash column chromatography eluting with methylene chloride/methanol (100/13). The purified product was triturated in boiling ether and the solid product collected by filtration to give 4-(6-cyanooxindol-3-yl)-6-methoxy-7-(3-morpholinopropoxy)quinazoline (36 mg, 13%) as an orange solid.

$^1$H NMR Spectrum: ($DMSOd_6$, $CF_3CO_2D$) 2.3(m, 2H); 3.1(m, 2H); 3.3(m, 2H); 3.5(m, 2H); 3.65(m, 2H); 3.85(s, 3H); 4.0(m, 2H); 4.3(m, 2H); 7.3(m, 3H); 7.7(m, 2H); 11.18(s, 1H).

MS: 460 $[MH]^+$

| Elemental analysis: | Found | C 64.0 | H 5.5 | N 15.2 |
|---|---|---|---|---|
| $C_{25}H_{25}N_5O_4$ 0.4$H_2O$ | Requires | C 64.3 | H 5.6 | N 15.0% |

EXAMPLE 60

A solution of 5-aminosulphonyloxindole (355 mg, 1.67 mmol) in DMF (3.5 ml) was added dropwise to sodium hydride (67 mg, 1.67 mmol, prewashed with THF) in DMF (5 ml). The mixture was stirred for 30 minutes at ambient temperature and a solution of 4-chloro-6-methoxy-7-(2-methoxyethoxy)quinazoline (150 mg, 0.56 mmol), (prepared as described for the starting material in Example 2), in DMF (3 ml) was added. The mixture was heated at 65° C. for 2.5 hours and then stirred overnight at ambient temperature. The mixture was partitioned between ethyl acetate and water, the aqueous layer was adjusted to pH7 with 1M hydrochloric acid and left standing for 2 hours. The resulting precipitate was collected by filtration, washed with water and ether, and dried under vacuum. The solid was dissolved in methylene chloride/methanol and 2.2M ethereal hydrogen chloride (1ml) was added. The volatiles were removed by evaporation, the solid residue was triturated with ether, collected by filtration and dried under vacuum to give 4-(5-aminosulphonyloxindol-3-yl)-6-methoxy-7-(2-methoxyethoxy)quinazoline hydrochloride (144 mg, 60%).

$^1$H NMR Spectrum: ($DMSOd_6$, $CF_3CO_2D$) 3.36(s, 3H); 3.77(t, 2H); 3.92(s, 3H); 4.35(t, 2H); 7.11 (d, 1H); 7.33(s, 1H); 7.61(d, 1H);, 7.71(s, 1H); 8.1(s, 1H); 8.76(s, 1H).

MS-ESI: 445 $[MH]^+$

| Elemental analysis: | Found | C 49.4 | H 4.5 | N 11.5 |
|---|---|---|---|---|
| $C_{20}H_{20}N_4O_6S$ 0.3$H_2O$ 0.95HCl | Requires | C 49.6 | H 4.5 | N 11.6% |

The starting material was prepared as follows:

Oxindole (2 g, 15 mmol) was added in portions to chlorosulphonic acid (5 ml, 75 mmol) cooled at 5° C. The mixture was stirred at ambient temperature for 10 minutes and then heated at 80° C. for 30 minutes. The mixture was allowed to cool, and then poured onto ice. The precipitate was collected by filtration, washed with water, and dried over phosphorus pentoxide to give 5-chlorosulphonyloxindole (2.8 g, 80%).

$^1$H NMR Spectrun: ($DMSOd_6$) 3.46(s, 2H); 6.72(d, 1H); 7.43(m, 2H); 10.43(br s, 1H).

MS-EI: 232 $[M]^+$

A solution of 5-chlorosulphonyloxindole (2 g, 0.86 mmol) in ethanol (30 ml), methylene chloride (150 ml) and 2.8M methanolic ammonia (6.2 ml, 17 mmol) was stirred overnight at ambient temperature. The volatiles were removed by evaporation and the solid residue was purified by column chromatography eluting with methanol/methylene chloride (15/85) to give 5-aminosulphonyloxindole (1.54 g, 84%).

$^1$H NMR Spectrum: ($DMSOd_6$) 3.58(s, 2H); 6.92(d, 1H); 7.18(s, 2H); 7.6–7.7(m, 2H); 10.73(s, 1H).

EXAMPLE 61

Using a procedure analogous to that described in Example 26, 6-phenyloxindole (300 mg, 1.4 mmol) was added to sodium hydride (90 mg, 2.25 mmol) in DMF (10 ml) and the solution was treated with 4-chloro-7-(3-morpholinopropoxy)quinazoline (210 mg, 0.73 mmol), (prepared as described for the starting material in Example 37), in DMF (10 ml) to give, after work-up and purification, 7-(3-morpholinopropoxy)4-(6-pbenyloxindol-3-yl)quinazoline (365 mg, 28%).

$^1$H NMR Spectrum: ($DMSOd_6CF_3CO_2D$) 2.2(m, 2H); 3.1(m, 2H); 3.3(t, 2H); 3.5(d, 2H); 3.65(t, 2H); 4.0(m, 2H); 4.25(t, 2H); 7.1(m, 2H); 7.15(d, 1H); 7.2(dd, 1H); 7.55(d, 1H); 8.4(d, 1H); 8.6(s, 1H); 9.8(br s, 1H); 11.0(s, 1H).

MS-ESI: 483 $[MH]^+$

| Elemental analysis: | Found | C 55.2 | H 4.5 | N 11.3 |
|---|---|---|---|---|
| $C_{23}H_{23}N_4O_3Br$ 1$H_2O$ | Requires | C 55.5 | H 5.0 | N 11.3% |

The starting material was prepared as follows:

6-Bromooxindole (800 mg, 3.8 mmol), (prepared as described for the starting material in Example 62), phenylboronic acid (500 mg, 4.1 mmol) sodium hydrogen carbonate (saturated aqueous solution, 50 ml) and 1,2-dimethoxyethane (100 ml) were mixed together and the solution was degassed using alternatively vacuum and argon. Tetrakis(triphenylphosphine)palladium(0) (50 mg) was added and the solution degassed again before heating it to reflux for 8 hours. The reaction mixture was evaporated to dryness using a rotary evaporator and the solid residue partitioned between water (75 ml) and ethyl acetate (100 ml). The aqueous phase was reextracted with more ethyl acetate (100 ml×3), the organic phases were combined, washed with brine and passed directly through a short plug of silica to remove the baseline impurities. The solvent was evaporated and the solid was triturated in ether and filtered to give 6-phenyloxindole as a pink solid (375 mg, 60%).

$^1$H NMR Spectrum: ($DMSOd_6$) 3.5(s, 2H); 7.0(s, 1H); 7.2(d, 1H); 7.25(d, 1H); 7.35(d, 1H); 7.45(t, 2H); 7.6(d, 2H); 10.42(br s, 1H).

MS-ESI: 208 $[M-H]^+$

EXAMPLE 62

Using a procedure analogous to that described in Example 26, 6-bromooxindole (1.16 g, 5.5 mmol) was added to sodium hydride (324 mg, 8.6 mmol) in DMF (20 ml) and the solution was treated with 4-chloro-7-(3-morpholinopropoxy)quinazoline (790 mg, 2.7 mmol), (prepared as described for the starting material in Example 37), in DMF (10 ml) to give, after work-up and purification, 4-(6-bromooxindol-3-yl)-7-(3-morpholinopropoxy) quinazoline (365 mg, 28%).

¹H NMR Spectrum: (DMSOd₆, CF₃CO₂D) 2.2(m, 2H); 3.1(m, 2H); 3.3(t, 2H); 3.5(d, 2H); 3.65(t, 2H); 4.0(m, 2H); 4.25(t, 2H); 7.1(m, 2H); 7.15(d, 1H); 7.2(dd, 1H); 7.55(d, 1H); 8.4(d, 1H); 8.6(s, 1H); 9.8(br s, 1H); 11.0(s, 1H).

MS-ESI: 483 [MH]⁺

| Elemental analysis: | Found | C 55.2 | H 4.5 | N 11.3 |
|---|---|---|---|---|
| C₂₃H₂₃N₄O₃Br 1H₂O | Requires | C 55.5 | H 5.0 | N 11.3% |

The starting material was prepared as follows:

2,5-Dibromonitrobenzene (41.5 g, 148 mmol) was dissolved in anhydrous DMF (500 ml) and sodium hydride (17.7 g of a 60% suspension in mineral oil, 443 mmol) was added under argon. Diethyl malonate (49.6 g, 295 mmol) was added dropwise over 10 minutes giving a strong exotherm (mixture rose to 60° C.). The reaction mixture was maintained at 60° C. for 6 hours then left to cool to ambient temperature and stirred for 18 hours. The resulting dark red solution was poured slowly into 2M hydrochloric acid (1500 ml) and extracted with ether (500 ml×4). The organic phases were combined, washed with brine, dried (MgSO₄) and the solvent removed by evaporation. The crude oil was purified by flash chromatography eluting with isohexanes/ethyl acetate (100/0, then 95/5 and finally 80/20) to give diethyl (4-bromo-2-nitrophenyl)malonate (51 g, 96%).

Using a procedure analogous to that described for the starting material in Example 57, diethyl(4-bromo-2-nitrophenyl)malonate (35 g, 97 mmol) was converted into ethyl (4-bromo-2-nitrophenyl)acetate (26 g, 93%).

Using a procedure analogous to that described for the starting material in Example 57, ethyl(4-bromo-2-nitrophenyl)acetate (26 g, 90 mmol) was treated with iron in acetic acid. The product thus obtained was recystallised from ether/isohexanes to give 6-bromooxindole (8.2 g, 42%).

¹H NMR Spectrum: (DMSOd₆) 3.45(s, 2H); 6.9(s, 1H); 7.1(m, 2H); 10.45(br s, 1H).

MS-ESI: 210 and 212 [M-H]⁺

EXAMPLE 63

Using a procedure analogous to that described in Example 26, 6-(1-t-butoxycarbonylpyrrol-2-yl)oxindole (500 mg, 1.7 mmol) was added to sodium hydride (90 mg, 2.25 mmol) in THF (10 ml) and the solution was treated with 4-chloro-6-methoxy-7-(3-morpholinopropoxy)quinazoline (250 mg, 0.74 mmol), (prepared as described for the starting material in Example 5), in DMF (2 ml) to give, after work-up and purification, 4-(6-(1-t-butoxycarbonylpyrrol-2-yl)oxindol-3-yl)-6-methoxy-7-(3-morpholinopropoxy)quinazoline (185 mg, 40%).

¹H NMR Spectrun: (DMSOd₆, CF₃CO₂D) 1.3(s, 9H); 2.2(m, 2H); 3.1(t, 2H); 3.3(t, 2H); 3.5(d, 2H); 3.6(t, 2H); 3.8(s, 3H); 3.9(d, 2H); 4.25(t, 2H); 6.2(m, 2H); 6.95(s, 1H); 7.0(d, 1H); 7.25(m, 2H); 7.6(d, 1H); 7.7(s, 1H); 8.95(s, 1H); 9.7(br s, 1H); 11.2(s, 1H).

MS-ESI: 600 [MH]⁺

| Elemental analysis: | Found | C 65.7 | H 5.9 | N 11.9 |
|---|---|---|---|---|
| C₃₃H₃₇N₅O₆ 0.4H₂O | Requires | C 65.3 | H 6.3 | N 11.5% |

The starting material was prepared as follows:

Triethylamine (13 ml, 93 mmol), 4-(N,N-dimethylamino)pyridine (100 mg), and di-t-butyl dicarbonate (18.1 g, 83 mmol) were added successively to a solution of pyrrole (5 g, 74.6 mmol) in acetonitrile (125 ml). The reaction mixture was then heated at 60° C. for 30 minutes. The reaction was allowed to cool and the solvent was removed by evaporation. The residue was purified by flash column chromatography eluting with isohexanes/ethyl acetate (100/0 and then 95/5) to give 1-t-butoxycarbonylpyrrole (8.74 g, 70%).

n-Butyllithium (29 ml of a 1.6M solution in hexane, 47.4 mmol) was added dropwise over 10 minutes to a solution of 2,2,6,6-tetramethylpiperidine (6.7 g, 47.4 mmol) in THF (175 ml) cooled to −78° C. A solution of 1-t-butoxycarbonylpyrrole (8.19 g, 49 mmol) in THF (25 ml) was added and the mixture was maintained below −70° C. The reaction mixture was stirred for 1.5 hours at −78° C. and tri-isopropyl borate (17 g, 90 mmol) was added. The reaction mixture was then allowed to warm to ambient temperature over 1 hour. The mixture was diluted with ether (500 ml) and washed with 1M potassium hydrogen sulphate solution (100 ml×3), 1M sodium hydrogen carbonate solution (100 ml×2) and brine (100 ml). The ether phase was dried (MgSO₄) and the solvent removed by evaporation. The residue was purified by flash column chromatography eluting with isohexanes/ethyl acetate (a gradient from 100/0 to 50/50) to give the 1-t-butoxycarbonylpyrrol-2-ylboronic acid (4.05 g, 43%).

1-t-Butoxycarbonylpyrrol-2-ylboronic acid (1.5 g, 7.1 mmol) and a saturated aqueous solution of sodium hydrogen carbonate (25 ml) were added to a solution of 6-bromooxindole (1.1 g, 5.2 mmol), (prepared as described for the starting material in Example 62), in 1,2-dimethoxyethane (75 ml). The reaction mixture was degassed and placed under argon and tetrakis (triphenylphosphine)palladium(0) (50 mg) was added and the mixture heated at reflux for 6 hours. The organic solvent was removed by evaporation and the reaction mixture partitioned between ethyl acetate and water. The organic phase was separated and the aqueous phase was re-extracted twice with ethyl acetate. The organic phases were combined, washed with brine, dried (MgSO₄), and the solvent removed by evaporation. The residue was triturated with ether/isohexanes (1/1) and collected by filtration to give 6-(1-t-butoxycarbonylpyrrol-2-yl)oxindole (1.11 g, 71%).

¹H NMR Spectrum: (DMSOd₆) 1.25(s, 9H); 3.45(s, 2H); 6.2(m, 2H); 6.65(s, 1H); 6.85(d, 1H); 7.15(d, 1H); 7.25(s, 1H); 10.35(br s, 1H).

EXAMPLE 64

4-(6-(1-t-Butoxycarbonylpyrrol-2-yl)oxindol-3-yl)-6-methoxy-7-(3-morpholinopropoxy)quinazoline (150 mg, 0.25 mmol), (prepared as described in Example 63), was dissolved in TFA (5 ml) and triethylsilane (0.5 ml) and the mixture stirred at ambient temperature for 2 hours. The volatiles were removed by evaporation and azeotroping with toluene. The residue suspended in methanol/methylene chloride and 1M ethereal hydrogen chloride (1.25 ml) was added and the volatiles were removed by evaporation. The residue was triturated with t-butyl methyl ether and collected by filtration to give 4-(6-(pyrrol-2-yl)oxindol-3-yl)-6-methoxy-7-(3-morpholinopropoxy)quinazoline hydrochloride (132 mg, 87%) as a dark purple solid.

$^1$H NMR Spectrum: (DMSOd$_6$, CF$_3$CO$_2$D) 2.3(m, 2H); 3.1(m, 2H); 3.25(m, 2H); 3.45(d, 2H); 3.8(m, 5H), 3.9(d, 2H); 4.25(t, 2H); 6.1(m, 1H); 6.4(m, 1H); 6.8(s, 1H); 7.2(s, 1H); 7.25(m, 2H); 7.6(d, 1H); 7.8(s, 1H); 8.55(s, 1H); 10.9(br s, 1H); 11.1(m, 1H); 11.3(br s, 1H).

MS-ESI: 500 [MH]$^+$

| Elemental analysis: | Found | C 55.7 | H 5.9 | N 11.4 |
|---|---|---|---|---|
| C$_{33}$H$_{37}$N$_5$O$_6$ 1.7H$_2$O 2HCl | Requires | C 55.8 | H 5.8 | N 11.6% |

EXAMPLE 65

A solution of oxindole (122 mg, 0.91 mmol) in DMF (1.5 ml) was added to a suspension of sodium hydride (37 mg, 0.91 mmol, prewashed with hexane) in DMF (3.5 ml). The mixture was stirred for 30 minutes at ambient temperature and 4-chloro-6-methoxy-7-(2-([N-methyl-N-(3-morpholinopropylsulphonyl)]amino)ethoxy)quinazoline (140 mg, 0.3 mmol) was added as a solid and the mixture stirred for 1.5 hours at ambient temperature. The mixture was poured onto a mixture of ether and water (50 ml/50 ml), the aqueous layer was adjusted to pH8 with 1M hydrochloric acid and was extracted with methylene chloride. The organic extract was washed with brine, dried (MgSO$_4$) and the solvent removed by evaporation. The residue was purified by column chromatography eluting with methylene chloride/methanol (95/5). The purified product was dissolved in methylene chloride (15 ml) and methanol (2 ml), and 2.2M ethereal hydrogen chloride (1 ml) was added. The mixture was stirred for 30 minutes at ambient temperature and the volatiles were removed by evaporation. The residue was triturated with ether, collected by filtration and dried under vacuum at 70° C. to give 6-methoxy-7-(2-([N-methyl-N-(3-morpholinopropylsulphonyl)]amino)ethoxy)4-(oxindol-3-yl)quinazoline hydrochloride (100 mg, 59%).

$^1$H NMR Spectrum: (DMSOd$_6$, CF$_3$CO$_2$D) 2.1–2.2(m, 2H); 3.01(s, 3H); 3.15(t, 2H); 3.25(t, 2H); 3.33(t, 2H); 3.46(d, 2H); 3.7–3.8(m, 4H); 3.89(s, 3H); 3.99(d, 2H); 4.36(t, 2H); 7.0–7.1(m, 2H); 7.18(t, 1H); 7.35(s, 1H); 7.71 (d, 1H); 7.79(s, 1H); 8.91(s, 1H).

MS-ESI: 556 [MH]$^+$

The starting material was prepared as follows:

Diethyl azodicarboxylate (679 mg, 3.9 mmol) was added dropwise to a suspension of 7-hydroxy-6-methoxy-3-((pivaloyloxy)methyl)-3,4-dihydroquinazolin4-one (918 mg, 3 mmol), (prepared as described for the starting material in Example 22), triphenylphosphine (1 g, 3.9 mmol) and 2-([N-(t-butylcarbonyl)-N-methyl]amino)ethanol (682 mg, 3.9 mmol), (Synth. Commun. 1993, 23, 2443), in methylene chloride (20 ml) and the mixture stirred for 1 hour at ambient temperature. Further 2-([N-(t-butylcarbonyl)-N-methyl] amino)ethanol (105 mg, 0.6 mmol), triphenylphosphine (786 mg, 3 mmol) and diethyl azodicarboxylate (522 mg, 3 mmol) were added and the mixture stirred for 30 minutes at ambient temperature. The mixture was concentrated to half volume by evaporation and purified by column chromatography eluting with methylene chloride/ether (7/3 increasing to 1/1) to give 6-methoxy-7-(2-([N-(t-butylcarbonyl)-N-methyl]amino)ethoxy)-3-((pivaloyloxy)methyl)-3,4-dihydroquinazolin-4-one (1.3 g, 98%).

$^1$H NMR Spectrum: (CDCl$_3$) 1.2(s, 9H); 1.45(s, 9H); 3.05(br s, 3H); 3.72(br s, 2H); 3.98(s, 3H); 4.25(br s, 2H); 5.95(s, 2H); 7.1(br s, 1H); 7.6(s, 1H); 8.2(s, 1H).

A solution of 6-methoxy-7-(2-([N-t-butylcarbonyl)-N-methyl]aminoethoxy)-3-((pivaloyloxy)methyl)-3,4-dihydroquinazolin4one (1.39 g, 3 mmol) in methylene chloride (4 ml) and TFA (4 ml) was stirred at ambient temperature for 1 hour. Toluene was added, and the volatiles were removed by evaporation. The residue was triturated with ether and the resulting solid was collected by filtration. The solid was dissolved in water, sodium hydrogen carbonate was added and the aqueous mixture was extracted with methylene chloride. The organic extract was dried (MgSO$_4$) and the solvent removed by evaporation. The residue was triturated with ether and the solid was collected by filtration to give 6-methoxy-7-(2-((methylaino)ethoxy)-3-((pivaloyloxy)methyl)-3,4-hydmquinazolin4-one (800 mg, 73%).

$^1$H NMR Spectrum: (DMSOd$_6$, CF$_3$CO$_2$D) 1.13(s, 9H); 2.72(s, 3H); 3.45(br s, 2H); 3.95(s, 3H); 4.5(t, 2H); 5.94(s, 2H); 7.31(s, 1H); 7.6(s, 1H); 8.47(s, 1H).

MS-ESI: 364 [MH]$^+$

3-Morpholinopropane sulphonyl chloride (280 mg, 1.1 mmol), (WO 93 01181) followed by triethylamine (336 µl, 2.4 mmol) was added to a solution of 6-methoxy-7-(2-(methylamino)ethoxy)-3-((pivaloyloxy)methyl)-3,4-dihydroquinazolin4-one (350 mg, 0.96 mmol) in methylene chloride (15 ml) and the mixture stirred for 30 minutes at ambient temperature. The mixture was partitioned between methylene chloride and water, the organic layer was separated, washed with brine, dried (MgSO$_4$) and the volatiles were removed by evaporation. The residue was purified by column chromatography eluting with ethyl acetate/methylene chloride (1/1) followed by methylene chloride/methanol (95/5). The purified product was triturated with ether, collected by filtration and dried under vacuum to give 6-methoxy-7-(2-([N-methyl-N-(3-morpholinopropylsulphonyl)]amino)ethoxy)-3-((pivaloyloxy)methyl)-3,4-dihydroquinazolin-4-one (320 mg, 60%).

$^1$H NMR Spectrum: (DMSOd$_6$) 1.11(s, 9H); 1.8–1.9(m, 2H); 2.25–2.35(m, 6H); 2.94(s, 3H); 3.19(t, 2H); 3.32(s, 3H); 3.51(t, 4H); 3.61(t, 2H); 3.9(s, 3H); 4.29(t, 2H); 5.9(s, 2H); 7.23(s, 1H); 7.52(s, 1H); 8.36(s, 1H).

MS-ESI: 577 [MNa]$^+$

A solution of 6-methoxy-7-(2-([N-methyl-N-(3-morpholinopropylsulphonyl)]amino)ethoxy)-3-((pivaloyloxy)methyl)-3,4-dihydroquinazolin-4-one (310 mg, 0.55 mmol) in saturated methanolic ammonia (15 ml) was stirred at ambient temperature overnight. The volatiles were removed by evaporation, the solid residue was triturated with ether, collected by filtration and dried under vacuum to give 6-methoxy-7-(2-([N-methyl-N(3-morpholinopropyisulphonyl)]amino)ethoxy)-3,4-dihydroquinazolin-4-one (245 mg, 100%).

$^1$H NMR Spectrum: (DMSOd$_6$) 1.8(t, 2H); 2.2–2.3(m, 6H); 2.94(s, 3H); 3.18(t, 2H); 3.15(t, 4H); 3.60(t, 2H); 3.88(s, 3H); 4.27(t, 2H); 7.18(s, 1H); 7.47(s, 1H); 7.99(s, 1H).

A solution of 6-methoxy-7-(2-(N-methyl-N-(3-morpholinopropylsulphonyl))amino)ethoxy)-3,4-dihydroquinazolin4-one (176 mg, 0.4 mmol) in thionyl chloride (4 ml) containing DMF (100 µl) was stirred at 45° C. for 1 hour. The volatiles were removed by evaporation and by azeotroping with toluene. The residue was partitioned between methylene chloride and water, the aqueous phase was adjusted to pH8 with saturated aqueous sodium hydrogen carbonate solution. The organic layer was separated, washed with brine, dried (MgSO₄) and the solvent removed by evaporation. The residue was purified by column chromatography eluting with methanol/methylene chloride (a gradient from 3/100 to 10/90). The purified product was triturated with ether, collected by filtration and dried under vacuum to give 4-chloro-6-methoxy-7-(2-(N-methyl-N-(3-morpholinopropylsulphonyl)]amino)ethoxy) quinazoline (153 mg, 71%).

¹H NMR Spectrum: (DMSOd₆) 1.75–1.85(m, 2H); 2.25–2.35(m, 6H); 2.96(s, 3H); 3.2(t, 2H); 3.51(t, 4H); 3.65(t, 2H); 4.01(s, 3H); 4.4(t, 2H); 7.43(s, 1H); 7.54(s, 1H); 8.89(s, 1H).

EXAMPLE 66

Using a procedure analogous to that described in Example 26, 6-(1-t-butoxycarbonylpyrrolidin-2-yl)oxindole (420 mg, 1.4 mmol) was added to sodium hydride (85 mg, 2.2 mmol) in THF (15 ml) and the solution was treated with 4-chloro-6-methoxy-7-(3-morpholinopropoxy)quinazoline (235 mg, 0.7 mmol), (prepared as described for the starting material in Example 5), in DMF (2 ml) to give, after work-up and purification, 4-(6-(1-t-butoxycarbonylpyrrolidin-2-yl) oxindol-3-yl)-6-methoxy-7-(3-morpholinopropoxy) quinazoline (135 mg, 32%).

¹H NMR Spectrum: (DMSOd₆, CF₃CO₂D) 1.1–1.4(m, 9H); 1.8(m, 3H); 2.3(m, 3H); 3.1(m, 2H); 3.4(t, 2H); 3.5(m, 4H); 3.8(m, 5H); 4.0(m, 2H); 4.3(t, 2H); 4.7–4.9(m, 1H); 6.9(m, 2H); 7.25(s, 1H); 7.6(d, 1H); 7.75(s, 1H); 8.95(s, 1H); 10.95(s, 1H).

MS-ESI: 604 [MH]⁺

| Elemental analysis: | Found | C 64.6 | H 6.9 | N 11.0 |
|---|---|---|---|---|
| C₃₃H₄₁N₅O₆ 0.7H₂O | Requires | C 64.3 | H 6.9 | N 11.4% |

The starting material was prepared as follows:

A mixture of 6-(1-t-butoxycarbonylpyrrol-2-yl)oxindole (560 mg, 1.9 mmol), (prepared as described for the starting material in Example 63), and 10% palladium-on-charcoal catalyst (50 mg) in ethyl acetate (30 ml) was stirred under hydrogen at 1 atmosphere pressure for 3 days. The catalyst was removed by filtration through diatomaceous earth, the solvent was removed by evaporation and the residue triturated with ether/isohexanes (1/5) and collected by filtration to give 6-(1-t-butoxycarbonylpyrrolidin-2-yl)oxindole (480 mg, 85%) as a pale yellow solid.

¹H NMR Spectrum: (DMSOd₆) 1.25(br s, 9H); 1.75(m, 3H); 2.3(m, 2H); 3.4(s, 2H); 3.45(m, 2H); 4.75(br s, 1H); 6.6(s, 1H); 6.75(d, 1H); 7.1(d, 2H); 10.1(br s, 1H).

MS-ESI: 301 [M-H]⁺

EXAMPLE 67

TFA (5 ml) and triethylsilane (0.5 g) were added to 4-(6-(1-t-butoxycarbonylpyrrolidin-2-yl)oxindol-3-yl)-6-methoxy-7-(3 -morpholinopropoxy)quinazoline (75 mg, 0.1 2 mmol), (prepared as described in Example 66), and the solution was stirred for 30 minutes. The volatiles were removed by evaporation and by azeotroping with toluene. The bright orange residue was dissolved in methanol and a solution of 1M ethereal hydrogen chloride was added. The resulting precipitate was collected by filtration, washed with ether and dried at 60° C. under vacuum for 2 hours to give 6-methoxy-7-(3-morpholinopropoxy)-4-(6-(pyrrolidin-2-yl) oxindol-3-yl)quinazoline hydrochloride (45 mg, 63%).

¹H NMR Spectrum: (DMSOd₆, CF₃CO₂D) 2.0(m, 3H); 2.3(m, 3H); 3.1(m, 2H); 3.3(m, 4H); 3.5(d, 2H); 3.75(t, 2H); 3.85(s, 3H); 4.0(d, 2H); 4.3(t, 2H); 4.5(m, 1H); 7.1(m, 2H);7.3(s, 1H); 7.7(d, 1H); 7.75(s, 1H); 8.8(m, 2H); 11.2(s, 1H).

MS-ESI: 504 [MH]⁻

| Elemental analysis: | Found | C 52.1 | H 5.6 | N 10.4 |
|---|---|---|---|---|
| C₂₈H₃₃N₅O₄ 0.7H₂O 3HCl | Requires | C 51.8 | H 6.2 | N 10.8% |

EXAMPLE 68

A solution of 5-aminosulphonyloxindole (283 mg, 1.3 mmol), (prepared as described for the starting material in Example 60), in DMF (3.5 ml) was added dropwise to a suspension of sodium hydride (53 mg, 1.3 mmol, prewashed with hexane) in DMF (1.5 ml). The mixture was stirred for 30 minutes at ambient temperature and a solution of 4-chloro-6-methoxy-7-(3-morpholinopropoxy)quinazoline (150 mg, 0.44 mmol), (prepared as described for the starting material in Example 5), in DMF (4 ml) was added. The mixture was stirred for 20 minutes at 65° C., DMSO (2 ml) was added and heating was continued for 1 hour at 65° C. The mixture was allowed to cool, the volatiles were removed by evaporation and the residue was partitioned between ether and water. The aqueous layer was adjusted to pH7.8 with 1M hydrochloric acid and the resulting precipitate was collected by filtration, washed with water and ether, and dried under vacuum. The solid was dissolved in methanol/ methylene chloride (1/1) and 2.2M ethereal hydrogen chloride (1 ml) was added. The mixture was stirred for 10 minutes at ambient temperature and the volatiles were removed by evaporation. The solid residue was triturated with ether, collected by filtration, washed with ether and dried under vacuum to give 4-(5-aminosulphonyloxindol-3-yl)-6-methoxy-7-(3-morpholinopropoxy)quinazoline hydrochloride (62 mg, 24%).

¹H NMR Spectrum: (DMSOd₆, CF₃CO₂D) 2.25–2.35(m, 2H); 3.15(t, 2H); 2H); 3.36(t, 2H); 3.55(d, 2H); 3.73(t, 2H); 3.93(s, 3H); 4.03(d, 2H); 4.33(t, 2H); 7.13(d, 1H); 7.35(s, 1H); 7.62(d,1H); 7.74(s, 1H); 8.1(s, 1H); 8.76(s, 1H).

MS-ESI: 514 [MH]⁺

| Elemental analysis: | Found | C 49.2 | H 5.2 | N 11.8 |
|---|---|---|---|---|
| C₂₄H₂₇N₅O₆S 1.0H₂O 1.4HCl | Requires | C 49.5 | H 5.3 | N 12.0% |

EXAMPLE 69

A solution of 5-methylaminosulphonyloxindole (262 mg, 1.16 mmol) in DMF (3.5 ml) was added dropwise to a suspension of sodium hydride (46 mg, 1.1 6 mmol, pre-washed with hexane) in DMF (1.5 ml). The mixture was stirred for 30 minutes at ambient temperature and 4-chloro-6-methoxy-7-(3-morpholinopropoxy)quinazoline (130 mg, 0.38 mmol), (prepared as described for the starting material in Example 5), was added as a solid. The mixture was stirred for 45 minutes at 60° C. and was then partitioned between ether and water. The aqueous layer was separated and was adjusted to pH7–8 with 1M hydrochloric acid. The precipitate was collected by filtration, washed with water and ether, and dried under vacuum. The solid was suspended in methylene chloride/methanol (1/1) and 2.2M ethereal hydrogen chloride (1.5 ml) was added. The mixture was stirred for 10 minutes at ambient temperature and the volatiles were removed by evaporation. The solid residue was triturated with ether, collected by filtration, washed with ether and dried under vacuum at 60° C. to give 6-methoxy-4-(5-methylaminosulphonyloxindol-3-yl)-7-(3-morpholinopropoxy)quinazoline hydrochloride (116 mg, 53%).

$^1$H NMR Spectrum: (DMSOd$_6$, CF$_3$CO$_2$D) 2.29(s, 3H); 3.16(t, 2H); 3.33(t, 2H); 3.54(d, 2H); 3.74(t, 2H); 3.93(s, 3H); 4.02(d, 2H); 4.33(t, 2H); 7.14(d, 1H); 7.34(s, 1H); 7.52(d, 1H); 7.76(s, 1H); 8.03(s, 1H); 8.67(s, 1H).

MS-ESI: 528 [MH]$^+$

| Elemental analysis: | Found | C 50.3 | H 5.4 | N 11.3 |
|---|---|---|---|---|
| C$_{25}$H$_{29}$N$_5$O$_6$S 0.85H$_2$O 1.6HCl | Requires | C .09 | H 5.4 | N 11.6% |

The starting material was prepared as follows:

Methylamine (2.7 ml of a 2.9M solution in chloroform) was added to a suspension of 5-chlorosulphonyloxindole (900 mg, 3.9 mmol), (prepared as described for the starting material in Example 60), in a mixture of methylene chloride (20 ml) and ethanol (20 ml). The mixture was stirred for 15 minutes at ambient temperature, the volatiles were removed by evaporation. The solid residue was suspended in water, collected by filtration, washed with water, ether, and dried under vacuum over phosphorus pentoxide to give 5-methylaminosulphonyloxindole (880 mg, 90%).

$^1$H NMR Spectrum: (DMSOd$_6$) 2.37(d, 3H); 3.58(s, 2H); 6.96(d, 1H); 7.25(br s, 1H); 7.58(s 1H); 7.60(d, 1H).

EXAMPLE 70

A solution of 5-methylaminosulphonyloxindole (252 mg, 1.1 mmol), (prepared as described for the starting material in Example 69), in DMF (2.5 ml) was added dropwise to a suspension of sodium hydride (45 mg, 1.1 mmol, prewashed with hexane) in DMF (1.5 ml). The mixture was stirred for 30 minutes at ambient temperature and 4-chloro-6-methoxy-7-(2-methoxyethoxy)quinazoline (100 mg, 0.37 mmol), (prepared as described for the starting material in Example 2), was added as a solid. The mixture was then stirred for 45 minutes at 60° C. and was then partitioned between ether and water. The aqueous layer was separated and was adjusted to pH7–8 with 1M hydrochloric acid. The precipitate was collected by filtration, washed with water and ether, and dried under vacuum. The solid was suspended in methylene chloride/methanol (1/1) and 2.2M ethereal hydrogen chloride (1.5 ml) was added. The mixture was stirred for 10 minutes at ambient temperature and the volatiles were removed by evaporation. The solid residue was triturated with ether, collected by filtration, washed with ether and dried under vacuum at 60° C. to give 6-methoxy-7-(2-methoxyethoxy)-4-(5-methylaminosulphonyloxindol-3-yl)quinazoline hydrochloride (123 mg, 68%).

$^1$H NMR Spectrum: (DMSOd$_6$, CF$_3$CO$_2$D) 2.29(s, 3H); 3.36(s, 3H); 3.79(t, 2H); 3.93(s, 3H); 4.35(t, 2H); 7.14(d, 1H); 7.32(s, 1H); 7.53(d, 1H); 7.73(s, 1H); 8.04(s, 1H); 8.73(s, 1H).

MS-ESI: 459 [MH]$^+$

| Elemental analysis: | Found | C 51.6 | H 4.8 | N 11.1 |
|---|---|---|---|---|
| C$_{21}$H$_{22}$N$_4$O$_6$S 0.5H$_2$O 0.65HCl | Requires | C 51.4 | H 4.9 | N 11.4% |

EXAMPLE 71

A solution of oxindole (116 mg, 0.87 mmol) in DMF (1.5 ml) was added to a suspension of sodium hydride (35 mg, 0.87 mmol, prewashed with hexane) in DMF (2.5 ml). The mixture was stirred for 30 minutes at ambient temperature and 4-chloro-6-methoxy-7-(2-([N-methyl-N-(1-methyl-1H-imidazol-4-ylsulphonyl)]amino)ethoxy)quinazoline (120 mg, 0.29 mmol) was added as a solid. The mixture was stirred for 10 minutes at ambient temperature followed by 20 minutes at 50° C. The mixture was allowed to cool, and was partitioned between ether and water. The aqueous layer was separated and adjusted to pH7.7 with 1M hydrochloric acid. The mixture was left to stand for 1.5 hours and the resulting precipitate was collected by filtration, washed with water, ether and dried under vacuum. The solid was purified by column chromatography eluting with methylene chloride/methanol (95/5 and then 90/10). The purified solid was dissolved in methylene chloride/methanol (2/1) and 2M ethereal hydrogen chloride (1.5 ml) was added. The mixture was stirred for 10 minutes at ambient temperature and the volatiles were removed by evaporation. The solid residue was triturated with ether, collected by filtration, washed with ether, dried under vacuum to give 6-methoxy-7-(2-([N-methyl-N-(1-methyl-1H-imidazol4-ylsulphonyl)]amino)ethoxy)-4-(oxindol-3-yl)quinazoline hydrochloride (106 mg, 65%).

$^1$H NMR Spectrum: (DMSOd$_6$, CF$_3$CO$_2$D) 2.89(s, 3H); 3.56(t, 2H); 3.72(s, 3H); 3.86(s, 3H); 4.39(t, 2H); 7–7.1(m, 2H); 7.17(t, 1H); 7.3(s, 1H); 7.71(d, 2H); 7.76(s, 1H); 7.89(d, 1H); 8.91(s, 1H).

MS-ESI: 509 [MH]$^+$

| Elemental analysis: | Found | C 51.3 | H 4.6 | N 14.8 |
|---|---|---|---|---|
| C$_{24}$H$_{24}$N$_6$O$_5$S 0.1H$_2$O 1.3HCl | Requires | C 51.7 | H 4.6 | N 15.0% |

The starting material was prepared as follows:

Using a procedure identical to that described for the synthesis of 6-methoxy-7-(2-([N-methyl-N-(3-morpholinopropyisulphonyl)]amino)ethoxy)-3-((pivaloyloxy)methyl)-3,4-dihydroquinazolin-4-one in Example 65, 6-methoxy-7-(2-(methylamino)ethoxy)-3-((pivaloyloxy)methyl)-3,4-dihydroquinazolin4-one (400 mg, 1.1 mmol), (prepared as described for the starting material in Example 65), was treated with (1-methyl-1H-imidazol-4 -yl)sulphonyl chloride (219 mg, 1.2 mmol) and purified by column chromatography eluting with methanol/acetonitrile/methylene chloride (5/35/60) to give 6-methoxy-7-(2-([N-methyl-N-(1-methyl-1H-imidazol-4-ylsulphonyl)]amino)ethoxy)-3-((pivaloyloxy)methyl)-3,4-dihydroquinazolin-4-one (507 mg, 73%).

$^1$H NMR Spectrum: (DMSOd$_6$) 1.12(s, 9H); 2.84(s, 3H); 3.48(t, 2H); 3.69(s, 3H); 3.89(s, 3H); 4.31(t, 2H); 5.90(s, 2H); 7.19(s, 1H); 7.51(s, 1H); 7.79(s, 1H); 7.83(s, 1H); 8.36(s, 1H).

To a solution of 6-methoxy-7-(2-([N-methyl-N-(1-methyl-1H-imidazol-4-ylsulphonyl)]amino)ethoxy)-3-

((pivaloyfoxy)methyl)-3,4-dihydroquinazl2in-4-one (470 mg, 0.93 mmol) in methylene chloride (15 ml) was added a saturated solution of methanolic ammonia (50 ml). The mixture was stirred for 2 days at ambient temperature and the volatiles were removed by evaporation. The solid residue was triturated with ether, collected by filtration, washed with ether and dried under vacuum to give 6-methoxy-7-(2-([N-methyl-N-(1-methyl-1H-imidazol-4-ylsulphonyl)]amino) ethoxy)-3,4-dihydroquinazolin-4-one (300 mg, 82%).

$^1$H NMR Spectrum: (DMSOd$_6$) 2.84(s, 3H); 3.48(t, 2H); 3.69(s, 3H); 3.87(s, 3H); 4.29(t, 2H); 7.14(s, 1H); 7.45(s, 1H); 7.79(s, 1H); 7.83(s, 1H); 7.98(s, 1H).

A solution of 6-methoxy-7-(2-([N-methyl-N-(1-methyl-1H-imidazol4-ylsulphonyl)]amino)ethoxy)-3,4-dihydroquinazolin4-one (250 mg, 0.64 mmol) in thionyl chloride (5 ml) containing DMF (150 µl) was heated at 50° C. for 20 minutes. The mixture was allowed to cool, toluene was added and the volatiles were removed by evaporation. The residue was dissolved in methylene chloride and cooled to 5° C. Saturated aqueous sodium hydrogen carbonate solution was added until the aqueous layer maintained pH7.7 and the aqueous layer was extracted with methylene chloride. The combined organic extract was washed with brine, dried (MgSO$_4$) and the solvent removed by evaporation. The residue was triturated with ether, collected by filtration and dried under vacuum to give 4-chloro-6-methoxy-7-(2-([N-methyl-N-(1-methyl-1H-imidazol-4-ylsulphonyl)]amino)ethoxy)quinazoline (285 mg, 91%).

$^1$H NMR Spectrum: (DMSOd$_6$) 2.86(s, 3H); 3.53(t, 2H); 3.68(s, 3H); 4.0(s, 3H); 4.42(t, 2H); 7.41(s, 1H); 7.49(s, 1H); 7.78(s, 1H); 7.83(s, 1H); 8.89(s, 1H).

EXAMPLE 72

Using a procedure analogous to that described in Example 26, oxindole (0.32 g, 2.4 mmol) was added to sodium hydride (110 mg, 2.8 mmol) in DMF (15 ml) and the solution was treated with 4-chloro-6-morpholinoquinazoline (200 mg, 8 mmol), (EP 0566226), in DMF (8 ml). The product so obtained was treated with ethereal hydrogen chloride to give 4-(oxindol-3-yl)-6-morpholinoquinazoline hydrochloride (120 mg, 43%).

$^1$H NMR Spectrum (DMSOd$_6$, CF$_3$CO$_2$D) 3.2(m, 4H); 3.7(m, 4H); 7.0(m, 2H); 7.15(t, 1H); 7.6(m, 4H); 8.9(s, 1H), 11.2(s, 1H).

MS-ESI: 347 [MH]$^+$

| Elemental analysis: | Found | C | 61.8 | H | 4.9 | N | 14.4 |
| C$_{20}$H$_{18}$N$_4$O$_2$ 0.3H$_2$O 1HCl | Requires | C | 61.9 | H | 5.1 | N | 14.4% |

EXAMPLE 73

A solution of 5-N,N-dimethylaminosulphonyloxindole (268 mg, 1.1lmmol) in DMF (3 ml) was added dropwise to a suspension of sodium hydride (45 mg, 1.1 mmol, prewashed with hexane) in DMF (1.5 ml). The mixture was stirred for 30 minutes at ambient temperature and 4-chloro-6-methoxy-7-(2-methoxyethoxy)quinazoline (100 mg, 0.37 mmol), (prepared as described for the starting material in Example 2), was added as a solid. The mixture was stirred for 10 minutes at ambient temperature and then 1 hour at 45° C. The mixture was allowed to cool and was partitioned between ether and water. The aqueous layer was separated, adjusted to pH7 with 1M hydrochloric acid and extracted with ethyl acetate. The organic extract was washed with brine, dried (MgSO$_4$) and the solvent removed by evaporation. The residue was purified by column chromatography eluting with methylene chloridelacetonitrile/methanol (60/36/4). The purified solid was collected, dried under vacuum and was dissolved in methylene chloride/methanol (3/1). 2.2M Ethereal hydrogen chloride (1 ml) was added and the mixture stirred for 10 minutes at ambient temperature. The volatiles were removed by evaporation, the solid residue was triturated with ether, collected by filtration and dried under vacuum to give 4-(5N,N-dimethylaminosulphonyloxindol-3-yl)-6-methoxy-7-(2-methoxyethoxy)quinazoline hydrochloride (75 mg, 41%).

$^1$H NMR Spectrum: (DMSOd$_6$, CF$_3$CO$_2$D) 2.50(s, 6H); 3.35(s, 3H); 3.77(t, 2H); 3.91(s, 1H).

MS-EI: 472 [M]$^+$

| Elemental analysis: | Found | C | 52.5 | H | 5.1 | N | 11.1 |
| C$_{22}$H$_{24}$N$_4$O$_6$S 0.5H$_2$O 0.7HCl | Requires | C | 52.1 | H | 5.1 | N | 11.0% |

The starting material was prepared as follows:

Dimethylamine (430 µl, 8.6 mmol) was added to a solution of 5-chlorosulphonyloxindole (990 mg, 4.3 mmol), (prepared as described for the starting material in Example 60), in a mixture of methylene chloride (20 ml), acetonitrile (20 ml) and ethanol (20 ml). The mixture was stirred for 1 hour at ambient temperature, dimethylamine (86 µl) was added and stirring continued for 30 minutes at ambient temperature. The volatiles were removed by evaporation and the residue was purified by column chromatography eluting with methylene chloride/methanol 97/3 to give 5-N,N-dimethylaminosulphonyloxindole (315 mg, 30%).

$^1$H NMR Spectrum: (DMSOd$_6$) 2.57(s, 6H); 3.60(s, 2H); 7.01(d, 1H); 7.55(s, 1H); 7.59(s, 1H).

EXAMPLE 74

A solution of oxindole (153 mg, 1.15 mmol) in DMF (3 ml) was added to a suspension of sodium hydride (46 mg, 1.15 mmol, prewashed with hexane) in DMF (1 ml) and the mixture was stirred for 30 minutes at ambient temperature. 4-Chloro-6-methoxy-7-(2-(2-methoxyethoxy)ethoxy) quinazoline (120 mg, 0.38 mmol) was added as a solid and the mixture was stirred for 10 minutes at ambient temperature and then for 45 minutes at 50° C. The mixture was allowed to cool and was partitioned between ether and water. The aqueous layer was separated and adjusted to pH7.5 with 1M hydrochloric acid. The resulting precipitate was collected by filtration washed with water followed by ether and dried over phosphorus pentoxide. The solid was dissolved in methylene chloride/methanol and 2.8M ethereal hydrogen chloride (1 ml) was added. The volatiles were removed by evaporation, the solid residue was triturated with ether, collected by filtration and dried under vacuum to give 6-methoxy-7-(2-(2-methoxyethoxy)ethoxy)-4-(oxindol-3-yl)quinazoline hydrochloride (124 mg, 73%).

$^1$H NMR Spectrum: (DMSOd$_6$, CF$_3$CO$_2$D) 3.27(s, 3H); 3.49(m, 2H); 3.64(m, 2H); 3.87(br s, 5H); 4.32(m, 2H); 7.0–7.1(m, 2H); 7.18(t, 1H); 7.75(d, 1H); 8.9(s, 1H).

MS-ESI: 410 [MH]$^+$

| Elemental analysis: | Found | C | 59.1 | H | 5.6 | N | 9.4 |
|---|---|---|---|---|---|---|---|
| C$_{22}$H$_{23}$N$_3$O$_5$ 0.4H$_2$O 0.75HCl | Requires | C | 59.5 | H | 5.6 | N | 9.5% |

The starting material was prepared as follows:

Diethyl azodicarboxylate (864μl, 5.5 mmol) was added dropwise to a mixture of 7-hydroxy-6-methoxy-3-((pivaloyloxy)methyl)-3,4-dihydroquinazolin-4-one (1.2 g, 3.9 mmol) (prepared as described for the starting material in Example 22), triphenylphosphine (1.44 g, 5.5 mmol) and 2-(2-methoxyethoxy)ethanol (653 μl, 5.5 mmol) in methylene chloride (70 ml) cooled at 0° C. The mixture was stirred for 1.5 hours at ambient temperature and the solvent was removed by evaporation. The residue was purified by column chromatography eluting with a mixture of ethyl acetate/methylene chloride (50/50 followed by 80/20). The purified solid was suspended in ether, collected by filtration and dried under vacuum to give 6-methoxy-7-(2-(2-methoxyethoxy)ethoxy)-3-((pivaloyloxy)methyl)-3,4-dihydroquinazolin-4-one (1.70 g, 100%).

$^1$H NMR Spectrum: (DMSOd$_6$) 1.13(s, 9 H); 3.26(s, 3H); 3.5(m, 2H); 3.65(m, 2H); 3.85(m, 2H); 3.91(s, 3H); 4.3(m, 2H); 5.9(s, 2H); 7.2(s, 1H); 7.5(s, 1H); 8.4(s, 1H).

Saturated methanolic ammonia (20 ml) was added to a solution of 6-methoxy-7-(2-(2-methoxyethoxy)ethoxy)-3-((pivaloyloxy)methyl)-3,4-dihydroquinazolin-4-one (2.26 g, 5.5 mmol) in a mixture of ethanol (40 ml) and methylene chloride (15 ml). The mixture was stirred for 24 hours at ambient temperature, and further methanolic ammonia (20 ml) was added. The mixture was stirred for a further 24 hours at ambient temperature and the volatiles were removed by evaporation. The residue was triturated with ether, collected by filtration, dried under vacuum to give 6-methoxy-7-(2-(2-methoxyethoxy)ethoxy)-3,4-dihydroquinazolin-4-one (975 mg, 78%).

$^1$H NMR Spectrum: (DMSOd$_6$) 3.25(s, 3H); 3.45(t, 2H); 3.6(t, 2H); 3.8(t, 2H); 3.9(s, 3H); 4.2(t, 2H); 7.15(s, 1H); 7.45(s, 1H); 8.0(s, 1H).

MS-EI: 294 [M]$^+$

A solution of 6-methoxy-7-(2-(2-methoxyethoxy)ethoxy)-3,4-dihydroquinazolin-4-one (930 mg, 3.16 mmol) in thionyl chloride (15 ml) and DMF (150 μl) was heated at 60° C. for 1.5 hours. The mixture was allowed to cool and the volatiles were removed by evaporation and by azeotroping with toluene. The residue was dissolved in methylene chloride and 5% aqueous sodium hydrogen carbonate solution was added until the aqueous layer was at pH8. The organic layer was separated, washed with brine, dried (MgSO$_4$) and the solvent removed by evaporation. The residue was purified by flash chromatography eluting with ethyl acetate to give 4-chloro-6-methoxy-7-(2-(2-methoxyethoxy)ethoxy)quinazoline (863 mg, 87%).

$^1$H NMR Spectrum: (DMSOd$_6$) 3.24(s, 3H); 3.47(m, 2H); 3.62(m, 2H); 3.84(t, 2H); 4.01(s, 3H); 4.25(t, 2H); 7.41(s, 1H); 7.49(s, 1H); 8.88(s, 1H).

EXAMPLE 75

A solution of 5-aminosulphonyloxindole (265 mg, 1.25 mmol), (prepared as described for the starting material in Example 60), in DMF (2.5 ml) was added to a suspension of sodium hydride (50 mg, 1.25 mmol, prewashed with pentane) in DMF (1.5 ml). The mixture was stirred for 30 minutes at ambient temperature and 4-chloro-6-methoxy-7-(2-(2-methoxyethoxy)ethoxy)quinazoline (265 mg, 1.25 mmol), (prepared as described for the starting material in Example 74), was added followed by DMF (2 ml) and DMSO (0.5 ml). The mixture was heated at 60° C. for 45 minutes, then allowed to cool and partitioned between ether and water. The aqueous layer was separated and adjusted to pH7 with 1M hydrochloric acid. The resulting precipitate was collected by filtration, washed with water and ether, and dried under vacuum. The solid was dissolved in methylene chloride/methanol and 2.8M ethereal hydrogen chloride (1 ml) was added. The volatiles were removed by evaporation, the solid was triturated with ether, collected by filtration and dried under vacuum to give 4-(5-aminosulphonyloxindol-3-yl)-6-methoxy-7-(2-(2-methoxyethoxy)ethoxy)quinazoline hydrochloride (106 mg, 50%).

$^1$H NMR Spectrum: (DMSOd$_6$, CF$_3$CO$_2$D) 3.26(s, 3H); 3.49(m, 2H); 3.64(m, 2H); 3.86(br s, 2H); 3.91(s, 3H); 4.34(m, 2H); 7.10(d, 1H); 7.31(s, 1H); 7.59(d, 1H); 7.71(s, 1H); 8.08(s, 1H); 8.71(s, 1H).

MS-ESI: 489 [MH]$^+$

| Elemental analysis: | Found | C | 51.4 | H | 4.9 | N | 10.8 |
|---|---|---|---|---|---|---|---|
| C$_{22}$H$_{24}$N$_4$O$_7$S 0.7H$_2$O 0.45HCl | Requires | C | 51.1 | H | 5.03 | N | 10.8% |

EXAMPLE 76

A solution of 5-N,N-dimethylaminosulphonyloxindole (256 mg, 1.07 mmol), (prepared as described for the starting material in Example 73), in DMF (3 ml) was added to a suspension of sodium hydride (43 mg, 1.07 mmol, prewashed with pentane) in DMF (2 ml). The mixture was stirred for 30 minutes at ambient temperature and 4-chloro-6-methoxy-7-(3-morpholinopropoxy)quinazoline (120 mg, 0.36 mmol), (prepared as described for the starting material in Example 5), was added. The mixture was heated at 65° C. for 1 hour, then allowed to cool and partitioned between ether and water. The aqueous layer was separated and was adjusted to pH8 with 1M hydrochloric acid. The aqueous layer was extracted with methylene chloride, the organic extracts were combined, washed with brine, dried (MgSO$_4$) and the solvent removed by evaporation. The residue was purified by column chromatography eluting with methylene chloride/methanol (94/6). The purified product was dissolved in methylene chloride/methanol (3/1) and 2.8M ethereal hydrogen chloride (1 ml) was added. The volatiles were removed by evaporation, the residue was triturated with ether, collected by filtration and dried under vacuum to give 4-(5-N,N-dimethylaminosulphonyloxindol-3-yl)-6-methoxy-7-(3-morpholinopropoxy)quinazoline hydrochloride (109 mg, 48%).

$^1$H NMR Spectrum: (DMSOd$_6$, CF$_3$CO$_2$D) 2.3–2.4(m, 2H); 2.51(s, 6H); 3.1–3.2(m, 2H); 3.3–3.4(m, 2H); 3.6(d, 2H); 3.73(t, 2H); 3.92(s, 3H); 4.05(d, 2H); 4.33(t, 2H);

7.17(d, 1H); 7.3(s, 1H); 7.46(d, 1H); 7.83(br s, 1H); 7.98(s, 1H); 8.67(s, 1H).

MS-EI: 541 [M]$^+$

| Elemental analysis: | Found | C | 50.3 | H | 5.9 | N | 10.9 |
|---|---|---|---|---|---|---|---|
| $C_{26}H_{31}N_5O_6S$ 1.5$H_2O$ 1.5HCl 0.17ether | Requires | C | 50.4 | H | 5.9 | N | 11.0% |

EXAMPLE 77

The following illustrate representative pharmaceutical dosage forms containing the compound of formula I, or a pharmaceutically acceptable salt thereof (hereafter compound X), for therapeutic or prophylactic use in humans:

| (a) | Tablet I | mg/tablet |
|---|---|---|
| | Compound X | 100 |
| | Lactose Ph.Eur | 182.75 |
| | Croscarmellose sodium | 12.0 |
| | Maize starch paste (5% w/v paste) | 2.25 |
| | Magnesium stearate | 3.0 |
| (b) | Tablet II | mg/tablet |
| | Compound X | 50 |
| | Lactose Ph.Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |
| (c) | Tablet III | mg/tablet |
| | Compound X | 1.0 |
| | Lactose Ph.Eur | 93.25 |
| | Croscarmellose sodium | 4.0 |
| | Maize starch paste (5% w/v paste) | 0.75 |
| | Magnesium stearate | 1.0 |
| (d) | Capsule | mg/capsule |
| | Compound X | 10 |
| | Lactose Ph.Eur | 488.5 |
| | Magnesium stearate | 1.5 |
| (e) | Injection I | (50 mg/ml) |
| | Compound X | 5.0% w/v |
| | 1N Sodium hydroxide solution | 15.0% v/v |
| | 0.1N Hydrochloric acid (to adjust pH to 7.6) | |
| | Polyethylene glycol 400 | 4.5% w/v |
| | Water for injection to 100% | |
| (f) | Injection II | 10 mg/ml) |
| | Compound X | 1.0% w/v |
| | Sodium phosphate BP | 3.6% w/v |
| | 0.1N Sodium hydroxide solution | 15.0% v/v |
| | Water for injection to 100% | |
| (g) | Injection III | (1 mg/ml, buffered to pH6) |
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

Note

The above formulations may be obtained by conventional procedures well known in the pharmaceutical art. The tablets (a)–(c) may be enteric coated by conventional means, for example to provide a coating of cellulose acetate phthalate.

What is claimed is:

1. A compound of the formula I:

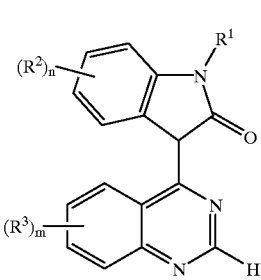

(I)

wherein:

$R^2$ represents hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylthio, $C_{1-4}$alkylsulphinyl, $C_{1-4}$alkylsulphonyl, carbamoyl, $\underline{N}$-$C_{1-4}$alkylcarbamoyl, $\underline{N},\underline{N}$-di($C_{1-4}$alkyl)carbamoyl, aminosulphonyl, $\underline{N}$-$C_{1-4}$alkylaminosulphonyl, $\underline{N},\underline{N}$-di($C_{1-4}$alkyl)aminosulphonyl, $C_{1-4}$alkylsulphonylamino, or a group $R^4X^1$ wherein $X^1$ represents a direct bond, $C_{2-4}$alkanoyl, —CONR$^5$R$^6$—, —SO$_2$NR$^7$R$^8$— or —SO$_2$R$^9$— (wherein $R^5$ and $R^7$, each independently represents hydrogen or $C_{1-2}$alkyl and $R^6$, $R^8$ and $R^9$ each independently represents $C_{1-4}$alkyl and wherein $R^4$ is linked to $R^6$, $R^8$ or $R^9$) and $R^4$ represents phenyl or a 5 or 6-membered heterocyclic group with one or two heteroatoms, selected independently from O, S and N, which heterocyclic group may be saturated or unsaturated and which phenyl or heterocyclic group may bear one or two substituents selected from hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxyearbonyl;

n is an integer from 0 to 4;

$R^1$ represents hydrogen, $C_{1-4}$alkyl, $C_{1-4}$alkoxymethyl, di($C_{1-4}$alkoxy)methyl or $C_{1-4}$alkanoyl;

m is an integer from 0 to 4; and $R^3$ represents hydroxy, halogeno, nitro, trifluoromethyl, $C_{1-3}$alkyl, cyano, amino or $R^{10}X^2$ wherein $X^2$ represents —O—, —CH$_2$—, —S—, —SO—, —SO$_2$—, —NR$^{11}$CO—, —CONR$^{12}$—, —SO$_2$NR$^{13}$—, —NR$^{14}$SO$_2$— or —NR$^{15}$— (wherein $R^{11}$, $R^{12}$, $R^{13}$, $R^{14}$ and $R^{15}$ each independently represents hydrogen, $C_{1-3}$alkyl or $C_{1-3}$alkoxy$C_{2-3}$alkyl), or $X^2$ represents a direct bond, and $R^{10}$ is selected from one of the following seventeen groups:

1) hydrogen or $C_{1-5}$alkyl which maybe unsubstituted or which may be substituted with one or more groups selected from hydroxy, fluoro and amino;
2) $C_{1-5}$alkyl$X^3$COR$^{16}$ (wherein $X^3$ represents —O— or —NR$^{17}$— (in which R$^{17}$ represents hydrogen, $C_{1-3}$alkyl or $C_{1-3}$alkoxy$C_{2-3}$alkyl) and R$^{16}$ represents $C_{1-3}$alkyl, —NR$^{18}$R$^{19}$— or —OR$^{20}$— (wherein R$^{18}$, R$^{19}$ and R$^{20}$ which may be the same or different each represents hydrogen, $C_{1-3}$alkyl or $C_{1-3}$alkoxy$C_{2-3}$alkyl));
3) $C_{1-5}$alkyl$X^4$R$^{21}$ (wherein $X^4$ represents —O—, —S—, —SO—, —SO$_2$—, —OCO—, —NR$^{22}$CO—, —CONR$^{23}$—, —SO$_2$NR$^{24}$—, —NR$^{25}$SO$_2$— or —NR$^{26}$— (wherein R$^{22}$, R$^{23}$, R$^{24}$, R$^{25}$ and R$^{26}$ each independently represents hydrogen, $C_{1-3}$alkyl or $C_{1-3}$alkoxy$C_{2-3}$alkyl) and R$^{21}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);
4) $C_{1-5}$alkyl$X^5C_{1-5}$alkyl$X^6R^{27}$ (wherein $X^5$ and $X^6$ which may be the same or different are each —O—, —S—, —SO—, —SO$_2$—, —NR$^{28}$CO—, —CONR$^{29}$—, —SO$_2$NR$^{30}$—, —NR$^{31}$SO$_2$— or —NR$^{32}$— (wherein R$^{28}$, R$^{29}$, R$^{30}$, R$^{31}$ and R$^{32}$ each independently represents hydrogen, $C_{1-3}$alkyl or $C_{1-3}$alkoxy$C_{2-3}$alkyl) and R$^{27}$ represents hydrogen or $C_{1-3}$alkyl);
5) $C_{1-5}$alkylR$^{33}$ (wherein R$^{33}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C^{1-4}$alkoxy);
6) $C_{2-5}$alkenylR$^{33}$ (wherein R$^{33}$ is as defined herein);
7) $C_{2-5}$alkynylR$^{33}$ (wherein R$^{33}$ is as defined herein);
8) R$^{34}$ (wherein R$^{34}$ represents a pyridone group, a phenyl group or a 5 or 6-membered aromatic heterocyclic group with 1 to 3 heteroatoms selected from O, N and S, which pyridone, phenyl or heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C^{1-4}$hydroxyalkoxy, carboxy, cyano, —CONR$^{35}$R$^{36}$ and —NR$^{37}$COR$^{38}$ (wherein R$^{35}$, R$^{36}$, R$^{37}$ and R$^{38}$, which may be the same or different, each represents hydrogen, $C_{1-4}$alkyl or $C_{1-3}$alkoxy$C_{2-3}$alkyl));
9) $C_{1-5}$alkylR$^{34}$ (wherein R$^{34}$ is as defined herein);
10) $C_{2-5}$alkenylR$^{34}$ (wherein R$^{34}$ is as defined herein);
11) $C_{2-5}$alkynylR$^{34}$ (wherein R$^{34}$ is as defined herein);
12) $C_{1-5}$alkyl$X^7$R$^{34}$ (wherein $X^7$ represents —O—, —S—, —SO—, —SO$_2$—, —NR$^{39}$CO—, —CONR$^{40}$—, —SO$_2$NR$^{41}$—, —NR$^{42}$SO$_2$— or —NR$^{43}$— (wherein R$^{39}$, R$^{40}$, R$^{41}$, R$^{42}$ and R$^{43}$ each independently represents hydrogen, $C_{1-3}$alkyl or $C_{1-3}$alkoxy$C_{2-3}$alkyl) and R$^{34}$ is as defined herein);
13) $C_{2-5}$alkenyl$X^8$R$^{34}$ (wherein $X^8$ represents —O—, —S—, —SO—, —SO$_2$—, —NR$^{44}$CO—, —CONR$^{45}$—, —SO$_2$NR$^{46}$—, —NR$^{47}$SO$_2$— or —NR$^{48}$— (wherein R$^{44}$, R$^{45}$, R$^{46}$, R$^{47}$ and R$^{48}$ each independently represents hydrogen, $C_{1-3}$alkyl or $C_{1-3}$alkoxy$C_{2-3}$alkyl) and R$^{34}$ is as defined herein);
14) $C_{2-5}$alkynyl$X^9$R$^{34}$ (wherein $X^9$ represents —O—, —S—, —SO—, —SO$_2$—, —NR$^{49}$CO—, —CONR$^{50}$—, —SO$_2$NR$^{51}$—, —NR$^{52}$SO$_2$— or —NR$^{53}$— (wherein R$^{49}$, R$^{50}$, R$^{51}$, R$^{52}$ and R$^{53}$ each independently represents hydrogen, $C_{1-3}$alkyl or $C_{1-3}$alkoxy$C_{2-3}$alkyl) and R$^{34}$ is as defined herein);
15) $C_{1-3}$alkyl$X^{10}C_{1-3}$alkylR$^{34}$ (wherein $X^{10}$ represents —O—, —S—, —SO—, —SO$_2$—, —NR$^{54}$CO—, —CONR$^{55}$—, —SO$_2$NR$^{56}$—, —NR$^{57}$SO$_2$— or —NR$^{58}$— (wherein R$^{54}$, R$^{55}$, R$^{56}$, R$^{57}$ and R$^{58}$ each independently represents hydrogen, $C_{1-3}$alkyl or $C_{1-3}$alkoxy$C_{2-3}$alkyl) and R$^{34}$ is as defined herein);
16) R$^{33}$ (wherein R$^{33}$ is as defined herein); and
17) $C_{1-3}$alkyl$X^{10}C_{1-3}$alkylR$^{33}$ (wherein $X^{10}$ and R$^{33}$ are as defined herein);

and salts thereof.

2. A compound as claimed in claim 1 wherein R$^1$ is hydrogen.

3. A compound as claimed in claim 1 or claim 2 wherein R$^2$ is halogeno, trifluoromethyl, cyano, nitro, $C_{2-3}$alkanoyl, $C_{1-3}$alkoxycarbonyl, $C_{1-3}$alkylsulphinyl, $C_{1-3}$alkylsulphonyl, carbamoyl, N-$C_{1-3}$alkylcarbamoyl, N,N-di($C_{1-3}$alkyl)carbamoyl, aminosulphonyl, N-$C_{1-3}$alkylaminosulphonyl, N,N-di($C_{1-3}$alkyl)aminosulphonyl, or a group R$^4$X$^1$, wherein X$^1$ is as defined in claim 1; and R$^4$ represents phenyl or a 5 or 6-membered heterocyclic group with one or two heteroatoms, selected independently from O, S and N, of which at least one is N, which heterocyclic group may be saturated or unsaturated and which phenyl or heterocyclic group may bear one or two substituents selected from hydroxy, halogeno, $C_{1-2}$alkyl, $C_{1-2}$alkoxy, $C_{1-2}$alkanoyloxy, trifluoromethyl, cyano, amino, nitro and $C_{1-4}$alkoxycarbonyl.

4. A compound as claimed in claim 1 or claim 2 wherein R$^3$ is hydroxy, halogeno, nitro, trifluoromethyl, $C_{1-3}$alkyl, cyano, amino or R$^{10}$X$^2$ wherein X$^2$ is as defined in claim 1 and R$^{10}$ is selected from one of the following fifteen groups:
1) $C_{1-3}$alkyl which may be unsubstituted or substituted with one or more fluorine atoms, or $C_{2-3}$alkyl which may be unsubstituted or substituted with one or two groups selected from hydroxy and amino;
2) 2-(3,3-dimethylureido)ethyl, 3-(3,3-dimethylureido)propyl, 2-(3-methylureido)ethyl, 3-(3-methylureido)propyl, 2-ureidoethyl, 3-ureidopropyl, 2-(N,N-

105 dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl;

3) $C_{2-3}$alkyl$X^4R^{21}$ (wherein $X^4$ is as defined in claim 1 and $R^{21}$ is a group selected from $C_{1-2}$alkyl, cyclopentyl, cyclohexyl, pyrrolidinyl and piperidinyl which group is linked to $X^4$ through a carbon atom and which $C_{1-2}$alkyl group may bear one or two substituents selected from hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{2-3}$alkyl$X^5C_{2-3}$alkyl$X^6R^{27}$ (wherein $X^5$ and $X^6$ are as defined in claim 1 and $R^{27}$ represents hydrogen or $C_{1-2}$alkyl);

5) $C_{1-2}$alkyl$R^{62}$ (wherein $R^{62}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-2}$alkyl through a carbon atom and which group may carry one substituent selected from oxo, hydroxy, halogeno, $C_{1-2}$alkyl, $C_{1-2}$hydroxyalkyl and $C_{1-2}$alkoxy) or $C_{2-3}$alkyl$R^{63}$ (wherein $R^{63}$ is a group selected from morpholino, thiomorpholino, piperidino, piperazin-1-yl and pyrrolidin-1-yl which group may carry one substituent selected from oxo, hydroxy, halogeno, $C_{1-2}$alkyl, $C_{1-2}$hydroxyalkyl and $C_{1-2}$alkoxy);

6) $R^{34}$ (wherein $R^{34}$ is as defined in claim 1);
7) $C_{1-4}$alkyl$R^{34}$ (wherein $R^{34}$ is as defined in claim 1);
8) 1-$R^{34}$but-2-en-4-yl (wherein $R^{34}$ is as defined in claim 1);
9) 1-$R^{34}$but-2-yn-4-yl (wherein $R^{34}$ is as defined in claim 1);
10) $C_{1-5}$alkyl$X^7R^{34}$ (wherein $X^7$ and $R^{34}$ are as defined in claim 1);
11) 1-($R^{34}X^8$)but-2-en-4-yl (wherein $X^8$ and $R^{34}$ are as defined in claim 1);
12) 1-($R^{34}X^9$)but-2-yn-4-yl (wherein $X^9$ and $R^{34}$ are as defined in claim 1);
13) ethyl$X^{10}$methyl$R^{34}$ (wherein $X^{10}$ and $R^{34}$ are as defined in claim 1);
14) $R^{33}$ (wherein $R^{33}$ is as defined in claim 1); and
15) ethyl$X^{10}$methyl$R^{33}$ (wherein $X^{10}$ and $R^{33}$ are as defined in claim 1).

5. A compound of the formula Ia:

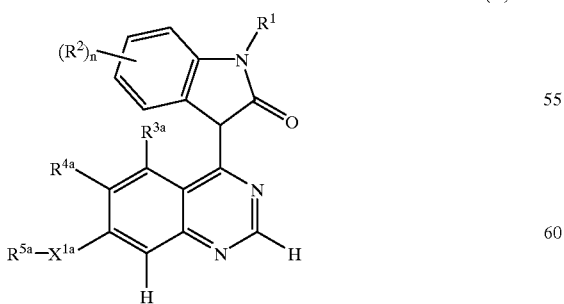

(Ia)

wherein:
$R^2$ represents hydroxy, halogeno, $C_{1-3}$alkyl, $C_{1-3}$alkoxy, $C_{1-3}$alkanoyloxy, trifluoromethyl, cyano,

106 amino, nitro, $C_{2-4}$alkanoyl, $C_{1-4}$alkanoylamino, $C_{1-4}$alkoxycarbonyl, $C_{1-4}$alkylthio, $C_{1-4}$alkylsulphinyl, $C_{1-4}$alkylsulphonyl, carbamoyl, N-$C_{1-4}$alkylcarbamoyl, N,N-di($C_{1-4}$alkyl)carbamoyl, aminosulphonyl, N-$C_{1-4}$alkylaminosulphonyl, N,N-di($C_{1-4}$alkyl)aminosulphonyl, $C_{1-4}$alkylsulphonylamino, or a group $R^4X^1$ wherein
$X^1$ represents a direct bond, $C_{2-4}$alkanoyl, —CONR$^5$R$^6$—, —SO$_2$NR$^7$R$^8$— or —SO$_2$R$^9$— (wherein $R^5$ and $R^7$, each independently represents hydrogen or $C_{1-2}$alkyl and $R^6$, $R^8$ and $R^9$ each independently represents $C_{1-4}$alkyl and wherein $R^4$ is linked to $R^6$, $R^8$ or $R^9$) and
$R^4$ represents phenyl or a 5 or 6-membered heterocyclic group with one or two heteroatoms, selected independently from O, S and N, which heterocyclic group may be saturated or unsaturated and which phenyl or heterocyclic group may bear one or two substituents selected from hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl;

n is an integer from 0 to 4;
$R^1$ represents hydrogen, $C_{1-4}$alkyl, $C_{1-4}$alkoxymethyl, di($C_{1-4}$alkoxy)methyl or $C_{1-4}$alkanoyl;
$R^{3a}$ represents hydrogen, hydroxy, methoxy, amino, nitro or halogeno;
$R^{4a}$ represents hydrogen, hydroxy, halogeno, cyano, nitro, trifluoromethyl, $C_{1-3}$alkyl, $C_{1-3}$alkoxy, $C_{1-3}$alkylthio, —NR$^{6a}$R$^{7a}$— (wherein $R^{6a}$ and $R^{7a}$, which may be the same or different, each represents hydrogen or $C_{1-3}$alkyl) or $R^{8a}(CH_2)_{za}X^{2a}$ (wherein $R^{8a}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy, za is an integer from 0 to 4 and $X^{2a}$ represents a direct bond, —O—, —CH$_2$—, —S—, —SO—, —SO$_2$—, —NR$^{9a}$CO—, —CONR$^{10a}$, —SO$_2$NR$^{11a}$—, —NR$^{12a}$SO$_2$— or —NR$^{13a}$— (wherein $R^{9a}$, $R^{10a}$, $R^{11a}$, $R^{12a}$ and $R^{13a}$ each independently represents hydrogen, $C_{1-3}$alkyl or $C_{1-3}$alkoxy$C_{2-3}$alkyl));
$X^{1a}$ represents —O—, —CH$_2$—, —S—, —SO—, —SO$_2$—, —NR$^{14a}$CO—, —CONR$^{15a}$—, —SO$_2$NR$^{16a}$—, —NR$^{17a}$SO$_2$— or —NR$^{18a}$— (wherein $R^{14a}$, $R^{15a}$, $R^{16a}$, $R^{17a}$ and $R^{18a}$ each independently represents hydrogen, $C_{1-3}$alkyl or $C_{1-3}$alkoxy$C_{2-3}$alkyl) or $X^{1a}$ represents a direct bond;
$R^{5a}$ is selected from one of the following seventeen groups:

1) hydrogen or $C_{1-5}$alkyl which may be unsubstituted or which may be substituted with one or more groups selected from hydroxy, fluoro and amino;
2) $C_{1-5}$alkyl$X^{3a}$COR$^{19a}$ (wherein $X^{3a}$ represents —O— or —NR$^{20a}$— (in which $R^{20a}$ represents hydrogen, $C_{1-3}$ alkyl or $C_{1-3}$ alkoxy$C_{2-3}$alkyl) and $R^{19a}$ represents $C_{1-3}$alkyl, —NR$^{21a}$R$^{22a}$— or —OR$^{23a}$— (wherein $R^{21a}$, $R^{22a}$ and $R^{23a}$ which may be the same or different each represents hydrogen, $C_{1-3}$alkyl or $C_{1-3}$alkoxy$C_{2-3}$alkyl));
3) $C_{1-5}$alkyl$X^{4a}R^{24a}$ (wherein $X^{4a}$ represents —O—, —S—, —SO—, —SO$_2$—, —OCO—, —NR$^{25a}$CO—, —CONR$^{26a}$—, —SO$_2$NR$^{27a}$—, —NR$^{28a}$SO$_2$— or —NR$_{29a}$— (wherein R$^{25a}$, R$^{26a}$, R$^{27a}$, R$^{28a}$ and R$^{29a}$ each independently represents hydrogen, C$_{1-3}$alkyl or C$_{1-3}$alkoxyC$_{2-3}$alkyl) and R$^{24a}$ represents hydrogen, C$_{1-3}$alkyl, cyclopentyl, cyclohexyl or a 5 or 6 membered saturated heterocyclic group with one or two heteroatoms, selected independently from O, S and N, which C$_{1-3}$alkyl group may bear one or two substituents selected from oxo, hydroxy, halogeno and C$_{1-4}$alkoxy and which cyclic group may bear one or two substituents selected from oxo, hydroxy, halogeno, C$_{1-4}$alkyl, C$_{1-4}$hydroxyalkyl and C$_{1-4}$alkoxy);

4) C$_{1-5}$alkylX$^{5a}$C$_{1-5}$alkylX$^{6a}$R$^{30a}$ (wherein X$^{5a}$ and X$^{6a}$ which may be the same or different are each —O—, —S—, —SO—, —SO$_2$—, —NR$^{31a}$CO—, —CONR$^{32a}$—, —SO$_2$NR$^{33a}$—, —NR$^{34a}$SO$_2$— or —NR$^{35a}$— (wherein R$^{31a}$, R$^{32a}$, R$^{33a}$, R$^{34a}$ and R$^{35a}$ each independently represents hydrogen, C$_{1-3}$alkyl or C$_{1-3}$alkoxyC$_{2-3}$alkyl) and R$^{30a}$ represents hydrogen or C$_{1-3}$alkyl);

5) C$_{1-5}$alkylR$^{36a}$ (wherein R$^{36a}$ is a 5 or 6 membered saturated heterocyclic group with one or two heteroatoms, selected independently from O, S and N, which heterocyclic group may bear one or two substituents selected from oxo, hydroxy, halogeno, C$_{1-4}$alkyl, C$_{1-4}$hydroxyalkyl and C$_{1-4}$alkoxy);

6) C$_{2-5}$alkenylR$^{36a}$ (wherein R$^{36a}$ is as defined herein);

7) C$_{2-5}$alkynylR$^{36a}$ (wherein R$^{36a}$ is as defined herein);

8) R$^{37a}$ (wherein R$^{37a}$ represents a pyridone group, a phenyl group or a 5 or 6-membered aromatic heterocyclic group with 1 to 3 heteroatoms selected from O, N and S, which pyridone, phenyl or heterocyclic group may carry up to 5 substituents selected from hydroxy, halogeno, amino, C$_{1-4}$alkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, carboxy, cyano, —CONR$^{38a}$R$^{39a}$ and —NR$^{40a}$COR$^{41a}$ (wherein R$^{38a}$, R$^{39a}$, R$^{40a}$ and R$^{41a}$, which may be the same or different, each represents hydrogen, C$_{1-4}$alkyl or C$_{1-3}$alkoxyC$_{2-3}$alkyl));

9) C$_{1-5}$alkylR$^{37a}$ (wherein R$^{37a}$ is as defined herein);

10) C$_{2-5}$alkenylR$^{37a}$ (wherein R$^{37a}$ is as defined herein);

11) C$_{2-5}$alkynylR$^{37a}$ (wherein R$^{37a}$ is as defined herein);

12) C$_{1-5}$alkylX$^{7a}$R$^{37a}$ (wherein X$^{7a}$ represents —O—, —S—, —SO—, —SO$_2$—, —NR$^{42a}$CO—, —CONR$^{43a}$—, —SO$_2$NR$^{44a}$—, —NR$^{45a}$SO$_2$— or NR$^{46a}$— (wherein R$^{42a}$, R$^{43a}$, R$^{44a}$, R$^{45a}$ and R$^{46a}$ each independently represents hydrogen, C$_{1-3}$alkyl or C$_{1-3}$alkoxyC$_{2-3}$alkyl) and R$^{37a}$ is as defined herein);

13) C$_{2-5}$alkenylX$^{8a}$R$^{37a}$ (wherein X$^{8a}$ represents —O—, —S—, —SO—, —SO$_2$—, —NR$^{47a}$CO—, —CONR$^{48a}$—, —SO$_2$NR$^{49a}$—, —NR$^{50a}$SO$_2$— or —NR$^{51a}$— (wherein R$^{47a}$, R$^{48a}$, R$^{49a}$, R$^{50a}$ and R$^{51a}$ each independently represents hydrogen, C$_{1-3}$alkyl or C$_{1-3}$alkoxyC$_{2-3}$alkyl) and R$^{37a}$ is as defined herein);

14) C$_{2-5}$alkynylX$^{9a}$R$^{37a}$ (wherein X$^{9a}$ represents —O—, —S—, —SO—, —SO$_2$—, —NR$^{52a}$CO—, —CONR$^{53a}$—, —SO$_2$NR$^{54a}$—, —NR$^{55a}$SO$_2$— or —NR$^{56a}$— (wherein R$^{52a}$, R$^{53a}$, R$^{54a}$, R$^{55a}$ and R$^{56a}$ each independently represents hydrogen, C$_{1-3}$alkyl or C$_{1-3}$alkoxyC$_{2-3}$alkyl) and R$^{37a}$ is as defined herein);

15) C$_{1-3}$alkylX$^{10a}$C$_{1-3}$alkylR$^{37a}$ (wherein X$^{10a}$ represents —O—, —S—, —SO—, —SO$_2$—, —NR$^{57a}$CO—, —CONR$^{58a}$—, —SO$_2$NR$^{59a}$—, —NR$^{60a}$SO$_2$— or —NR$^{61a}$— (wherein R$^{57a}$, R$^{58a}$, R$^{59a}$, R$^{60a}$ and R$^{61a}$ each independently represents hydrogen, C$_{1-3}$alkyl or C$_{1-3}$alkoxyC$_{2-3}$alkyl) and R$^{37a}$ is as defined herein);

16) R$^{36a}$ (wherein R$^{36a}$ is as defined herein); and

17) C$_{1-3}$alkylX$^{10a}$C$_{1-3}$alkylR$^{36a}$ (wherein X$^{10a}$ and R$^{36a}$ are as defined herein);

and salts thereof.

6. A compound as claimed in claim 5 wherein R$^1$ is hydrogen.

7. A compound as claimed in claim 5 or claim 6 wherein R$^2$ is halogeno, trifluoromethyl, cyano, nitro, C$_{2-3}$alkanoyl, C$_{1-3}$alkoxycarbonyl, C$_{1-3}$alkylsulphinyl, C$_{1-3}$alkylsulphonyl, carbamoyl, N-C$_{1-3}$alkylcarbamoyl, N,N-di(C$_{1-3}$alkyl)carbamoyl, aminosulphonyl, N-C$_{1-3}$alkylaminosulphonyl, N,N-di(C$_{1-3}$alkyl)aminosulphonyl, or a group R$^4$X$^1$ (wherein X$^1$ is as defined in claim 5 and R$^4$ represents phenyl or a 5 or 6-membered heterocyclic group with one or two heteroatoms, selected independently from O, S and N, of which at least one is N, which heterocyclic group may be saturated or unsaturated and which phenyl or heterocyclic group may bear one or two substituents selected from hydroxy, halogeno, C$_{1-2}$alkyl, C$_{1-2}$alkoxy, C$_{1-2}$alkanoyloxy, trifluoromethyl, cyano, amino, nitro and C$_{1-4}$alkoxycarbonyl).

8. A compound as claimed in claim 5 or claim 6 wherein R$^{3a}$ is hydrogen.

9. A compound as claimed in claim 5 or claim 6 wherein R$^{4a}$ is hydrogen, hydroxy, cyano, nitro, trifluoromethyl, methyl, ethyl, methoxy, ethoxy, or R$^{8a}$(CH$_2$)$_{za}$X$^{2a}$ (wherein R$^{8a}$ is a group selected from pyrrolidinyl, piperazinyl, piperidinyl, morpholino and thiomorpholino which group may carry one or two substituents selected from oxo, hydroxy, halogeno, C$_{1-2}$alkyl, C$_{1-2}$hydroxyalkyl and C$_{1-2}$alkoxy, X$^{2a}$ is —O—, —S—, —NR$^{9a}$CO—, —NR$^{12a}$SO$_2$— (wherein R$^{9a}$ and R$^{12a}$ each independently represents hydrogen or C$_{1-2}$alkyl) or NH and za is an integer from 1 to 3).

10. A compound as claimed in claim 5 or claim 6 wherein X$^{1a}$ is —O—, —S—, —NR$^{14a}$CO—, —NR$^{17a}$SO$_2$— (wherein R$^{14a}$ and R$^{17a}$ each independently represents hydrogen or C$_{1-2}$alkyl) or NH.

11. A compound as claimed in claim 5 or claim 6 wherein R$^{5a}$ is selected from one of the following fifteen groups:

1) C$_{1-3}$alkyl which may be unsubstituted or substituted with one or more fluorine atoms, or C$_{2-3}$alkyl which may be unsubstituted or substituted with one or two groups selected from hydroxy and amino;

2) 2-(3,3-dimethylureido)ethyl, 3-(3,3-dimethylureido) propyl, 2-(3-methylureido)ethyl, 3-(3-methylureido) propyl, 2-ureidoethyl, 3-ureidopropyl, 2-(N,N-dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl;

3) C$_{2-3}$alkylX$^{4a}$R$^{24a}$ (wherein X$^{4a}$ is as defined in claim 5 and R$^{24a}$ is a group selected from C$_{1-2}$alkyl, cyclopentyl, cyclohexyl, pyrrolidinyl and piperidinyl which group is linked to $X^{4a}$ through a carbon atom and which $C_{1-2}$alkyl group may bear one or two substituents selected from hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{2-3}$alkyl$X^{5a}C_{2-3}$alkyl$X^{6a}R^{30a}$ (wherein $X^{5a}$ and $X^{6a}$ are as defined in claim 5 and $R^{30a}$ represents hydrogen or $C_{1-2}$alkyl);

5) $C_{1-2}$alkyl$R^{65a}$ (wherein $R^{65a}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-2}$alkyl through a carbon atom and which group may carry one substituent selected from oxo, hydroxy, halogeno, $C_{1-2}$alkyl, $C_{1-2}$hydroxyalkyl and $C_{1-2}$alkoxy) or $C_{2-3}$alkyl$R^{66a}$ (wherein $R^{66a}$ is a group selected from morpholino, thiomorpholino, piperidino, piperazin-1-yl and pyrrolidin-1-yl which group may carry one substituent selected from oxo, hydroxy, halogeno, $C_{1-2}$alkyl, $C_{1-2}$hydroxyalkyl and $C_{1-2}$alkoxy);

6) $R^{37a}$ (wherein $R^{37a}$ is as defined in claim 5);

7) $C_{1-4}$alkyl$R^{37a}$ (wherein $R^{37a}$ is as defined in claim 5);

8) 1-$R^{37a}$but-2-en-4-yl (wherein $R^{37a}$ is as defined in claim 5);

9) 1-$R^{37a}$but-2-yn-4-yl (wherein $R^{37a}$ is as defined in claim 5);

10) $C_{1-5}$alkyl$X^{7a}R^{37a}$ (wherein $X^{7a}$ and $R^{37a}$ are as defined in claim 5);

11) 1-($R^{37a}X^{8a}$)but-2-en-4-yl (wherein $X^{8a}$ and $R^{37a}$ are as defined in claim 5);

12) 1-($R^{37a}X^{9a}$)but-2-yn-4-yl (wherein $X^{9a}$ and $R^{37a}$ are as defined in claim 5);

13) ethyl$X^{10a}$methyl$R^{37a}$ (wherein $X^{10a}$ and $R^{37a}$ are as defined in claim 5);

14) $R^{36a}$ (wherein $R^{36a}$ is as defined in claim 5); and 15) ethyl$X^{10a}$methyl$R^{36a}$ (wherein $X^{10a}$ and $R^{36a}$ are as defined in claim 5).

12. A compound of the formula Ib:

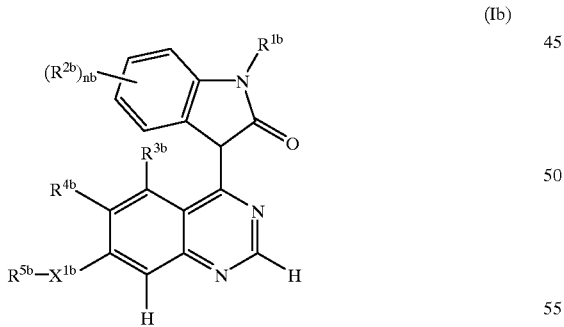

(Ib)

wherein:
$R^{1b}$ represents hydrogen;
$R^{2b}$ represents halogeno, trifluoromethyl, cyano, nitro, $C_{2-3}$alkanoyl, $C_{1-3}$alkoxycarbonyl, $C_{1-3}$alkylsulphinyl, $C_{1-3}$alkylsulphonyl, carbamoyl, N-$C_{1-3}$alkylcarbamoyl, N,N-di($C_{1-3}$alkyl)carbamoyl, aminosulphonyl, N-$C_{1-3}$alkylaminosulphonyl, N,N-di($C_{1-3}$alkyl)aminosulphonyl, or a group $R^{6b}X^{2b}$ (wherein $X^{2b}$ represents a direct bond, $C_{2-4}$alkanoyl, —CONR$^{7b}$R$^{8b}$—, —SO$_2$NR$^{9b}$R$^{10b}$— or —SO$_2$R$^{11b}$— (wherein R$^{7b}$ and R$^{9b}$, each independently represents hydrogen and R$^{8b}$, R$^{10b}$ and R$^{11b}$ each independently represents $C_{1-3}$alkyl and wherein R$^{6b}$ is linked to R$^{8b}$, R$^{10b}$ or R$^{11b}$) and R$^{6b}$ represents pyrrolidinyl, piperazinyl, piperidinyl, morpholino, thiomorpholino, imidazolyl or triazolyl which heterocyclic group is linked to $X^{2b}$ via a nitrogen atom and which heterocyclic group may bear one or two substituents selected from hydroxy, halogeno, $C_{1-2}$alkyl, $C_{1-2}$alkoxy, $C_{1-2}$alkanoyloxy, trifluoromethyl, cyano, amino, nitro and $C_{1-4}$alkoxycarbonyl);

nb is an integer from 0 to 2;
$R^{3b}$ represents hydrogen;
$R^{4b}$ represents hydrogen, hydroxy, cyano, nitro, trifluoromethyl, methyl, methoxy or a group $R^{12b}(CH_2)_{zb}X^{3b}$ (wherein $R^{12b}$ represents a group selected from pyrrolidinyl, piperazinyl, piperidinyl, morpholino and thiomorpholino which group may carry one or two substituents selected from oxo, hydroxy, halogeno, $C_{1-2}$alkyl, $C_{1-2}$hydroxyalkyl and $C_{1-2}$alkoxy, zb is an integer from 1 to 3 and $X^{3b}$ represents —O— or —NR$^{13}$CO— (wherein $R^{13b}$ represents hydrogen or $C_{1-2}$alkyl));
$X^{1b}$ represents —O— or —NR$^{14b}$CO— (wherein $R^{14b}$ represents hydrogen or $C_{1-2}$alkyl); and
$R^{5b}$ represents methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl 2-(4-pyridyloxy)ethyl, 2-(4-pyridylamino)ethyl, 2-(4-oxo-1,4-dihydro-1-pyridyl)ethyl, 2-thiomorpholinoethyl, 3-thiomorpholinopropyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 2-(2-methylimidazol-1-yl)ethyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 2-((N-methyl-N-4-pyridyl)amino)ethyl or 3-(4-oxidomorpholino)propyl;
and salts thereof.

13. A compound as claimed in claim 1 selected from:
6,7-dimethoxy-4-(6-fluorooxindol-3-yl)quinazoline;
6,7-dimethoxy-4-(oxindol-3-yl)quinazoline;
7-(2-methoxyethoxy)-4-(oxindol-3-yl)quinazoline;
4-(5-bromooxindol-3-yl)-6-methoxy-7-(2-methoxyethoxy)quinazoline;

4-(5-hydroxyoxindol-3-yl)-6-methoxy-7-(3-morpholinopropoxy)quinazoline;
6-methoxy-7-(3-morpholinopropoxy)-4-(6-trifluoromethyloxindol-3-yl)quinazoline;
4-(5-aminosulponyloxindol-3-yl)-6-methoxy-7-(2-methoxyethoxy)quinazoline;
4-(5-cyanooxindol-3-yl)-7-(3-morpholinopropoxy)quinazoline;
6-methoxy-7-(2-(2-methoxyethoxy)ethoxy)-4-(oxindol-3-yl)quinazoline; and
4-(5-aminosulphonyloxindol-3-yl)-6-methoxy-7-(2-(2-methoxyethoxy)ethoxy)quinazoline;
and salts thereof.

14. A compound as claimed in claim 1 selected from:
4-(5-fluorooxindol-3-yl)-6-methoxy-7-(3-morpholinopropoxy)quinazoline;
4-(5-fluorooxindol-3-yl)-6-methoxy-7-(2-methoxyethoxy)quinazoline;
4-(5-cyanooxindol-3-yl)-7-(2-(imidazol-1-yl)ethoxy)-6-methoxyquinazoline; and
7-(3-morpholinopropoxy)-4-(6-trifluoromethyloxindol-3-yl)quinazoline;
and salts thereof.

15. A compound as claimed in claim 1 selected from:
4-(6-fluorooxindol-3-yl)-6-methoxy-7-(3-morpholinopropoxy)quinazoline;
6-methoxy-7-(2-methoxyethoxy)-4-(oxindol-3-yl)quinazoline; and
6-methoxy-7-(3-morpholinopropoxy)-4-(oxindol-3-yl)quinazoline;
and salts thereof.

16. A compound as claimed in any one of claims 1, 5 and 12–15 in the form of a pharmaceutically acceptable salt.

17. A process for the preparation of a compound of formula I or salt thereof (as defined in claim 1) which comprises:

(a) the reaction of a compound of the formula III:

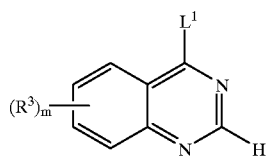

(III)

(wherein $R^3$ and m are as defined in claim 1 and $L^1$ is a displaceable moiety), with a compound of the formula IV:

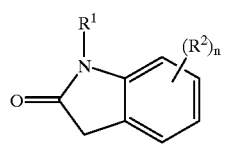

(IV)

(wherein $R^1$, $R^2$ and n are as defined in claim 1) whereby to obtain compounds of the formula I and salts thereof;

(b) the deprotection of a compound of formula V:

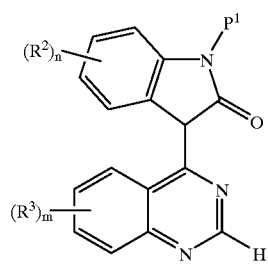

(V)

(wherein $R^2$, $R^3$, n and m are as defined in claim 1 and $P^1$ represents a protecting group);

(c) for the preparation of compounds of formula I and salts thereof wherein $R^1$ is hydrogen, the reduction and cyclisation of a compound of formula VI:

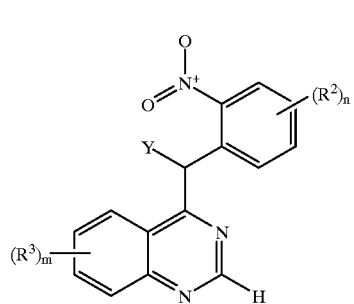

(VI)

(wherein $R^2$, $R^3$, m and n are as defined in claim 1 and Y represents cyano, carboxy or $C_{1-4}$alkoxycarbonyl);

(d) for the preparation of compounds of formula I and salts thereof wherein at least one of the $R^2$ groups is hydroxy the deprotection of a compound of formula VII:

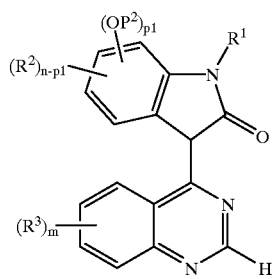

(VII)

(wherein $R^1$, $R^2$, $R^3$, n and m are as defined in claim 1, $P^2$ represents a phenolic hydroxy protecting group and p1 is an integer from 1 to 4 equal to the number of protected hydroxy groups and such that n–p1 is equal to the number of $R^2$ substituents which are not protected hydroxy);

(e) for the preparation of those compounds of formula I and salts thereof wherein at least one $R^3$ is $R^{10}X^2$ wherein $R^{10}$ is as defined in claim 1 and $X^2$ is —O—, —S—, —SO$_2$—, —CONR$^{12}$—, —SO$_2$NR$^{13}$— or —NR$^{15}$— (wherein $R^{12}$, $R^{13}$ and $R^{15}$ each independently represents hydrogen, $C_{1-3}$alkyl or $C_{1-3}$alkoxyC$_2$-

₃alkyl), the reaction, of a compound of the formula VIII:

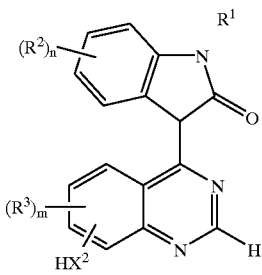

(VIII)

(wherein $R^1$, $R^2$, $R^3$, n and $X^2$ are as defined in claim 1 and s is an integer from 0 to 3) with a compound of formula IX:

 (IX)

(wherein $R^{10}$ is as defined in claim 1 and $L^1$ is as herein defined);

(f) for the preparation of compounds of formula I and salts thereof wherein at least one $R^3$ is $R^{10}X^2$ wherein $R^{10}$ is as defined in claim 1 and $X^2$ is —O—, —S—, or —$NR^{15}$— (wherein $R^{15}$ represents hydrogen, $C_{1-3}$alkyl or $C_{1-3}$alkoxy$C_{2-3}$alkyl), the reaction of a compound of the formula X:

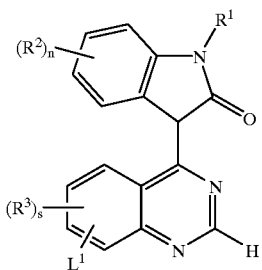

(X)

with a compound of the formula XI:

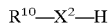 (XI)

(wherein $L^1$ and s are as defined herein and $R^1$, $R^2$, $R^3$, $R^{10}$, n, and $X^2$ are all as defined in claim 1);

(g) for the preparation of compounds of formula I and salts thereof wherein at least one $R^3$ is $R^{10}X^2$ wherein $X^2$ is as defined in claim 1 and $R^{10}$ is $C_{1-5}$alkyl$R^{65}$, reacting a compound of the formula XII:

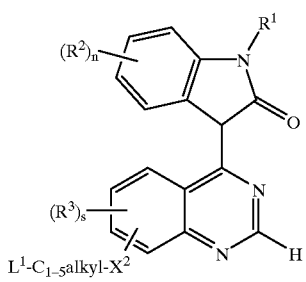

(XII)

(wherein $L^1$ and s are as herein defined and $X^2$, $R^1$, $R^2$, $R^3$ and n are as defined in claim 1) with a compound of the formula XIII:

 (XIII)

(wherein $R^{65}$ is as defined herein) to give a compound of formula I or salt thereof;

(h) for the preparation of those compounds of formula I and salts thereof wherein one or more of the substituents $(R^3)_m$ is represented by —$NR^{79}R^{80}$—, where one or both of $R^{79}$ and $R^{80}$ are $C_{1-3}$alkyl, the reaction of a compound of formula I wherein the substituent $(R^3)_m$ is an amino group and an alkylating agent;

for the preparation of compounds of formula I and salts thereof wherein one or more of the substituents $R^2$ or $R^3$ is an amino group the reduction of a corresponding compound of formula I wherein the substituent(s) at the corresponding position(s) of the quinazoline and/or benz ring of the oxindole group is/are a nitro group(s);

and when a salt of a compound of formula I is required, reaction of the compound obtained with an acid or base whereby to obtain the desired salt.

18. A pharmaceutical composition which comprises as active ingredient a compound of formula I as defined in claim 1 or a pharmaceutically acceptable salt thereof in association with a pharmaceutically acceptable excipient or carrier.

19. A method for producing an antiangiogenic and/or vascular permeability reducing effect in a warm-blooded animal in need of such treatment which comprises administering to said animal an effective amount of a compound of formula I as defined in any one of claims 1, and 13–15, or a pharmaceutically acceptable salt thereof.

* * * * *